US011684673B2

(12) United States Patent
Bakaletz et al.

(10) Patent No.: US 11,684,673 B2
(45) Date of Patent: Jun. 27, 2023

(54) PEPTIDES AND ANTIBODIES FOR THE REMOVAL OF BIOFILMS

(71) Applicant: RESEARCH INSTITUTE AT NATIONWIDE CHILDREN'S HOSPITAL, Columbus, OH (US)

(72) Inventors: Lauren O. Bakaletz, Hilliard, OH (US); Steven D. Goodman, Hilliard, OH (US)

(73) Assignee: Research Institute at Nationwide Children's Hospital, Columbus, OH (US)

(*) Notice: Subject to any disclaimer, the term of this patent is extended or adjusted under 35 U.S.C. 154(b) by 0 days.

(21) Appl. No.: 17/150,731

(22) Filed: Jan. 15, 2021

(65) Prior Publication Data

US 2021/0228716 A1     Jul. 29, 2021

Related U.S. Application Data

(63) Continuation of application No. 15/744,713, filed as application No. PCT/US2016/045032 on Aug. 1, 2016, now Pat. No. 10,940,204.

(60) Provisional application No. 62/361,400, filed on Jul. 12, 2016, provisional application No. 62/387,562, filed on Dec. 23, 2015, provisional application No. 62/199,957, filed on Jul. 31, 2015.

(51) Int. Cl.

| | |
|---|---|
| *A61K 39/40* | (2006.01) |
| *C07K 16/18* | (2006.01) |
| *C12N 15/62* | (2006.01) |
| *A61L 27/54* | (2006.01) |
| *A61L 29/16* | (2006.01) |
| *A61Q 11/00* | (2006.01) |
| *A61Q 17/00* | (2006.01) |
| *C07K 16/12* | (2006.01) |
| *A61K 8/64* | (2006.01) |
| *A61K 39/395* | (2006.01) |
| *A61K 39/12* | (2006.01) |
| *A61P 31/04* | (2006.01) |
| *A61K 39/00* | (2006.01) |

(52) U.S. Cl.
CPC ............... *A61K 39/40* (2013.01); *A61K 8/64* (2013.01); *A61K 39/12* (2013.01); *A61K 39/395* (2013.01); *A61L 27/54* (2013.01); *A61L 29/16* (2013.01); *A61P 31/04* (2018.01); *A61Q 11/00* (2013.01); *A61Q 17/005* (2013.01); *C07K 16/12* (2013.01); *C07K 16/1217* (2013.01); *C07K 16/1232* (2013.01); *C07K 16/1242* (2013.01); *C07K 16/1271* (2013.01); *C07K 16/1275* (2013.01); *C07K 16/18* (2013.01); *C12N 15/62* (2013.01); *A61K 2039/507* (2013.01); *A61L 2300/404* (2013.01); *C07K 2317/34* (2013.01); *C07K 2317/76* (2013.01)

(58) Field of Classification Search
None
See application file for complete search history.

(56) References Cited

U.S. PATENT DOCUMENTS

| | | |
|---|---|---|
| 4,659,678 A | 4/1987 | Forrest et al. |
| 4,914,023 A | 4/1990 | Philo |
| 6,551,795 B1 | 4/2003 | Rubenfield et al. |
| 6,663,863 B2 | 12/2003 | Horvath et al. |
| 6,696,550 B2 | 2/2004 | Larosa et al. |
| 6,846,651 B2 | 1/2005 | Fleischmann et al. |
| 7,241,867 B2 | 7/2007 | Bakaletz et al. |
| 7,413,868 B2 | 8/2008 | Kauvar et al. |
| 7,638,282 B2 | 12/2009 | Bakaletz et al. |
| 7,811,591 B2 | 10/2010 | Bakaletz et al. |
| 7,816,086 B2 | 10/2010 | Bakaletz et al. |
| 7,939,344 B2 | 5/2011 | Kauvar et al. |
| 7,998,490 B2 | 8/2011 | Bakaletz et al. |
| 8,236,494 B2 | 8/2012 | Bakaletz et al. |
| 8,283,114 B2 | 10/2012 | Bakaletz et al. |
| 8,628,917 B2 | 1/2014 | Bakaletz et al. |
| 8,652,773 B2 | 2/2014 | Bakaletz et al. |
| 8,758,764 B2 | 6/2014 | Masignani et al. |
| 8,933,029 B2 | 1/2015 | McNicol et al. |
| 8,999,291 B2 | 4/2015 | Goodman et al. |
| 9,017,656 B2 | 4/2015 | Hancock et al. |
| 9,034,642 B2 | 5/2015 | Bakaletz et al. |
| 9,155,792 B2 | 10/2015 | Cottarel et al. |
| 9,745,366 B2 | 8/2017 | Goodman et al. |

(Continued)

FOREIGN PATENT DOCUMENTS

| | | |
|---|---|---|
| JP | 2005-519998 A | 7/2005 |
| JP | 2006-506441 A | 2/2006 |

(Continued)

OTHER PUBLICATIONS

U.S. Appl. No. 14/493,051, filed Sep. 22, 2014, Goodman et al.
U.S. Appl. No. 14/535,254, filed Nov. 6, 2014, University of Southern California et al.
U.S. Appl. No. 14/885,800, filed Oct. 16, 2015m Goodman et al.
U.S. Appl. No. 14/967,228, filed Dec. 11, 2015, Goodman et al.
U.S. Appl. No. 15/078,987, filed Mar. 23, 2016, The Research Institute at Nationwide Children's Hospital.
U.S. Appl. No. 15/744,713, filed Jan. 12, 2018, The Research Institute at Nationwide Children's Hospital.

(Continued)

*Primary Examiner* — Brian Gangle
(74) *Attorney, Agent, or Firm* — Foley & Lardner LLP

(57) ABSTRACT

This disclosure provides isolated or recombinant polypeptides that are useful to vaccinate individuals suffering from chronic/recurrent biofilm disease or as a therapeutic for those with an existing infection. The individual's immune system will then naturally generate antibodies which prevent or clear these bacteria from the host by interfering with the construction and or maintenance of a functional protective biofilm. Alternatively, antibodies to the polypeptides can be administered to treat or prevent infection. Bacteria that are released from the biofilm by our technology are more readily cleared by the remainder of the host's immune system.

26 Claims, 33 Drawing Sheets

Specification includes a Sequence Listing.

(56) References Cited

U.S. PATENT DOCUMENTS

| | | |
|---|---|---|
| 10,233,234 B2 | 3/2019 | Kauvar et al. |
| 10,570,193 B2 | 2/2020 | Kauvar et al. |
| 10,595,530 B2 | 3/2020 | Goodman et al. |
| 10,940,204 B2 | 3/2021 | Bakaletz et al. |
| 11,104,723 B2 | 8/2021 | Goodman et al. |
| 11,248,040 B2 | 2/2022 | Kauvar et al. |
| 2002/0132753 A1 | 9/2002 | Rosen et al. |
| 2003/0060410 A1 | 3/2003 | Tracey et al. |
| 2003/0099602 A1 | 5/2003 | Levin et al. |
| 2003/0229065 A1 | 12/2003 | Levy et al. |
| 2004/0202670 A1 | 10/2004 | Apicella |
| 2005/0049402 A1 | 3/2005 | Babcook et al. |
| 2005/0131222 A1 | 6/2005 | Fleischmann et al. |
| 2005/0221439 A1 | 10/2005 | Bakaletz et al. |
| 2006/0030539 A1 | 2/2006 | Nick et al. |
| 2006/0099207 A1 | 5/2006 | Wu et al. |
| 2006/0121047 A1 | 6/2006 | Tracey |
| 2006/0228384 A1 | 10/2006 | Eldridge |
| 2006/0240045 A1 | 10/2006 | Berthet et al. |
| 2007/0154529 A1 | 7/2007 | Bullerdiek |
| 2007/0264256 A1 | 11/2007 | Bakaletz et al. |
| 2009/0029929 A1 | 1/2009 | Nakajima et al. |
| 2009/0297555 A1 | 12/2009 | Kemble et al. |
| 2009/0324651 A1 | 12/2009 | Old et al. |
| 2010/0166771 A1 | 7/2010 | Bakaletz et al. |
| 2010/0291177 A1 | 11/2010 | Hermans et al. |
| 2010/0310569 A1 | 12/2010 | Bakaletz et al. |
| 2011/0135646 A1 | 6/2011 | Bakaletz et al. |
| 2011/0236306 A1 | 9/2011 | Goodman et al. |
| 2011/0293624 A1 | 12/2011 | Bakaletz et al. |
| 2012/0128701 A1 | 5/2012 | Goodman et al. |
| 2012/0148615 A1 | 6/2012 | Masignani et al. |
| 2013/0017204 A1 | 1/2013 | Bakaletz et al. |
| 2013/0078254 A1 | 3/2013 | Bakaletz et al. |
| 2013/0183323 A1 | 7/2013 | Wang |
| 2014/0120107 A1 | 5/2014 | Bakaletz et al. |
| 2014/0127221 A1 | 5/2014 | Bakaletz et al. |
| 2014/0287426 A1 | 9/2014 | Arnold et al. |
| 2014/0356389 A1 | 12/2014 | Masignani et al. |
| 2015/0086542 A1 | 3/2015 | Goodman et al. |
| 2015/0086561 A1 | 3/2015 | Kauvar et al. |
| 2015/0166641 A1 | 6/2015 | Goodman et al. |
| 2015/0197558 A1 | 7/2015 | Kauvar et al. |
| 2015/0218231 A1 | 8/2015 | Bakaletz et al. |
| 2015/0299298 A1 | 10/2015 | Kauvar et al. |
| 2016/0095316 A1 | 4/2016 | Goodman et al. |
| 2016/0175440 A1 | 6/2016 | Goodman et al. |
| 2016/0194384 A1 | 7/2016 | Goodman et al. |
| 2016/0237145 A1 | 8/2016 | Kauvar et al. |
| 2016/0244489 A1 | 8/2016 | Masignani et al. |
| 2016/0289278 A1 | 10/2016 | Bakaletz et al. |
| 2018/0303900 A1 | 10/2018 | Bakaletz et al. |
| 2019/0000971 A1 | 1/2019 | Bakaletz et al. |
| 2019/0337996 A1 | 11/2019 | Bakaletz et al. |
| 2019/0338018 A1 | 11/2019 | Bakaletz et al. |
| 2020/0002409 A1 | 1/2020 | Goodman et al. |
| 2020/0190170 A1 | 6/2020 | Kauvar et al. |
| 2021/0206841 A1 | 7/2021 | Goodman et al. |

FOREIGN PATENT DOCUMENTS

| | | |
|---|---|---|
| JP | 2006-506467 A | 2/2006 |
| JP | 2008-520552 A | 6/2008 |
| JP | 2013-529893 A | 7/2013 |
| WO | WO-00/47104 A2 | 8/2000 |
| WO | WO-02/085295 A2 | 10/2002 |
| WO | WO-03/026691 A1 | 4/2003 |
| WO | WO-03/026691 A2 | 4/2003 |
| WO | WO-2004/014418 A2 | 2/2004 |
| WO | WO-2004/044001 A2 | 5/2004 |
| WO | WO-2004/072094 A2 | 8/2004 |
| WO | WO-2005/025604 A2 | 3/2005 |
| WO | WO-2005/111066 A2 | 11/2005 |
| WO | WO-2006/017816 A2 | 2/2006 |
| WO | WO-2006/083301 A2 | 8/2006 |
| WO | WO-2006/114805 A2 | 11/2006 |
| WO | WO-2006/138527 A2 | 12/2006 |
| WO | WO-2007/001422 A2 | 1/2007 |
| WO | WO-2011/123396 A1 | 10/2011 |
| WO | WO-2012/034090 A1 | 3/2012 |
| WO | WO-2014/016417 A1 | 1/2014 |
| WO | WO-2014/201305 A1 | 12/2014 |
| WO | WO-2015/038339 A1 | 3/2015 |
| WO | WO-2015/048484 A2 | 4/2015 |
| WO | WO-2015/089502 A2 | 6/2015 |
| WO | WO-2016/154491 A1 | 9/2016 |
| WO | WO-2016/184795 A1 | 11/2016 |
| WO | WO-2017/023863 A1 | 2/2017 |
| WO | WO-2017/066719 A2 | 4/2017 |
| WO | WO-2017/192594 A1 | 11/2017 |
| WO | WO-2018/129078 A1 | 7/2018 |
| WO | WO-2018/129092 A1 | 7/2018 |
| WO | WO-2018/170178 A1 | 9/2018 |
| WO | WO-2020/038963 A1 | 2/2020 |
| WO | WO-2020/092554 A1 | 5/2020 |
| WO | WO-2021/007260 A2 | 1/2021 |

OTHER PUBLICATIONS

U.S. Appl. No. 15/999,215, filed Aug. 16, 2018, Goodman et al.
U.S. Appl. No. 16/297,094, filed Mar. 8, 2019, Goodman et al.
U.S. Appl. No. 16/475,654, filed Jul. 2, 2019, Bakaletz et al.
U.S. Appl. No. 16/475,656, filed Jul. 2, 2019, Bakaletz et al.
U.S. Appl. No. 16/492,582, filed Sep. 9, 2019, Goodman et al.
Adams et al., "D-158. Epitope-mapping the immune response of children with otitis media and adults with chronic obstructive pulmonary disease to the PilA protein of nontypeable Haemophilus influenzae type IV pilus," 107th General Meeting, American Society for Microbiology; Toronto, ON, 2007, 1 page.
Adams et al., "Epitope-mapping the immune response of children with otitis media and adults with chronic obstructive pulmonary disease to the PilA protein of nontypeable Haemophilus influenzae type IV pilus," Immunology, 9th International Symposium on Recent Advances in Otitis Media; St. Pete Beach, FL, 2007, p. 356, 1 page.
Andersson et al., "High Mobility Group 1 Protein (HMG-1) Stimulates Proinflammatory Cytokine Synthesis in Human Monocytes", The Journal of Experimental Medicine, vol. 192, No. 4, Aug. 21, 2000, pp. 565-570.
Andersson, U. et al. (2011) "HMGB1 Is a Therapeutic Target for Sterile Inflammation and Infection," Annu. Rev. Immunol. 29:139-162.
Bakaletz et al., "New strategies to target bacterial biofilms", 28th Annual North American Cystic Fibrosis Conference (NACFC), Atlanta, GA, Oct. 9-11, 2014 (presentation), 2 pages.
Bakaletz et al., "Relative immunogenicity and efficacy of two synthetic chimeric peptides of fimbrin as vaccinogens against nasopharyngeal colonization by nontypeable Haemophilus influenzae in the chincilla," Vaccine, vol. 15, No. 9, 1997, pp. 955-961.
Bakaletz et al., "Protection against Development of Otitis Media Induced by Nontypeable Haemophilus influenzae by Both Active and Passive Immunization in a Chinchilla Model of Virus-Bacterium Superinfection," Infecion and Immunity, vol. 67, No. 6, Jun. 1999, pp. 2746-2762.
Bakaletz, "Biofilms can be dispersed by focusing the immune system on a common family of bacterial nucleoid associated proteins", 6th ASM Conference on Biofilms, Miami, FL, Sep. 29-Oct. 4, 2012 (presentation), 5 pages.
Bakaletz, L.O., Targeting the biofilm for development of novel preventative and therapeutic vaccine candidates to prevent otitis media, 6th ASM Conference on Biofilms, Miami, FL, Sep. 29-Oct. 4, 2012 (presentation), 5 pages.
Barve et al., "Cloning and characterization of the mating type (MAT) locus from Ascochyta rabiei (teleomorph: Didymella rabiei) and a MAT phylogeny of legume-associated *Ascochyta* spp.," Fungal Genetics and Biology, vol. 39, No. 2, Feb. 10, 2003, pp. 151-167.
Bass, J.I.F. et al. (2010) "Extracellular DNA: A Major Proinflammatory Component of Pseudomonas aeruginosa Biofilms," The Journal of Immunology 184:6386-6395.

(56) References Cited

OTHER PUBLICATIONS

Beech, I.B. et al. (2005) "Microbe-surface interactions in biofouling and biocorrosion processes," International Microbiology 8:157-168.

Bjarnsholt, T. (2013) "The role of bacterial biofilms in chronic infections," APMIS 121(Suppl. 136):1-51.

Boles, B.R. et al. (2011) "Staphylococcal biofilm disassembly," Trends in Microbiology 19(9):449-455.

Brady, R.A. et al. (2006) "Identification of *Staphylococcus aureus* Proteins Recognized by the Antibody-Mediated Immune Response to a Biofilm Infection," Infection and Immunity 74(6):3415-3426.

Brandstetter et al., "Antibodies Directed Against Integration Host Factor Mediate Biofilm Clearance From Nasopore," The Laryngoscope, vol. 12, No. 11, Nov. 2013, pp. 2626-2632.

Brockson et al., "Evaluation of the kinetics and mechanism of action of anti-integration host factor-mediated disruption of bacterial biofilms," Molecular Microbiology, vol. 93, No. 6, Aug. 19, 2014, pp. 1246-1258, Supplementary Material, 6 pages.

Brockson et al., "Evaluation of the kinetics and mechanism of action of anti-integration host factor-mediated disruption of bacterial biofilms," Molecular Microbiology, vol. 93, No. 6, Aug. 19, 2014, pp. 1246-1258.

Brockson ME, Novotny LA, Mokrzan EM, Malhotra S, Jurcisek JA, Akbar R, Devaraj A, Goodman SD, Bakaletz LO, Evaluation of the kinetics and mechanism of action of anti-integration host factor-mediated disruption of bacterial biofilms. Molecular microbiology. 2014;93(6): 1246-58. Epub Jul. 30, 2014, doi: 10.1 1 1 1/mmi. 12735, PubMed PMID: 25069521; PMCID: 4160410.

Brown et al., "Tolerance to Single, but Not Multiple, Amino Acid Replacements in Antibody VHCDR2", J Immunol. May 1996, 155(9), pp. 3285-3291.

Catlin, "Extracellular Deoxyribonucleic Acid of Bacteria and a Deoxyribonuclease Inhibitor," Science, vol. 124, Sep. 7, 1956, pp. 441-442.

Ceri, H. et al. (1999) "The Calgary Biofilm Device: New Technology for Rapid Determination of Antibiotic Susceptibilities of Bacterial Biofilms," Journal of Clinical Microbiology 37(6):1771-1776.

Chen et al., "Novel Strategies for the Prevention and Treatment of Biofilm Related Infections," Int. J. Mol. Sci., vol. 14, Sep. 6, 2013, pp. 18488-18501.

Chen, C. et al. (2004) "Substrate specificity of Helicobacter pylori histone-like HU protein is determined by insufficient stabilization of DNA flexure points," Biochem J. 383:343-351.

Cho et al., "The modulation of the biological activities of mitochondrial histone Abf2p by yeast PKA and its possible role in the regulation of mitochondrial DNA content during glucose repression," Biochimica et Biophysica Acta, vol. 1522, No. 3, Oct. 4, 2001, pp. 175-186.

Coenye, T. et al. (2010) "In vitro and in vivo model systems to study microbial biofilm formation," Journal of Microbiological Methods 83:89-105.

Cohavy, O. et al. (1999) "Identification of a Novel Mycobacterial Histone H1 Homologue (HupB) as an Antigenic Target of pANCA Monoclonal Antibody and Serum Immunoglobulin A from Patients with Cohn's Disease," Infection and Immunity 67(12):6510-6517.

Collarini, E.J. et al. (2009) "Potent High-Affinity Antibodies for Treatment and Prophylaxis of Respiratory Syncytial Virus Derived from B Cells of Infected Patients," J Immunol 183:6338-6345.

Dalai, B. et al. (2009) "Histone-like protein H-NS regulates biofilm formation and virulence of Actinobacillus pheuropneumonia," Microbial Pathogenesis 46:128-134.

Darouiche, R.O. et al. (2004) "Treatment of Infections Associated with Surgical Implants," N Engl J Med 350:1422-1429.

De La Fuente-Nunez et al., "Broad-Spectrum Anti-biofilm Peptide That Targets a Cellular Stress Response," PLoS Pathog., vol. 10, No. 5, May 2014, pp. 1-12.

Devaraj A, justice SS, Bakaletz LO, Goodman SD. DNABII proteins play a central role in UPEC biofilm structure. Molecular microbiology. 2015. doi: 10.1111/mmi.12994. PubMed PMID: 25757804.

Devaraj et al., "DNABII proteins play a central role in UPEC biofilm structure", Molecular Microbiology, 2017, vol. 96, vol. 6, Jun. 2015, pp. 1119-1135.

Dominguez-Herrera, J. et al. (2011) "Efficacy of Daptomycin versus Vancomycin in an Experimental Model of Foreign-Body and Systemic Infection Caused by Biofilm Producers and Methicillin-Resistant *Staphylococcus epidermidis*," Antimicrobial Agents and Chemotherapy 56(2):613-617.

Donlan, R.M. et al. (2002) "Biofilms: Survival Mechanisms of Clinically Relevant Microorganisms," Clinical Microbiology Reviews 15(2):167-193.

Durocher et al., "High-level and high-throughput recombinant protein production by transient transfection of suspension-growing human 293-EBNA1 cells," Nucleic Acids Research, vol. 30, No. 2, e9, Nov. 11, 2001, 9 pages.

Eboigbodin, K.E. et al. (2008) "Characterization of the Extracellular Plymeric Substances Produced by *Escherichia coli* Using Infrared Spectroscopic, Proteomic, and Aggregation Studies," Biomacromolecules 9:686-695.

Estelles et al., "A High-Affinity Native Human Antibody Disrupts Biofilm from *Staphylococcus aureus* Bacteria and Potentiates Antibiotic Efficacy in a Mouse Implant Infection Model," Antimicrobial Agents and Chemotherapy, vol. 60, No. 4, Apr. 2016, pp. 2292-2301.

Estrela et al., "Combining Biofilm-Controlling Compounds and Antibiotics as a Promising New Way to Control Biofilm Infections," Pharmaceuticals, vol. 3, May 11, 2010, pp. 1374-1393.

Extended European Search Report issued in EP 16833687.3 dated Feb. 14, 2019, 13 pages.

Falciola et al., "Mutational analysis of the DNA binding domain A of chromosomal protein HMG1," Nucleic Acids Research, vol. 22, No. 3, Jan. 10, 1994, pp. 285-292.

Fan, Z. et al. (2002) "HMG2 Interacts with the Nucleosome Assembly Protein SET and Is a Target of the Cytotoxic T-Lymphocyte Protease Granzyme A," Molecular and Cellular Biology 22(8):2810-2820.

Final Office Action in U.S. Appl. No. 14/493,051 dated Oct. 7, 2016, 6 pages.

Final Office Action in U.S. Appl. No. 14/885,800 dated May 4, 2017, 17 pages.

Final Office Action in U.S. Appl. No. 15/078,987 dated Dec. 28, 2016, 12 pages.

Final Office Action issued in U.S. Appl. No. 15/336,726 dated Sep. 11, 2018, 10 pages.

Final Office Action on U.S. Appl. No. 14/885,800 dated May 29, 2018, 24 pages.

Final Office Action on U.S. Appl. No. 14/967,228 dated Nov. 22, 2017, 26 pages.

Final Office Action on U.S. Appl. No. 13/073,782 dated Mar. 27, 2014, 8 pages.

Final Office Action on U.S. Appl. No. 13/229,575 dated Aug. 29, 2013, 17 pages.

Final Office Action on U.S. Appl. No. 13/229,575 dated Sep. 19, 2014, 34 pages.

Final Office Action on U.S. Appl. No. 15/744,713 dated May 4, 2020, 10 pages.

Final Official Action issued in Japan Patent Application No. 2016-519661 dated Mar. 7, 2019, 5 pages (English Translation).

First Examination Report on AU Application No. 2018202762 dated May 10, 2019, 4 pages.

Garcia-Contreras et al., "Protein Translation and Cell Death: The Role of Rare tRNAs in Biofilm Formation and in Activating Dormant Phage Killer Genes," PLoS ONE, vol. 3, No. 6, Jun. 11, 2008, e2394, 17 pages.

George et al., "Cystic fibrosis infections: treatment strategies and prospects," FEMS Microbiol Lett., vol. 300, Jun. 15, 2009, pp. 153-164.

Gerstel et al., "Complex Regulation of csgD Promoter Activity by Global Regulatory Proteins," Molecular Microbiology, vol. 49, No. 3, Aug. 2003, pp. 639-654.

Goldenberg et al., "Genetic and biochemical analysis of IHF/HU hybrid proteins", BioChimie, vol. 76, No. 10-11, Jan. 1, 1994, pp. 941-950.

(56) References Cited

OTHER PUBLICATIONS

Good et al., "Synthetic RNA silencing in bacteria-antimicrobial discovery and resistance breaking," Frontiers in Microbiology, vol. 2, No. 185, Sep. 12, 2011, pp. 1-11.
Goodman et al., "Biofilms can be dispersed by focusing the immune system on a common family of bacterial nucleoid-associated proteins," Mucosal Immunology, vol. 4, No. 6, Nov. 2011, pp. 625-637.
Goodman et al., "In Vitro Selection of Integration Host Factor Binding Sites," Journal of Bacteriology, vol. 181, No. 10, May 1999, pp. 3246-3255.
Goodman et al., "Replacement of Integration Host Factor Protein-induced DNA Bending by Flexible Regions of DNA," The Journal of Biological Chemistry, vol. 274, No. 52, Aug. 6, 1999, pp. 37004-37011.
Goodman S D et al., "Biofilms can be dispersed by focusing the immune system on a common family of bacterial nucleoid-associated proteins", Mucosal Immuno, Nature Publishing Group, vol. 4, No. 6, Nov. 1, 2011, pp. 625-637.
Goodman SD, Obergfell KP, Jurcisek JA, Novotny LA, Downey JS, Ayala EA, Tjokro N, Li B, Justice SS, Bakaletz LO. Biofilms can be dispersed by focusing the immune system on a common family of bacterial nucleoid-associated proteins. Mucosal immunology. 2011;4(6):625-37. Epub Jul. 1, 2011. doi: 10.1038/mi.2011.27. PubMed PMID: 21716265.
Goodman, "A new immunotherapeutic approach that disperses biofilms, Banff Conference on Infectious Diseases", Banff, Alberta, Canada, May 18, 2012 (presentation), 9 pages.
Goodman, "Making and breaking biofilms", Ohio Branch American Society for Microbiology Annual Meeting, Columbus, OH, Apr. 11-12, 2014 (presentation), 12 pages.
Goodman, "Nucleoprotein complexes in the extracellular matrix are critical for the structural integrity of bacterial biofilms", 112th General Meeting, American Society for Microbiology, San Francisco, CA, Jun. 18, 2012 (presentation), 9 pages.
Goodman, "The DNABII family of proteins: Diagnostic markers and therapeutic targets of bacterial biofilms", International Congress on Bacteriology and Infectious Disease, Baltimore, MD, Nov. 21, 2013, 7 pages.
Goshima et al., "Chimeric HU-IHF proteins that alter DNA-binding ability," Gene, vol. 118, No. 1, Sep. 1, 1992, pp. 97-102.
Govan et al., "Microbial pathogenesis in cystic fibrosis: mucoid Pseudomonas aeruginosa and Burkholderia cepacia," Microbiol. Rev., vol. 60, No. 3, Sep. 1996, pp. 539-574.
Granston et al., "Characterization of a Set of Integration Host Factor Mutants Deficient for DNA Binding," J. Mol. Biol., vol. 234, Jun. 21, 1993, pp. 45-59.
Greenspan et al., "Defining epitopes: It's not as easy as it seems," Nature Biotechnology, vol. 17, Oct. 1999, pp. 936-937.
Gustave et al., "Targeting bacterial integration host factor to disrupt biofilms associated with cystic fibrosis," Journal of Cystic Fibrosis, vol. 12, No. 4, Nov. 17, 2012, pp. 384-389.
Gustave et al., Biofilms recovered from the sputum of CF patients contain the bacterial protein integration host factor (IHF), 25th Annual North American Cystic Fibrosis Conference, Anaheim, CA, Nov. 3-5, 2011 (poster), 1 page.
Gustave JE, Jurcisek JA, McCoy KS, Goodman SD, Bakaletz LO. Targeting bacterial integration host factor to disrupt biofilms associated with cystic fibrosis. Journal of cystic fibrosis: official journal of the European Cystic Fibrosis Society.2013;12(4):384-9. Epub Nov. 22, 2012. doi: 10.1016/j.jcf.2012.10.011. PubMed PMID: 23168017; PMCID: 3582735.
Hall-Stoodley et al., "Bacterial Biofilms: From the Natural Environment to Infectious Diseases," Nature Reviews, Microbiology, vol. 2, Feb. 2004, pp. 95-108.
Hall-Stoodley et al., "Direct Detection of Bacterial Biofilms on the Middle-Ear Mucosa of Children With Chronic Otitis Media," JAMA, vol. 296, No. 2, Jun. 1, 2007, pp. 202-211.
Hall-Stoodley et al., "Evolving concepts in biofilm infections", Cellular Microbiology, vol. 11, No. 7, 2009, pp. 1034-1043.
Hall-Stoodley et al., "Characterization of biofilm matrix, degradation by DNase treatment and evidence of capsule downregulation in Streptococcus pneumoniae clinical isolates," BMC Microbiology, vol. 8, No. 173, Oct. 8, 2008, 16 pages.
Haluzi et al., "Genes Coding for Integration Host Factor Are Conserve in Gram-Negative Bacteria," Journal of Bacteriology, vol. 173, No. 19, Oct. 1991, pp. 6297-6299.
Harley et al., "The Molecular Action and Regulation of the Testis-Determining Factors, SRY (Sex-Determining Region on the Y Chromosome) and SOX9 [SRY-Related High-Mobility Group (HMG) Box 9]," Endocrine Reviews, vol. 24, No. 4, Aug. 2003, pp. 466-487.
Harriman, W.D. et al. (2008) "Antibody discovery via multiplexed single cell characterization," Journal of Immunological Methods 341:135-145.
Harrison, J.J. et al. (2010) "Microtiter susceptibility testing of microbes growing on peg lids: a miniaturized biofilm model for high-throughput screening," Nature Protocols 5(7):1236-1254.
Haruta et al., "A possible role of histone-like DNA-binding protein of Streptococcus intermedius in the pathogenesis of bile duct damage in primary biliary cirrhosis," Clinical Immunology, vol. 127, No. 2, Mar. 11, 2008, pp. 245-251.
Haruta et al.,"Long-term bacterial exposure can trigger nonsuppurative destructive cholangitis associated with multifocal epithelial inflammation," Laboratory Investigation, vol. 90, Apr. 2010, pp. 577-588.
Haurum. "Recombinant polyclonal antibodies: the next generation of antibody therapeutics?" Drug Discovery Today. Jul. 2006;11(13-14):655-60.
Hoyle et al., "Bacterial Resistance to Antibiotics: The Role of Biofilms," Prog. Drug Res., vol. 37, 1991, pp. 91-105.
International Preliminary Report on Patentability on PCT Application No. PCT/US2017/030648 dated Nov. 15, 2018, 7 pages.
International Search Report and Written Opinion (ISA/US) on PCT Application No. PCT/US2016/045032 dated Jan. 13, 2017, 32 pages.
International Search Report and Written Opinion for PCT Application No. PCT/US2011/030212 dated Aug. 9, 2011, 18 pages.
International Search Report and Written Opinion for PCT Application No. PCT/US2011/051107, dated Jan. 25, 2012, 15 pages.
International Search Report and Written Opinion for PCT Patent Application No. PCT/US2014/042201, dated Nov. 28, 2014, 16 pages.
International Search Report and Written Opinion issued in PCT Application No. PCT/US2014/057771 dated Mar. 20, 2015, 13 pages.
International Search Report and Written Opinion on PCT Application No. PCT/US2018/012235 dated Apr. 26, 2018, 19 pages.
International Search Report and Written Opinion on PCT Application No. PCT/US2016/024107 dated Jul. 27, 2016, 8 pages.
International Search Report and Written Opinion on PCT Application No. PCT/US2016/57237 dated Apr. 5, 2017, 15 pages.
International Search Report and Written Opinion on PCT Application No. PCT/US2017/030648 dated Aug. 3, 2017, 10 pages.
International Search Report and Written Opinion on PCT Application No. PCT/US2018/012255 dated Apr. 26, 2018, 14 pages.
International Search Report and Written Opinion on PCT Application No. PCT/US2018/022508 dated Jul. 18, 2018, 17 pages.
International Search Report and Written Opinion on PCT PCT/US2019/044998 dated Oct. 24, 2019.
Janeway, "Manipulating the immune response to fight infection," Immunobiology: The Immune System in Health and Disease, 5th ed.; retrieved online from https://www.ncbi.nlm.nih.gov/books/NBK27131/, 2001, 13 pages.
Jiao et al., "Identification of Biofilm Matrix-Associated Proteins from an Acid Mine Drainage Microbial Community," Appl & Environ Microbiol., vol. 77, Aug. 2011, pp. 5230-5237.
Jodar et al., "Development of vaccines against meningococcal disease," Lancet, vol. 359, Apr. 27, 2002, pp. 1499-1508.
John, A-K. et al. (2011) "Reversible Daptomycin Tolerance of Adherent Staphylococci in an Implant Infection Model," Antimicrobial Agents and Chemotherapy 55(7):3510-3516.

(56) References Cited

OTHER PUBLICATIONS

Johnson et al., "Chapter 8: Bending and Compaction of DNA by Proteins," Protein-Nucleic Acid Interactions: Structural Biology, 2008, pp. 176-220.
Joo, H-S. et al. (2012) "Molecular Basis of In Vivo Formation by Bacterial Pathogens," Chemistry & Biology 19:1503-1513.
Jurcisek et al., "Role of Sialic Acid and Complex Carbohydrate Biosynthesis in Biofilm Formation by Nontypeable Haemophilus influenzae in the Chinchilla Middle Ear," Infection and Immunity, vol. 73, Jun. 2005, pp. 3210-3218.
Jurcisek et al., "Biofilms Formed by Nontypeable Haemophilus influenzae In Vivo Contain both Double-Stranded DNA and Type IV Pilin Protein," Journal of Bacteriology, vol. 189, No. 10, Feb. 15, 2007, pp. 3868-3875.
Justice et al., "Aberrant Community Architecture and Attenuated Persistence of Uropathogenic *Escherichia coli* in the Absence of Individual IHF Subunits," PLoS ONE, vol. 7, No. 10, Oct. 2012, pp. 1-11.
Kadajji et al., "Water Soluble Polymers for Pharmaceutical Applications", Polymers, vol. 3, No. 4, Nov. 11, 2011, pp. 1972-2009.
Kamashev et al., "The histone-like protein HU binds specifically to DNA recombination and repair intermediates," The EMBO Journal, vol. 19, No. 23, Oct. 13, 2000, pp. 6527-6535.
Kennedy et al., "Passive Transfer of Antiserum Specific for Immunogens Derived from a Nontypeable Haemophilus influenzae Adhesin and Lipoprotein D Prevents Otitis Media after Heterologous Challenge," Infection and Immunity, vol. 68, No. 5, May 2000, pp. 2756-2765.
Khrapunov, S. et al. (2006) "Binding then bending: A mechanism for wrapping DNA," PNAS 103(51):19217-19218.
Kim et al., "Beta-Arm flexibility of HU from *Staphylococcus aureus* dictates the DNA-binding and recognition mechanism," Acta Cryst., D70, Oct. 30, 2014, pp. 3273-3289.
Kim et al., "Proteins Released by Helicobacter pylori In Vitro," Journal of Bacteriology, vol. 184, No. 22, Nov. 2002, pp. 6155-6162.
Kirketerp-Moller et al., "Distribution, Organization, and Ecology of Bacteria in Chronic Wounds," Journal of Clinical Microbiology, vol. 46, No. 8, Aug. 2008, pp. 2717-2722.
Kornblit et al., "The genetic variation of the human HMG1 gene," Tissue Antigens, vol. 70, Apr. 12, 2007, pp. 151-156.
Kristian, S.A. et al. (2003) "Alanylation of Teichoic Acids Protects *Staphylococcus aureus* against Toll-like Receptor 2-Dependent Host Defense in a Mouse Tissue Cage Infection Model," The Journal of Infectoius Diseases 188:414-423.
Kyd et al., "Efficacy of the 26-Kilodalton Outer Membrane Protein and Two P5 Fimbrin-Derived Immunogens to Induce Clearance of Nontypeable Haemophilus influenzae from the Rat Middle Ear and Lungs as Well as from the Chinchilla Middle Ear and Nasopharynx," Infection and Immunity, vol. 71, No. 8, Aug. 2003, pp. 4691-4699.
Labbé et al., "Association of Smads with lymphoid enhancer binding factor 1/T cell-specific factor mediates cooperative signaling by the transforming growth factor-β and Wnt pathways," Proc. Natl. Acad. Sci. USA, vol. 97, No. 15, Jul. 18, 2000, pp. 8358-8363.
Laura A. Novotny et al., "Monoclonal antibodies against DNA-binding tips of DNABII proteins disrupt biofilms in vitro and induce bacterial clearance in vivo", EBIOMedicine, vol. 10, Aug. 1, 2016, pp. 33-44.
Lebeaux et al., "From in vitro to in vivo Models of Bacterial Biofilm-Related Infections," Pathogens, vol. 2, May 13, 2013, pp. 288-356.
Li et al., "Retroviral eDNA Integration: Stimulation by HMG I Family Proteins," Journal of Virology, vol. 74, No. 23, Dec. 2000, pp. 10965-10974.
Liu et al., "The essentiality and involvement of *Streptococcus intermedius* histone-like DNA-binding protein in bacterial viability and normal growth," Molecular Microbiology, vol. 68, No. 5, Apr. 21, 2008, pp. 1268-1282.
Liu, D. et al. (2008) "Histone-like DNA binding protein of *Streptococcus intermedius* induces the expression of pro-inflammatory cytokines in human monocytes via activation of ERK1/2 and JNK pathways," Cellular Microbiology 10(1):262-276.
Lunsford et al., "DNA-Binding Activities in *Streptococcus gordonii*: Indentification of a Receptor-Nickase and a Histonelike Protein," Current Microbiology, vol. 32, 1996, pp. 95-100.
Lutz, H.U. et al. (1990) "Covalent binding of detergent-solubilized membrane glycoproteins to 'Chemobond' plates for ELISA," Journal of Immunological Methods 129:211-220.
M. Elizabeth Brockson et al., "Evaluation of the kinetics and mechanism of action anti-integration host factor-mediated disruption of bacterial biofilms: Anti-IHF-mediated biofilm collapse", Molecular Microbiology., Aug. 19, 2014, pp. 1-22.
Malhotra et al., "Defining the functional epitopes of Integration Host Factor (IHF) to develop a novel biofilm-focused immunotherapeutic against nontypeable Haemophilus influenzae-induced chronic and recurrent otitis media", 18th International Symposium on Recent Advances in Otitis Media, National Harbor, MD, Jun. 7-11, 2015 (poster), 1 page.
Malhotra et al., "Fine mapping the functional epitopes within integration host factor, a novel therapeutic target for nontypeable Haemophilus influenza-induced diseases of the respiratory tract", Abst. 12th Annual AMA Research Symposium, Dallas, TX, Nov. 7, 2014, 1 page.
Malhotra et al., Identification of immunoprotective domains within the bacterial DNA-binding protein, integration host factor, 20th Annual Midwest Microbial Pathogenesis Meeting. The Ohio State University, Columbus, OH, Aug. 23-25, 2013 (poster), 1 page.
Malhotra et al., Identification of immunoprotective domains within the bacterial DNA-binding protein, integration host factor, Abst. Seventh Extraordinary International Symposium on Recent Advances in Otitis Media, Stockholm, Sweden, Jun. 12, 2013, 20 pages.
Malhotra et al., Identification of immunoprotective domains within the bacterial DNA-binding protein, integration host factor, Seventh Extraordinary International Symposium on Recent Advances in Otitis Media, Stockholm, Sweden, Jun. 15, 2013 (presentation).
Mann, E.E. et al. (2009) "Modulation of eDNA Release and Degradation Affects *Staphylococcus aureus* Biofilm Maturation," PLoS ONE 4(6):e5822, 1-12.
Martinez-Antonio A et al. (2008), "Functional organization of *Escherichia coli* transcriptional regulatory network", J. Mol. Biol. vol. 381, p. 238-247.
Meluleni et al., (1995) "Mucoid Pseudomonas aeruginosa Growing in a Biofilm In Vitro Are Killed by Opsonic Antibodies to the Mucoid Exopolysaccharide Capsule but Not by Antibodies Produced During Chronic Lung Infection in Cystic Fibrosis Patients," J. Immunology, 155:2029-2038.
Mouw et al., "Shaping the Borrelia burgdorferi genome: crystal structure and binding properties of the DNA-bending protein Hbb," Molecular Microbiology, vol. 63, No. 5, Jan. 22, 2007, pp. 1319-1330.
Mukherjee et al., "Quantitative protein expression and cell surface characteristics of *Escherichia coli* MG1655 biofilms," Proteomics, vol. 11, Nov. 1, 2010, pp. 339-351.
Murphy et al., "Microbial Interactions in the Respiratory Tract," The Pediatric Infectious Disease Journal, vol. 28, No. 10, Oct. 2009, pp. S121-S126.
Murphy, T.F. et al. (2002) "Biofilm formation by nontypeable Haemophilus influenzae: strain variablitiy, outer membrane antigen expression and role of pili," BMC Microbiology 2:7, 1-8.
Nakamura et al., "HMG Box A in HMG3 Protein Functions as a Mediator of DNA Structural Alteration Together with Box B," J. Biochem., vol. 129, No. 4, Feb. 5, 2001, pp. 643-651.
Nakashima, N. et al., "Bacterial Cellular Engineering by Genome Editing and Gene Silencing," Int. J. Mol. Sci., vol. 15, Feb. 18, 2014, pp. 2773-2793.
Nash et al., "Overproduction of *Escherichia coli* Integration Host Factor, a Protein with Nonidentical Subunits," Journal of Bacteriology, vol. 169, No. 9, Sep. 1987, pp. 4124-4127.
NCBI Gen Bank Accession No. ACE63256 (Apr. 1, 2009), 2 pages.
NCBI Gen Bank Accession No. NP_418813.1 (Aug. 8, 2016), 3 pages.
NCBI GenBank Accession No. BAA03950 (Feb. 16, 2008), 2 pages.

(56) References Cited

OTHER PUBLICATIONS

NCBI GenBank Accession No. CAA47740 (Nov. 11, 1998), 1 page.
NCBI GenBank Accession No. CAA49169(Feb. 5, 2003), 2 pages.
NCBI Genebank: P0A6Y1 (Sep. 13, 2005), 7 pages.
Non-Final Office Action for U.S. Appl. No. 14/493,051, dated Oct. 8, 2015, 8 pages.
Non-Final Office Action for U.S. Appl. No. 14/493,051 dated Mar. 12, 2015, 8 pages.
Non-Final Office Action in U.S. Appl. No. 13/073,782, dated Jun. 10, 2013, 15 pages.
Non-Final Office Action in U.S. Appl. No. 14/493,051 dated Apr. 28, 2016, 7 pages.
Non-Final Office Action in U.S. Appl. No. 14/885,800 dated Oct. 31, 2016, 22 pages.
Non-Final Office Action in U.S. Appl. No. 15/078,987 dated Jul. 14, 2016, 15 pages.
Non-Final Office Action in U.S. Appl. No. 15/078,987 dated Jun. 14, 2017, 26 pages.
Non-Final Office Action in U.S. Appl. No. 15/078,987, dated Mar. 16, 2018, 18 pages.
Non-Final Office Action in U.S. Appl. No. 13/073,782, dated Jun. 25, 2014, 5 pages.
Non-Final Office Action in U.S. Appl. No. 13/229,575, dated Jan. 10, 2013, 18 pages.
Non-Final Office Action in U.S. Appl. No. 13/229,575 dated Mar. 31, 2014, 32 pages.
Non-Final Office Action issued in U.S. Appl. No. 14/535,254 dated Mar. 25, 2016, 7 pages.
Non-Final Office Action on U.S. Appl. No. 14/493,051 dated Jan. 10, 2017, 4 pages.
Non-Final Office Action on U.S. Appl. No. 14/535,254 dated Jan. 26, 2018, 9 pages.
Non-Final Office Action on U.S. Appl. No. 14/535,254 dated Jul. 10, 2017, 5 pages.
Non-Final Office Action on U.S. Appl. No. 14/535,254 dated Sep. 9, 2015, 10 pages.
Non-Final Office Action on U.S. Appl. No. 14/885,800 dated Dec. 15, 2017, 16 pages.
Non-Final Office Action on U.S. Appl. No. 14/967,228 dated May 19, 2017, 21 pages.
Non-Final Office Action on U.S. Appl. No. 15/336,726 dated Mar. 7, 2018, 9 pages.
Non-Final Office Action on U.S. Appl. No. 14/535,254 dated Aug. 12, 2016, 8 pages.
Non-Final Office Action on U.S. Appl. No. 14/885,800 dated Aug. 8, 2019, 9 pages.
Non-Final Office Action on U.S. Appl. No. 15/144,681 dated Jan. 31, 2018, 18 pages.
Non-Final Office Action on U.S. Appl. No. 15/744,713 dated Nov. 8, 2019, 12 pages.
Notice of Allowability for U.S. Appl. No. 13/073,782 dated Mar. 4, 2015, 4 pages.
Notice of Allowability on U.S. Appl. No. 14/885,800 dated Jan. 3, 2020, 3 pages.
Notice of Allowance in U.S. Appl. No. 14/493,051 dated Apr. 25, 2017, 8 pages.
Notice of Allowance in U.S. Appl. No. 13/073,782, dated Aug. 19, 2014, 11 pages.
Notice of Allowance on U.S. Appl. No. 14/493,051 dated Jan. 27, 2017, 9 pages.
Notice of Allowance on U.S. Appl. No. 15/144,681 dated Oct. 30, 2018, 10 pages.
Notice of Allowance on U.S. Appl. No. 15/744,713 dated Oct. 2, 2020.
Notice of Allowance on U.S. Appl. No. 15/744,713 dated Oct. 6, 2020.
Notice of Allowance on U.S. Appl. No. 14/885,800 dated Nov. 13, 2019, 8 pages.
Notice of Allowance on U.S. Appl. No. 16/181,260 dated Oct. 18, 2019, 9 pages.

Novotny et al., "Antibodies against the majority subunit of Type 1V pili disperse nontypeable Haemophilus influenza biofilms in a LuxS-dependent manner and confer therapeutics resolution of experimental otitis media," Mol. Microbiol., vol. 96, No. 2, Apr. 2015, pp. 1-32.
Novotny et al., "Epitope mapping immunodominant regions of the PilA protein of nontypeable Haemophilus influenzae (NTHI) to facilitate the design of two novel chimeric vaccine candidates," Vaccine, vol. 28, No. 1, pp. 279-289 (Dec. 10, 2009).
Novotny et al., "Monoclonal antibodies against DNA-binding tips of DNABII proteins disrupt biofilms in vitro and induce bacterial clearance in vivo," EBIOMedicine, vol. 10, pp. 33-44 (Aug. 1, 2016).
Novotny et al., "Structural Stability of Burkholderia cenocepacia Biofilms Is Reliant on eDNA Structure and Presence of a Bacterial Nucleic Acid Binding Protein," PLOS ONE, vol. 8, No. 6, e67629, Jun. 2013, 15 pages.
Novotny et al., "Detection and characterization of pediatric serum antibody to the OMP P5-homologous adhesin of nontypeable Haemophilus influenzae during acute otitis media," Vaccine, vol. 20, No. 29-30, Jun. 8, 2002, pp. 3590-3597.
Novotny et al., "Epitope mapping immunodominant regions of the PilA protein of nontypeable Haemophilus influenzae (NTHI) to facilitate the design of two novel chimeric vaccine candidates," Vaccine, vol. 28, No. 1, Aug. 22, 2009, pp. 279-289.
Novotny et al., "Epitope mapping of the Outer Membrane Protein P5-Homologous Fimbrin Adhesin of Nontypeable Haemophilus influenzae," Infection and Immunity, vol. 68, No. 4, Apr. 2000, pp. 2119-2128.
Novotny et al., "Passive immunization with human anti-protein D antibodies induced by polysaccharide protein D conjugates protects chinchillas against otitis media after intranasal challenge with Haemophilus influenzae," Vaccine, vol. 24, No. 22, Mar. 27, 2006, pp. 4804-4811.
Novotny et al., "The Fourth Surface-Exposed Region of the Outer Membrane Protein P5-Homologous Adhesin of the Nontypable Haemophilus influenzae Is an Immunodominant but Nonprotective Decoying Epitope," The Journal of Immunology, vol. 171, No. 4, Jun. 10, 2003, pp. 1978-1983.
Novotny LA, Amer AO, Brockson ME, Goodman SD, Bakaletz LO. Structural stability of Burkholderia cenocepacia biofilms is reliant on eDNA structure and presence of a bacterial nucleic acid binding protein. PloS one.2013;8(6):e67629. Epub Jun. 27, 2013. doi: 10.1371/journal.pone.0067629. PubMed PMID: 23799151; PMCID: 3682984.
Novotny, "Development of a novel biofilm-focused immunotherapeutic against NTHI-induced otitis media", 18th International Symposium on Recent Advances in Otitis Media, National Harbor, MD, Jun. 7-11, 2015 (presentation), 3 pages.
Novotny, L.A. et al. (2016) "Monoclonal antibodies against DNA-binding tips of DNABII proteins disrupt biofilms in vitro and induce bacterial clearance in vivo," EBioMedicine 10:33-44.
Oberto et al., "Histones, HMG, HU, IHF: Même combat," Biochimie, vol. 76, 1994, pp. 901-908.
Official Action on JP Application No. 2017-109356 dated Jul. 26, 2019, 15 pages (English Translation).
Official Action on JP Application No. 2018-187557 dated Jul. 11, 2019, 4 pages (English Translation).
Ordway et al., "Evaluation of Standard Chemotherapy in the Guinea Pig Model of Tuberculosis," Antimicrobial Agents and Chemotherapy, vol. 54, May 2010, pp. 1820-1833.
Otto, "*Staphylococcus epidermidis*—the 'accidental' pathogen," Nature Reviews Microbiology, vol. 7, Aug. 2009, pp. 555-567.
PDB ID: 1IHF: Rice, P.A. et al. (1996), 1 page; retrieved online from http://www.rcsb.org/pdb/explore.do?structureId=IHF, 2 pages.
Pedulla et al., "A novel host factor for integration of mycobacteriophage L5," Proc. Natl. Acad. Sci. USA, vol. 93, Dec. 1996, pp. 15411-15416.
Percival, S.L. et al. (2015) "Biofilms and Wounds: An Overview of the Evidence," Advances in Wound Care 4(7):373-381.
Petersen et al., "Biofilm Mode of Growth of *Streptococcus intermedius* Favoreed by a Competence-Stimulating Signaling Peptide," Journal of Bacteriology, vol. 186, No. 18, Sep. 2004, pp. 6327-6331.

(56) References Cited

OTHER PUBLICATIONS

Pethe et al., "*Mycobacterium smegmatis* laminin-binding glycoprotein shares epitopes with *Mycobacterium tuberculosis* heparin-binding haemagglutinin," Molecular Microbiology, vol. 39, No. 1, 2001, pp. 89-99.
Prymula et al., "Pneumococcal capsular polysaccharides conjugated to protein D for prevention of acute otitis media caused by both *Streptococcus pneumoniae* and non-typable Haemophilus influenzae: a randomized double-blind efficacy study," Lancet, vol. 367, No. 9512, Mar. 4, 2006, pp. 740-748.
Reffuveille et al., "A Broad-Spectrum Antibiofilm Peptide Enhances Antibiotic Action against Bacterial Biofilms", Antimicrobial Agents and Chemotherapy, vol. 58, No. 9, Sep. 2014, pp. 5363-5371.
Restriction Requirement on U.S. Appl. No. 14/493,051 dated Nov. 7, 2014, 6 pages.
Restriction Requirement on U.S. Appl. No. 15/744,713 dated Jul. 29, 2019, 10 pages.
Rice et al., "Crystal Structure of an IHF-DNA Complex: A Protein-Induced DNA U-Turn," Cell, vol. 87, No. 7, pp. 1295-1306 (Dec. 27, 1996).
Rice et al., "Crystal Structure of an IHF-DNA Complex: A Protein-Induced DNA U-Turn," Cell, vol. 87, No. 7, Dec. 27, 1996, pp. 1295-1306.
Rocco et al., "Natural antigenic differences in the fucntionally equivalent extracellular DNABI I proteins of bacterial biofilms provide a means for targeted biofilm therapeutics," Molecular Oral Microbiology, vol. 32, No. 2, Apr. 2017, pp. 1-21.
Rudikoff et al., "Single amino acid substitution altering antigen-binding specificity," Proc. Natl. Acad. Sci. USA, vol. 79, No. 6, Mar. 1982, pp. 1979-1983.
Salmeron, "Fermented cereal beverages: from probiotic, prebioticand synbiotic towards Nanoscience designed healthy drinks", Letters in Applied Microbiology, vol. 65, Mar. 31, 2017, pp. 114-124.
Sapi et al., "Characterization of Biofilm Formation by Borrelia burgdorferi In Vitro," PLOS One, vol. 7, No. 10, Oct. 2012, pp. 1-11.
Schwartz, K. et al. (2012) "Functional Amyloids Composed of Phenol Soluble Modulins Stabilize *Staphylococcus aureus* Biofilms," PLOS Pathogens 8:e1002744, 1-11.
Segall et al., "Architectural elements in nucleoprotein complexes: interchangeability of specific and non-specific DNA binding proteins," The EMBO Journal, vol. 13, No. 19, 1994, pp. 4536-4548.
Shahrooei et al., "Inhibition of *Staphylococcus epidermidis* Biofilm Formation by Rabbit Polyclonal Antibodies against the SesC Protein," Infection and Immunity, vol. 77, No. 9, Sep. 2009, pp. 3670-3678.
Shields, R.C. et al. (2013) "Efficacy of a Marine Bacterial Nuclease against Biofilm Forming Microorganisms Isolated from Chronic Rhinosinusitis," PLoS ONE 8(2):e55339, 1-13.
Singh et al.,"Quorum-sensing signals indicate that cystic fibrosis lungs are infected with bacterial biofilms," Nature, vol. 407, No. 12, Oct. 12, 2000, pp. 762-764.
Sioud, "siRNA and miRNA Gene Silencing: From Bench to Bedside", Methods in Mol. Biol., vol. 487, Humana Press., 2009, pp. 1-281, 290 pages.
Skolnick, J. et al. (2000) "From genes to protein structure and function: novel applications of computational approaches in the genomic era," Trends in Biotechnology 18:34-39.
Smith et al., "Cystic Fibrosis Airway Epithelia Fail to Kill Bacteria Because of Abnormal Airway Surface Fluid," Cell, vol. 85, Apr. 19, 1996, pp. 229-236.
Stinson, M.W. et al. (1998) "Streptococcal Histone-Like Protein: Primary Structure of hlpA and Protein Binding to Lipoteichoic Acid and Epithelial Cells," Infection and Immunity 66(1):259-265.
Stoltz et al., "Cystic Fibrosis Pigs Develop Lung Disease and Exhibit Defective Bacterial Eradication at Birth," www.ScienceTranslationMedicine.org, vol. 2, No. 29, Apr. 28, 2010, pp. 1-8.
Stros et al., "The HMG-box: a versatile protein domain occurring in a wide variety of DNA-binding proteins," Cell. Mol. Life Sci., vol. 64, No. 19-20, Jun. 29, 2007, pp. 2590-2606.
Sun et al.,"Inhibition of Biofilm Formation by Monoclonal Antibodies against *Staphylococcus epidermindis* RP62A Accumulation-Associated Protein," Clinical & Diagnostic Laboratory Immunology, vol. 12, No. 1, Jan. 2005, pp. 93-100.
Swinger et al., "IHF and HU: flexible architects of bent DNA," Current Opinion in Structural Biology, vol. 14, No. 1, 2004, pp. 28-35.
Takeda, "Polyhistidine Affinity Chromatography for Purification and Biochemical Analysis of Fungal Cell Wall-Degrading Enzymes," Affinity Chromatography, Dr. Sameh Magdeldin (Ed.), ISBN: 978-953-51-0325-7, In Tech, 2012, pp. 177-186.
Taudte et al., "Alanine mutagenesis of high-mobility-group-protein-1 box B (HMG1-B)," Biochem. J., vol. 347, Feb. 25, 2000, pp. 807-814.
Teter et al., "DNA Bending and Twisting Properties of Integration Host Factor Determined by DNA Cyclization," Plasmid, vol. 43, 2000, pp. 73-84.
Tetz et al., "Effect of DNase and Antibiotics on Biofilm Characteristics," Antimicrobial Agents and Chemotherapy, vol. 53, No. 3, Mar. 2009, pp. 1204-1209.
Third Office Action on CA Application No. 2794305 dated Jun. 18, 2019, 5 pages.
Thomas, "HMG1 and 2: architectural DNA-binding proteins," Biochemical Society Transactions, vol. 29, Pt. 4, Apr. 12, 2001, pp. 395-401.
Thurnheer et al., "Colonisation of gingival epithelia by subgingival biofilms in vitro: role of 'red complex' bacteria", Arch Oral Biol., vol. 59, No. 9, Sep. 2014, pp. 1-24.
UniProtKB/TrEMBL A0A0E4BIL9. Putative DNA-binding protein HU (Sep. 16, 2015) [Retrieved from the Internet Jan. 12, 2017: ],1 page.
Vajdos et al. "Comprehensive Functional Maps of the Antigen-binding Site of an Anti-ErbB2 Antibody Obtained with Shotgun Scanning Mutagenesis", J Mol. Biol., Jul. 5, 2002, 320(2), pp. 415-428.
Van Schaik et al., "DNA Binding: a Novel Function of Pseudomonas aeruginosa Type IV Pili," Journal of Bacteriology, vol. 187, No. 4, Feb. 2005, pp. 1455-1464.
Whitchurch et al., "Extracellular DNA Required for Bacterial Biofilm Formation," Science, vol. 295, No. 5559, Feb. 22, 2002, p. 1487, 1 page.
Whitchurch et al., "Extracellular DNA Required for Bacterial Biofilm Formation," Science, vol. 295, No. 5559, Feb. 22, 2002, Supplementary Material, 2 pages.
Wiedenheft et al., "RNA-guided genetic silencing systems in bacteria and archaea," Nature, vol. 482, No. 7385, Feb. 16, 2012, pp. 331-338.
Winters et al., "Isolation and Characterization of a *Streptococcus pyogenes* Protein that Binds to Basal Laminae of Human Cardiac Muscle," Infection and Immunity, vol. 61, No. 8, Aug. 1993, pp. 3259-3264.
Winther et al., "Location of Bacterial Biofilm in the Mucus Overlying the Adenoid by Light Microscopy," Head & Neck Surgery, vol. 135, No. 12, Dec. 2009, pp. 1239-1245.
Woischnig et al., "High Affinity Native Human Monoclonal Antibody with Broad Cross-Species Biofilm Disrupting Activity" poster presented at ICAAC Meeting on Sep. 20, 2015, available at www.trellisbio.com/assets/docs/ICAAC%20Biofilm%20Poster%2020150920.pdf., 1 page.
Wu et al., "Preparation of sodium fluoride-loaded gelatin microspheres, characterization and cariostatic studies", J. Microencapsul., vol. 21, No. 8, Dec. 2004, Abstract, 1 page.
Xiong et al., "A Human Biofilm-Disrupting Monoclonal Antibody Potentiates Antibiotic Efficacy in Rodent Models of both *Staphylococcus aureus* and Acinetobacter baumannii Infections," Antimicrob. Agents Chemother., vol. 61, No. 10, Oct. 2017, pp. 1-10.
Yoshida, M. (1996) Seikagaku Biochemistry 68(12):1829-1834.
Zimmerli et al., "Pathogenesis of Foreign Body Infection: Description and Characteristics of an Animal Model," The Journal of Infectious Diseases, vol. 146, No. 4, Oct. 1982, pp. 487-497.

(56) References Cited

OTHER PUBLICATIONS

Zimmerli, W. et al. (1984) "Pathogenesis of Foreign Body Infection," J. Clin. Invest. 73:1191-1200.

Zulianello et al., "The HimA and HimD subunits of integration host factor can specifically bind to DNA as homodimers," The EMBO Journal, vol. 13, No. 4, Apr. 1, 1994, pp. 1534-1540.

Novotny, et al., "Kinetic analysis and evaluation of the mechanisms involved in the resolution of experimental nontypeable Haemophilus influenzae-induced otitis media after transcutaneous immunization", Vaccine 31, Jul. 25, 2013, pp. 3417-3426.

Novotny, et al., "Transcutaneous immunization as preventative and therapeutic regimens to protect against experimental otitis media due to nontypeable Haemophilus influenzae", Mucosal Immunol vol. 5 No. 1, Jul. 2011, pp. 456-467.

U.S. Final Office Action dated May 2, 2022, from U.S. Appl. No. 16/475,656.

U.S. Non-Final Office Action dated Apr. 7, 2022, from U.S. Appl. No. 16/475,654.

U.S. Final Office Action dated Nov. 25, 2022, from U.S. Appl. No. 16/475,654.

Medium     Naive rabbit serum

Biofilm reversal assay

1:50 dilution of serum

Rabbit anti-IHF$_{E.\ coli}$     Rabbit anti-IHF$_{NTHI}$     Rabbit anti-HU$_{NTHI}$

5.0 µg IgG1/well      5.0 µg IgG2a/well

IhfA3$_{NTHI}$+IhfB2$_{NTHI}$   IhfA5$_{NTHI}$+IhfB4$_{NTHI}$   IhfA5$_{NTHI}$+IhfmB4$_{NTHI}$ 5.0 µg mAb IhfA3$_{NTHI}$/well      5.0 µg mAb IhfA5$_{NTHI}$/well 5.0 µg mAb IhfB2$_{NTHI}$/well 5.0 µg mAb IhfB4$_{NTHI}$/well 5.0 µg mAb IhfmB4$_{NTHI}$/well

| Peptide | Image | AA Sequence |
|---|---|---|
| IhfA-3NTHI | 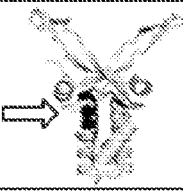 | FLEEIRLSLESGQDVKLSGF<br>(negative control 20-mer peptide) |
| IhfA-5NTHI | 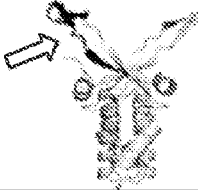 | RPGRNPKTGDVVPVSARRVV |
| HuA-5NTHI |  | RTGRNPQTGAEIQIAASKVP |

| Peptide | Image | AA Sequence |
|---|---|---|
| IhfB-2NTHI | 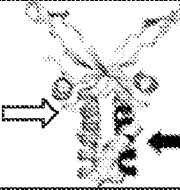 | TLSAKEIENMVKDILEFISQ<br>(negative control 20-mer peptide) |
| IhfB-4NTHI | 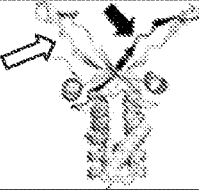 | RGFGSFSLHHRQPRLGRNPK |
| mIhfB-4NTHI | 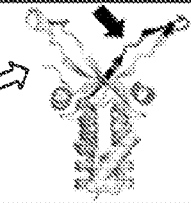 | FSLHHRQPRLGRNPKTGDSV<br>(removed 5 residues at N-terminus and extended 5-residues C-terminally) |

FIG. 8B

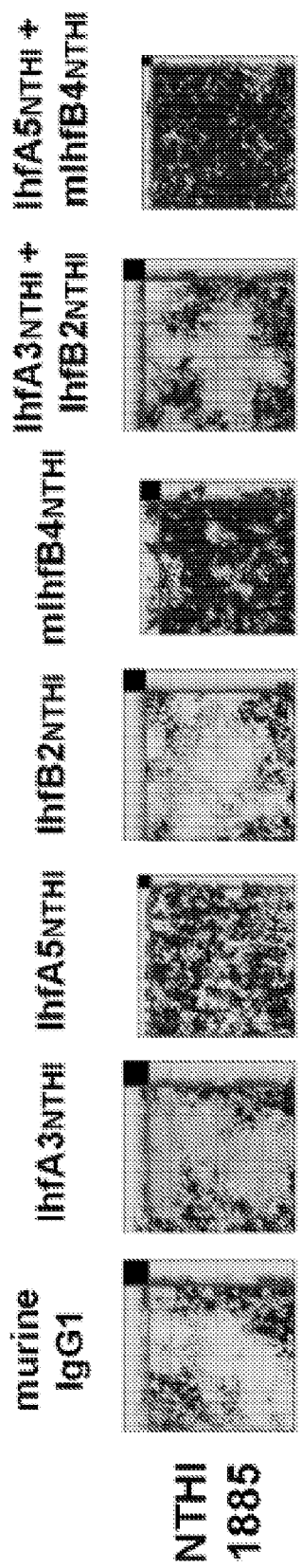
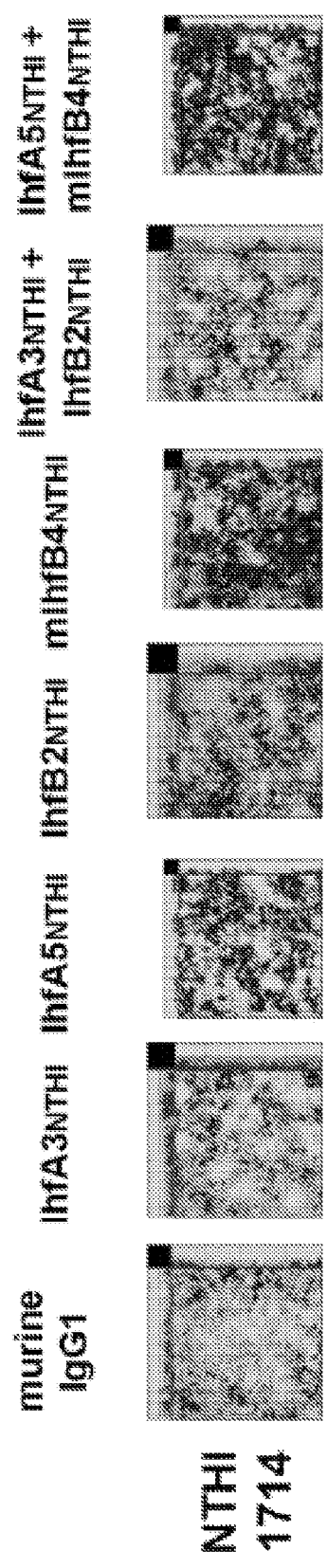
FIG. 9A
FIG. 9B

| Cohort | Mean aggregates per FOV |
|---|---|
| Prior to treatment | 9.6 ± 1.2 |
| Murine IgG1 + IgG2a | 8.9 ± 0.6 |
| Tail-directed MAbs | 8.7 ± 0.5 |
| Tip-directed MAbs | 1.2 ± 0.1 |

PEPTIDES AND ANTIBODIES FOR THE REMOVAL OF BIOFILMS

CROSS-REFERENCE TO RELATED APPLICATIONS

This application is a continuation of U.S. application Ser. No. 15/744,713, filed Jan. 12, 2018, now U.S. Pat. No. 10,940,204, issued Mar. 9, 2021, which is a national stage entry under 35 U.S.C. § 371 of International Application No. PCT/US2016/045032, filed Aug. 1, 2016, which in turn claims priority under 35 U.S.C. § 119(e) to U.S. Provisional Patent Application Nos. 62/199,957, filed Jul. 31, 2015; 62/387,562, filed Dec. 23, 2015; and 62/361,400, filed Jul. 12, 2016; the contents of each of which are hereby incorporated by reference in their entireties.

STATEMENT OF GOVERNMENT SUPPORT

This invention was made with government support under Contract No. R01DC011818 awarded by the National Institute of Deafness and Communication Disorders (NIDCD) at the National Institutes of Health. The government has certain rights in the invention.

FIELD

The present disclosure generally relates to the methods and compositions to lessen and/or cure bacterial biofilms and treat diseases or disorders associated with biofilms.

SEQUENCE LISTING

The instant application contains a Sequence Listing which has been submitted electronically in ASCII format and is hereby incorporated by reference in its entirety. Said ASCII copy, created on Jul. 28, 2016, is named 106887-0360_SL.txt and is 73,105 bytes in size.

BACKGROUND

At least one protein from the DNABII family of proteins is found in all known eubacteria and are naturally found outside of the bacterial cell. While they elicit a strong innate immune response, host subjects fail to naturally produce specific protective antibody to family members as a result of infection. The DNABII protein and extracellular DNA (eDNA) contribute to the lattice structure of a "biofilm." The major problem with bacterial biofilms is the inability of the host immune system and/or antibiotics and other antimicrobials to gain access to the bacteria protected within the biofilm.

Biofilms are present in an industrial setting as well. For example, biofilms are implicated in a wide range of petroleum process problems, from the production field to the gas station storage tank. In the field, sulfate reducing biofilm bacteria produce hydrogen sulfide (soured oil). In the process pipelines, biofilm activity develops slimes which impede filters and orifices. Biofilm and biofilm organisms also cause corrosion of pipeline and petroleum process equipment. These problems can be manifested throughout an oil or gas production facility to the point where fouling and corrosive biofilm organisms have even been found on the surfaces of final product storage tanks.

In the home, biofilms are found in or on any surface that supports microbial growth, e.g., in drains, on food preparation surfaces, in toilets, and in swimming pools and spas. Biofilms are implicated in a wide range of water processes, both domestic and industrial. They can grow on the surface of process equipment and impede the performance of the equipment, such as degradation of heat transfer or plugging of filters and membranes. Biofilms growing on a cooling tower fill can add enough weight to cause collapse of the fill. Biofilms cause corrosion of even highly specialized stainless steels. Biofilms in a water process can degrade the value of a final product such as biofilm contamination in a paper process or the attachment of even a single cell on a silicon chip. Biofilms growing in drinking water distribution systems can harbor potential pathogenic organisms, corrosive organisms or bacteria that degrade the aesthetic quality of the water.

PARTIAL SEQUENCE LISTING

SEQ ID NO. 1: Full Length Wild type (wt) 86-028NP *Haemophilus influenzae* IhfA; Genbank Accession No.: AAX88425.1, last accessed Mar. 21, 2011:

```
MATITKLDIIEYLSDKYHLSKQDTKNVVENFLEEIRLSLESGQDVKLSG

FGNFELRDKSSRPGRNPKTGDVVPVSARRVVITKPGQKLRARVEKIK.
```

SEQ ID NO. 2: Full Length Wild type (wt) 86-028NP *Haemophilus influenzae* IhfB; Genbank Accession No.: AAX88699.1, last accessed May 13, 2015:

```
MTKSELMEKLSAKQPTLSAKEIENMVKDILEFISQSLENGDRVEVRGF

GSFSLHHRQPRLGRNPKTGDSVNLSAKSVPYFKAGKELKARVDVQA.
```

SEQ ID NO. 3: Full Length wt 86-028NP *Haemophilus influenzae* HU, Genbank Accession No.: YP_248142.1, last accessed Mar. 21, 2011:

```
MRFVTIFINHAFNSSQVRLSFAQFLRQIRKDTFKESNFLFNRRYKFMNK

TDLIDAIANAAELNKKQAKAALEATLDAITASLKEGEPVQLIGFGTFKV

NERAARTGRNPQTGAEIQIAASKVPAFVSGKALKDAIK.
```

SEQ ID NO. 4: Full Length wt 82846 *Haemophilus influenzae* IhfA, Genbank Accession No.: ADO96375, last accessed Mar. 21, 2011:

```
MATITKLDIIEYLSDKYHLSKQDTKNVVENFLEEIRLSLESGQDVKLSGF

GNFELRDKSSRPGRNPKTGDVVPVSARRVVTFKPGQKLRARVEKTK.
```

SEQ ID NO. 5: Full Length wt Rd *Haemophilus influenzae* IhfA; Genbank Accession No.: AAC22959.1, last accessed Mar. 21, 2011:

```
MATITKLDIIEYLSDKYHLSKQDTKNVVENFLEEIRLSLESGQDVKLSGF

GNFELRDKSSRPGRNPKTGDVVPVSARRVVTFKPGQKLRARVEKTK.
```

SEQ ID NO. 6: Full Length wt *E. coli* K12 IhfA; Genbank Accession No.: AAC74782.1, last accessed Mar. 21, 2011:

```
MALTKAEMSEYLFDKLGLSKRDAKELVELFFEEIRRALENGEQVKLSGFG

NFDLRDKNQRPGRNPKTGEDIPITARRVVTFRPGQKLKSRVENASPKDE;

DNA Genbank No. NC_000913.
```

SEQ ID NO. 7: Full Length wt E. coli K12 IhfB; Genbank Accession No.: BAA35656, last accessed May 19, 2015:

MTKSELIERLATQQSHIPAKTVEDAVKEMLEHMASTLAQGERIEIRGFGS

FSLHYRAPRTGRNPKTGDKVELEGKYVPHFKPGKELRDRANIYG.

SEQ ID NO. 8: E. coli hupA, Genbank Accession No.: AP_003818, Last accessed Mar. 21, 2011:

MNKTQLIDVIAEKAELSKTQAKAALESTLAAITESLKEGDAVQLVGFGTF

KVNHRAERTGRNPQTGKEIKIAAANVPAFVSGKALKDAVK.

SEQ ID NO. 9: E. coli hupB, Genbank Accession No.: AP_001090.1, Last accessed Mar. 21, 2011:

MNKSQLIDKIAAGADISKAAAGRALDAIIASVTESLKEGDDVALVGFGTF

AVKERAARTGRNPQTGKEIAAAKVPSFRAGKALKDAVN.

SEQ ID NO. 10: Full Length wt P. aeruginosa PA 01 IhfA; Genbank Accession No.: AAG06126.1, last accessed Mar. 21, 2011:

MGALTKAEIAERLYEELGLNKREAKELVELFFEEIRQALEHNEQVKLSGF

GNFDLRDKRQRPGRNPKTGEEIPITARRVVTFRPGQKLKARVEAYAG

TKS.

SEQ ID NO. 11: Full Length wt P. aeruginosa PA 01 IhfB; Genbank Accession No.: AAF72950.1, last accessed May 19, 2015:

MTKSELIERIVTHQGQLSAKDVELAIKTMLEQMSQALATGDRIEIRGFGS

FSLHYRAPRVGRNPKTGESVRLDGKFVPHFKPGKELRDRVNEPE.

SEQ ID NO. 12: Haemophilus influenzae IhfA, A-3 fragment:

FLEEIRLSLESGQDVKLSGF.

SEQ ID NO. 13: Haemophilus influenzae IhfA, A5 fragment:

RPGRNPKTGDVVPVSARRVV.

SEQ ID NO. 14: Haemophilus influenzae HU, A5 fragment:

RTGRNPQTGAEIQIAASKVP.

SEQ ID NO. 15: Haemophilus influenzae IhfB, B2 fragment:

TLSAKEIENMVKDILEFISQ.

SEQ ID NO. 16: Haemophilus influenzae IhfB, B4 fragment:

RGFGSFSLHHRQPRLGRNPK.

SEQ ID NO. 17: Haemophilus influenzae IhfB, modified B4 (mB4) fragment:

FSLHHRQPRLGRNPKTGDSV.

SEQ ID NO. 18: Haemophilus influenzae IhfA, A-1 fragment:

MATITKLDIIEYLSDKYHLS.

SEQ ID NO. 19: Haemophilus influenzae IhfA, A2 fragment:

KYHLSKQDTKNVVENFLEEI.

SEQ ID NO. 20: Haemophilus influenzae IhfA, A4 fragment:

KLSGFGNFELRDKSSRPGRN.

SEQ ID NO. 21: Haemophilus influenzae IhfA, A6 fragment:

ARRVVTFKPGQKLRARVEKTK.

SEQ ID NO. 22: Haemophilus influenzae IhfB, B1 fragment:

MTKSELMEKLSAKQPTLSAK.

SEQ ID NO. 23: Haemophilus influenzae IhfB, B3 fragment:

EFISQSLENGDRVEVRGFGS.

SEQ ID NO. 24: Haemophilus influenzae IhfB, B5 fragment:

GRNPKTGDSVNLSAKSVPYF.

SEQ ID NO. 25: Haemophilus influenzae IhfB, B6 fragment:

SVPYFKAGKELKARVDVQA.

SEQ ID NO. 26: Haemophilus influenzae IhfA, A tip fragment:

NFELRDKSSRPGRNPKTGDVV.

SEQ ID NO. 27: Haemophilus influenzae IhfB, B tip fragment:

SLHHRQPRLGRNPKTGDSVNL.

SEQ ID NO. 28 Haemophilus influenzae HU, fragment:

MNKTDLIDAIANAAELNKKQAK.

SEQ ID NO. 29 *Haemophilus influenzae* HU, fragment:

KKQAKAALEATLDAITASLKEG.

SEQ ID NO. 30 *Haemophilus influenzae* HU, fragment:

SLKEGEPVQLIGFGTFKVNERA.

SEQ ID NO. 31 *Haemophilus influenzae* HU, fragment:

VNERAARTGRNPQTGAEIQIAA.

SEQ ID NO. 32 *Haemophilus influenzae* HU, fragment:

IQIAASKVPAFVSGKALKDAIK.

SEQ ID NO. 33: *Haemophilus influenzae* HU, A3 fragment:

KKQAKAALEATLDAITASLKEG.

SEQ ID NO. 34: Human IgD constant region, Uniprot: P01880:

APTKAPDVFPIISGCRHPKDNSPVVLACLITGYHPTSVTVTWYMGTQSQP
QRTFPEIQRRDSYYMTSSQLSTPLQQWRQGEYKCVVQHTASKSKKEIFRW
PESPKAQASSVPTAQPQAEGSLAKATTAPATTRNTGRGGEEKKKEKEKEE
QEERETKTPECPSHTQPLGVYLLTPAVQDLWLRDKATFTCFVVGSDLKDA
HLTWEVAGKVPTGGVEEGLLERHSNGSQSQHSRLTLPRSLWNAGTSVTCT
LNHPSLPPQRLMALREPAAQAPVKLSLNLLASSDPPEAASWLLCEVSGFS
PPNILLMWLEDQREVNTSGFAPARPPPQPGSTTFWAWSVLRVPAPPSPQP
ATYTCVVSHEDSRTLLNASRSLEVSYVTDHGPMK.

SEQ ID NO. 35: Human IgG1 constant region, Uniprot: P01857:

ASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKKVEP
KSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGK
EYKCKVSNKALPAPIEKTISKAKGQPREPQVYTLPPSRDELTKNQVSLTC
LVKGFYPSDIAVEWESNGQPENNYKTTPPVLDSDGSFFLYSKLTVDKSRW
QQGNVFSCSVMHEALHNHYTQKSLSLSPGK.

SEQ ID NO. 36: Human IgG2 constant region, Uniprot: P01859:

ASTKGPSVFPLAPCSRSTSESTAALGCLVKDYFPEPVTVSWNSGALTSGV
HTFPAVLQSSGLYSLSSVVTVPSSNFGTQTYTCNVDHKPSNTKVDKTVER
KCCVECPPCPAPPVAGPSVFLFPPKPKDTLMISRTPEVTCVVVDVSHEDP
EVQFNWYVDGVEVHNAKTKPREEQFNSTFRVVSVLTVVHQDWLNGKEYKC
KVSNKGLPAPIEKTISKTKGQPREPQVYTLPPSREEMTKNQVSLTCLVKG
FYPSDISVEWESNGQPENNYKTTPPMLDSDGSFFLYSKLTVDKSRWQQGN
VFSCSVMHEALHNHYTQKSLSLSPGK.

SEQ ID NO. 37: Human IgG3 constant region, Uniprot: P01860:

ASTKGPSVFPLAPCSRSTSGGTAALGCLVKDYFPEPVTVSWNSGALTSGV
HTFPAVLQSSGLYSLSSVVTVPSSSLGTQTYTCNVNHKPSNTKVDKRVEL
KTPLGDTTHTCPRCPEPKSCDTPPPCPRCPEPKSCDTPPPCPRCPEPKSC
DTPPPCPRCPAPELLGGPSVFLFPPKPKDTLMISRTPEVTCVVVDVSHED
PEVQFKWYVDGVEVHNAKTKPREEQYNSTFRVVSVLTVLHQDWLNGKEYK
CKVSNKALPAPIEKTISKTKGQPREPQVYTLPPSREEMTKNQVSLTCLVK
GFYPSDIAVEWESSGQPENNYNTTPPMLDSDGSFFLYSKLTVDKSRWQQG
NIFSCSVMHEALHNRFTQKSLSLSPGK.

SEQ ID NO. 38: Human IgM constant region, Uniprot: P01871:

GSASAPTLFPLVSCENSPSDTSSVAVGCLAQDFLPDSITLSWKYKNNSDI
SSTRGFPSVLRGGKYAATSQVLLPSKDVMQGTDEHVVCKVQHPNGNKEKN
VPLPVIAELPPKVSVFVPPRDGFFGNPRKSKLICQATGFSPRQIQVSWLR
EGKQVGSGVTTDQVQAEAKESGPTTYKVTSTLTIKESDWLGQSMFTCRVD
HRGLTFQQNASSMCVPDQDTAIRVFAIPPSFASIFLTKSTKLTCLVTDLT
TYDSVTISWTRQNGEAVKTHTNISESHPNATFSAVGEASICEDDWNSGER
FTCTVTHTDLPSPLKQTISRPKGVALHRPDVYLLPPAREQLNLRESATIT
CLVTGFSPADVFVQWMQRGQPLSPEKYVTSAPMPEPQAPGRYFAHSILTV
SEEEWNTGETYTCVAHEALPNRVTERTVDKSTGKPTLYNVSLVMSDTAGT
CY.

SEQ ID NO. 39: Human IgG4 constant region, Uniprot: P01861:

ASTKGPSVFPLAPCSRSTSESTAALGCLVKDYFPEPVTVSWNSGALTSGV
HTFPAVLQSSGLYSLSSVVTVPSSSLGTKTYTCNVDHKPSNTKVDKRVES
KYGPPCPSCPAPEFLGGPSVFLFPPKPKDTLMISRTPEVTCVVVDVSQED
PEVQFNWYVDGVEVHNAKTKPREEQFNSTYRVVSVLTVLHQDWLNGKEYK
CKVSNKGLPSSIEKTISKAKGQPREPQVYTLPPSQEEMTKNQVSLTCLVK
GFYPSDIAVEWESNGQPENNYKTTPPVLDSDGSFFLYSRLTVDKSRWQEG
NVFSCSVMHEALHNHYTQKSLSLSLGK.

SEQ ID NO. 40: Human IgA1 constant region, Uniprot: P01876:

ASPTSPKVFPLSLCSTQPDGNVVIACLVQGFFPQEPLSVTWSESGQGVTA
RNFPPSQDASGDLYTTSSQLTLPATQCLAGKSVTCHVKHYTNPSQDVTVP
CPVPSTPPTPSPSTPPTPSPSCCHPRLSLHRPALEDLLLGSEANLTCTLT
GLRDASGVTFTWTPSSGKSAVQGPPERDLCGCYSVSSVLPGCAEPWNHGK

-continued

TFTCTAAYPESKTPLTATLSKSGNTFRPEVHLLPPPSEELALNELVTLTC
LARGFSPKDVLVRWLQGSQELPREKYLTWASRQEPSQGTTTFAVTSILRV
AAEDWKKGDTFSCMVGHEALPLAFTQKTIDRLAGKPTHVNVSVVMAEVDG
TCY.

SEQ ID NO. 41: Human IgA2 constant region, Uniprot: P01877:

ASPTSPKVFPLSLDSTPQDGNVVVACLVQGFFPQEPLSVTWSESGQNVTA
RNFPPSQDASGDLYTTSSQLTLPATQCPDGKSVTCHVKHYTNPSQDVTVP
CPVPPPPPCCHPRLSLHRPALEDLLLGSEANLTCTLTGLRDASGATFTWT
PSSGKSAVQGPPERDLCGCYSVSSVLPGCAQPWNHGETFTCTAAHPELKT
PLTANITKSGNTFRPEVHLLPPPSEELALNELVTLTCLARGFSPKDVLVR
WLQGSQELPREKYLTWASRQEPSQGTTTFAVTSILRVAAEDWKKGDTFSC
MVGHEALPLAFTQKTIDRMAGKPTHVNVSVVMAEVDGTCY.

SEQ ID NO. 42: Human Ig kappa constant region, Uniprot: P01834:

TVAAPSVFIFPPSDEQLKSGTASVVCLLNNFYPREAKVQWKVDNALQSGN
SQESVTEQDSKDSTYSLSSTLTLSKADYEKHKVYACEVTHQGLSSPVTKS
FNRGEC.

SEQ ID NO. 43: Non-limiting exemplary linker:

GPSLKL.

SEQ ID NO. 44: Non-limiting exemplary linker:

GGG.

SEQ ID NO. 45: Non-limiting exemplary linker:

GPSL.

SEQ ID NO. 46: Non-limiting exemplary linker:

GPS.

SEQ ID NO. 47: Non-limiting exemplary linker:

PSLK.

SEQ ID NO. 48: Non-limiting exemplary linker:

GPSLK.

SEQ ID NO. 49: Non-limiting exemplary linker:

SLKL.

SEQ ID NO. 50: Non-limiting exemplary heavy chain variable region nucleotide sequence, IhfA5 fragment:

GAGGTGCAGCTGCAGGAGTCTGGACCTGGCCTGGTGACGCCCTCACAGAG
CCTGTCCATGACTTGCACTGTCTCTGGGTTTTCATTAACCAGCTATAGTG
TACACTGGGTTCGCCAGCCTCCAGGAAAGAGTCTGGAGTGGCTGGGAGTA
ATATGGGCTGGTGGAAGCACAAATTATAATTCGGCTCTCATGTCCAGACT
GAGCATCAGCAAAGACAACTCCAAGAGCCAAGTTTTCTTAAAAATGGACA
GTCTGCAAACTGATGACACAGCCATATACTACTGTGCCAGAGAGGACTCC
TGGGGTCAAGGAACCTCAGTCACCGTCTCCTCA.

SEQ ID NO. 51: Non-limiting exemplary heavy chain variable region amino acid sequence, IhfA5 fragment:

EVQLQESGPGLVTPSQSLSMTCTVSGFSLTSYSVHWVRQPPGKSLEWLGV
IWAGGSTNYNSALMSRLSISKDNSKSQVFLKMDSLQTDDTAIYYCAREDS
WGQGTSVTVSS.

SEQ ID NO. 52: Non-limiting exemplary heavy chain variable region nucleotide sequence, IhfmB4 fragment:

GAGGTGCAGCTGCAGGAGTCTGGGGCAGAGCTTGTGAGGTCAGGGGCCTC
AGTCAAGTTGTCCTGCACAGCTTCTGGCTTCAACATTAAAGACTACTATA
TGCACTGGGTGAAGCAGAGGCCTGAACAGGGCCTGGAGTGGATTGGATGG
ATTGATCCTGAAAATGATGATACTGAATATGTCCCGAAGTTCCAGGGCAA
GGCCAGTATGACTGCAGACACATCCTCCAACACAGCCTACCTGCAGCTCA
GCAGCCTGACATCTGAGGACACTGCCGTCTATTACTGTACAGAGCTCGGA
GCTTACTGGGGCCAGGGGACTCTGGTC.

SEQ ID NO. 53: Non-limiting exemplary heavy chain variable region amino acid sequence, IhfmB4 fragment:

EVQLQESGAELVRSGASVKLSCTASGFNIKDYYMHWVKQRPEQGLEWIGW
IDPENDDTEYVPKFQGKASMTADTSSNTAYLQLSSLTSEDTAVYYCTELG
AYWGQGTLV.

SEQ ID NO. 54: Non-limiting exemplary light chain variable region nucleotide sequence, IhfA5 fragment:

GACATTGTGATGACCCAGTCTCAAAAATTCATGTCCACATCAGTAGGAGA
CAGGGTCAGCGTCACCTGCAAGGCCAGTCAGAATGTGGGTACTAATGTAG
CCTGGTATCAACAGAAACCAGGGCAATCTCCTAAAGCACTGATTTACTCG
GCATCCTACCGGTACAGTGGAGTCCCTGATCGCTTCACAGGCAGTGGATC
TGGGACAGATTTCACTCTCACCATCAGCAATGTGCAGTCTGAAGACTTGG
CAGAGTATTTCTGTCAGCAATATAACAGCTATCCCACGTTCGGAGGGGGG
ACCAAGTTGGAAATAAAA.

SEQ ID NO. 55: Non-limiting exemplary light chain variable region amino acid sequence, IhfA5 fragment:

DIVMTQSQKFMSTSVGDRVSVTCKASQNVGTNVAWYQQKPGQSPKALIYS
ASYRYSGVPDRFTGSGSGTDFTLTISNVQSEDLAEYFCQQYNSYPTFGGG
TKLEIK.

SEQ ID NO. 56: Non-limiting exemplary light chain variable region nucleotide sequence, IhfmB4 fragment:

GATGTTGTGATGACCCAGATTCCACTCACTTTGTCGGTTACCATTGGACA
ACCAGCCTCCATCTCTTGCAAGTCAAGTCAGAGCCTCTTAGATAGTAATG
GAAAGACATATTTGAATTGGTTGTTTCAGAGGCCAGGCCAGTCTCCAAAG
CGCCTAATCTATCTGGTGTCTAAACTGGACTCTGGAGTCCCTGACAGGTT
CACTGGCAGTGGATCAGGGACAGATTTCACACTGAAAATCAGCAGAGTTG
AGGCTGAGGATTGGGAATTTATTATTGCTGGCAAAGTACACATTTTCCT
CACACGTTCGGAGGGGGACCAAGTTGGAAATCAAA.

SEQ ID NO. 57: Non-limiting exemplary light chain variable region amino acid sequence, IhfmB4 fragment:

DVVMTQIPLTLSVTIGQPASISCKSSQSLLDSNGKTYLNWLFQRPGQSPK
RLIYLVSKLDSGVPDRFTGSGSGTDFTLKISRVEAEDLGIYYCWQSTHFP
HTFGGGTKLEIK.

SEQ ID NO. 58: Partial non-limiting exemplary CDRH1 sequence, IhfA5 fragment:

FSLTSYS.

SEQ ID NO. 59: Partial non-limiting exemplary CDRH1 sequence, IhfA5 fragment:

FSLTSYSV.

SEQ ID NO. 60: Partial non-limiting exemplary CDRH1 sequence, IhfA5 fragment:

FSLTSYSVH.

SEQ ID NO. 61: Partial non-limiting exemplary CDRH1 sequence, IhfA5 fragment:

GFSLTSYS.

SEQ ID NO. 62: Partial non-limiting exemplary CDRH2 sequence, IhfA5 fragment:

IWAGGST.

SEQ ID NO. 63: Partial non-limiting exemplary CDRH2 sequence, IhfA5 fragment:

VIWAGGST.

SEQ ID NO. 64: Partial non-limiting exemplary CDRH2 sequence, IhfA5 fragment:

GVIWAGGST.

SEQ ID NO. 65: Partial non-limiting exemplary CDRH2 sequence, IhfA5 fragment:

LGVIWAGGST.

SEQ ID NO. 66: Partial non-limiting exemplary CDRH2 sequence, IhfA5 fragment:

WLGVIWAGGST.

SEQ ID NO. 67: Partial non-limiting exemplary CDRH2 sequence, IhfA5 fragment:

IWAGGSTN.

SEQ ID NO. 68: Partial non-limiting exemplary CDRH2 sequence, IhfA5 fragment:

VIWAGGSTN.

SEQ ID NO. 69: Partial non-limiting exemplary CDRH2 sequence, IhfA5 fragment:

GVIWAGGSTN.

SEQ ID NO. 70: Partial non-limiting exemplary CDRH2 sequence, IhfA5 fragment:

LGVIWAGGSTN.

SEQ ID NO. 71: Partial non-limiting exemplary CDRH2 sequence, IhfA5 fragment:

WLGVIWAGGSTN.

SEQ ID NO. 72: Partial non-limiting exemplary CDRH2 sequence, IhfA5 fragment:

IWAGGSTNY.

SEQ ID NO. 73: Partial non-limiting exemplary CDRH2 sequence, IhfA5 fragment:

VIWAGGSTNY.

SEQ ID NO. 74: Partial non-limiting exemplary CDRH2 sequence, IhfA5 fragment:

GVIWAGGSTNY.

SEQ ID NO. 75: Partial non-limiting exemplary CDRH2 sequence, IhfA5 fragment:

LGVIWAGGSTNY.

SEQ ID NO. 76: Partial non-limiting exemplary CDRH2 sequence, IhfA5 fragment:

WLGVIWAGGSTNY

SEQ ID NO. 77: Partial non-limiting exemplary CDRH3 sequence, IhfA5 fragment:

REDS.

SEQ ID NO. 78: Partial non-limiting exemplary CDRH3 sequence, IhfA5 fragment:

```
AREDS.
```

SEQ ID NO. 79: Partial non-limiting exemplary CDRL1 sequence, IhfA5 fragment:

```
QNVGTN.
```

SEQ ID NO. 80: Partial non-limiting exemplary CDRL1 sequence, IhfA5 fragment:

```
QNVGTNV.
```

SEQ ID NO. 81: Partial non-limiting exemplary CDRL1 sequence, IhfA5 fragment:

```
QNVGTNVA.
```

SEQ ID NO. 82: Partial non-limiting exemplary CDRL2 sequence, IhfA5 fragment:

```
SAS.
```

SEQ ID NO. 83: Partial non-limiting exemplary CDRL2 sequence, IhfA5 fragment:

```
YSAS.
```

SEQ ID NO. 84: Partial non-limiting exemplary CDRL2 sequence, IhfA5 fragment:

```
IYSAS
```

SEQ ID NO. 85: Partial non-limiting exemplary CDRL2 sequence, IhfA5 fragment:

```
LIYSAS.
```

SEQ ID NO. 86: Partial non-limiting exemplary CDRL2 sequence, IhfA5 fragment:

```
ALIYSAS.
```

SEQ ID NO. 87: Partial non-limiting exemplary CDRL2 sequence, IhfA5 fragment:

```
SASY.
```

SEQ ID NO. 88: Partial non-limiting exemplary CDRL2 sequence, IhfA5 fragment:

```
YSASY.
```

SEQ ID NO. 89: Partial non-limiting exemplary CDRL2 sequence, IhfA5 fragment:

```
IYSASY.
```

SEQ ID NO. 90: Partial non-limiting exemplary CDRL2 sequence, IhfA5 fragment:

```
LIYSASY.
```

SEQ ID NO. 91: Partial non-limiting exemplary CDRL2 sequence, IhfA5 fragment:

```
ALIYSASY.
```

SEQ ID NO. 92: Partial non-limiting exemplary CDRL2 sequence, IhfA5 fragment:

```
SASYR.
```

SEQ ID NO. 93: Partial non-limiting exemplary CDRL2 sequence, IhfA5 fragment:

```
YSASYR.
```

SEQ ID NO. 94: Partial non-limiting exemplary CDRL2 sequence, IhfA5 fragment:

```
IYSASYR.
```

SEQ ID NO. 95: Partial non-limiting exemplary CDRL2 sequence, IhfA5 fragment:

```
LIYSASYR.
```

SEQ ID NO. 96: Partial non-limiting exemplary CDRL2 sequence, IhfA5 fragment:

```
ALIYSASYR.
```

SEQ ID NO. 97: Partial non-limiting exemplary CDRL2 sequence, IhfA5 fragment:

```
SASYRY.
```

SEQ ID NO. 98: Partial non-limiting exemplary CDRL2 sequence, IhfA5 fragment:

```
YSASYRY.
```

SEQ ID NO. 99: Partial non-limiting exemplary CDRL2 sequence, IhfA5 fragment:

```
IYSASYRY.
```

SEQ ID NO. 100: Partial non-limiting exemplary CDRL2 sequence, IhfA5 fragment:

```
LIYSASYRY.
```

SEQ ID NO. 101: Partial non-limiting exemplary CDRL2 sequence, IhfA5 fragment:

```
ALIYSASYRY.
```

SEQ ID NO. 102: Partial non-limiting exemplary CDRL2 sequence, IhfA5 fragment:

SASYRYS.

SEQ ID NO. 103: Partial non-limiting exemplary CDRL2 sequence, IhfA5 fragment:

YSASYRYS.

SEQ ID NO. 104: Partial non-limiting exemplary CDRL2 sequence, IhfA5 fragment:

IYSASYRYS.

SEQ ID NO. 105: Partial non-limiting exemplary CDRL2 sequence, IhfA5 fragment:

LIYSASYRYS.

SEQ ID NO. 106: Partial non-limiting exemplary CDRL2 sequence, IhfA5 fragment:

ALIYSASYRYS.

SEQ ID NO. 107: Non-limiting exemplary linker:

GGSGGS.

SEQ ID NO. 108: Partial non-limiting exemplary CDRL3 sequence, IhfA5 fragment:

QQYNSYP.

SEQ ID NO. 109: Partial non-limiting exemplary CDRL3 sequence, IhfA5 fragment:

QQYNSYPT.

SEQ ID NO. 110: Partial non-limiting exemplary CDRH1 sequence, IhfmB4 fragment:

FNIKDYY.

SEQ ID NO. 111: Partial non-limiting exemplary CDRH1 sequence, IhfmB4 fragment:

FNIKDYYM.

SEQ ID NO. 112: Partial non-limiting exemplary CDRH1 sequence, IhfmB4 fragment:

FNIKDYYMH.

SEQ ID NO. 113: Partial non-limiting exemplary CDRH1 sequence, IhfmB4 fragment:

GFNIKDYY.

SEQ ID NO. 114: Partial non-limiting exemplary CDRH2 sequence, IhfmB4 fragment:

IDPENDDT.

SEQ ID NO. 115: Partial non-limiting exemplary CDRH2 sequence, IhfmB4 fragment:

WIDPENDDT.

SEQ ID NO. 116: Partial non-limiting exemplary CDRH2 sequence, IhfmB4 fragment:

GWIDPENDDT

SEQ ID NO. 117: Partial non-limiting exemplary CDRH2 sequence, IhfmB4 fragment:

IGWIDPENDDT

SEQ ID NO. 118: Partial non-limiting exemplary CDRH2 sequence, IhfmB4 fragment:

WIGWIDPENDDT.

SEQ ID NO. 119: Partial non-limiting exemplary CDRH2 sequence, IhfmB4 fragment:

IDPENDDTE.

SEQ ID NO. 120: Partial non-limiting exemplary CDRH2 sequence, IhfmB4 fragment:

WIDPENDDTE.

SEQ ID NO. 121: Partial non-limiting exemplary CDRH2 sequence, IhfmB4 fragment:

GWIDPENDDTE.

SEQ ID NO. 122: Partial non-limiting exemplary CDRH2 sequence, IhfmB4 fragment:

IGWIDPENDDTE.

SEQ ID NO. 123: Partial non-limiting exemplary CDRH2 sequence, IhfmB4 fragment:

WIGWIDPENDDTE.

SEQ ID NO. 124: Partial non-limiting exemplary CDRH2 sequence, IhfmB4 fragment:

IDPENDDTEY.

SEQ ID NO. 125: Partial non-limiting exemplary CDRH2 sequence, IhfmB4 fragment:

WIDPENDDTEY.

SEQ ID NO. 126: Partial non-limiting exemplary CDRH2 sequence, IhfmB4 fragment:

GWIDPENDDTEY.

SEQ ID NO. 127: Partial non-limiting exemplary CDRH2 sequence, IhfmB4 fragment:

IGWIDPENDDTEY.

SEQ ID NO. 128: Partial non-limiting exemplary CDRH2 sequence, IhfmB4 fragment:

WIGWIDPENDDTEY.

SEQ ID NO. 129: Partial non-limiting exemplary CDRH3 sequence, IhfmB4 fragment:

TELGAY.

SEQ ID NO. 130: Partial non-limiting exemplary CDRL1 sequence, IhfmB4 fragment:

QSLLDSNGKTY.

SEQ ID NO. 131: Partial non-limiting exemplary CDRL1 sequence, IhfmB4 fragment:

QSLLDSNGKTYL.

SEQ ID NO. 132: Partial non-limiting exemplary CDRL1 sequence, IhfmB4 fragment:

QSLLDSNGKTYLN.

SEQ ID NO. 133: Partial non-limiting exemplary CDRL2 sequence, IhfmB4 fragment:

LVS.

SEQ ID NO. 134: Partial non-limiting exemplary CDRL2 sequence, IhfmB4 fragment:

YLVS.

SEQ ID NO. 135: Partial non-limiting exemplary CDRL2 sequence, IhfmB4 fragment:

IYLVS.

SEQ ID NO. 136: Partial non-limiting exemplary CDRL2 sequence, IhfmB4 fragment:

LIYLVS.

SEQ ID NO. 137: Partial non-limiting exemplary CDRL2 sequence, IhfmB4 fragment:

RLIYLVS.

SEQ ID NO. 138: Partial non-limiting exemplary CDRL2 sequence, IhfmB4 fragment:

LVSK.

SEQ ID NO. 139: Partial non-limiting exemplary CDRL2 sequence, IhfmB4 fragment:

YLVSK.

SEQ ID NO. 140: Partial non-limiting exemplary CDRL2 sequence, IhfmB4 fragment:

IYLVSK.

SEQ ID NO. 141: Partial non-limiting exemplary CDRL2 sequence, IhfmB4 fragment:

LIYLVSK.

SEQ ID NO. 142: Partial non-limiting exemplary CDRL2 sequence, IhfmB4 fragment:

RLIYLVSK.

SEQ ID NO. 143: Partial non-limiting exemplary CDRL2 sequence, IhfmB4 fragment:

LVSKL.

SEQ ID NO. 144: Partial non-limiting exemplary CDRL2 sequence, IhfmB4 fragment:

YLVSKL.

SEQ ID NO. 145: Partial non-limiting exemplary CDRL2 sequence, IhfmB4 fragment:

IYLVSKL.

SEQ ID NO. 146: Partial non-limiting exemplary CDRL2 sequence, IhfmB4 fragment:

LIYLVSKL.

SEQ ID NO. 147: Partial non-limiting exemplary CDRL2 sequence, IhfmB4 fragment:

RLIYLVSKL.

SEQ ID NO. 148: Partial non-limiting exemplary CDRL2 sequence, IhfmB4 fragment:

LVSKLD.

SEQ ID NO. 149: Partial non-limiting exemplary CDRL2 sequence, IhfmB4 fragment:

YLVSKLD.

SEQ ID NO. 150: Partial non-limiting exemplary CDRL2 sequence, IhfmB4 fragment:

IYLVSKLD.

SEQ ID NO. 151: Partial non-limiting exemplary CDRL2 sequence, IhfmB4 fragment:

LIYLVSKLD.

SEQ ID NO. 152: Partial non-limiting exemplary CDRL2 sequence, IhfmB4 fragment:

RLIYLVSKLD.

SEQ ID NO. 153: Partial non-limiting exemplary CDRL2 sequence, IhfmB4 fragment:

LVSKLDS

SEQ ID NO. 154: Partial non-limiting exemplary CDRL2 sequence, IhfmB4 fragment:

YLVSKLDS.

SEQ ID NO. 155: Partial non-limiting exemplary CDRL2 sequence, IhfmB4 fragment:

IYLVSKLDS.

SEQ ID NO. 156: Partial non-limiting exemplary CDRL2 sequence, IhfmB4 fragment:

LIYLVSKLDS.

SEQ ID NO. 157: Partial non-limiting exemplary CDRL2 sequence, IhfmB4 fragment:

RLIYLVSKLDS.

SEQ ID NO. 158: Partial non-limiting exemplary CDRL3 sequence, IhfmB4 fragment:

WQSTHFPH.

SEQ ID NO. 159: Partial non-limiting exemplary CDRL3 sequence, IhfmB4 fragment:

WQSTHFPHT.

DESCRIPTION OF TABLES

Table 1 is a listing of hybridomas producing non-limiting exemplary antibodies.

Table 2 is a non-limiting listing of the antibodies and combinations thereof used in Example 3.

Table 3 is a non-limiting listing of antibodies used in Example 4.

Table 4 is a summary of the scoring methodology used in the otitis media model of Example 4.

Table 5 is a description of the cohorts studied in Example 7.

Table 6 is a non-limiting list of exemplary antibodies and their corresponding CDRs.

Table 7 is a non-limiting list of exemplary antibodies and their corresponding heavy chain and light chain variable regions.

SUMMARY

Within bacterial cells, the DNABII proteins are DNA binding proteins that necessarily bend DNA substrates upon binding. Similarly, DNA that is already in a bent conformation is an exemplary substrate as the energy required for bending is rendered unnecessary.

The DNABII family is a member of a class of proteins referred to as nucleoid associated proteins (NAPs), bacterial proteins that, in part, shape the intracellular bacterial nucleoid (Browning et al. (2010) Curr. Opin. Microbiol. 13:773-780). In addition, this family is ubiquitous, expressed by virtually all eubacteria. All characterized family members to date function as either a homodimer or heterodimer of subunits. The family is divided into two types, HU (histone-like protein) and IHF (integration host factor). The primary distinction between these family members is that HU binds DNA in a sequence independent manner, while IHF binds a consensus sequence (WATCAANNNNTTR where W is A or T and R is a purine (SEQ ID NO. 160)) conserved across genera (Swinger et al. (2004) Curr. Opin. Struct. Biol. 14:28-35). All DNABII proteins bind to and bend DNA considerably, e.g., E. coli IHF can bend DNA into a virtual U-turn (Rice et al. (1996) Cell 87:1295-1306). In addition, all family members have a preference for pre-bent or curved DNA structures, e.g., Holliday junctions, a cruciform-like structure central to DNA recombination. In fact, DNABII proteins function as accessory factors facilitating all intracellular DNA functions, including gene expression, recombination, repair and replication (Swinger et al. (2004) Curr. Opin. Struct. Biol. 14:28-35).

The DNABII family of proteins is found outside of bacterial cells in the biofilm state. Applicants have shown that these proteins are in fact bound to the extracellular DNA at critical branched junctions. In one aspect, Applicants have shown that by delivering to the host antibodies specific to DNABII, the host is able to significantly reduce or eradicate a pre-formed biofilm.

Aspects of this disclosure relate to one or more antibodies or antigen binding fragments that are specific to a DNABII polypeptide. In certain aspects, this polypeptide is derived from the IHF or HU sequence of Haemophilus influenzae. In some aspects, the antibody or antigen binding fragment may have affinity for a specific region of the alpha or beta subunit of IHF, such as but not limited to a polypeptide comprising, or alternatively consisting essentially of, or yet further comprising a proline comprising loop; in some aspects, the antibody or antigen binding fragment may have affinity for a specific region of HU, such as but not limited to the flexible arms of its 3D structure.

In certain aspects, the disclosure relates to an antibody or antigen binding fragment that specifically recognizes or binds an isolated or recombinant polypeptide consisting essentially of an amino acid sequence selected from: SEQ ID NOs. 12 to 17, SEQ ID NO. 31, SEQ ID NO. 33, a polypeptide comprising the amino acid sequence NPXT, or an equivalent of each thereof. In a further aspect, the isolated or recombinant polypeptide comprises at least 15, or alternatively at least 18, or alternatively at least 20 amino acids in total. In a further aspect, the NPXT sequence is not the terminal amino acids of the polypeptide. In some embodiments, the antibody or antigen binding fragment is not a polyclonal antibody.

In alternate aspect, the disclosure provides an antibody or an antigen binding fragment that can be administered alone or in combination with each other, with a pharmaceutically acceptable carrier. Some aspects of the disclosure also relate to a composition comprising, or alternatively consisting essentially thereof, or yet further consisting of these combinations. Further aspects relate to the use of the antibodies or antigen binding fragments in, for example, diagnostic, therapeutic, industrial, veterinary and functional assays as disclosed herein that include but are not limited to the use of antibodies or antigen binding fragments in the treatment of, and/or visualization and/or detection of biofilms. They also are useful to treat microbial infections caused by biofilms.

This disclosure also provides isolated or recombinant polypeptides comprising, or alternatively consisting essentially of, or yet further consisting of an amino acid sequence selected from: SEQ ID NOs. 12 to 17, SEQ ID NO. 31, SEQ ID NO. 33, a polypeptide comprising the amino acid sequence NPXT, or an equivalent of each thereof. Use of the isolated or recombinant polypeptides as immunogens is disclosed herein. In some method aspects, such isolated or recombinant polypeptides are used to generate antibodies that specifically recognize or bind these amino acid sequences. In addition, the isolated or recombinant polypeptides can be used in vaccine formulations and immunization methods. They also are useful to treat microbial infections caused by biofilms.

This disclosure also provides isolated or recombinant polynucleotides encoding one or more of the above-identified isolated or recombinant polypeptides or antibodies or a fragment of each thereof. Vectors comprising the isolated polynucleotides are further provided that in one aspect further contain regulatory sequences operative linked to the polynucleotides for the replication and/or expression thereof. In aspects involving more than one isolated polypeptide disclosed herein, the isolated polynucleotides may be contained within a polycistronic vector.

Isolated host cells comprising one or more of isolated or recombinant polypeptides or isolated or recombinant polynucleotides or the vectors, described herein are further provided.

The polynucleotides, polypeptides, antibodies, antigen binding fragment, or vectors or host cells can father comprise a detectable label and/or a purification label. In one aspect, the detectable label is not a naturally occurring, detectable compound such as a fluorescent polynucleotide or amino acid. In a further aspect, the detectable label is a naturally occurring molecule that is located in a non-naturally occurring position on the polypeptide or polynucleotide.

Compositions comprising, or alternatively consisting essentially of, or yet further consisting of, a carrier and one or more of an isolated or recombinant polypeptide disclosed herein, an isolated or recombinant polynucleotide disclosed herein, a vector disclosed herein, an isolated host cell disclosed herein, or an antibody or fragment thereof as disclosed herein, are also provided. The carriers can be one or more of a solid support, a medical device like a stent or dental implant, or a liquid such as a pharmaceutically acceptable carrier. The compositions can further comprise an adjuvant, an antimicrobial or an antigenic peptide or an antimicrobial other than the disclosed antibodies or fragments thereof.

The compositions can further comprise additional biologically active agents.

Non-limiting examples of such include an antimicrobial agent, one or more antibodies to vaccine antigens, or antimicrobial peptides. In some embodiments, these exemplary biologically active agents are used in combination with one or more antibodies disclosed herein. In further embodiments, such a combination may be used as a therapeutic composition in any of the methods disclosed herein.

Further non-limiting examples include vaccine components (i.e., antigenic peptides) such as surface antigens, e.g., an OMP P5, rsPilA, OMP 26, OMP P2, or Type IV Pilin protein (see Jurcisek and Bakaletz (2007) J. of Bacteriology 189(10):3868-3875, Murphy et al. (2009) The Pediatric infectious Disease Journal, 28:S121-S126, and Novotny et al. (2015) Mol. Microbiol. 96(2):276-92) and antimicrobial agents. In some embodiments, these exemplary biologically active agents are used in combination with one or more isolated or recombinant polypeptides disclosed herein. In further embodiments, such a combination may be used as a vaccine composition in any of the methods disclosed herein.

Additional non-limiting agents include additional antibodies, fragments, derivatives or polypeptides as disclosed herein or as disclosed in U.S. Pat. Application Publication No. 2011/0236306 and PCT International Pat. Application Publication No. WO/2014/201305. As is apparent to the skilled artisan, the selection and amount of agents will vary with the purpose of the treatment, the general health, sex, gender and species (e.g., human or animal).

This disclosure also provides a method for producing an antigenic peptide by growing or culturing a host cell comprising an isolated polynucleotide encoding an antigenic peptide as described above under conditions that favor the expression of the polynucleotide. Also provided are vectors comprising polynucleotide encoding the antigenic polypeptide that in one aspect further contain regulatory sequences operatively linked to the polynucleotides for the replication and/or expression thereof. The polypeptide produced by this method can be isolating for further in vitro or in vivo use. Alternatively, the polypeptides can be produced using chemical synthetic methods known to those of skill in the art.

A kit is also provided for diagnostic or therapeutic use comprising a composition as described herein and instructions for use. A kit is also provided to perform screens for new drugs and/or combination therapies as provided herein.

BRIEF DESCRIPTION OF THE DRAWINGS

FIGS. 8A-8B depict computer models of the 3 dimensional (3D) structures of DNABII proteins, highlighting the predicted position of the amino acids within the peptides used for antibody generation. FIG. 8A depicting top down and front views of specific IHFB epitopes and FIG. 8B depicting 3D structures of IHFA, HU, and IHFB epitopes; the epitopes are highlighted (with an arrow pointing to the highlighted region). Figure discloses SEQ ID NOs. 12-17, respectively, in order of appearance.

FIG. 9A depicts the disruption of biofilms formed by *Haemophilus influenzae* NTHI strain #1885 upon incubation with monoclonal anti-IHF and combinations thereof. FIG. 9B depicts the disruption of biofilms formed by *Haemophilus influenzae* NTHI strain #1714 upon incubation with monoclonal anti-IHF and combinations thereof.

(FIG. 12A) Multiple bacterial aggregates were observed throughout the lungs of mice prior to treatment (yellow, aggregates encircled) and (FIG. 12B) in lungs after receipt of nonspecific murine IgG1+IgG2a (FIG. 12C) or a cocktail of the tail-directed MAbs $IhfA3_{NTHI}$+$IhfB2_{NTHI}$. FIG. 12F—treatment with nonspecific murine IgG1+IgG2a; G—treatment with tail-directed MAbs $IhfA3_{NTHI}$+$IhfB2_{NTHI}$ and H—treatment with tip-directed MAbs $IhfA5_{NTHI}$+$mIhfB4_{NTHI}$ (*P. aeruginosa* aggregates were labeled with fluorescently tagged rabbit antibody to whole *P. aeruginosa* which labels both the bacteria themselves as well as bacterial proteins contained within the biofilm matrix hence the inability to readily resolve individual bacterial cells)]. Note that aggregates in FIGS. 12A, 12B & 12C and 12E, 12F & 12G are similar in size whereas those imaged in lungs treated with the cocktail of tip-directed MAbs appear as single bacterial cells (FIGS. 12D & H); scale bars, 5 μm. A representative TEM image of a *P. aeruginosa* aggregate as shown in FIGS. 12A, 12B & 12C or 12E, 12F & 12G is presented in FIG. 12I. Bacterial cells are pseudo-colored green and mouse lung tissue is pseudo-colored blue to aid in visualization. Bacterial aggregates within lungs from mice that received murine IgG or tail-directed MAbs typically contained 50-100 bacteria. The relatively limited number of very small clusters or presence of only single bacteria resident within lungs from micetreated with tip-directed MAbs precluded visualization by TEM; Scale bar, 2 μm. Legend: FOV—field of view.

DETAILED DESCRIPTION

Figure 1:
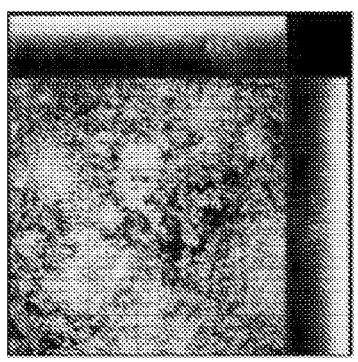
FIG. 1 depicts the reduction of biofilms formed by *Haemophilus influenzae* upon incubation with polyclonal rabbit anti-IHF or anti-HU compared to incubation with naïve rabbit serum.
Figure 1:
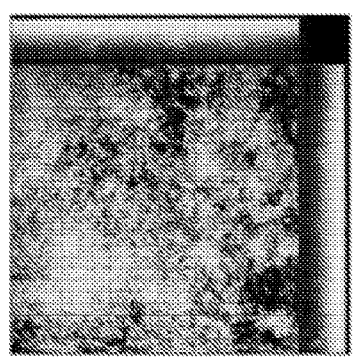
Figure 1:
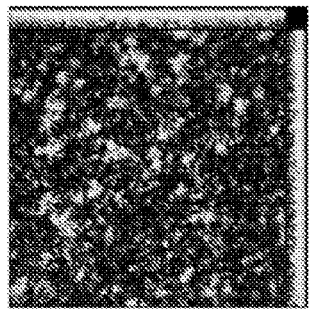
Figure 1:
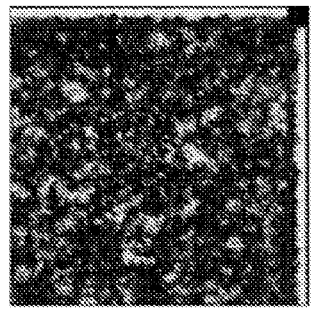
Figure 1:
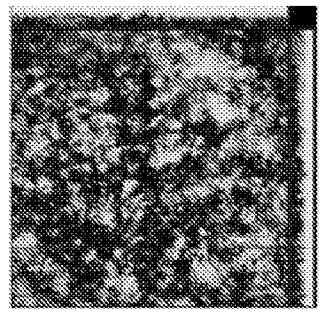
Figure 2A:
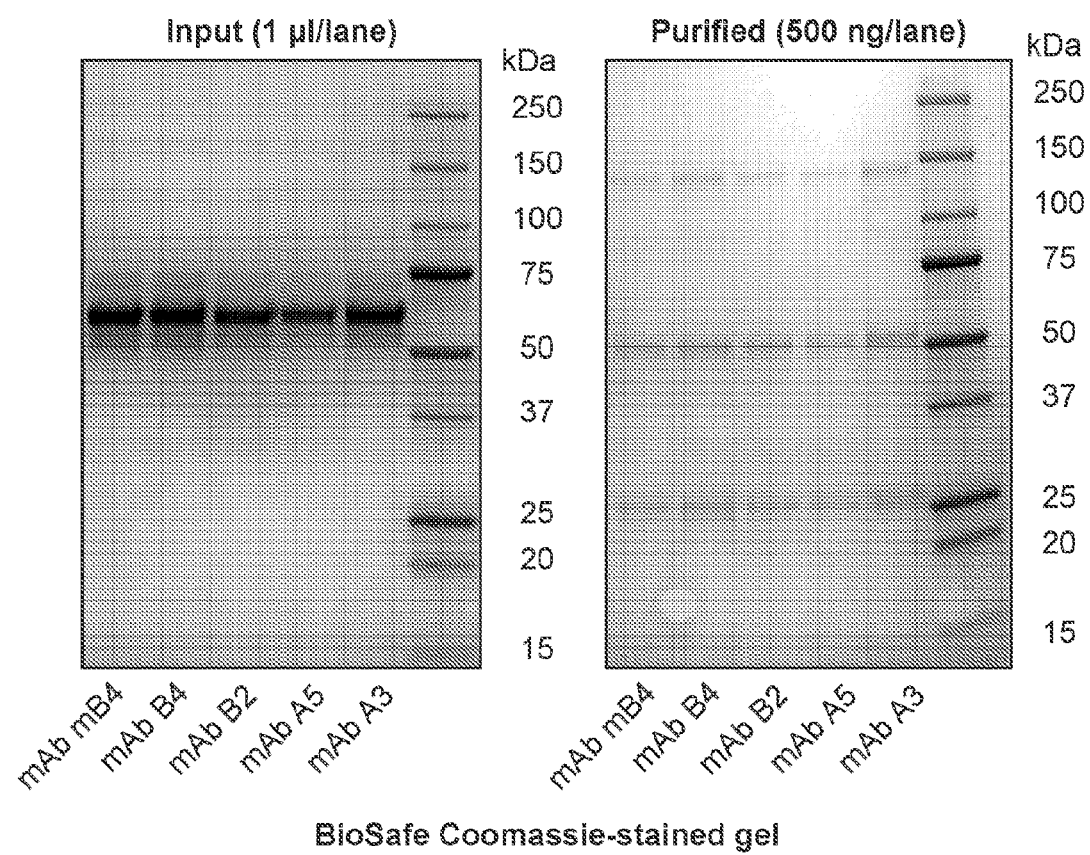
FIG. 2A shows the results of culture and purification of monoclonal antibodies generated against *Haemophilus influenzae* IHF and HU.
Figure 2B:
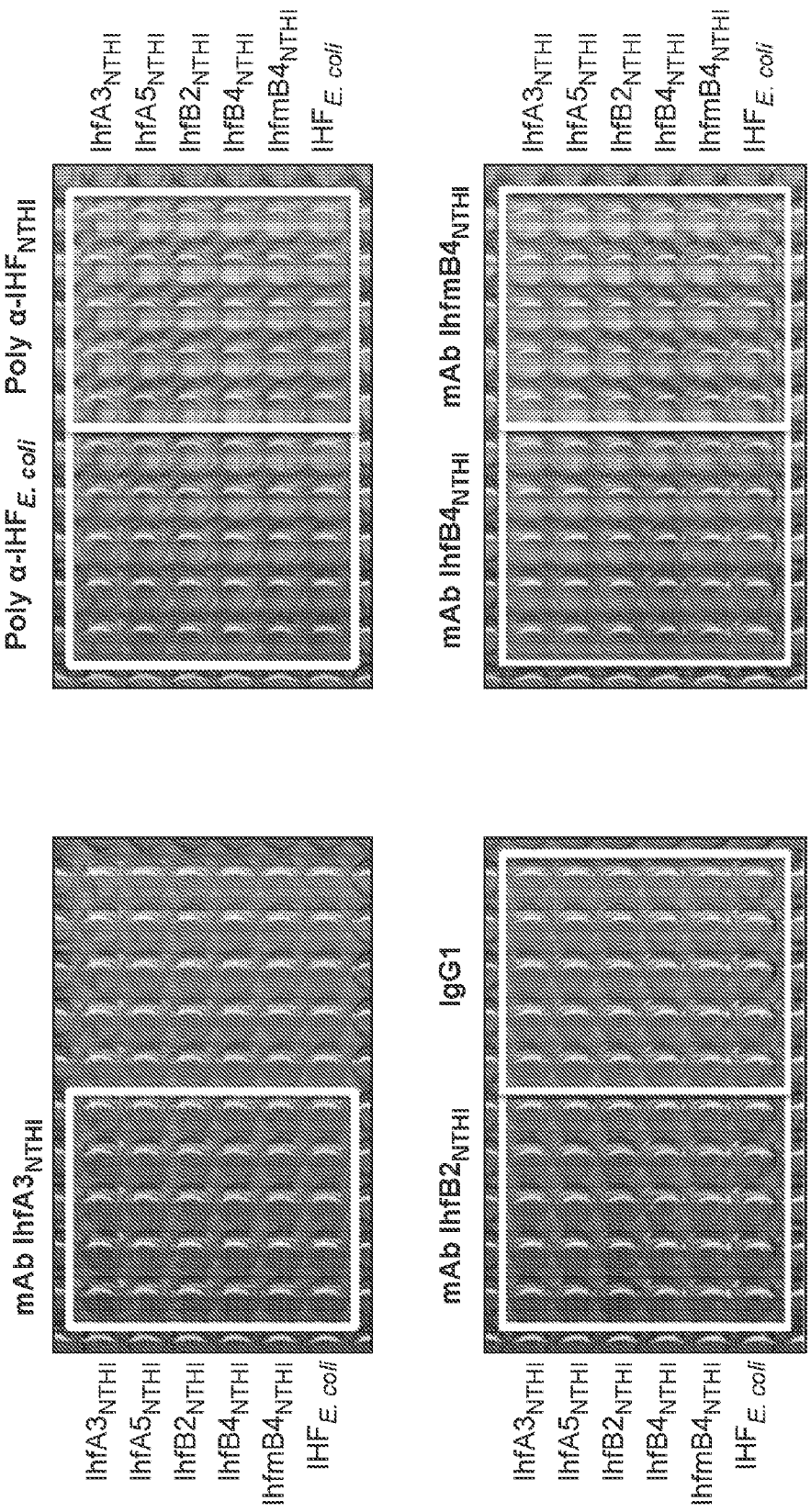
FIG. 2B shows ELISA results confirming the specificity of each respective antibody to its corresponding epitope.
Figure 2C:
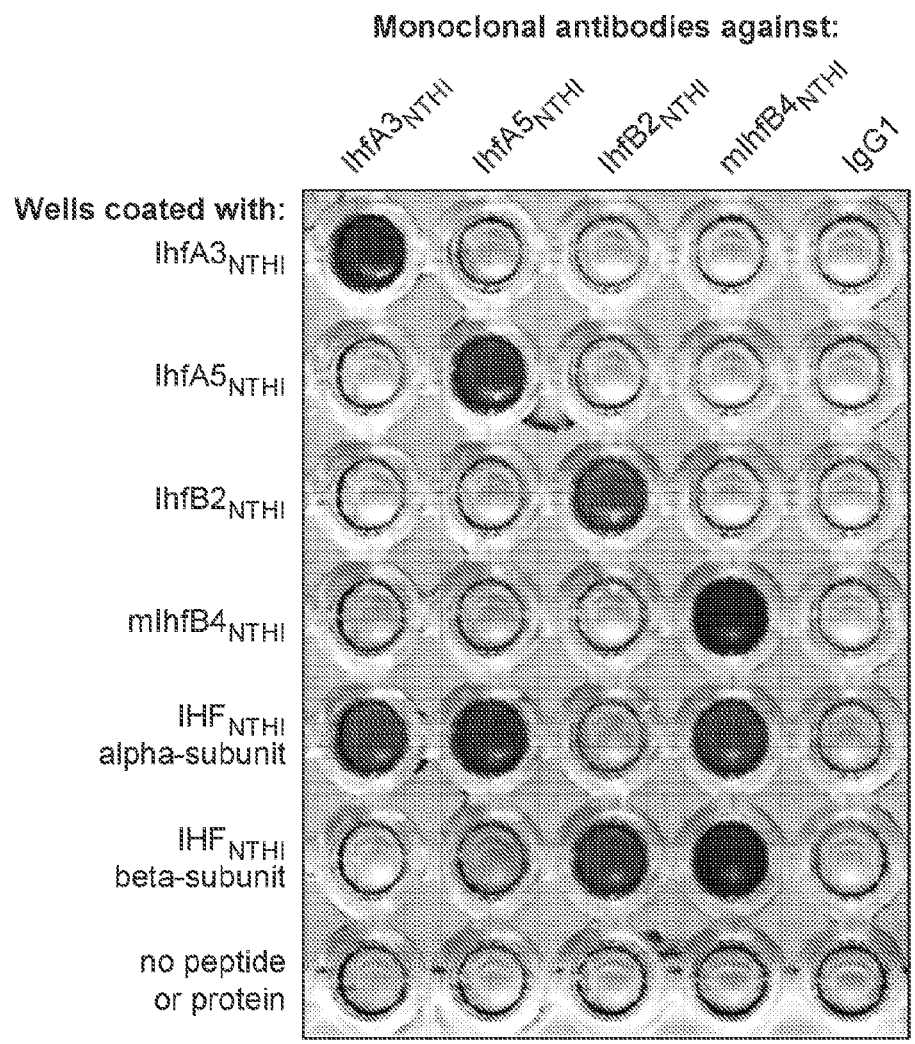
FIG. 2C depicts the specificity of IHF$_{NTHI}$ monoclonal antibodies to the IHF fragment against which it is directed (e.g., A3, A5, B2, B4) and IHF$_{NTHI}$ protein subunit (i.e., IHF alpha subunit or IHF beta subunit) from which they were derived. Dark-colored wells within the scanned image of a representative ELISA plate displayed reactivity of monoclonal antibodies to their respective peptide and protein subunit.

Unless defined otherwise, all technical and scientific terms used herein have the same meanings as commonly understood by one of ordinary skill in the art to which this disclosure belongs. All nucleotide sequences provided herein are presented in the 5' to 3' direction. Although any methods and materials similar or equivalent to those described herein can be used in the practice or testing of the present disclosure, particular, non-limiting exemplary methods, devices, and materials are now described. All technical and patent publications cited herein are incorporated herein by reference in their entirety. Nothing herein is to be construed as an admission that the disclosure is not entitled to antedate such disclosure by virtue of prior invention.

The practice of the present disclosure will employ, unless otherwise indicated, conventional techniques of tissue culture, immunology, molecular biology, microbiology, cell biology and recombinant DNA, which are within the skill of the art. See, e.g., Green and Sambrook eds. (2012) Molecular Cloning: A Laboratory Manual, 4$^{th}$ edition; the series Ausubel et al. eds. (2015) Current Protocols in Molecular Biology; the series Methods in Enzymology (Academic Press, Inc., N.Y.); MacPherson et al. (2015) PCR 1: A Practical Approach (IRL Press at Oxford University Press); MacPherson et al. (1995) PCR 2: A Practical Approach; McPherson et al. (2006) PCR: The Basics (Garland Science); Harlow and Lane eds. (1999) Antibodies, A Laboratory Manual; Greenfield ed. (2014) Antibodies, A Laboratory Manual; Freshney (2010) Culture of Animal Cells: A Manual of Basic Technique, 6$^{th}$ edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Herdewijn ed. (2005) Oligonucleotide Synthesis: Methods and Applications; Hames and Higgins eds. (1984) Transcription and Translation; Buzdin and Lukyanov ed. (2007) Nucleic Acids Hybridization: Modern Applications; Immobilized Cells and Enzymes (IRL Press (1986)); Grandi ed. (2007) In Vitro Transcription and Translation Protocols, 2$^{nd}$ edition; Guisan ed. (2006) Immobilization of Enzymes and Cells; Perbal (1988) A Practical Guide to Molecular Cloning, 2$^{nd}$ edition; Miller and Calos eds, (1987) Gene Transfer Vectors for Mammalian Cells (Cold Spring Harbor Laboratory); Makrides ed. (2003) Gene Transfer and Expression in Mammalian Cells; Mayer and Walker eds. (1987) Immunochemical Methods in Cell and Molecular Biology (Academic Press, London); Lundblad and Macdonald eds. (2010) Handbook of Biochemistry and Molecular Biology, 4$^{th}$ edition; and Herzenberg et al. eds (1996) Weir's Handbook of Experimental Immunology, 5$^{th}$ edition.

All numerical designations, e.g., pH, temperature, time, concentration, and molecular weight, including ranges, are approximations which are varied (+) or (−) by increments of 1.0 or 0.1, as appropriate or alternatively by a variation of +/−15%, or alternatively 10% or alternatively 5% or alternatively 2%. It is to be understood, although not always explicitly stated, that all numerical designations are preceded by the term "about". It also is to be understood, although not always explicitly stated, that the reagents described herein are merely exemplary and that equivalents of such are known in the art.

As used in the specification and claims, the singular form "a", "an" and "the" include plural references unless the context clearly dictates otherwise. For example, the term "a polypeptide" includes a plurality of polypeptides, including mixtures thereof.

As used herein, the term "comprising" is intended to mean that the compositions and methods include the recited elements, but do not exclude others. "Consisting essentially of" when used to define compositions and methods, shall mean excluding other elements of any essential significance to the combination for the intended use. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions disclosed herein. Embodiments defined by each of these transition terms are within the scope of this disclosure.

A "biofilm" intends an organized community of microorganisms that at times adhere to the surface of a structure, that may be organic or inorganic, together with the polymers such as DNA that they secrete and/or release. The biofilms are very resistant to microbiotics and antimicrobial agents. They live on gingival tissues, teeth and restorations, causing caries and periodontal disease, also known as periodontal plaque disease. They also cause middle ear infections. Biofilms can also form on the surface of dental implants, stents, catheter lines and contact lenses. They grow on pacemakers, heart valve replacements, artificial joints and other surgical implants. The Centers for Disease Control) estimate that over 65% of nosocomial (hospital-acquired) infections are caused by biofilms. They cause vaginal infections and lead to life-threatening systemic infections in people with hobbled immune systems. Biofilms also are involved in numerous diseases, including but not limited to those caused by *Aggregatibacter actinomycetemcomitans, Borrelia burgdorferi* (e.g., B31), *Bordetella pertussis* (e.g., Tohama I), *Burkholderia pseudomallei* (e.g., 668), *Burkholderia cenocepacia* (e.g., HI2424), *Escherichia coli* (e.g., K12 MG1655), *Enterococcus faecalis* (e.g., V583), *Haemophilus influenzae* (e.g., Rd KW20), *Helicobacter pylori* (e.g., 26695), *Klebsiella pneumoniae, Moraxella catarrhalis* (e.g., RH4), *Mycobacterium smegmatis* (e.g., MC2), *Mycobacterium tuberculosis* (e.g., CDC1551), *Neisseria gonorrhoeae* (e.g., FA1090), *Neisseria meningitidis* (e.g., MC58), *Pseudomonas aeruginosa, Porphyromonas gingivalis* (e.g., W83), *Prevotella intermedia* (e.g., 17), *Prevotella melaninogenica* (e.g., ATCC® 25845), *Staphylococcus aureus* (e.g., MW2), *Staphylococcus epidermidis* (e.g., RP62A), *Streptococcus agalactiae* (e.g., 2603V/R), *Streptococcus bovis, Streptococcus gallolyticus* (e.g., UCN34), *Streptococcus gordonii* (e.g., NCTC 7868 (Challis)), *Streptococcus mutans* (e.g., UA159), *Streptococcus pneumoniae* (e.g., R6), *Streptococcus pyogenes* (e.g., MGAS10270), *Streptococcus sobrinus* (e.g., 6715), *Salmonella enterica* (e.g., typhi, CT18), *Treponema denticola* (e.g., ATCC® 35405), *Treponema palladum* (e.g., Nichols), *Vibrio cholera* (e.g., El Tor, N16961). Additional organisms known to associate with and/or form biofilms include but are not limited to *Campylobacter* spp., *Candida* spp., *Legionella pneumophila*, and *Listeria monocytogenes*. For instance, cystic fibrosis patients have *Pseudomonas* infections that often result in antibiotic resistant biofilms. Other diseases associated with biofilms include, but are not limited to, lung infections of cystic fibrosis patients, otitis media, post-tympanostomy tube ottorhea, chronic suppurative otitis media, native valve infectious endocarditis, osteomyelitis, rhinosinositis, prostatitis, urinary tract infection, wounds, dental caries and periodontitis. Foodborne pathogens, such as but not limited to some of the above listed organisms (e.g., *Listeria monocytogenes, Escherichia coli, Salmonella enterica*) may also form biofilms on the food which they contaminate. Disease causing biofilms in animals (e.g., *Escherichia coli, Salmonella*, and *Shigella* species) may also cause downstream food contamination and/or disease in human hosts. Further, biofilms need not be of one homogeneous microbial population and may incorporate other pathogens and even host cells. In addition to being associated with disease—both nosocomial and otherwise—and food contamination, biofilms are often causes of industrial contamination, most notably in relation to process waters and surfaces in contact therewith. Complications involving organisms that form biofilm as industrial contaminants include but are not limited to biocorrosion, biofouling, and equipment damage as a result of biofilm formation. Non-limiting exemplary organisms associated with biofilms in industrial settings include those disclosed in Ferrera et al. (2015) Biofouling 31(2): 173-180 and *Desulfovibrio* species. Additional details regarding biofilms may be found in, for example, Donlan (2002) Emerging Infectious Diseases 8(9):881-890.

The term "inhibiting, competing or titrating" intends a prevention, reduction, or disruption in the formation of, or structure of, the DNA/protein matrix that is a component of a microbial biofilm.

The term "nucleoid associated protein" or "NAP" as used herein refers to a class of proteins that carry of the dynamic spatial organization of nucleic acids in the nucleoid of prokaryotic cells. These proteins organize the genome through effecting DNA bending, binding and aggregation. Certain NAPs are DNA binding proteins and may be associated with the biofilm including, DNABII proteins, DPS (Genbank Accession No.: CAA49169), H-NS (Genbank Accession No.: CAA47740), Hfq (Genbank Accession No.: ACE63256), CbpA (Genbank Accession No.: BAA03950) and CbpB (Genbank Accession No.: NP_418813). NAPs generally have strong sequence identity with alpha helical dimerization domains of DNABII proteins and may comprise anti-parallel beta ribbons, which often have NPXT comprising tips that bind and intercalate into the minor groove of DNA and kink it. The functional protomer is a dimer of identical or homologous subunits.

A "DNABII polypeptide or protein" intends a DNA binding protein or polypeptide that is composed of DNA-binding domains and thus have a specific or general affinity for microbial DNA. In one aspect, they bind DNA in the minor grove. Non-limiting examples of DNABII proteins are an integration host factor (IHF) protein and a histone-like protein (HU).

An "integration host factor" or "IHF" protein is a bacterial protein that is used by bacteriophages to incorporate their DNA into the host bacteria. They also bind extracellular microbial DNA. The genes that encode the IHF protein subunits in *E. coli* are himA (Genbank Accession No.: POA6X7.1) and himD (POA6Y1.1) genes. Homologs for these genes are found in other organisms, and peptides corresponding to these genes from other organisms can be found in Table 10 of U.S. Pat. No. 8,999,291, incorporated herein by reference.

"HMGB1" is a high mobility group box (HMGB) 1 protein that is reported to bind to and distort the minor groove of DNA and is an example of an interfering agent. Recombinant or isolated protein and polypeptide are commercially available from Atgenglobal, ProSpecBio, Protein1 and Abnova.

"HU" or "histone-like protein" refers to a class of heterodimeric proteins typically associate with *E. coli*. HU proteins are known to bind DNA junctions. Related proteins have been isolated from other microorganisms. The complete amino acid sequence of *E. coli* HU was reported by Laine et al. (1980) Eur. J. Biochem 103(3):447-481. The genes that encode the HU protein subunits in *E. coli* are hupA and hupB corresponding to SEQ ID NOs. 8 and 9, respectively. A *Haemophilus influenzae* homolog derived from non-typeable *Haemophilus influenzae* (NTHI) corresponds to SEQ ID NO. 3. Homologs for these genes are found in other organisms, and peptides corresponding to these genes from other organisms can be found in Table 10 of U.S. Pat. No. 8,999,291, incorporated herein by reference.

The term "surface antigens" or "surface proteins" refers to proteins or peptides on the surface of cells such as bacterial cells. Examples of surface antigens are outer membrane proteins such as OMP P5 (Genbank Accession No.: YP_004139079.1), OMP P2 (Genbank Accession No.: ZZX87199.1), OMP P26 (Genbank Accession No.: YP_665091.1), rsPilA or recombinant soluble PilA (Genbank Accession No.: EFU96734.1) and Type IV Pilin (Genbank Accession No.: Yp_003864351.1).

The term "*Haemophilus influenzae*" refers to pathogenic bacteria that can cause many different infections such as, for example, ear infections, eye infections, and sinusitis. Many different strains of *Haemophilus influenzae* have been isolated and have an IhfA gene or protein. Some non-limiting examples of different strains of *Haemophilus influenzae* include Rd KW20, 86-028NP, R2866, PittGG, PittEE, R2846, and 2019.

"Microbial DNA" intends single or double stranded DNA from a microorganism that produces a biofilm.

"Inhibiting, preventing or breaking down" a biofilm intends the prophylactic or therapeutic reduction in the structure of a biofilm. An example of breaking down or reducing a biofilm is shown in FIG. 1. Methods to determine if a biofilm has been inhibited, prevented or broken down are known in the art and include in vivo and ex vivo assays, as well as a reduction in the clinical symptoms of an infection or disease associated with a biofilm.

"Treating an infection" intends a reduction in the number of microbes, e.g., bacteria, associated with the formation of a biofilm. Methods to determine if the number of microbes has been reduced are known in the art and include in vivo and ex vivo assays, as well as a reduction in the clinical symptoms of an infection. Because bacteria are protected by the biofilms, the bacteria become resistance to the use of antibacterials. By breaking down the biofilm one can reduce or inhibit bacterial resistance to antibacterial and other agents.

An "interfering agent" intends an agent that any one or more of competes, inhibits, prevents, titrates a DNABII polypeptide such as IHF or HU to a microbial DNA or breaks down a microbial biofilm (e.g., by disrupting the structural integrity of the eDNA based extracellular matrix). It can be any one or more of a chemical or biological molecule. For example, IHF can specifically bind, bend or distort DNA structures such as DNA containing four-way junctions, cis-platinum adducts, DNA loop or base bulges. Examples of such agents, without limitation, include (1) small molecules that inhibit the DNA-binding activity of IHF, (2) small molecules such as polyamines and spermine that compete with IHF or HU in DNA binding, (3) polypeptides such as peptide fragments of IHF or HU that compete with IHF or HU in DNA binding, (4) antibodies or fragments thereof directed to IHF or HU, or (5) a four-way or bent polynucleotides or other types of polynucleotides containing bent or distorted DNA structures that compete in IHF or HU-binding. A "small molecule that inhibits the binding of an IHF or HU to a nucleic acid" refers to (1) or (2) above and includes those that bind DNA in the minor grove, i.e., minor groove binding molecules. A "four-way polynucleotide" intends a polynucleotide that contains a four-way junction, also known as the Holliday junction, between four strands of DNA.

A "bent polynucleotide" intends a double strand polynucleotide that contains a small loop on one strand which does not pair with the other strand. In some embodiments, the loop is from 1 base to about 20 bases long, or alternatively from 2 bases to about 15 bases long, or alternatively from about 3 bases to about 12 bases long, or alternatively from about 4 bases to about 10 bases long, or alternatively has about 4, 5, or 6, or 7, or 8, or 9, or 10 bases.

"Polypeptides that compete with DNABII proteins in DNA binding" intend proteins or peptides that compete with IHF or HU in binding bent or distorted DNA structures but do not form a biofilm with the DNA. Examples, without limitation, include fragments of IHF that include one or more DNA binding domains of the IHF, or the biological equivalents thereof.

As used herein, the term "specifically recognize or bind" intends that the binding agent, e.g., monoclonal antibody, is more likely than not to bind to its intended target or binding partner.

A "subject" of diagnosis or treatment is a cell or an animal such as a mammal, or a human. Non-human animals subject to diagnosis or treatment and are those subject to infections or animal models, for example, simians, murines, such as, rats, mice, chinchilla, canine, such as dogs, leporids, such as rabbits, livestock, sport animals, and pets.

The term "protein", "peptide" and "polypeptide" are used interchangeably and in their broadest sense to refer to a compound of two or more subunit amino acids, amino acid analogs or peptidomimetics. The subunits may be linked by peptide bonds. In another embodiment, the subunit may be linked by other bonds, e.g., ester, ether, etc. A protein or peptide must contain at least two amino acids and no limitation is placed on the maximum number of amino acids which may comprise a protein's or peptide's sequence. As used herein the term "amino acid" refers to either natural and/or unnatural or synthetic amino acids, including glycine and both the D and L optical isomers, amino acid analogs and peptidomimetics.

A "C-terminal polypeptide" intends at least the 10, or alternatively at least the 15, or alternatively at least 20, or at least the 25 C-terminal amino acids or alternatively half of a polypeptide. In another aspect, for polypeptides containing 90 amino acids, the C-terminal polypeptide would comprise amino acids 46 through 90. In one aspect, the term intends the C-terminal 20 amino acids from the carboxy terminus.

The terms "polynucleotide" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, RNAi, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment disclosed herein that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching.

The term "isolated" or "recombinant" as used herein with respect to nucleic acids, such as DNA or RNA, refers to molecules separated from other DNAs or RNAs, respectively that are present in the natural source of the macromolecule as well as polypeptides. The term "isolated or recombinant nucleic acid" is meant to include nucleic acid fragments which are not naturally occurring as fragments and would not be found in the natural state. The term "isolated" is also used herein to refer to polynucleotides, polypeptides and proteins that are isolated from other cellular proteins and is meant to encompass both purified and recombinant polypeptides. In other embodiments, the term "isolated or recombinant" means separated from constituents, cellular and otherwise, in which the cell, tissue, polynucleotide, peptide, polypeptide, protein, antibody or fragment(s) thereof, which are normally associated in nature. For example, an isolated cell is a cell that is separated from tissue or cells of dissimilar phenotype or genotype. An isolated polynucleotide is separated from the 3' and 5' contiguous nucleotides with which it is normally associated in its native or natural environment, e.g., on the chromosome. As is apparent to those of skill in the art, a non-naturally occurring polynucleotide, peptide, polypeptide, protein, antibody or fragment(s) thereof, does not require "isolation" to distinguish it from its naturally occurring counterpart.

It is to be inferred without explicit recitation and unless otherwise intended, that when the present disclosure relates to a polypeptide, protein, polynucleotide or antibody, an equivalent or a biologically equivalent of such is intended within the scope of this disclosure. As used herein, the term "biological equivalent thereof" is intended to be synonymous with "equivalent thereof" when referring to a reference protein, antibody, fragment, polypeptide or nucleic acid, intends those having minimal homology while still maintaining desired structure or functionality. Unless specifically recited herein, it is contemplated that any polynucleotide, polypeptide or protein mentioned herein also includes equivalents thereof. In one aspect, an equivalent polynucleotide is one that hybridizes under stringent conditions to the polynucleotide or complement of the polynucleotide as described herein for use in the described methods. In another aspect, an equivalent antibody or antigen binding polypeptide intends one that binds with at least 70%, or alternatively at least 75%, or alternatively at least 80%, or alternatively at least 85%, or alternatively at least 90%, or alternatively at least 95% affinity or higher affinity to a reference antibody or antigen binding fragment. In another aspect, the equivalent thereof competes with the binding of the antibody or antigen binding fragment to its antigen tinder a competitive ELISA assay. In another aspect, an equivalent intends at least about 80% homology or identity and alternatively, at least about 85%, or alternatively at least about 90%, or alternatively at least about 95%, or alternatively 98% percent homology or identity and exhibits substantially equivalent biological activity to the reference protein, polypeptide or nucleic acid. Examples of biologically equivalent polypeptides are provided in Table 9 of U.S. Pat. No. 8,999,291, incorporated herein by reference, which identify conservative amino acid substitutions to the disclosed amino acid sequences.

A polynucleotide or polynucleotide region (or a polypeptide or polypeptide region) having a certain percentage (for example, 80%, 85%, 90%, or 95%) of "sequence identity" to another sequence means that, when aligned, that percentage of bases (or amino acids) are the same in comparing the two sequences. The alignment and the percent homology or sequence identity can be determined using software programs known in the art, for example those described in Current Protocols in Molecular Biology (Ausubel et al., eds. 1987) Supplement 30, section 7.7.18, Table 7.7.1. In certain embodiments, default parameters are used for alignment. A non-limiting exemplary alignment program is BLAST, using default parameters. In particular, exemplary programs include BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.gov/cgi-bin/BLAST. Sequence identity and percent identity were determined by incorporating them into clustalW (available at the web address:align.genome.jp, last accessed on Mar. 7, 2011.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, or alternatively less than 25% identity, with one of the sequences of the present disclosure.

"Homology" or "identity" or "similarity" can also refer to two nucleic acid molecules that hybridize under stringent conditions.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Examples of stringent hybridization conditions include: incubation temperatures of about 25° C. to about 37° C.; hybridization buffer concentrations of about 6×SSC to about 10×SSC; formamide concentrations of about 0% to about 25%; and wash solutions from about 4×SSC to about 8×SSC. Examples of moderate hybridization conditions include: incubation temperatures of about 40° C. to about 50° C.; buffer concentrations of about 9×SSC to about 2×SSC; formamide concentrations of about 30% to about 50%; and wash solutions of about 5×SSC to about 2×SSC. Examples of high stringency conditions include: incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water. In general, hybridization incubation times are from 5 minutes to 24 hours, with 1, 2, or more washing steps, and wash incubation times are about 1, 2, or 15 minutes. SSC is 0.15 M NaCl and 15 mM citrate buffer. It is understood that equivalents of SSC using other buffer systems can be employed.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in an eukaryotic cell.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

As used herein, the terms "treating," "treatment" and the like are used herein to mean obtaining a desired pharmacologic and/or physiologic effect. The effect may be prophylactic in terms of completely or partially preventing a disorder or sign or symptom thereof, and/or may be therapeutic in terms of a partial or complete cure for a disorder and/or adverse effect attributable to the disorder. Methods to determine if treatment has occurred are known in the art and briefly described herein.

To prevent intends to prevent a disorder or effect in vitro or in vivo in a system or subject that is predisposed to the disorder or effect. An example of such is preventing the formation of a biofilm in a system that is infected with a microorganism known to produce one.

A "composition" is intended to mean a combination of active agent and another compound or composition, inert (for example, a detectable agent or label) or active, such as an adjuvant.

A "pharmaceutical composition" is intended to include the combination of an active agent with a carrier, inert or active, making the composition suitable for diagnostic or therapeutic use in vitro, in vivo or ex vivo.

"Pharmaceutically acceptable carriers" refers to any diluents, excipients, or carriers that may be used in the compositions disclosed herein. Pharmaceutically acceptable carriers include ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, microspheres, microparticles, or nanoparticles (comprising e.g., biodegradable polymers such as Poly(Lactic Acid-co-Glycolic Acid)), and wool fat. Suitable pharmaceutical carriers are described in Remington's Pharmaceutical Sciences, Mack Publishing Company, a standard reference text in this field. They may be selected with respect to the intended form of administration, that is, oral tablets, capsules, elixirs, syrups and the like, and consistent with conventional pharmaceutical practices.

A "biologically active agent" or an active agent disclosed herein intends one or more of an isolated or recombinant polypeptide, an isolated or recombinant polynucleotide, a vector, an isolated host cell, or an antibody, as well as compositions comprising one or more of same.

"Administration" can be effected in one dose, continuously or intermittently throughout the course of treatment. Methods of determining the most effective means and dosage of administration are known to those of skill in the art and will vary with the composition used for therapy, the purpose of the therapy, the target cell being treated, and the subject being treated. Single or multiple administrations can be carried out with the dose level and pattern being selected by the treating physician. Suitable dosage formulations and methods of administering the agents are known in the art. Route of administration can also be determined and method of determining the most effective route of administration are known to those of skill in the art and will vary with the composition used for treatment, the purpose of the treatment, the health condition or disease stage of the subject being treated, and target cell or tissue. Non-limiting examples of route of administration include oral administration, nasal administration, inhalation, injection, and topical application. Administration can be for use in industrial as well as therapeutic applications.

An agent (antibody or fragment thereof, polypeptide or polynucleotide, or cell) of the present disclosure can be administered for therapy by any suitable route of administration. It will also be appreciated that the optimal route will vary with the condition and age of the recipient, and the disease being treated. The agent may be used in industrial settings and for the treatment of animals. When used in industrial settings, the biofilm is contacted with the agent, e.g., antibody.

The term "effective amount" refers to a quantity sufficient to achieve a desired effect. In the context of therapeutic or prophylactic applications, the effective amount will depend on the type and severity of the condition at issue and the characteristics of the individual subject, such as general health, age, sex, body weight, species, and tolerance to pharmaceutical compositions. In the context of an immunogenic composition, in some embodiments the effective amount is the amount sufficient to result in breaking down a biofilm. In other aspects, the amount is effective to treat a bacterial infection associated with a biofilm in a subject. In other embodiments, the effective amount of an agent or an immunogenic composition is the amount sufficient to result in antibody generation against the antigen. In some embodiments, the effective amount is the amount required to confer passive immunity on a subject in need thereof. With respect to immunogenic compositions, in some embodiments the effective amount will depend on the intended use, the degree of immunogenicity of a particular antigenic compound, and the health/responsiveness of the subject's immune system, in addition to the factors described above. The skilled artisan will be able to determine appropriate amounts depending on these and other factors.

In the case of an in vitro application, in some embodiments the effective amount will depend on the size and nature of the application in question. It will also depend on the nature and sensitivity of the in vitro target and the methods in use. The skilled artisan will be able to determine the effective amount based on these and other considerations. The effective amount may comprise one or more administrations of a composition depending on the embodiment.

The term "conjugated moiety" refers to a moiety that can be added to an isolated chimeric polypeptide by forming a covalent bond with a residue of chimeric polypeptide. The moiety may bond directly to a residue of the chimeric polypeptide or may form a covalent bond with a linker which in turn forms a covalent bond with a residue of the chimeric polypeptide.

A "peptide conjugate" refers to the association by covalent or non-covalent bonding of one or more polypeptides and another chemical or biological compound. In a non-limiting example, the "conjugation" of a polypeptide with a chemical compound results in improved stability or efficacy of the polypeptide for its intended purpose. In one embodiment, a peptide is conjugated to a carrier, wherein the carrier is a liposome, a micelle, or a pharmaceutically acceptable polymer.

"Liposomes" are microscopic vesicles consisting of concentric lipid bilayers. Structurally, liposomes range in size and shape from long tubes to spheres, with dimensions from a few hundred Angstroms to fractions of a millimeter. Vesicle-forming lipids are selected to achieve a specified degree of fluidity or rigidity of the final complex providing the lipid composition of the outer layer. These are neutral (cholesterol) or bipolar and include phospholipids, such as phosphatidylcholine (PC), phosphatidylethanolamine (PE), phosphatidylinositol (PI), and sphingomyelin (SM) and other types of bipolar lipids including but not limited to dioleoylphosphatidylethanolamine (DOPE), with a hydrocarbon chain length in the range of 14-22, and saturated or with one or more double C=C bonds. Examples of lipids capable of producing a stable liposome, alone, or in combination with other lipid components are phospholipids, such as hydrogenated soy phosphatidylcholine (HSPC), lecithin, phosphatidylethanolamine, lysolecithin, lysophosphatidylethanol-amine, phosphatidylserine, phosphatidylinositol, sphingomyelin, cephalin, cardiolipin, phosphatidic acid, cerebrosides, di stearoylphosphatidylethanolamine (DSPE), dioleoylphosphatidylcholine (DOPC), dipalmitoylphosphatidylcholine (DPPC), palmitoyloteoylphosphatidylcholine (POPC), palmitoyloleoylphosphatidylethanolamine (POPE) and dioleoylphosphatidylethanolamine 4-(N-maleimido-triethyl)cyclohexane-1-carboxylate (DOPE-mal). Additional non-phosphorous containing lipids that can become incorporated into liposomes include stearylamine, dodecylamine, hexadecylamine, isopropyl myristate, triethanolamine-lauryl sulfate, alkyl-aryl sulfate, acetyl palmitate, glycerol ricinoleate, hexadecyl stereate, amphoteric acrylic polymers, polyethyloxylated fatty acid amides, and the cationic lipids mentioned above (DDAB, DODAC, DMRIE, DMTAP, DOGS, DOTAP (DOTMA), DOSPA, DPTAP, DSTAP, DC-Chol). Negatively charged lipids include phosphatidic acid (PA), dipalmitoylphosphatidylglycerol (DPPG), dioteoylphosphatidylglycerol and (DOPG), dicetylphosphate that are able to form vesicles. Typically, liposomes can be divided into three categories based on their overall size and the nature of the lamellar structure. The three classifications, as developed by the New York Academy Sciences Meeting, "Liposomes and Their Use in Biology and Medicine," December 1977, are multi-lamellar vesicles (MLVs), small uni-lamellar vesicles (SUVs) and large uni-lamellar vesicles (LUVs). The biological active agents can be encapsulated in such for administration in accordance with the methods described herein.

A "micelle" is an aggregate of surfactant molecules dispersed in a liquid colloid. A typical micelle in aqueous solution forms an aggregate with the hydrophilic "head" regions in contact with surrounding solvent, sequestering the hydrophobic tail regions in the micelle center. This type of micelle is known as a normal phase micelle (oil-in-water micelle). Inverse micelles have the head groups at the center with the tails extending out (water-in-oil micelle). Micelles can be used to attach a polynucleotide, polypeptide, antibody or composition described herein to facilitate efficient delivery to the target cell or tissue.

The phrase "pharmaceutically acceptable polymer" refers to the group of compounds which can be conjugated to one or more polypeptides or antibodies described here. It is contemplated that the conjugation of a polymer to the polypeptide or antibody is capable of extending the half-life of the polypeptide in vivo and in vitro. Non-limiting examples include polyethylene glycols, polyvinylpyrrolidones, polyvinylalcohols, cellulose derivatives, polyacrylates, polymethacrylates, sugars, polyols and mixtures thereof. The biological active agents can be conjugated to a pharmaceutically acceptable polymer for administration in accordance with the methods described herein.

A "gene delivery vehicle" is defined as any molecule that can carry inserted polynucleotides into a host cell. Examples of gene delivery vehicles are liposomes, micelles biocompatible polymers, including natural polymers and synthetic polymers; lipoproteins; polypeptides; polysaccharides; lipopolysaccharides; artificial viral envelopes; metal particles; and bacteria, or viruses, such as baculovirus, adenovirus and retrovirus, bacteriophage, cosmid, plasmid, fungal vectors and other recombination vehicles typically used in the art which have been described for expression in a variety of eukaryotic and prokaryotic hosts, and may be used for gene therapy as well as for simple protein expression.

A polynucleotide disclosed herein can be delivered to a cell or tissue using a gene delivery vehicle. "Gene delivery," "gene transfer," "transducing," and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extra-chromosomal replicon (e.g., a plasmid) or a nuclear or mitochondrial chromosome. A number of vectors are known to be capable of mediating transfer of genes to mammalian cells, as is known in the art and described herein.

As used herein the term "eDNA" refers to extracellular DNA found as a component to pathogenic biofilms.

A "plasmid" is an extra-chromosomal DNA molecule separate from the chromosomal DNA which is capable of replicating independently of the chromosomal DNA. In many cases, it is circular and double-stranded. Plasmids provide a mechanism for horizontal gene transfer within a population of microbes and typically provide a selective advantage under a given environmental state. Plasmids may carry genes that provide resistance to naturally occurring antibiotics in a competitive environmental niche, or alternatively the proteins produced may act as toxins under similar circumstances.

"Plasmids" used in genetic engineering are called "plasmid vectors". Many plasmids are commercially available for such uses. The gene to be replicated is inserted into copies of a plasmid containing genes that make cells resistant to particular antibiotics and a multiple cloning site (MCS, or polylinker), which is a short region containing several commonly used restriction sites allowing the easy insertion of DNA fragments at this location. Another major use of plasmids is to make large amounts of proteins. In this case, researchers grow bacteria containing a plasmid harboring the gene of interest. Just as the bacterium produces proteins to confer its antibiotic resistance, it can also be induced to produce large amounts of proteins from the inserted gene. This is a cheap and easy way of mass-producing a gene or the protein it then codes for.

A "yeast artificial chromosome" or "YAC" refers to a vector used to clone large DNA fragments (larger than 100 kb and up to 3000 kb). It is an artificially constructed chromosome and contains the telomeric, centromeric, and replication origin sequences needed for replication and preservation in yeast cells. Built using an initial circular plasmid, they are linearized by using restriction enzymes, and then DNA ligase can add a sequence or gene of interest within the linear molecule by the use of cohesive ends. Yeast expression vectors, such as YACs, YIps (yeast integrating plasmid), and YEps (yeast episomal plasmid), are extremely useful as one can get eukaryotic protein products with posttranslational modifications as yeasts are themselves eukaryotic cells, however YACs have been found to be more unstable than BACs, producing chimeric effects.

A "viral vector" is defined as a recombinantly produced virus or viral particle that comprises a polynucleotide to be delivered into a host cell, either in vivo, ex vivo or in vitro. Examples of viral vectors include retroviral vectors, adenovirus vectors, adeno-associated virus vectors, alphavirus vectors and the like. Infectious tobacco mosaic virus (TMV)-based vectors can be used to manufacturer proteins and have been reported to express Griffithsin in tobacco leaves (O'Keefe et al. (2009) Proc. Nat. Acad. Sci. USA 106(15):6099-6104). Alphavirus vectors, such as Semliki Forest virus-based vectors and Sindbis virus-based vectors, have also been developed for use in gene therapy and immunotherapy. See, Schlesinger & Dubensky (1999) Curr. Opin. Biotechnol. 5:434-439 and Ying et al. (1999) Nat. Med. 5(7):823-827. In aspects where gene transfer is mediated by a retroviral vector, a vector construct refers to the polynucleotide comprising the retroviral genome or part thereof, and a therapeutic gene. Further details as to modern methods of vectors for use in gene transfer may be found in, for example, Kotterman et al. (2015) Viral Vectors for Gene Therapy: Translational and Clinical Outlook Annual Review of Biomedical Engineering 17.

As used herein, "retroviral mediated gene transfer" or "retroviral transduction" carries the same meaning and refers to the process by which a gene or nucleic acid sequences are stably transferred into the host cell by virtue of the virus entering the cell and integrating its genome into the host cell genome. The virus can enter the host cell via its normal mechanism of infection or be modified such that it binds to a different host cell surface receptor or ligand to enter the cell. As used herein, retroviral vector refers to a viral particle capable of introducing exogenous nucleic acid into a cell through a viral or viral-like entry mechanism.

Retroviruses carry their genetic information in the form of RNA; however, once the virus infects a cell, the RNA is reverse-transcribed into the DNA form which integrates into the genomic DNA of the infected cell. The integrated DNA form is called a provirus.

In aspects where gene transfer is mediated by a DNA viral vector, such as an adenovirus (Ad) or adeno-associated virus (AAV), a vector construct refers to the polynucleotide comprising the viral genome or part thereof, and a transgene. Adenoviruses (Ads) are a relatively well characterized, homogenous group of viruses, including over 50 serotypes. See, e.g., PCT International Pat. Application Publication No. WO 95/27071. Ads do not require integration into the host cell genome. Recombinant Ad derived vectors, particularly those that reduce the potential for recombination and generation of wild-type virus, have also been constructed. See, PCT International Pat. Application Publication Nos. WO 95/00655 and WO 95/11984, Wild-type AAV has high infectivity and specificity integrating into the host cell's genome. See, Hermonat & Muzyczka (1984) Proc. Natl. Acad. Sci. USA 81:6466-6470 and Lebkowski et al. (1988) Mol. Cell. Biol. 8:3988-3996.

Vectors that contain both a promoter and a cloning site into which a polynucleotide can be operatively linked are well known in the art. Such vectors are capable of transcribing RNA in vitro or in vivo, and are commercially available from sources such as Stratagene (La Jolla, Calif.) and Promega Biotech (Madison, Wis.). In order to optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression.

Gene delivery vehicles also include DNA/liposome complexes, micelles and targeted viral protein-DNA complexes. Liposomes that also comprise a targeting antibody or fragment thereof can be used in the methods disclosed herein. In addition to the delivery of polynucleotides to a cell or cell population, direct introduction of the proteins described herein to the cell or cell population can be done by the non-limiting technique of protein transfection, alternatively culturing conditions that can enhance the expression and/or promote the activity of the proteins disclosed herein are other non-limiting techniques.

As used herein, the terms "antibody," "antibodies" and "immunoglobulin" includes whole antibodies and any antigen binding fragment or a single chain thereof. Thus the term "antibody" includes any protein or peptide containing molecule that comprises at least a portion of an immunoglobulin molecule. The terms "antibody," "antibodies" and "immunoglobulin" also include immunoglobulins of any isotype, fragments of antibodies which retain specific binding to antigen, including, but not limited to, Fab, Fab', $F(ab)_2$, Fv, scFv, dsFv, Fd fragments, dAb, VH, VL, VhH, and V-NAR domains; minibodies, diabodies, triabodies, tetrabodies and kappa bodies; multispecific antibody fragments formed from antibody fragments and one or more isolated. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, at least one portion of a binding protein, chimeric antibodies, humanized antibodies, species-ized antibodies, single-chain antibodies, and fusion proteins comprising an antigen-binding portion of an antibody and a non-antibody protein. The variable regions of the heavy and light chains of the immunoglobulin molecule contain a binding domain that interacts with an antigen. The constant regions of the antibodies (Abs) may mediate the binding of the immunoglobulin to host tissues. The term "anti-" when used before a protein name, anti-IHF, anti-HU, anti-OMP P5, for example, refers to a monoclonal or polyclonal antibody that binds and/or has an affinity to a particular protein. For example, "anti-IHF" refers to an antibody that binds to the IHF protein. The specific antibody may have affinity or bind to proteins other than the protein it was raised against. For example, anti-IHF, while specifically raised against the IHF protein, may also bind other proteins that are related either through sequence homology or through structure homology.

The antibodies can be polyclonal, monoclonal, multispecific (e.g., bispecific antibodies), a diabody, and antibody fragments, so long as they exhibit the desired biological activity. Antibodies can be isolated from any suitable biological source, e.g., a human, a murine, rat, sheep and canine.

As used herein, "monoclonal antibody" refers to an antibody obtained from a substantially homogeneous antibody population. Monoclonal antibodies are highly specific, as each monoclonal antibody is directed against a single determinant on the antigen. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like.

Monoclonal antibodies may be generated using hybridoma techniques or recombinant DNA methods known in the art. A hybridoma is a cell that is produced in the laboratory from the fusion of an antibody-producing lymphocyte and a non-antibody producing cancer cell, usually a myeloma or lymphoma. A hybridoma proliferates and produces a continuous sample of a specific monoclonal antibody. Alternative techniques for generating or selecting antibodies include in vitro exposure of lymphocytes to antigens of interest, and screening of antibody display libraries in cells, phage, or similar systems.

The term "human antibody" as used herein, is intended to include antibodies having variable and constant regions derived from human germline immunoglobulin sequences. The human antibodies disclosed herein may include amino acid residues not encoded by human germline immunoglobulin sequences (e.g., mutations introduced by random or site-specific mutagenesis in vitro or by somatic mutation in vivo). However, the term "human antibody" as used herein, is not intended to include antibodies in which CDR sequences derived from the germline of another mammalian species, such as a mouse, have been grafted onto human framework sequences. Thus, as used herein, the term "human antibody" refers to an antibody in which substantially every part of the protein (e.g., CDR, framework, $C_L$, $C_H$ domains (e.g., $C_{H1}$, $C_{H2}$, $C_{H3}$), hinge, (VL, VH)) is substantially non-immunogenic in humans, with only minor sequence changes or variations. Similarly, antibodies designated primate (monkey, baboon, chimpanzee, etc.), rodent (mouse, rat, rabbit, guinea pig, hamster, and the like) and other mammals designate such species, sub-genus, genus, sub-family, family specific antibodies. Further, chimeric antibodies include any combination of the above. Such changes or variations optionally retain or reduce the immunogenicity in humans or other species relative to non-modified antibodies. Thus, a human antibody is distinct from a chimeric or humanized antibody. It is pointed out that a human antibody can be produced by a non-human animal or prokaryotic or eukaryotic cell that is capable of expressing functionally rearranged human immunoglobulin (e.g., heavy chain and/or light chain) genes. Further, when a human antibody is a single chain antibody, it can comprise a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin.

As used herein, a human antibody is "derived from" a particular germline sequence if the antibody is obtained from a system using human immunoglobulin sequences, e.g., by immunizing a transgenic mouse carrying human immunoglobulin genes or by screening a human immunoglobulin gene library. A human antibody that is "derived from" a human germline immunoglobulin sequence can be identified as such by comparing the amino acid sequence of the human antibody to the amino acid sequence of human germline immunoglobulins. A selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

A "human monoclonal antibody" refers to antibodies displaying a single binding specificity which have variable and constant regions derived from human germline immunoglobulin sequences. The term also intends recombinant human antibodies. Methods to making these antibodies are described herein.

The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the antibody, e.g., from a transfectoma, antibodies isolated from a recombinant, combinatorial human antibody library, and antibodies prepared, expressed, created or isolated by any other means that involve splicing of human immunoglobulin gene sequences to other DNA sequences. Such recombinant human antibodies have variable and constant regions derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. Methods to making these antibodies are described herein.

As used herein, chimeric antibodies are antibodies whose light and heavy chain genes have been constructed, typically by genetic engineering, from antibody variable and constant region genes belonging to different species.

As used herein, the term "humanized antibody" or "humanized immunoglobulin" refers to a human/non-human chimeric antibody that contains a minimal sequence derived from non-human immunoglobulin. For the most part, humanized antibodies are human immunoglobulins (recipient antibody) in which residues from a variable region of the recipient are replaced by residues from a variable region of a non-human species (donor antibody) such as mouse, rat, rabbit, or non-human primate having the desired specificity, affinity and capacity. Humanized antibodies may comprise residues that are not found in the recipient antibody or in the donor antibody. The humanized antibody can optionally also comprise at least a portion of an immunoglobulin constant region (Fc), typically that of a human immunoglobulin, a non-human antibody containing one or more amino acids in a framework region, a constant region or a CDR, that have been substituted with a correspondingly positioned amino acid from a human antibody. In general, humanized antibodies are expected to produce a reduced immune response in a human host, as compared to a non-humanized version of the same antibody. The humanized antibodies may have conservative amino acid substitutions which have substantially no effect on antigen binding or other antibody functions. Conservative substitutions groupings include: glycine-alanine, valine-leucine-isoleucine, phenylalanine-tyrosine, lysine-arginine, alanine-valine, serine-threonine and asparagine-glutamine. The term "species-ized" refers to antibodies that have been modified in the same or a similar manner for a non-human species.

The terms "polyclonal antibody" or "polyclonal antibody composition" as used herein refer to a preparation of antibodies that are derived from different B-cell lines. They are a mixture of immunoglobulin molecules secreted against a specific antigen, each recognizing a different epitope. In some embodiments, the antibody or antigen binding fragment is not a polyclonal antibody.

As used herein, the term "antibody derivative", comprises a full-length antibody or a fragment of an antibody, wherein one or more of the amino acids are chemically modified by alkylation, pegylation, acylation, ester formation or amide formation or the like, e.g., for linking the antibody to a second molecule. This includes, but is not limited to, pegylated antibodies, cysteine-pegylated antibodies, and variants thereof.

As used herein, the term "label" intends a directly or indirectly detectable compound or composition that is conjugated directly or indirectly to the composition to be detected, e.g., N-terminal histidine tags (N-His), magnetically active isotopes, e.g., $^{115}$Sn, $^{117}$Sn and $^{119}$Sn, a non-radioactive isotopes such as $^{13}$C and $^{15}$N, polynucleotide or protein such as an antibody so as to generate a "labeled" composition. The term also includes sequences conjugated to a polynucleotide that will provide a signal upon expression of the inserted sequences, such as green fluorescent protein (GFP) and the like. While the term "label" generally intends compositions covalently attached to the composition to be detected, in one aspect it specifically excludes naturally occurring nucleosides and amino acids that are known to fluoresce under certain conditions (e.g., temperature, pH, etc.) when positioned within the polynucleotide or protein in its native environment and generally any natural fluorescence that may be present in the composition to be detected. The label may be detectable by itself (e.g., radioisotope labels or fluorescent labels) or, in the case of an enzymatic label, may catalyze chemical alteration of a substrate compound or composition which is detectable. The labels can be suitable for small scale detection or more suitable for high-throughput screening. As such, suitable labels include, but are not limited to magnetically active isotopes, non-radioactive isotopes, radioisotopes, fluorochromes, chemiluminescent compounds, dyes, and proteins, including enzymes. The label may be simply detected or it may be quantified. A response that is simply detected generally comprises a response whose existence merely is confirmed, whereas a response that is quantified generally comprises a response having a quantifiable (e.g., numerically reportable) value such as an intensity, polarization, and/or other property. In luminescence or fluorescence assays, the detectable response may be generated directly using a luminophore or fluorophore associated with an assay component actually involved in binding, or indirectly using a luminophore or fluorophore associated with another (e.g., reporter or indicator) component. Examples of luminescent labels that produce signals include, but are not limited to bioluminescence and chemiluminescence. Detectable luminescence response generally comprises a change in, or an occurrence of a luminescence signal. Suitable methods and luminophores for luminescently labeling assay components are known in the art and described for example in Haugland, Richard P. (1996) Handbook of Fluorescent Probes and Research Chemicals ($6^{th}$ ed). Examples of luminescent probes include, but are not limited to, aequorin and luciferases.

As used herein, the term "immunoconjugate" comprises an antibody or an antibody derivative associated with or linked to a second agent, such as a cytotoxic agent, a detectable agent, a radioactive agent, a targeting agent, a human antibody, a humanized antibody, a chimeric antibody, a synthetic antibody, a semisynthetic antibody, or a multispecific antibody.

Examples of suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, and Texas Red. Other suitable optical dyes are described in the Haugland, Richard P. (1996) Handbook of Fluorescent Probes and Research Chemicals ($6^{th}$ ed.).

In another aspect, the fluorescent label is functionalized to facilitate covalent attachment to a cellular component present in or on the surface of the cell or tissue such as a cell surface marker. Suitable functional groups, including, but not are limited to, isothiocyanate groups, amino groups, haloacetyl groups, maleimides, succinimidyl esters, and sulfonyl halides, all of which may be used to attach the fluorescent label to a second molecule. The choice of the functional group of the fluorescent label will depend on the site of attachment to either a linker, the agent, the marker, or the second labeling agent.

"Eukaryotic cells" comprise all of the life kingdoms except monera. They can be easily distinguished through a membrane-bound nucleus. Animals, plants, fungi, and protists are eukaryotes or organisms whose cells are organized into complex structures by internal membranes and a cytoskeleton. The most characteristic membrane-bound structure is the nucleus. Unless specifically recited, the term "host" includes a eukaryotic host, including, for example, yeast, higher plant, insect and mammalian cells. Non-limiting examples of eukaryotic cells or hosts include simian, bovine, porcine, murine, rat, avian, reptilian and human.

"Prokaryotic cells" that usually lack a nucleus or any other membrane-bound organelles and are divided into two domains, bacteria and archaea. In addition to chromosomal DNA, these cells can also contain genetic information in a circular loop called on episome. Bacterial cells are very small, roughly the size of an animal mitochondrion (about 1-2 µm in diameter and 10 µm long). Prokaryotic cells feature three major shapes: rod shaped, spherical, and spiral. Instead of going through elaborate replication processes like eukaryotes, bacterial cells divide by binary fission. Examples include but are not limited to *Bacillus* bacteria, *E. coli* bacterium, and *Salmonella* bacterium.

A "native" or "natural" antigen is a polypeptide, protein or a fragment which contains an epitope, which has been isolated from a natural biological source, and which can specifically bind to an antigen receptor, in particular a T cell antigen receptor (TCR), in a subject.

The terms "antigen" and "antigenic" refer to molecules with the capacity to be recognized by an antibody or otherwise act as a member of an antibody-ligand pair. "Specific binding" refers to the interaction of an antigen with the variable regions of immunoglobulin heavy and light chains. Antibody-antigen binding may occur in vivo or in vitro. The skilled artisan will understand that macromolecules, including proteins, nucleic acids, fatty acids, lipids, lipopolysaccharides and polysaccharides have the potential to act as an antigen. The skilled artisan will further understand that nucleic acids encoding a protein with the potential to act as an antibody ligand necessarily encode an antigen. The artisan will further understand that antigens are not limited to full-length molecules, but can also include partial molecules. The term "antigenic" is an adjectival reference to molecules having the properties of an antigen. The term encompasses substances which are immunogenic, i.e., immunogens, as well as substances which induce immunological unresponsiveness, or anergy, i.e., anergens.

An "altered antigen" is one having a primary sequence that is different from that of the corresponding wild-type antigen. Altered antigens can be made by synthetic or recombinant methods and include, but are not limited to, antigenic peptides that are differentially modified during or after translation, e.g., by phosphorylation, glycosylation, cross-linking, acylation, proteolytic cleavage, linkage to an antibody molecule, membrane molecule or other ligand (Ferguson et al. (1988) Ann. Rev. Biochem. 57:285-320). A synthetic or altered antigen disclosed herein is intended to bind to the same TCR as the natural epitope.

A "self-antigen" also referred to herein as a native or wild-type antigen is an antigenic peptide that induces little or no immune response in the subject due to self-tolerance to the antigen. An example of a self-antigen is the melanoma specific antigen gp100.

"Immune response" broadly refers to the antigen-specific responses of lymphocytes to foreign substances. The terms "immunogen" and "immunogenic" refer to molecules with the capacity to elicit an immune response. All immunogens are antigens; however, not all antigens are immunogenic. An immune response disclosed herein can be humoral (via antibody activity) or cell-mediated (via T cell activation). The response may occur in vivo or in vitro. The skilled artisan will understand that a variety of macromolecules, including proteins, nucleic acids, fatty acids, lipids, lipopolysaccharides and polysaccharides have the potential to be immunogenic. The skilled artisan will further understand that nucleic acids encoding a molecule capable of eliciting an immune response necessarily encode an immunogen. The artisan will further understand that immunogens are not limited to full-length molecules, but may include partial molecules.

The term "passive immunity" refers to the transfer of immunity from one subject to another through the transfer of antibodies. Passive immunity may occur naturally, as when maternal antibodies are transferred to a fetus. Passive immunity may also occur artificially as when antibody compositions are administered to non-immune subjects. Antibody donors and recipients may be human or non-human subjects. Antibodies may be polyclonal or monoclonal, may be generated in vitro or in vivo, and may be purified, partially purified, or unpurified depending on the embodiment. In some embodiments described herein, passive immunity is conferred on a subject in need thereof through the administration of antibodies or antigen binding fragments that specifically recognize or bind to a particular antigen. In some embodiments, passive immunity is conferred through the administration of an isolated or recombinant polynucleotide encoding an antibody or antigen binding fragment that specifically recognizes or binds to a particular antigen.

As used herein, the term "inducing an immune response in a subject" is a term well understood in the art and intends that an increase of at least about 2-fold, at least about 5-fold, at least about 10-fold, at least about 100-fold, at least about 500-fold, or at least about 1000-fold or more in an immune response to an antigen (or epitope) can be detected or measured, after introducing the antigen (or epitope) into the subject, relative to the immune response (if any) before introduction of the antigen (or epitope) into the subject. An immune response to an antigen (or epitope), includes, but is not limited to, production of an antigen-specific (or epitope-specific) antibody, and production of an immune cell expressing on its surface a molecule which specifically binds to an antigen (or epitope). Methods of determining whether an immune response to a given antigen (or epitope) has been induced are well known in the art. For example, antigen-specific antibody can be detected using any of a variety of immunoassays known in the art, including, but not limited to, ELISA, wherein, for example, binding of an antibody in a sample to an immobilized antigen (or epitope) is detected with a detectably-labeled second antibody (e.g., enzyme-labeled mouse anti-human Ig antibody).

As used herein, "solid phase support" or "solid support", used interchangeably, is not limited to a specific type of support. Rather a large number of supports are available and are known to one of ordinary skill in the art. Solid phase supports include silica gels, resins, derivatized plastic films, glass beads, cotton, plastic beads, alumina gels. As used herein, "solid support" also includes synthetic antigen-presenting matrices, cells, and liposomes. A suitable solid phase support may be selected on the basis of desired end use and suitability for various protocols. For example, for peptide synthesis, solid phase support may refer to resins such as polystyrene (e.g., PAM-resin obtained from Bachem Inc., Peninsula Laboratories, etc.), POLYHIPE® resin (polymerized high internal-phase emulsion resin) (obtained from Aminotech, Canada), polyamide resin (obtained from Peninsula Laboratories), polystyrene resin grafted with polyethylene glycol (TENTAGEL®, Rapp Polymere, Tubingen, Germany) or polydimethylacrylamide resin (obtained from Milligen/Biosearch, Calif.).

An example of a solid phase support include glass, polystyrene, polypropylene, polyethylene, dextran, nylon, amylases, natural and modified celluloses, polyacrylamides, gabbros, and magnetite. The nature of the carrier can be either soluble to some extent or insoluble. The support material may have virtually any possible structural configuration so long as the coupled molecule is capable of binding to a polynucleotide, polypeptide or antibody. Thus, the support configuration may be spherical, as in a bead, or cylindrical, as in the inside surface of a test tube, or the external surface of a rod. Alternatively, the surface may be flat such as a sheet, test strip, etc. or alternatively polystyrene beads. Those skilled in the art will know many other suitable carriers for binding antibody or antigen, or will be able to ascertain the same by use of routine experimentation.

Antibodies, Fragments and Derivatives Thereof

This disclosure provides an antibody that binds and/or specifically recognizes and binds an isolated polypeptide for use in the methods disclosed herein. The antibody can be any of the various antibodies described herein, non-limiting examples of such include a polyclonal antibody, a monoclonal antibody, a chimeric antibody, a human antibody, a veneered antibody, a diabody, a humanized antibody, an antibody derivative, a recombinant humanized antibody, or a derivative or fragment of each thereof. In one aspect, the fragment comprises, or alternatively consists essentially of, or yet further consists of the CDR of the antibody, examples of such are provided herein. In one aspect, the antibody is detectably labeled or further comprises a detectable and/or purification label conjugated to it. Also provided is a hybridoma cell line that produces a monoclonal antibody disclosed herein. Compositions comprising, or alternatively consisting essentially of, or yet further consisting of, one or more of the above embodiments are further provided herein. Further provided are polynucleotides that encode the amino acid sequence of the antibodies and fragments as well as methods to produce recombinantly or chemically synthesize the antibody polypeptides and fragments thereof. The antibody polypeptides can be produced in a eukaryotic or prokaryotic cell, or by other methods known in the art and briefly described herein. Antibodies disclosed herein may be selected such that they have a high level of epitope binding specificity and high binding affinity to the biofilm. In general, the higher the binding affinity of an antibody, the more stringent wash conditions can be performed in an immunoassay to remove nonspecifically bound material without removing the target. Accordingly, the antibodies of the present technology useful in the disclosed methods usually have binding affinities of at least $10^{-6}$, $10^{-7}$, $10^{-8}$, $10^{-9}$, $10^{-10}$, $10^{-11}$, or $10^{-12}$M. In certain aspects, the antibodies have a sufficient kinetic on-rate to reach equilibrium under standard conditions in at least 12 hours, at least 5 hours, at least 1 hour, or at least 30 minutes. In another aspect, the affinity of the antibody or antigen binding fragment is less than or about 1000 picoMole (pM), less than about 900 pM, less than about 800 pM, less than about 700 pM, less than about 600 pM, less than about 500 pM, less than about 400 pM, less than about 300 pM, less than about 200 pM, less than about 100 pM, less than about 50 pM, less than about 40 pM, less than about 30 pM, less than about 20 pM, or about 10 pM, or about 9 pM, or about 8 pM, or alternatively less than about 4 pM, or alternatively less than about 2 pM.

Antibodies, such as equivalent antibodies, also can be generated using conventional techniques known in the art and are well-described in the literature. Several methodologies exist for production of polyclonal antibodies. For example, polyclonal antibodies are typically produced by immunization of a suitable mammal such as, but not limited to, chickens, goats, guinea pigs, hamsters, horses, mice, rats, and rabbits. An antigen is injected into the mammal, induces the B-lymphocytes to produce immunoglobulins specific for the antigen. Immunoglobulins may be purified from the mammal's serum. Antibodies specific to an IHFα and/or an IHFβ subunit can be generated by injection of polypeptides corresponding to different epitopes of IHFα and IHFβ. For example, antibodies can be generated using the 20 amino acids of each subunit such as SEQ ID NOs. 12 and 13 for IHFα (fragments A3 and A5 of IHF, respectively), SEQ ID NO. 14 for HU (fragment A5 of HU), SEQ ID NOs. 15 to 17 for IHFβ (fragments B2, B4, and mB4 of IHF).

In addition, antibodies can be generated against the "tip" region of an DNABII protein, that in one aspect contains or is altered to contain turn of the antiparallel beta ribbon and/or the sequence NPXT, wherein "X" refers to any amino acid. In some embodiments, X is selected from the amino acids Q, R, K, S, or T. Such antibodies may be generated using a fragment of the DNABII protein comprising the NPXT sequence, optionally flanked by between about 0, 1, 2, 3, 4, 5, 6, 7, 8, 9, 10, 11, 12, 13, 14, 15, or 16 amino acids on one or both sides of said sequence. Non-limiting examples of such are disclosed herein with the consensus amino acid sequence NPXT, in underlined and bolded text. In another aspect, antibodies may be generated against the tip region of a DNABII protein providing the consensus sequence NPXT, wherein "X" is any amino acid or alternatively X is selected from the amino acids Q, R, K, S, or T. A skilled artisan will appreciate that in any one of these sequences, the residue in the X position (marked with a doubleunderline in the below examples) may be substituted with any amino acid—e.g., Q, R, K, S, or T. Examples include:

SEQ ID NO. 13: *Haemophilus influenzae* IhfA, A5 fragment:

RPGRNPKTGDVVPVSARRVV.

SEQ ID NO. 14: *Haemophilus influenzae* HU, A5 fragment:

RTGRNPQTGAEIQIAASKVP.

SEQ ID NO. 17: *Haemophilus influenzae* IhfB, modified B4 (mB4) fragment:

FSLHHRQPRLGRNPKTGDSV.

SEQ ID NO. 26: *Haemophilus influenzae* IhfA, A tip fragment:

NFELRDKSSRPGRNPKTGDVV.

SEQ ID NO. 27: *Haemophilus influenzae* IhfB, B tip fragment:

SLHHRQPRLGRNPKTGDSVNL.

SEQ ID NO. 31 *Haemophilus influenzae* HU, fragment:

VNERAARTGRNPQTGAEIQIAA.

In some embodiments, the polypeptide comprising NPXT is at least about 20 amino acids long and the NPXT is centrally in the sequence. Non-limiting examples of such sequences include SEQ ID NOs. 13, 14, and 31. Alternatively, the polypeptides having the NPXT motif (e.g., as noted above) can be modified to remove the NPXT motif either by substitution or deletion of one or more amino acids and monoclonal antibodies can be raised against these polypeptides. Applicants have determined that antibodies raised against DNABII polypeptides lacking the NPXT motif are useful in diagnostic methods to image and monitor biofilm formation and/or disruption. In one aspect, a kit is provided comprising an antibody raised against or that binds a DNABII having the NPXT motif and an antibody raised against or binds a DNABII (e.g. a modified or naturally occurring polypeptide) that lacks the NPXT motif. For example a kit can comprise an antibody that recognizes and bind the polypeptide A5, B4, or mB4 (therapeutic) can be combined in a kit with an antibody that recognizes and bind the polypeptide A3 or B2 (diagnostic). The kit is useful for diagnosis, treatment and monitoring biofilm treatment.

Variations of this methodology include modification of adjuvants, routes and site of administration, injection volumes per site and the number of sites per animal for optimal production and humane treatment of the animal. For example, adjuvants typically are used to improve or enhance an immune response to antigens. Most adjuvants provide for an injection site antigen depot, which allows for a stow release of antigen into draining lymph nodes. Other adjuvants include surfactants which promote concentration of protein antigen molecules over a large surface area and immunostimulatory molecules. Non-limiting examples of adjuvants for polyclonal antibody generation include Freund's adjuvants, Ribi adjuvant system, MPL derived adjuvants, those derived from the heat labile enterotoxin of *E. coli* (e.g., dmLT=double mutant labile toxin), and Titermax. Polyclonal antibodies can be generated using methods known in the art some of which are described in U.S. Pat. Nos. 7,279,559; 7,119,179; 7,060,800; 6,709,659; 6,656,746; 6,322,788; 5,686,073; and 5,670,153.

Monoclonal antibodies can be generated using conventional hybridoma techniques known in the art and well-described in the literature. For example, a hybridoma is produced by fusing a suitable immortal cell line (e.g., a myeloma cell line such as, but not limited to, Sp2/0, Sp2/0-AG14, NSO, NS1, NS2, AE-1, L.5, P3X63Ag8,653, Sp2 SA3, Sp2 MAI, Sp2 SS1, Sp2 SA5, U397, MIA 144, ACT IV, MOLT4, DA-1, JURKAT, WEHI, K-562, COS, RAJI, NIH 313, HL-60, MLA 144, NAMAIWA, NEURO 2A, CHO, PerC.6, YB2/O) or the like, or heteromyelomas, fusion products thereof, or any cell or fusion cell derived there from, or any other suitable cell line as known in the art (see, those at the following web addresses, e.g., atcc.org, lifetech.com, last accessed on Nov. 26, 2007), with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. Antibody producing cells can also be obtained from the peripheral blood or, in particular embodiments, the spleen or lymph nodes, of humans or other suitable animals that have been immunized with the antigen of interest. Any other suitable host cell can also be used for expressing-heterologous or endogenous nucleic acid encoding an antibody, specified fragment or variant thereof, of the present disclosure. The fused cells (hybridomas) or recombinant cells can be isolated using selective culture conditions or other suitable known methods, and cloned by limiting dilution or cell sorting, or other known methods. Some embodiments disclosed herein relate to specific hybridomas that produce monoclonal antibodies to IHF fragments; non-limiting examples include IhfA5 NTHI 14G8.F5.G6 (ATCC No. PTA-122334), IhfB4 NTHI 4E11.E5.G2 (ATCC No. PTA-122336), mIhfB4 NTHI 12E6.F8.D12.D5 (ATCC No. PTA-122335).

Other suitable methods of producing or isolating antibodies of the requisite specificity can be used, including, but not limited to, methods that select recombinant antibody from a peptide or protein library (e.g., but not limited to, a bacteriophage, ribosome, oligonucleotide, cDNA, or the like, display library; e.g., as available from various commercial vendors such as MorphoSys (Martinsreid/Planegg, Del.), BioInvent (Lund, Sweden), Affitech (Oslo, Norway) using methods known in the art. Art known methods are described in the patent literature some of which include U.S. Pat. Nos. 4,704,692; 5,723,323; 5,763,192; 5,814,476; 5,817,483; 5,824,514; 5,976,862. Alternative methods rely upon immunization of transgenic animals (e.g., SCID mice, Nguyen et al. (1977) Microbiol. Immunol. 41:901-907 (1997); Sandhu et al. (1996) Crit. Rev. Biotechnol. 16:95-118; Eren et al. (1998) Mumma 93:154-161) that are capable of producing a repertoire of human antibodies, as known in the art and/or as described herein. Such techniques, include, but are not limited to, ribosome display, e.g., Wanes et al. (1997) Proc. Natl. Acad. Sci. USA, 94:4937-4942; Hanes et al. (1998) Proc. Natl. Acad. Sci. USA 95:14130-14135); single cell antibody producing technologies (e.g., selected lymphocyte antibody method ("SLAM") (U.S. Pat. No. 5,627,052, Wen et al. (1987) J. Immunol 17:887-892; Babcook et al. (1996) Proc. Natl. Acad. Sci. USA 93:7843-7848); gel microdroplet and flow cytometry (Powell et al. (1990) Biotechnol. 8:333-337; One Cell Systems, (Cambridge, Mass.); Gray et al. (1995) J. Imm. Meth. 182:155-163; and Kenny et al. (1995) Bio. Technol. 13:787-790); B-cell selection (Steenbakkers et al. (1994) Molec. Biol. Reports 19:125-134).

Antibodies may also be produced by inducing in vivo production in the lymphocyte population or by screening recombinant immunoglobulin libraries or panels of highly specific binding reagents (Orlandi et al. (1989) PNAS 86: 3833-3837; Winter et al. (1991) Nature 349: 293-299).

Alternatively, techniques for the production of single chain antibodies may be used. Single chain antibodies (scF$_v$s) comprise a heavy chain variable region and a light chain variable region connected with a linker peptide (typically around 5 to 25 amino acids in length). In the scF$_v$, the variable regions of the heavy chain and the light chain may be derived from the same antibody or different antibodies. scF$_v$s may be synthesized using recombinant techniques, for example by expression of a vector encoding the scF$_v$ in a host organism such as *E. coli*. DNA encoding scF$_v$ can be obtained by performing amplification using a partial DNA encoding the entire or a desired amino acid sequence of a DNA selected from a DNA encoding the heavy chain or the variable region of the heavy chain of the above-mentioned antibody and a DNA encoding the light chain or the variable region of the light chain thereof as a template, by PCR using a primer pair that defines both ends thereof, and further performing amplification combining a DNA encoding a polypeptide linker portion and a primer pair that defines both ends thereof, so as to ligate both ends of the linker to the heavy chain and the light chain, respectively. An expression vector containing the DNA encoding scF$_v$ and a host transformed by the expression vector can be obtained according to conventional methods known in the art.

Antigen binding fragments may also be generated, for example the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed to allow rapid and easy identification of monoclonal Fab fragments with the desired specificity (Huse et al. (1989) Science 256:1275-1281).

Antibody derivatives of the present disclosure can also be prepared by delivering a polynucleotide encoding an antibody or fragment thereof disclosed herein to a suitable host such as to provide transgenic animals or mammals, such as goats, cows, horses, sheep, and the like, that produce such antibodies in their milk. These methods are known in the art and are described for example in U.S. Pat. Nos. 5,827,690; 5,849,992; 4,873,316; 5,849,992; 5,994,616; 5,565,362; and 5,304,489.

The term "antibody derivative" includes post-translational modification to linear polypeptide sequence of the antibody or fragment. For example, U.S. Pat. No. 6,602,684 B 1 describes a method for the generation of modified glycol-forms of antibodies, including whole antibody molecules, antibody fragments, or fusion proteins that include a region equivalent to the Fc region of an immunoglobulin, having enhanced Fe-mediated cellular toxicity, and glycoproteins so generated.

The antibodies disclosed herein also include derivatives that are modified by the covalent attachment of any type of molecule to the antibody such that covalent attachment does not prevent the antibody from generating an anti-idiotypic response. Antibody derivatives include, but are not limited to, antibodies that have been modified by glycosylation, acetylation, pegylation, phosphorylation, amidation, derivatization by known protecting/blocking groups, proteolytic cleavage, linkage to a cellular ligand or other protein, etc. Non-limiting examples of the modified antibodies contemplated herein are agylcosylated whole antibody molecules, antibody fragments, or fusion proteins that include a region equivalent to the Fc region of an immunoglobulin. Such aglycosyltae forms can be generated, for example, in host cells that lack the ability to modify proteins with N-linked glycans or by mutating N-linked consensus sites on the antibody of interest. Additionally, the derivatives may contain one or more non-classical amino acids.

Antibody derivatives also can be prepared by delivering a polynucleotide disclosed herein to provide transgenic plants and cultured plant cells (e.g., but not limited to tobacco, maize, and duckweed) that produce such antibodies, specified portions or variants in the plant parts or in cells cultured therefrom. For example, Cramer et al. (1999) Curr. Top. Microbol. Immunol. 240:95-118 and references cited therein, describe the production of transgenic tobacco leaves expressing large amounts of recombinant proteins, e.g., using an inducible promoter. Transgenic maize have been used to express mammalian proteins at commercial production levels, with biological activities equivalent to those produced in other recombinant systems or purified from natural sources. See, e.g., Hood et al. (1999) Adv. Exp. Med. Biol. 464:127-147 and references cited therein. Antibody derivatives have also been produced in large amounts from transgenic plant seeds including antibody fragments, such as single chain antibodies (scFv's), including tobacco seeds and potato tubers. See, e.g., Conrad et al. (1998) Plant Mol.

Biol. 38:101-109 and references cited therein. Thus, antibodies can also be produced using transgenic plants, according to know methods.

Antibody derivatives also can be produced, for example, by adding exogenous sequences to modify immunogenicity or to reduce, enhance or modify binding, affinity, on-rate, off-rate, avidity, specificity, half-life, or any other suitable characteristic. Generally part or all of the non-human or human CDR sequences are maintained while the non-human sequences of the variable and constant regions are replaced with human or other amino acids.

In general, the CDR residues are directly and most substantially involved in influencing antigen binding. Humanization or engineering of antibodies can be performed using any known method such as, but not limited to, those described in U.S. Pat. Nos. 5,723,323; 5,976,862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; and 4,816,567.

The general structure of antibodies is known in the art and will only be briefly summarized here. An immunoglobulin monomer comprises two heavy chains and two light chains connected by disulfide bonds. Each heavy chain is paired with one of the light chains to which it is directly bound via a disulfide bond. Each heavy chain comprises a constant region (which varies depending on the isotype of the antibody) and a variable region. The variable region comprises three hypervariable regions (or complementarity determining regions) which are designated CDRH1, CDRH2 and CDRH3 and which are supported within framework regions. Each light chain comprises a constant region and a variable region, with the variable region comprising three hypervariable regions (designated CDRL1, CDRL2 and CDRL3) supported by framework regions in an analogous manner to the variable region of the heavy chain.

The hypervariable regions of each pair of heavy and light chains mutually cooperate to provide an antigen binding site that is capable of binding a target antigen. The binding specificity of a pair of heavy and light chains is defined by the sequence of CDR1, CDR2 and CDR3 of the heavy and light chains. Thus once a set of CDR sequences (i.e., the sequence of CDR1, CDR2 and CDR3 for the heavy and light chains) is determined which gives rise to a particular binding specificity, the set of CDR sequences can, in principle, be inserted into the appropriate positions within any other antibody framework regions linked with any antibody constant regions in order to provide a different antibody with the same antigen binding specificity.

In certain aspects, the disclosure relates to an antibody or antigen binding fragment that specifically recognizes or binds an isolated or recombinant polypeptide that comprises or consisting essentially of an amino acid sequence selected from: SEQ ID NOs. 12 to 17, SEQ ID NO. 31, SEQ ID NO. 33, a polypeptide comprising the amino acid sequence NPXT, or an equivalent each thereof. In some embodiments, the antibody or antigen binding fragment is not a polyclonal antibody. Non-limiting exemplary antibodies produced by the disclosed hybridomas are disclosed in Table 1. The hybridoma cell lines that produce monoclonal antibodies that specifically recognize and bind *Haemophilus influenzae* IhfA fragment A5 (SEQ ID NO. 13), IhfB fragment B4 (SEQ ID NO. 16), and IhfB fragment mB4 (SEQ ID NO. 17) were deposited with American Type Culture Collection (ATCC) under the listed Accession Numbers in Table 1 and pursuant to the provisions of the Budapest Treaty on Jul. 30, 2015; the respective hybridoma cell lines are listed in Table 1. Further non-limiting exemplary antibodies include those that specifically recognize and bind *Haemophilus influenzae* IhfA fragment A3 (SEQ ID NO. 12) or IhfB fragment B2 (SEQ ID NO. 15) produced by hybridoma cell lines IhfA3 NTHI 9B10.F2.H3, IhfB2 NTHI 7A4.E4.G4, and IhfB2 NTHI 7A4.E4.G11 (these hybridomas were deposited with American Type Culture Collection (ATCC) under the Accession Numbers listed in Table 1 and pursuant to the provisions of the Budapest Treaty on Aug. 1, 2016); and an antibody that specifically recognizes or binds a polypeptide comprising SEQ ID NO. 31, SEQ ID NO. 33, a polypeptide comprising the amino acid sequence NPXT, or an equivalent of each thereof

TABLE 1

| Specificity | SEQ ID NO. | ATCC Accession No. | Hybridoma Cell Line |
| --- | --- | --- | --- |
| IhfA frag. A5 | SEQ ID NO. 13 | PTA-122334 | IhfA5 NTHI 14G8.F5.G6 |
| IhfB frag. B4 | SEQ ID NO. 16 | PTA-122336 | IhfB4 NTHI 4E11.E5.G2 |
| IhfB frag. mB4 | SEQ ID NO. 17 | PTA-122335 | mIhfB4 NTHI 12E6.F8.D12.D5 |
| IhfA frag. A3 | SEQ ID NO. 12 | | IhfA3 NTHI 9B10.F2.H3 |
| IhfB frag. B2 | SEQ ID NO. 15 | | IhfB2 NTHI 7A4.E4.G4 IhfB2 NTHI 7A4.E4.G11 |

In one aspect, the present disclosure provides an isolated antibody that is at least 85% identical to an antibody selected from the group consisting of (i) the antibody produced by hybridoma cell line IhfA5 NTHI 14G8.F5.G6, (ii) the antibody produced by hybridoma cell line IhfB4 NTHI 4E11.E5.G2, and (iii) the antibody produced by hybridoma cell line mIhfB4 NTHI 12E6.F8.D12.D5.

In one aspect, the present disclosure provides an isolated antibody comprising the CDRs of (i) the antibody produced by hybridoma cell line IhfA5 NTHI 14G8.F5.G6, (ii) the antibody produced by hybridoma cell line IhfB4 NTHI 4E11.E5.G2, or (iii) the antibody produced by hybridoma cell line mIhfB4 NTHI 12E6.F8.D12.D5. In one aspect, the present disclosure provides an isolated antibody that has CDR that are at least 85% identical to (i) the antibody produced by hybridoma cell line IhfA5 NTHI 14G8.F5.G6, (ii) the antibody produced by hybridoma cell line IhfB4 NTHI 4E11.E5.G2, or (iii) the antibody produced by hybridoma cell line mIhfB4 NTHI 12E6.F8.D12.D5.

In some aspects of the antibodies provided herein, the HC variable domain sequence comprises the HC variable domain sequence of (i) the antibody produced by hybridoma cell line IhfA5 NTHI 14G8.F5.G6, (ii) the antibody produced by hybridoma cell line IhfB4 NTHI 4E11.E5.G2, or (iii) the antibody produced by hybridoma cell line MIhfB4 NTHI 12E6.F8.D12.D5; and/or the LC variable domain sequence comprises the LC variable domain sequence of (i) the antibody produced by hybridoma cell line IhfA5 NTHI 14G8.F5.G6, (ii) the antibody produced by hybridoma cell line IhfB4 NTHI 4E11.E5.G2, or (iii) the antibody produced by hybridoma cell line mIhfB4 NTHI 12E6.F8.D12.D5.

In some aspects of the antibodies provided herein, the HC variable domain sequence comprises a HC variable domain sequence at least 85% identical to a HC variable domain sequence of (i) the antibody produced by hybridoma cell line IhfA5 NTHI 14G8.F5.G6, (ii) the antibody produced by hybridoma cell line IhfB4 NTHI 4E11.E5.G2, and (iii) the antibody produced by hybridoma cell line mIhfB4 NTHI 12E6.F8.D12.D5; and/or the LC variable domain sequence comprises a LC variable domain sequence at least 85% identical to the of LC variable domain sequence (i) the antibody produced by hybridoma cell line IhfA5 NTHI 14G8.F5.G6, (ii) the antibody produced by hybridoma cell line IhfB4 NTHI 4E11.E5.G2, and (iii) the antibody produced by hybridoma cell line mIhfB4 NTHI 12E6.F8.D12.D5.

In one aspect, the present disclosure provides an isolated antibody comprising a heavy chain (HC) variable domain sequence and a light chain (LC) variable domain sequence, wherein the heavy chain and light chain immunoglobulin variable domain sequences form an antigen binding site that binds to an epitope of a DNABII protein.

In some embodiments, the heavy chain variable region comprises a CDRH1 sequence comprising, or alternatively consisting essentially of, or yet further consisting of, an amino acid sequence comprising the CDRH1 of any one of the following antibodies: (i) the antibody produced by hybridoma cell line IhfA5 NTHI 14G8.F5.G6, (ii) the antibody produced by hybridoma cell line IhfB4 NTHI 4E11.E5.G2, and (iii) the antibody produced by hybridoma cell line mIhfB4 NTHI 12E6.F8.D12.D5.

In some embodiments, the heavy chain variable region comprises a CDRH2 sequence comprising, or alternatively consisting essentially of, or yet further consisting of, an amino acid sequence comprising the CDRH2 of any one of the following antibodies: (i) the antibody produced by hybridoma cell line IhfA5 NTHI 14G8.F5.G6, (ii) the antibody produced by hybridoma cell line IhfB4 NTHI 4E11.E5.G2, and (iii) the antibody produced by hybridoma cell line mIhfB4 NTHI 12E6.F8.D12.D5.

In some embodiments, the heavy chain variable region comprises a CDRH3 sequence comprising, or alternatively consisting essentially of, or yet further consisting of, an amino acid sequence comprising the CDRH3 of any one of the following antibodies: (i) the antibody produced by hybridoma cell line IhfA5 NTHI 14G8.F5.G6, (ii) the antibody produced by hybridoma cell line IhfB4 NTHI 4E11.E5.G2, and (iii) the antibody produced by hybridoma cell line mIhfB4 NTHI 12E6.F8.D12.D5.

In some embodiments, the heavy chain variable region comprises, or alternatively consists essentially of, or yet further consists of, the amino acid sequence comprising the heavy chain variable region sequence of any one of the following antibodies: (i) the antibody produced by hybridoma cell line IhfA5 NTHI 14G8.F5.G6, (ii) the antibody produced by hybridoma cell line IhfB4 NTHI 4E11.E5.G2, and (iii) the antibody produced by hybridoma cell line mIhfB4 NTHI 12E6.F8.D12.D5.

In some embodiments, the light chain variable region comprises a CDRL1 sequence comprising, or alternatively consisting essentially of, or yet further consisting of, an amino acid sequence comprising the CDRL1 of any one of the following antibodies: (i) the antibody produced by hybridoma cell line IhfA5 NTHI 14G8.F5.G6, (ii) the antibody produced by hybridoma cell line IhfB4 NTHI 4E11.E5.G2, and (iii) the antibody produced by hybridoma cell line mIhfB4 NTHI 12E6.F8.D12.D5.

In some embodiments, the light chain variable region comprises a CDRL2 sequence comprising, or alternatively consisting essentially of, or yet further consisting of, an amino acid sequence comprising the CDRL2 of any one of the following antibodies: (i) the antibody produced by hybridoma cell line IhfA5 NTHI 14G8.F5.G6, (ii) the antibody produced by hybridoma cell line IhfB4 NTHI 4E11.E5.G2, and (iii) the antibody produced by hybridoma cell line mIhfB4 NTHI 12E6.F8.D12.D5.

In some embodiments, the light chain variable region comprises a CDRL3 sequence comprising, or alternatively consisting essentially of, or yet further consisting of, an amino acid sequence comprising the CDRL3 of any one of the following antibodies: (i) the antibody produced by hybridoma cell line IhfA5 NTHI 14G8.F5.G6, (ii) the antibody produced by hybridoma cell line IhfB4 NTHI 4E11.E5.G2, and (iii) the antibody produced by hybridoma cell line mIhfB4 NTHI 12E6.F8.D12.D5.

In some embodiments, the light chain variable region comprises, or alternatively consists essentially of, or yet further consists of, the polypeptide encoded by the polynucleotide sequence comprising the light chain variable region sequence of any one of the following antibodies: (i) the antibody produced by hybridoma cell line IhfA5 NTHI 14G8.F5.G6, (ii) the antibody produced by hybridoma cell line IhfB4 NTHI 4E11.E5.G2, and (iii) the antibody produced by hybridoma cell line mIhfB4 NTHI 12E6.F8.D12.D5.

In some embodiments, the heavy chain variable region of the antibody or fragment thereof comprises a CDRH1 sequence comprising, or alternatively consisting essentially of, or yet further consisting of, an amino acid sequence comprising FSLTSYS (SEQ ID NO. 58), such as but not limited to an amino acid sequence beginning with, ending with, or consisting essentially of FSLTSYSV (SEQ ID NO. 59), FSLTSYSVH (SEQ ID NO. 60), GFSLTSYS (SEQ ID NO. 61), or a biological equivalent each thereof.

In some embodiments, the heavy chain variable region of the antibody or fragment thereof comprises a CDRH1 sequence comprising, or alternatively consisting essentially of, or yet further consisting of, an amino acid sequence comprising FNIKDYY (SEQ ID NO. 110), such as but not limited to an amino acid sequence beginning with, ending with, or consisting essentially of FNIKDYYM (SEQ ID NO. 111), FNIKDYYMH (SEQ ID NO. 112), GFNIKDYY (SEQ ID NO. 113), or a biological equivalent each thereof.

In some embodiments, the heavy chain variable region of the antibody or a fragment thereof comprises a CDRH2 sequence comprising, or alternatively consisting essentially of, or yet further consisting of, an amino acid sequence comprising IWAGGST (SEQ ID NO. 62), such as but not limited to an amino acid sequence beginning with, ending with, or consisting essentially of VIWAGGST (SEQ ID NO. 63), GVIWAGGST (SEQ ID NO. 64), LGVIWAGGST (SEQ ID NO. 65), WLGVIWAGGST (SEQ ID NO. 66), IWAGGSTN (SEQ ID NO. 67), VIWAGGSTN (SEQ ID NO. 68), GVIWAGGSTN (SEQ ID NO. 69), LGVIWAGGSTN (SEQ ID NO. 70), WLGVIWAGGSTN (SEQ ID NO. 71), IWAGGSTNY (SEQ ID NO. 72), VIWAGGSTNY (SEQ ID NO. 73), GVIWAGGSTNY (SEQ ID NO. 74), LGVIWAGGSTNY (SEQ ID NO. 75), WLGVIWAGGSTNY (SEQ ID NO. 76), or a biological equivalent each thereof.

In some embodiments, the heavy chain variable region of the antibody or a fragment thereof comprises a CDRH2 sequence comprising, or alternatively consisting essentially of, or yet further consisting of, an amino acid sequence comprising IDPENDDT (SEQ ID NO. 114), such as but not limited to an amino acid sequence beginning with, ending with, or consisting essentially of WIDPENDDT (SEQ ID NO. 115), GWIDPENDDT (SEQ ID NO. 116), IGWIDPENDDT (SEQ ID NO. 117), WIGWIDPENDDT (SEQ ID NO. 118), IDPENDDTE (SEQ ID NO. 119), WIDPENDDTE (SEQ ID NO. 120), GWIDPENDDTE (SEQ ID NO. 121), IGWIDPENDDTE (SEQ ID NO. 122), WIGWIDPENDDTE (SEQ ID NO. 123), IDPENDDTEY (SEQ ID NO. 124), WIDPENDDTEY (SEQ ID NO. 125) GWIDPENDDTEY (SEQ ID NO. 126), IGWIDPENDDTEY (SEQ ID NO. 127), WIGWIDPENDDTEY (SEQ ID NO. 128), or a biological equivalent each thereof.

In some embodiments, the heavy chain variable region of the antibody or a fragment thereof comprises a CDRH3 sequence comprising, or alternatively consisting essentially of, or yet further consisting of, an amino acid sequence comprising REDS (SEQ ID NO. 77), such as but not limited to an amino acid sequence beginning with, ending with, or consisting essentially of AREDS (SEQ ID NO. 78) or a biological equivalent thereof.

In some embodiments, the heavy chain variable region of the antibody or a fragment thereof comprises a CDRH3 sequence comprising, or alternatively consisting essentially of, or yet further consisting of, an amino acid sequence comprising TELGAY (SEQ ID NO. 129) or a biological equivalent thereof.

In some embodiments, the heavy chain variable region of the antibody or a fragment thereof comprises, or alternatively consists essentially of, or yet further consists of, the polypeptide encoded by the below noted polynucleotide sequences: GAGGTGCAGCTGCAGGAGTCTGGACCTGGCCTGGTGACGCCCTCACAGAGCCTG TCCATGACTTGCACTGTCTCTGGGTTTTCATTAACCAGCTATAGTGTACACTGGGT TCGCCAGCCTCCAGGAAAGAGTCTGGAGTGGCTGGGAGTAATATGGGCTGGTGG AAGCACAAATTATAATTCGGCTCTCATGTCCAGACTGAGCATCAGCAAAGACAA CTCCAAGAGCCAAGTTTTCTTAAAAATGGACAGTCTGCAAACTGATGACACAGCC ATATACTACTGTGCCAGAGAGGACTCCTGGGGTCAAGGAACCTCAGTCACCGTCT CCTCA (SEQ ID NO. 50) or a biological equivalent thereof.

In some embodiments, the heavy chain variable region of the antibody or a fragment thereof comprises, or alternatively consists essentially of, or yet further consists of, the amino acid sequence: EVQLQESGPGLVTPSQSLSMTCTVSGFSLTSYSVHWVRQPPGKSLEWLGVIWAGGST NYNSALMSRLSISKDNSKSQVFLKMDSLQTDDTAIYYCAREDSWGQGTSVTVSS (SEQ ID NO. 51) or a biological equivalent thereof.

In some embodiments, the heavy chain variable region of the antibody or a fragment thereof comprises, or alternatively consists essentially of, or yet further consists of, the polypeptide encoded by the below noted polynucleotide sequences: GAGGTGCAGCTGCAGGAGTCTGGGGCAGAGCTTGTGAGGTCAGGGGCCTCAGTC AAGTTGTCCTGCACAGCTTCTGGCTTCAACATTAAAGACTACTATATGCACTGGG TGAAGCAGAGGCCTGAACAGGGCCTGGAGTGGATTGGATGGATTGATCCTGAAA ATGATGATACTGAATATGTCCCGAAGTTCCAGGGCAAGGCCAGTAT GACTGCAG ACACATCCTCCAACACAGCCTACCTGCAGCTCAGCAGCCTGACATCTGAGGACA CTGCCGTCTATTACTGTACAGAGCTCGGAGCTTACTGGGGCCAGGGGACTCTGGT C (SEQ ID NO. 52) or a biological equivalent thereof.

In some embodiments, the heavy chain variable region of the antibody or a fragment thereof comprises, or alternatively consists essentially of, or yet further consists of, the amino acid sequence: EVQLQESGAELVRSGASVKLSCTASGFNIKDYYMHWVKQRPEQGLEWIGWIDPEND DTEYVPKFQGKASMTADTSSNTAYLQLSSLTSEDTAVYYCTELGAYWGQGTLV (SEQ ID NO. 53) or a biological equivalent thereof.

In some embodiments, the light chain variable region of the antibody or a fragment thereof comprises a CDRL1 sequence comprising, or alternatively consisting essentially of, or yet further consisting of, an amino acid sequence comprising QNVGTN (SEQ ID NO. 79), such as but not limited to an amino acid sequence beginning with, ending with, or consisting essentially of QNVGTNV (SEQ ID NO. 80), QNVGTNVA (SEQ ID NO. 81), or a biological equivalent each thereof.

In some embodiments, the light chain variable region of the antibody or a fragment thereof comprises a CDRL1 sequence comprising, or alternatively consisting essentially of, or yet further consisting of, an amino acid sequence comprising QSLLDSNGKTY (SEQ ID NO. 130), such as but not limited to an amino acid sequence beginning with, ending with, or consisting essentially of QSLLDSNGKTYL (SEQ ID NO. 131), QSLLDSNGKTYLN (SEQ ID NO. 132), or a biological equivalent each thereof.

In some embodiments, the light chain variable region of the antibody or a fragment thereof comprises a CDRL2 sequence comprising, or alternatively consisting essentially of, or yet further consisting of, an amino acid sequence comprising SAS (SEQ ID NO. 82), such as but not limited to an amino acid sequence beginning with, ending with, or consisting essentially of YSAS (SEQ ID NO. 83), IYSAS (SEQ ID NO. 84), LIYSAS (SEQ ID NO. 85), ALIYSAS (SEQ ID NO. 86), SASY (SEQ ID NO. 87), YSASY (SEQ ID NO. 88), IYSASY (SEQ ID NO. 89), LIYSASY (SEQ ID NO. 90), ALIYSASY (SEQ ID NO. 91), SASYR (SEQ ID NO. 92), YSASYR (SEQ ID NO. 93), IYSASYR (SEQ ID NO. 94), LIYSASYR (SEQ ID NO. 95), ALIYSASYR (SEQ ID NO. 96), SASYRY (SEQ ID NO. 97), YSASYRY (SEQ ID NO. 98), IYSASYRY (SEQ ID NO. 99), LIYSASYRY (SEQ ID NO. 100), ALIYSASYRY (SEQ ID NO. 101), SASYRYS (SEQ ID NO. 102), YSASYRYS (SEQ ID NO. 103), IYSASYRYS (SEQ ID NO. 104), LIYSASYRYS (SEQ ID NO. 105), ALIYSASYRYS (SEQ ID NO. 106), or a biological equivalent each thereof.

In some embodiments, the light chain variable region of the antibody or a fragment thereof comprises a CDRL2 sequence comprising, or alternatively consisting essentially of, or yet further consisting of, an amino acid sequence comprising LVS (SEQ ID NO. 133), such as but not limited to an amino acid sequence beginning with, ending with, or consisting essentially of YLVS (SEQ ID NO. 134), IYLVS (SEQ ID NO. 135), LIYLVS (SEQ ID NO. 136), RLIYLVS (SEQ ID NO. 137), LVSK (SEQ ID NO. 138), YLVSK (SEQ ID NO. 139), IYLVSK (SEQ ID NO. 140), LIYLVSK (SEQ ID NO. 141), RLIYLVSK (SEQ ID NO. 142), LVSKL (SEQ ID NO. 143), YLVSKL (SEQ ID NO. 144), IYLVSKL (SEQ ID NO. 145), LIYLVSKL (SEQ ID NO. 146), RLIYLVSKL (SEQ ID NO. 147), LVSKLD (SEQ ID NO. 148), YLVSKLD (SEQ ID NO. 149), IYLVSKLD (SEQ ID NO. 150), LIYLVSKLD (SEQ ID NO. 151), RLIYLVSKLD (SEQ ID NO. 152), LVSKLDS (SEQ ID NO. 153), YLVSKLDS (SEQ ID NO. 154), IYLVSKLDS (SEQ ID NO. 155), LIYLVSKLDS (SEQ ID NO. 156), RLIYLVSKLDS (SEQ ID NO. 157), or a biological equivalent each thereof.

In some embodiments, the light chain variable region of the antibody or a fragment thereof comprises a CDRL3 sequence comprising, or alternatively consisting essentially of, or yet further consisting of, an amino acid sequence comprising QQYNSYP (SEQ ID NO. 108), such as but not limited to an amino acid sequence beginning with, ending with, or consisting essentially of QQYNSYPT (SEQ ID NO. 109), or a biological equivalent thereof.

In some embodiments, the light chain variable region of the antibody or a fragment thereof comprises a CDRL3 sequence comprising, or alternatively consisting essentially of, or yet further consisting of, an amino acid sequence comprising WQSTHFPH (SEQ ID NO. 158), such as but not limited to an amino acid sequence beginning with, ending with, or consisting essentially of WQSTHFPHT (SEQ ID NO. 159) or a biological equivalent thereof.

In some embodiments, the light chain variable region of the antibody or fragment thereof comprises, or alternatively consists essentially of, or yet further consists of, the polypeptide encoded by the polynucleotide sequence: GACATTGTGATGACCCAGTCTCAAAAATTCATGTCCACATCAGTAGGAGACAGGGTCAGCGTCACCTGCAAGGCCAGTCAGAATGTGGGTACTAATGTAGCCTGGTATCAACAGAAACCAGGGCAATCTCCTAAAGCACTGATTTACTCGGCATCCTACCGGTA CAGTGGAGTCCCTGATCGCTTCACAGGCAGTGGATCTGGGACAGATTTCACTCTCACCATCAGCAATGTGCAGTCTGAAGACTTGGCAGAGTATTTCTGTCAGCAATATAACAGCTATCCACGTTCGGAGGGGGGACCAAGTTGGAAATAAAA (SEQ ID NO. 54) or a biological equivalent thereof.

In some embodiments, the light chain variable region of the antibody or fragment thereof comprises, or alternatively consists essentially of, or yet further consists of, the amino acid sequence: DIVMTQSQKFMSTSVGDRVSVTCKASQNVGTNVAWYQQKPGQSPKALIYSASYRYSGVPDRFTGSGSGTDFTLTISNVQSEDLAEYFCQQYNSYPTFGGGTKLEIK (SEQ ID NO. 55) or a biological equivalent thereof.

In some embodiments, the light chain variable region comprises, or alternatively consists essentially of, or yet further consists of, the polypeptide encoded by the polynucleotide sequence: GATGTTGTGATGACCCAGATTCCACTCACTTTGTCGGTTACCATTGGACAACCAGCCTCCATCTCTTGCAAGTCAAGTCAGAGCCTCTTAGATAGTAATGGAAAGACATA TTTGAATTGGTTGTTTCAGAGGCCAGGCCAGTCTCAAAGCGCCTAATCTATCTGGTGTCTAAACTGGACTCTGGAGTCCCTGACAGGTTCACTGGCAGTGGATCAGGGA CAGATTTCACACTGAAAATCAGCAGAGTTGAGGCTGAGGATTTGGGAATTTATTATTGCTGGCAAAGTACACATTTTCCTCACACGTTCGGAGGGGGGACCAAGTTGGAA ATCAAA (SEQ ID NO. 56) or a biological equivalent thereof.

In some embodiments, the light chain variable region comprises, or alternatively consists essentially of, or yet further consists of, the amino acid sequence: DVVMTQIPLTLSVTIGQPASISCKSSQSLLDSNGKTYLNWLFQRPGQSPKRLIYLVSKLDSGVPDRFTGSGSGTDFTLKISRVEAEDLGIYYCWQSTHFPHTFGGGTKLEIK (SEQ ID NO. 57) or a biological equivalent thereof.

Exemplary antibodies comprising the disclosed CDR sequences and heavy and light chain variable sequences are disclosed in Table 6 and Table 7, respectively. Alternate CDR predictions may be made based on the heavy and/or light chain sequences—e.g., based on the Kabat, Clothia, AbM, or contact definitions of CDR specificity; details of these CDR prediction methods are known in the art (see, e.g., bioinf org.uk/abs/#cdrid) and/or commercially available. Those disclosed in Table 6 are the result of utilizing the CDR prediction algorithms provided by the Ofran Lab (Paratome available at ofranservices.biu.ac.il/site/services/paratome/index.html) and Green Mountain Antibodies' CDR prediction program.

TABLE 6

| ANTIBODY | CDRH1 | CDRH2 | CDRH3 | CDRL1 | CDRL2 | CDRL3 |
| --- | --- | --- | --- | --- | --- | --- |
| Ihf A5 | SEQ ID NO. 60 or SEQ ID NO. 61 | SEQ ID NO. 62 or SEQ ID NO. 76 | SEQ ID NO. 77 or SEQ ID NO. 78 | SEQ ID NO. 79 or SEQ ID NO. 81 | SEQ ID NO. 82 or SEQ ID NO. 106 | SEQ ID NO. 108 or SEQ ID NO. 109 |
| Ihf mB4 | SEQ ID NO. 112 or SEQ ID NO. 113 | SEQ ID NO. 114 or SEQ ID NO. 128 | SEQ ID NO. 129 | SEQ ID NO. 131 or SEQ ID NO. 132 | SEQ ID NO. 133 or SEQ ID NO. 157 | SEQ ID NO. 158 or SEQ ID NO. 159 |

TABLE 7

| ANTIBODY | Heavy Chain Variable Region | Light Chain Variable Region |
| --- | --- | --- |
| Ihf A5 | SEQ ID NO. 51 | SEQ ID NO. 55 |
| Ihf mB4 | SEQ ID NO. 53 | SEQ ID NO. 57 |

In one aspect, the present disclosure provides an isolated antibody that is at least 85%, or alternatively at least 90%, or alternatively at least 95%, identical to an antibody selected from the group consisting of Ihf A5, Ihf mB4, or a biological equivalent each thereof.

In one aspect, the present disclosure provides an isolated antibody comprising the CDRs of Ihf A5. In one aspect, the present disclosure provides an isolated antibody that is at least 85%, or alternatively at least 90%, or alternatively at least 95%, identical to Ihf A5 or a biological equivalent thereof.

In one aspect, the present disclosure provides an isolated antibody comprising the CDRs of Ihf mB4. In one aspect, the present disclosure provides an isolated antibody that is at least 85%, or alternatively at least 90%, or alternatively at least 95%, identical to Ihf mB4 or a biological equivalent thereof.

In some aspects of the antibodies provided herein, the HC variable domain sequence comprises a variable domain sequence of Ihf A5 and the LC variable domain sequence comprises a variable domain sequence of Ihf A5.

In some aspects of the antibodies provided herein, the HC variable domain sequence comprises a variable domain sequence of Ihf mB4 and the LC variable domain sequence comprises a variable domain sequence of Ihf mB4.

Further provided herein are isolated polynucleotides encoding the above noted polypeptides, vector and host cells containing same, as well as methods for recombinant production of the polypeptides using recombinant cell systems as known in the art and described herein.

In another aspect of the present technology, the isolated antibody includes one or more of the following characteristics:

(a) the light chain immunoglobulin variable domain sequence comprises one or more CDRs that are at least 85%, or alternatively at least 90%, or alternatively at least 95% identical to a CDR of a light chain variable domain of any of the disclosed light chain sequences;

(b) the heavy chain immunoglobulin variable domain sequence comprises one or more CDRs that are at least 85%, or alternatively at least 90%, or alternatively at least 95% identical to a CDR of a heavy chain variable domain of any of the disclosed heavy chain sequences;

(c) the light chain immunoglobulin variable domain sequence is at least 85%, or alternatively at least 90%, or alternatively at least 95% identical to a light chain variable domain of any of the disclosed light chain sequences;

(d) the HC immunoglobulin variable domain sequence is at least 85%, or alternatively at least 90%, or alternatively at least 95% identical to a heavy chain variable domain of any of the disclosed light chain sequences; and (e) the antibody binds an epitope that overlaps with an epitope bound by any of the disclosed sequences.

In some of the aspects of the antibodies provided herein, the antibody binds a DNABII protein with a dissociation constant ($K_D$) of less than $10^{-4}$M, $10^{-5}$M, $10^{-6}$ M, $10^{-7}$ M, $10^{-8}$ M, $10^{-9}$ M, $10^{-10}$ M, $10^{-11}$ M, or $10^{-12}$M. In some of the aspects of the antibodies provided herein, the antigen binding site specifically binds to a DNABII protein. In another aspect, the affinity of the antibody or antigen binding fragment is less than or about 1000 picoMole (pM), 900 pM, 800 pM, 700 pM, 600 pM, 500 pM, 400 pM, 300 pM, 200 pM, about 100 pM, 50 pM, 40 pM, 30 pM, 20 pM, 10 pM, 9 pM, and 8 pM.

In some of the aspects of the antibodies provided herein, the antibody is soluble Fab.

In some of the aspects of the antibodies provided herein, the HC and LC variable domain sequences are components of the same polypeptide chain. In some of the aspects of the antibodies provided herein, the HC and LC variable domain sequences are components of different polypeptide chains.

In some of the aspects of the antibodies provided herein, the antibody is a full-length antibody.

In some of the aspects of the antibodies provided herein, the antibody is a monoclonal antibody.

In some of the aspects of the antibodies provided herein, the antibody is chimeric or humanized.

In other aspects, the antibodies provided herein are diabodies.

In some of the aspects of the antibodies provided herein, the antibody is selected from the group consisting of Fab, F(ab)'2, Fab', scF$_v$, and F$_v$.

In some of the aspects of the antibodies provided herein, the antibody comprises an Fc domain. In some of the aspects of the antibodies provided herein, the antibody is a rabbit antibody. In some of the aspects of the antibodies provided herein, the antibody is a human or humanized antibody or is non-immunogenic in a human.

In some of the aspects of the antibodies provided herein, the antibody comprises a human antibody framework region (e.g., a humanized antibody). In some aspects of the antibodies provided herein, the antibody comprises an antibody framework region from a non-human species such as a simian, equine, feline, canine, bovine, porcine, caprine, or ovine. In some aspects of the antibodies provided herein, the antibody is a chimeric antibody. In any one or more of these aspects, the antibody may further comprise one or more of the CDR regions and/or the heavy and/or light chains disclosed herein.

In other aspects, one or more amino acid residues in a CDR of the antibodies provided herein are substituted with another amino acid. The substitution may be "conservative" in the sense of being a substitution within the same family of amino acids. The naturally occurring amino acids may be divided into the following four families and conservative substitutions will take place within those families.

1) Amino acids with basic side chains: lysine, arginine, histidine.

2) Amino acids with acidic side chains: aspartic acid, glutamic acid.

3) Amino acids with uncharged polar side chains: asparagine, glutamine, serine, threonine, tyrosine.

4) Amino acids with nonpolar side chains: glycine, alanine, valine, leucine, isoleucine, proline, phenylalanine, methionine, tryptophan, cysteine.

In another aspect, one or more amino acid residues are added to or deleted from one or more CDRs of an antibody. Such additions or deletions occur at the N or C termini of the CDR or at a position within the CDR.

By varying the amino acid sequence of the CDRs of an antibody by addition, deletion or substitution of amino acids, various effects such as increased binding affinity for the target antigen may be obtained.

It is to be appreciated that antibodies of the present disclosure comprising such varied CDR sequences still bind a DNABII protein with similar specificity and sensitivity profiles as the disclosed antibodies. This may be tested by way of the binding assays.

The constant regions of antibodies may also be varied. For example, antibodies may be provided with Fc regions of any isotype: IgA (IgA1, IgA2), IgD, IgE, IgG (IgG1, IgG2, IgG3, IgG4) or IgM. The constant regions of antibodies may further be adapted for specific therapeutic indications, e.g., according to the teachings of Irani et al. (2015) Molecular Immunol. 67:171-182.

As noted in Irani (2015), Fc engineering is important in developing therapeutic antibodies with potent and specific activity, therefore reducing both dosage and potential side-effects. An understanding of the differences across the IgG subclasses has been used in Fc engineering and studies have shown that introducing specific residues from one subclass to another can transform certain effector functions, while retaining others (Armour et al. (1999) Eur. J. Immunol. 29:2613-2624; Armour et al. (2003) Mol. Immunol. 40:585-593; Hessell et al. (2007) Nature 449:101-104; Redpath et al. (1998) Hum. Immunol. 59:720-727; Vafa et al. (2014) Methods (San Diego, Calif.) 65:114-126). These Fc engineering approaches are pertinent in the context of infectious diseases, as specific antibody effector function is often critical in efficient pathogen clearance.

The structural and functional properties of the IgG subclasses vary, as do their response profiles to different infectious diseases, and these differences can be utilized in the development of effective therapeutic antibodies (Carter (2006) Nat. Rev. Immunol. 6:343-357; Jefferis (2012) Arch. Biochem. Biophys. 526:159-166). Although the heavy chains share greater than 90% sequence identity across IgG sub classes (Rispens and Vidarsson (2014) Nimmerjahn, M. E. A. (Ed.), Chapter 9—Human IgG Subclasses. Academic Press. Boston. pp. 159-177), there are differences in surface exposed residues on the constant (CH1, CH2 and CH3) domains, as well as substantial variation within the hinge region. It is the hinge structure that confers many of the unique properties to each IgG subclass such as stability, flexibility and distances spanned by the two Fabs and the attendant Fc (Liu and May (2012) mAbs 4:17-23; Roux et al. (1997) J. Immunol. (Baltimore, Md.: 1950) 159:3372-3382; Tian et al. (2014) Pharm. Sci. 103:1701-1710). Importantly, some areas of the Fc and the hinge that differ between IgG subclasses clearly overlap with residues known to be involved with binding to both activating and inhibitory Fcγ receptors (FcγR), the neonatal receptor for IgG (FcRn) and complement component C1q. The occurrence of key amino acid differences within the binding sites of these effector molecules helps explain the observed differences in the effector properties of the IgG subclasses. This structural and molecular information is important when choosing a subclass backbone for a therapeutic antibody or introducing changes in key amino acids to tailor antibodies for a specific purpose.

Among the licensed antibodies majority are IgG1, probably due to its potent effector functions. IgG2 or IgG4 has been used when a lack of specific cellular activity is desirable. There are no approved IgG3 therapeutic antibodies, with suggestions that this may be because of (i) an increased likelihood for proteolysis due to an extensive hinge region (Carter (2006), (ii) the many IgG3 allotypes across populations, (iii) IgG3 cannot be purified with protein A, or (iv) the reduced serum half-life of IgG3 compared to other subclasses, in spite of its higher antibody-dependent cellular cytotoxicity (ADCC). IgG1 is the predominant class antibody in therapeutic antibodies approved or in review in the EU or the USA, as well as therapeutic antibodies being generated to infectious diseases caused particularly by gram positive and negative bacteria.

Non-limiting examples of constant region sequences include:

Human IgD constant region, Uniprot: P01880 SEQ ID NO. 34:

APTKAPDVFPIISGCRHPKDNSPVVLACLITGYHPTSVTVTWYMGTQSQP

QRTFPEIQRRDSYYMTSSQLSTPLQQWRQGEYKCVVQHTASKSKKEIFRW

PESPKAQASSVPTAQPQAEGSLAKATTAPATTRNTGRGGEEKKKEKEKEE

QEERETKTPECPSHTQPLGVYLLTPAVQDLWLRDKATFTCFVVGSDLKDA

HLTWEVAGKVPTGGVEEGLLERHSNGSQSQHSRLTLPRSLWNAGTSVTCT

LNHPSLPPQRLMALREPAAQAPVKLSLNLLASSDPPEAASWLLCEVSGFS

PPNILLMWLEDQREVNTSGFAPARPPPQPGSTTFWAWSVLRVPAPPSPQP

ATYTCVVSHEDSRTLLNASRSLEVSYVTDHGPMK.

Human IgG1 constant region, Uniprot: P01857 SEQ ID NO. 35:

ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK.

Human IgG2 constant region, Uniprot: P01859 SEQ ID NO. 36:

ASTKGPSVFPLAPCSRSTSESTAALGCLVKDYFPEPVTVSWNSGALTSGV

HTFPAVLQSSGLYSLSSVVTVPSSNFGTQTYTCNVDHKPSNTKVDKTVER

KCCVECPPCPAPPVAGPSVFLFPPKPKDTLMISRTPEVTCVVVDVSHEDP

EVQFNWYVDGVEVHNAKTKPREEQFNSTFRVVSVLTVVHQDWLNGKEYKC

KVSNKGLPAPIEKTISKTKGQPREPQVYTLPPSREEMTKNQVSLTCLVKG

FYPSDISVEWESNGQPENNYKTTPPMLDSDGSFFLYSKLTVDKSRWQQGN

VFSCSVMHEALHNHYTQKSLSLSPGK.

Human IgG3 constant region, Uniprot: P01860 SEQ ID NO. 37:

ASTKGPSVFPLAPCSRSTSGGTAALGCLVKDYFPEPVTVSWNSGALTSGV

HTFPAVLQSSGLYSLSSVVTVPSSSLGTQTYTCNVNHKPSNTKVDKRVEL

KTPLGDTTHTCPRCPEPKSCDTPPPCPRCPEPKSCDTPPPCPRCPEPKSC

DTPPPCPRCPAPELLGGPSVFLFPPKPKDTLMISRTPEVTCVVVDVSHED

PEVQFKWYVDGVEVHNAKTKPREEQYNSTFRVVSVLTVLHQDWLNGKEYK

CKVSNKALPAPIEKTISKTKGQPREPQVYTLPPSREEMTKNQVSLTCLVK

GFYPSDIAVEWESSGQPENNYNTTPPMLDSDGSFFLYSKLTVDKSRWQQG

NIFSCSVMHEALHNRFTQKSLSLSPGK.

Human IgM constant region, Uniprot: P01871 SEQ ID NO. 38:

GSASAPTLFPLVSCENSPSDTSSVAVGCLAQDFLPDSITLSWKYKNNSDI

SSTRGFPSVLRGGKYAATSQVLLPSKDVMQGTDEHVVCKVQHPNGNKEKN

VPLPVIAELPPKVSVFVPPRDGFFGNPRKSKLICQATGFSPRQIQVSWLR

EGKQVGSGVTTDQVQAEAKESGPTTYKVTSTLTIKESDWLGQSMFTCRVD

HRGLTFQQNASSMCVPDQDTAIRVFAIPPSFASIFLTKSTKLTCLVTDLT

TYDSVTISWTRQNGEAVKTHTNISESHPNATFSAVGEASICEDDWNSGER

FTCTVTHTDLPSPLKQTISRPKGVALHRPDVYLLPPAREQLNLRESATIT

CLVTGFSPADVFVQWMQRGQPLSPEKYVTSAPMPEPQAPGRYFAHSILTV

SEEEWNTGETYTCVAHEALPNRVTERTVDKSTGKPTLYNVSLVMSDTAGT

CY.

Human IgG4 constant region, Uniprot: P01861 SEQ ID NO. 39:

ASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVES

KYGPPCPSCPAPEFLGGPSVFLFPPKPKDTLMISRTPEVTCVVVDVSQED

PEVQFNWYVDGVEVHNAKTKPREEQFNSTYRVVSVLTVLHQDWLNGKEYK

-continued

CKVSNKGLPSSIEKTISKAKGQPREPQVYTLPPSQEEMTKNQVSLTCLVK

GFYPSDIAVEWESNGQPENNYKTTPPVLDSDGSFFLYSRLTVDKSRWQEG

NVFSCSVMHEALHNHYTQKSLSLSLGK.

Human IgA1 constant region, Uniprot: P01876 SEQ ID NO. 40:

ASPTSPKVFPLSLCSTQPDGNVVIACLVQGFFPQEPLSVTWSESGQGVTA

RNFPPSQDASGDLYTTSSQLTLPATQCLAGKSVTCHVKHYTNPSQDVTVP

CPVPSTPPTPSPSTPPTPSPSCCHPRLSLHRPALEDLLLGSEANLTCTLT

GLRDASGVTFTWTPSSGKSAVQGPPERDLCGCYSVSSVLPGCAEPWNHGK

TFTCTAAYPESKTPLTATLSKSGNTFRPEVHLLPPPSEELALNELVTLTC

LARGFSPKDVLVRWLQGSQELPREKYLTWASRQEPSQGTTTFAVTSILRV

AAEDWKKGDTFSCMVGHEALPLAFTQKTIDRLAGKPTHVNVSVVMAEVDG

TCY.

Human IgA2 constant region, Uniprot: P01877 SEQ ID NO. 41:

ASPTSPKVFPLSLDSTPQDGNVVVACLVQGFFPQEPLSVTWSESGQNVTA

RNFPPSQDASGDLYTTSSQLTLPATQCPDGKSVTCHVKHYTNPSQDVTVP

CPVPPPPPCCHPRLSLHRPALEDLLLGSEANLTCTLTGLRDASGATFTWT

PSSGKSAVQGPPERDLCGCYSVSSVLPGCAQPWNHGETFTCTAAHPELKT

PLTANITKSGNTFRPEVHLLPPPSEELALNELVTLTCLARGFSPKDVLVR

WLQGSQELPREKYLTWASRQEPSQGTTTFAVTSILRVAAEDWKKGDTFSC

MVGHEALPLAFTQKTIDRMAGKPTHVNVSVVMAEVDGTCY.

Human Ig kappa constant region, Uniprot: P01834 SEQ ID NO. 42:

TVAAPSVFIFPPSDEQLKSGTASVVCLLNNFYPREAKVQWKVDNALQSGN

SQESVTEQDSKDSTYSLSSTLTLSKADYEKHKVYACEVTHQGLSSPVTKS

FNRGEC.

In some embodiments, the antibodies are specific to the IhfA fragment A5 (SEQ ID NO. 13) and comprise constant regions derived from IgM or IgG, such as but not limited to IgG2 (in certain aspects IgG2a). In instances where the antibody is a monoclonal antibody, exemplary isotypes include, but are not limited to, IgG such as IgG1, IgG2, IgG3, and IgG4, IgM, IgA such as IgA1 and IgA2, IgD, and IgE and can preferably include IgG and IgM. The isotype and subclass of the monoclonal antibody can be determined by, for example, an Ouchterlony test, ELISA, or radio immunoassay (hereinafter, referred to as "RIA"). A commercially available kit for identification (e.g., Mouse Typer Kit; Bio-Rad Laboratories, Inc., and RAT MONOCLONAL ANTIBODY ISOTYPING TEST KIT: AbD Serotec) may be used.

In some embodiments, the antibodies are specific to the IhfB fragment mB4 (SEQ ID NO. 17) and comprise constant regions derived from IgG, such as but not limited to IgG1.

In some aspects, the antibodies comprise a heavy chain constant region that is at least 80% identical to the heavy chain constant region sequence of any one of the following antibodies: (i) the antibody produced by hybridoma cell line IhfA5 NTHI 14G8.F5.G6, (ii) the antibody produced by hybridoma cell line IhfB4 NTHI 4E11.E5.G2, and (iii) the antibody produced by hybridoma cell line mIhfB4 NTHI 12E6.F8.D12.D5.

In some aspects, the antibodies comprise a light chain constant region that is at least 80% identical to the light chain constant region sequence of any one of the following antibodies: (i) the antibody produced by hybridoma cell line IhfA5 NTHI 14G8.F5.G6, (ii) the antibody produced by hybridoma cell line IhfB4 NTHI 4E11.E5.G2, and (iii) the antibody produced by hybridoma cell line mIhfB4 NTHI 12E6.F8.D12.D5.

In some aspects of the antibodies provided herein, the antibody binds to the epitope bound by DNABII antibodies.

In some aspects of the antibodies provided herein, the antibody contains structural modifications to facilitate rapid binding and cell uptake and/or slow release. In some aspects, the DNABII antibody contains a deletion in the CH2 constant heavy chain region of the antibody to facilitate rapid binding and cell uptake and/or slow release. In some aspects, a Fab fragment is used to facilitate rapid binding and cell uptake and/or slow release. In some aspects, a F(ab)'2 fragment is used to facilitate rapid binding and cell uptake and/or slow release.

The antibodies, fragments, and equivalents thereof can be combined with a carrier, e.g., a pharmaceutically acceptable carrier or other agents to provide a formulation for use and/or storage.

Chimeric, humanized or primatized antibodies of the present disclosure can be prepared based on the sequence of a reference monoclonal antibody prepared using standard molecular biology techniques. DNA encoding the heavy and light chain immunoglobulins can be obtained from the hybridoma of interest and engineered to contain non-reference (e.g., human) immunoglobulin sequences using standard molecular biology techniques. For example, to create a chimeric antibody, the murine variable regions can be linked to human constant regions using methods known in the art (U.S. Pat. No. 4,816,567). To create a humanized antibody, the murine CDR regions can be inserted into a human framework using methods known in the art (U.S. Pat. Nos. 5,225,539 and 5,530,101; 5,585,089; 5,693,762; and 6,180, 370). Similarly, to create a primatized antibody the murine CDR regions can be inserted into a primate framework using methods known in the art (PCT International Pat. Application Publication Nos. WO 93/02108 and WO 99/55369).

Techniques for making partially to fully human antibodies are known in the art and any such techniques can be used. According to one embodiment, fully human antibody sequences are made in a transgenic mouse which has been engineered to express human heavy and light chain antibody genes. Multiple strains of such transgenic mice have been made which can produce different classes of antibodies. B cells from transgenic mice which are producing a desirable antibody can be fused to make hybridoma cell lines for continuous production of the desired antibody. (See, for example, Russel et al. (2000) Infection and Immunity April 2000:1820-1826; Gallo et al. (2000) European J. of Immun. 30:534-540; Green (1999) J. of Immun. Methods 231:11-23; Yang et al. (1999A) J. of Leukocyte Biology 66:401-410; Yang (1999B) Cancer Research 59(6):1236-1243; Jakobovits (1998) Advanced Drug Reviews 31:33-42; Green and Jakobovits (1998) J. Exp. Med. 188(3):483-495; Jakobovits (1998) Exp. Opin. Invest. Drugs 7(4):607-614; Tsuda et al. (1997) Genomics 42:413-421; Sherman-Gold (1997)

Genetic Engineering News 17(14); Mendez et al. (1997) Nature Genetics 15:146-156; Jakobovits (1996) Weir's Handbook of Experimental Immunology, The Integrated Immune System Vol. IV, 194.1-194.7; Jakobovits (1995) Current Opinion in Biotechnology 6:561-566; Mendez et al. (1995) Genomics 26:294-307; Jakobovits (1994) Current Biology 4(8):761-763; Arbones et al. (1994) Immunity 1(4):247-260; Jakobovits (1993) Nature 362(6417):255-258; Jakobovits et al. (1993) Proc. Natl. Acad. Sci. USA 90(6):2551-2555; and U.S. Pat. No. 6,075,181.)

The antibodies disclosed herein also can be modified to create chimeric antibodies. Chimeric antibodies are those in which the various domains of the antibodies' heavy and light chains are coded for by DNA from more than one species. See, e.g., U.S. Pat. No. 4,816,567.

Alternatively, the antibodies disclosed herein can also be modified to create veneered antibodies. Veneered antibodies are those in which the exterior amino acid residues of the antibody of one species are judiciously replaced or "veneered" with those of a second species so that the antibodies of the first species will not be immunogenic in the second species thereby reducing the immunogenicity of the antibody. Since the antigenicity of a protein is primarily dependent on the nature of its surface, the immunogenicity of an antibody could be reduced by replacing the exposed residues which differ from those usually found in another mammalian species antibodies. This judicious replacement of exterior residues should have little, or no, effect on the interior domains, or on the interdomain contacts. Thus, ligand binding properties should be unaffected as a consequence of alterations which are limited to the variable region framework residues. The process is referred to as "veneering" since only the outer surface or skin of the antibody is altered, the supporting residues remain undisturbed.

The procedure for "veneering" makes use of the available sequence data for human antibody variable domains compiled by Kabat et al. (1987) Sequences of Proteins of Immunological interest, 4th ed., Bethesda, Md., National Institutes of Health, updates to this database, and other accessible U.S. and foreign databases (both nucleic acid and protein). Non-limiting examples of the methods used to generate veneered antibodies include EP 519596; U.S. Pat. No. 6,797,492; and described in Padlan et al. (1991) Mol. Immunol. 28(4-5):489-498.

The term "antibody derivative" also includes "diabodies" which are small antibody fragments with two antigen-binding sites, wherein fragments comprise a heavy chain variable domain (VH) connected to a light chain variable domain (VL) in the same polypeptide chain. (See for example, EP 404,097; WO 93/11161; and Hollinger et al. (1993) Proc. Natl. Acad. Sci. USA 90:6444-6448.) By using a linker that is too short to allow pairing between the two domains on the same chain, the domains are forced to pair with the complementary domains of another chain and create two antigen-binding sites. (See also, U.S. Pat. No. 6,632,926 to Chen et al., which discloses antibody variants that have one or more amino acids inserted into a hypervariable region of the parent antibody and a binding affinity for a target antigen which is at least about two fold stronger than the binding affinity of the parent antibody for the antigen). A non-limiting exemplary method for generating diabodies employs an expression vector encoding the diabody and transfecting it into a bacterial host. Methods such as immobilized metal ion affinity chromatography, culture and ELISA, and other known purification techniques may be used to isolate the diabodies from the resulting bacterial periplasm. These isolate diabodies may then be characterized by, for example, immunoblotting or gel filtration. Additional methods for producing diabodies are known in the art and include, but are not limited to, those disclosed in Takemura et al. (2000) Protein Eng. 13(8):583-588 and Methods in Molecular Biology (2012) 907:713-727.

In some embodiments, the antibody derivative is a diabody, wherein the heavy chain variable domain (VH) and the light chain variable domain (VL) are the same as any one of the antibodies disclosed herein above. In some embodiments, the diabody is specific to IhfA fragment A5 (SEQ ID NO. 13). In some embodiments, the diabody is specific to IhfB fragment mB4 (SEQ ID NO. 17).

The term "antibody derivative" further includes engineered antibody molecules, fragments and single domains such as scFv, dAbs, nanobodies, minibodies, Unibodies, and Affibodies & Hudson (2005) Nature Biotech 23(9):1126-36; U.S. Pat. Application Publication No. 2006/0211088; PCT International Pat. Application Publication No. WO 2007/059782; U.S. Pat. No. 5,831,012).

The term "antibody derivative" further includes "linear antibodies". The procedure for making linear antibodies is known in the art and described in Zapata et al. (1995) Protein Eng. 8(10):1057-1062. Briefly, these antibodies comprise a pair of tandem Ed segments ($V_H$-$C_H$1-VH-$C_H$1) which form a pair of antigen binding regions. Linear antibodies can be bispecific or monospecific.

The antibodies disclosed herein can be recovered and purified from recombinant cell cultures by known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be used for purification.

Antibodies of the present disclosure include naturally purified products, products of chemical synthetic procedures, and products produced by recombinant techniques from a eukaryotic host, including, for example, yeast, higher plant, insect and mammalian cells, or alternatively from a prokaryotic host as described above. A number of antibody production systems are described in Birch & Radner (2006) Adv. Drug Delivery Rev. 58:671-685.

If an antibody being tested binds with protein or polypeptide, then the antibody being tested and the antibodies provided by this disclosure are equivalent. It also is possible to determine without undue experimentation, whether an antibody has the same specificity as the antibody disclosed herein by determining whether the antibody being tested prevents an antibody disclosed herein from binding the protein or polypeptide with which the antibody is normally reactive. If the antibody being tested competes with the antibody disclosed herein as shown by a decrease in binding by the monoclonal antibody disclosed herein, then it is likely that the two antibodies bind to the same or a closely related epitope. Alternatively, one can pre-incubate the antibody disclosed herein with a protein with which it is normally reactive, and determine if the antibody being tested is inhibited in its ability to bind the antigen. If the antibody being tested is inhibited then, in all likelihood, it has the same, or a closely related, epitopic specificity as the antibody disclosed herein.

The term "antibody" also is intended to include antibodies of all immunoglobulin isotypes and subclasses. Particular isotypes of a monoclonal antibody can be prepared either directly by selecting from an initial fusion, or prepared secondarily, from a parental hybridoma secreting a monoclonal antibody of different isotype by using the sib selection technique to isolate class switch variants using the procedure described in Steplewski et al. (1985) Proc. Natl. Acad. Sci. USA 82:8653 or Spira et al. (1984) J. Immunol. Methods 74:307. Alternatively, recombinant DNA techniques may be used.

The isolation of other monoclonal antibodies with the specificity of the monoclonal antibodies described herein can also be accomplished by one of ordinary skill in the art by producing anti-idiotypic antibodies. Herlyn et al. (1986) Science 232:100. An anti-idiotypic antibody is an antibody which recognizes unique determinants present on the monoclonal antibody of interest.

In some aspects disclosed herein, it will be useful to detectably or therapeutically label the antibody. Suitable labels are described supra. Methods for conjugating antibodies to these agents are known in the art. For the purpose of illustration only, antibodies can be labeled with a detectable moiety such as a radioactive atom, a chromophore, a fluorophore, or the like. Such labeled antibodies can be used for diagnostic techniques, either in vivo, or in an isolated test sample.

The coupling of antibodies to low molecular weight haptens can increase the sensitivity of the antibody in an assay. The haptens can then be specifically detected by means of a second reaction. For example, it is common to use haptens such as biotin, which reacts avidin, or dinitrophenol, pyridoxal, and fluorescein, which can react with specific anti-hapten antibodies. See, Harlow and Lane (1988) supra.

The variable region of the antibodies of the present disclosure can be modified by mutating amino acid residues within the VH and/or VL CDR 1, CDR 2 and/or CDR 3 regions to improve one or more binding properties (e.g., affinity) of the antibody. Mutations may be introduced by site-directed mutagenesis or PCR-mediated mutagenesis and the effect on antibody binding, or other functional property of interest, can be evaluated in appropriate in vitro or in vivo assays. In certain embodiments, conservative modifications are introduced and typically no more than one, two, three, four or five residues within a CDR region are altered. The mutations may be amino acid substitutions, additions or deletions.

Framework modifications can be made to the antibodies to decrease immunogenicity, for example, by "backmutating" one or more framework residues to the corresponding germline sequence.

In addition, the antibodies disclosed herein may be engineered to include modifications within the Fc region to alter one or more functional properties of the antibody, such as serum half-fife, complement fixation, Fc receptor binding, and/or antigen-dependent cellular cytotoxicity. Such modifications include, but are not limited to, alterations of the number of cysteine residues in the hinge region to facilitate assembly of the light and heavy chains or to increase or decrease the stability of the antibody (U.S. Pat. No. 5,677, 425) and amino acid mutations in the Fc hinge region to decrease die biological half-life of the antibody (U.S. Pat. No. 6,165,745).

Additionally, the antibodies disclosed herein may be chemically modified. Glycosylation of an antibody can be altered, for example, by modifying one or more sites of glycosylation within the antibody sequence to increase the affinity of the antibody for antigen (U.S. Pat. Nos. 5,714,350 and 6,350,861). Alternatively, to increase antibody-dependent cell-mediated cytotoxicity, a hypofucosylated antibody having reduced amounts of fucosyl residues or an antibody having increased bisecting GlcNac structures can be obtained by expressing the antibody in a host cell with altered glycosylation mechanism (Shields et al. (2002) J. Biol. Chem. 277:26733-26740; Umana et al. (1999) Nat. Biotech. 17:176-180).

The antibodies disclosed herein can be pegylated to increase biological half-life by reacting the antibody or fragment thereof with polyethylene glycol (PEG) or a reactive ester or aldehyde derivative of PEG, under conditions in which one or more PEG groups become attached to the antibody or antibody fragment. Antibody pegylation may be carried out by an acylation reaction or an alkylation reaction with a reactive PEG molecule (or an analogous reactive water soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. The antibody to be pegylated can be an aglycosylated antibody. Methods for pegylating proteins are known in the art and can be applied to the antibodies disclosed herein (EP 0154316 and EP 0401384).

Additionally, antibodies may be chemically modified by conjugating or fusing the antigen-binding region of the antibody to serum protein, such as human serum albumin, to increase half-life of the resulting molecule. Such approach is for example described in EP 0322094 and EP 0486525.

The antibodies or fragments thereof of the present disclosure may be conjugated to a diagnostic agent and used diagnostically, for example, to monitor the development or progression of a disease and determine the efficacy of a given treatment regimen. Examples of diagnostic agents include enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody or fragment thereof, or indirectly, through a linker using techniques known in the art. Examples of suitable enzymes include horseradish peroxidase, alkaline phosphatase, beta-galactosidase, or acetylcholinesterase. Examples of suitable prosthetic group complexes include streptavidin/biotin and avidin/biotin. Examples of suitable fluorescent materials include umbelliferone, fluorescein, fluorescein isothiocyanate, rhodamine, dichlorotriazinylamine fluorescein, dansyl chloride or phycoerythrin. An example of a luminescent material includes luminol. Examples of bioluminescent materials include luciferase, luciferin, and aequorin. Examples of suitable radioactive material include $^{125}$I, $^{131}$I, Indium-111, Lutetium-171, Bismuth-212, Bismuth-213, Astatine-211, Copper-62, Copper-64, Copper-67, Yttrium-90, Iodine-125, Iodine-131, Phosphorus-32, Phosphorus-33, Scandium-47, Silver-111, Gallium-67, Praseodymium-142, Samarium-153, Terbium-161, Dysprosium-166, Holmium-166, Rhenium-186, Rhenium-188, Rhenium-189, Lead-212, Radium-223, Actinium-225, Iron-59, Selenium-75, Arsenic-77, Strontium-89, Molybdenum-99, Rhodium-1105, Palladium-109, Praseodymium-143, Promethium-149, Erbium-169, Iridium-194, Gold-198, Gold-199, and Lead-211. Monoclonal antibodies may be indirectly conjugated with radiometal ions through the use of bifunctional chelating agents that are covalently linked to the antibodies. Chelating agents may be attached through amities (Meares et al. (1984) Anal. Biochem. 142:68-78); sulfhydryl groups (Koyama 1994 Chem. Abstr. 120: 217262t) of amino acid residues and carbohydrate groups (Rodwell et al. (1986) PNAS USA 83:2632-2636; Quadri et al. (1993) Nucl. Med. Biol. 20:559-570).

Further, the antibodies or fragments thereof of the present disclosure may be conjugated to a therapeutic agent. Suitable therapeutic agents include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin, antimetabolites (such as methotrexate, 6-mercaptopurine, 6-thioguanine, cytarabine, fludarabin, 5-fluorouracil, decarbazine, hydroxyurea, asparaginase, gemcitabinc, cladribine), alkylating agents (such as mechlorethamine, thioepa, chloramhucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin), antibiotics (such as dactinomycin (formerly actinomycin), bleomycin, daunorubicin (formerly daunomycin), doxorubicin, idarubicin, mithramycin, mitomycin, mitoxantrone, plicamycin, anthramycin (AMC), diphtheria toxin and related molecules (such as diphtheria A chain and active fragments thereof and hybrid molecules), ricin toxin (such as ricin A or a deglycosylated ricin A chain toxin), cholera toxin, a Shiga-like toxin (SLT-I, SLT-II, SLT-IIV), LT toxin, C3 toxin, Shiga toxin, pertussis toxin, tetanus toxin, soybean Bowman-Birk protease inhibitor, *Pseudomonas* exotoxin, alorin, saporin, modeccin, gelanin, abrin A chain, modeccin A chain, alpha-sarcin, *Aleurites fordii* proteins, dianthin proteins, *Phytolacca americana* proteins (PAPI, PAPII, and PAP-S), *Momordica charantia* inhibitor, curcin, crotin, *Sapaonaria officinalis* inhibitor, gelonin, mitogellin, restrietocin, phenomycin, enomycin toxins mixed toxins, and antimicrobial or host defense peptides (e.g., specifically targeted antimicrobial peptides (STAMPs)).

Additional suitable conjugated molecules include ribonuclease (RNase), DNase, an antisense nucleic acid, an inhibitory RNA molecule such as a siRNA molecule, an immunostimulatory nucleic acid, aptamers, ribozymes, triplex forming molecules, and external guide sequences. Aptamers are small nucleic acids ranging from 15-50 bases in length that fold into defined secondary and tertiary structures, such as stem-loops or G-quartets, and can bind small molecules, such as ATP (U.S. Pat. No. 5,631,146) and theophiline (U.S. Pat. No. 5,580,737), as well as large molecules, such as reverse transcriptase (U.S. Pat. No. 5,786,462) and thrombin (U.S. Pat. No. 5,543,293). Ribozymes are nucleic acid molecules that are capable of catalyzing a chemical reaction, either intra-molecularly or inter-molecularly. Ribozymes typically cleave nucleic acid substrates through recognition and binding of the target substrate with subsequent cleavage. Triplex forming function nucleic acid molecules can interact with double-stranded or single-stranded nucleic acid by forming a triplex, in which three strands of DNA form a complex dependent on both Watson-Crick and Hoogsteen base-pairing. Triplex molecules can bind target regions with high affinity and specificity. Suitable conjugated molecules may further include any protein that binds to DNA provided that it does not create or stabilize biofilm architecture; it is envisioned that at least a subset of such proteins may facilitate the kinetics of binding for the interfering agents disclosed herein.

The functional nucleic acid molecules may act as effectors, inhibitors, modulators, and stimulators of a specific activity possessed by a target molecule, or the functional nucleic acid molecules may possess a de novo activity independent of any other molecules.

The therapeutic agents can be linked to the antibody directly or indirectly, using any of a large number of available methods. For example, an agent can be attached at the hinge region of the reduced antibody component via disulfide bond formation, using cross-linkers such as N-succinyl 3-(2-pyridyldithio) proprionate (SPDP), or via a carbohydrate moiety in the Fc region of the antibody (Yu et al. (1994) Int. J. Cancer 56: 244; Upeslacis et al., "Modification of Antibodies by Chemical Methods," in Monoclonal antibodies: principles and applications, Birch et al. (eds.), pages 187-230 (Wiley-Liss, Inc. 1995); Price, "Production and Characterization of Synthetic Peptide-Derived Antibodies," in Monoclonal antibodies: Production, Engineering and Clinical Application, Ritter et al. (eds.), pages 60-84 (Cambridge University Press 1995)).

Techniques for conjugating therapeutic agents to antibodies are well known (Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al, (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody in Cancer Therapy", in Monoclonal Antibodies For Cancer Detection And Therapy, Baldwin et al. (eds.), pp. 303-16 (Academic Press 1985), and Thorpe et al. (1982) Immunol. Rev. 62:119-58).

The antibodies disclosed herein or antigen-binding regions thereof can be linked to another functional molecule such as another antibody or ligand for a receptor to generate a bi-specific or multi-specific molecule that binds to at least two or more different binding sites or target molecules. Linking of the antibody to one or more other binding molecules, such as another antibody, antibody fragment, peptide or binding mimetic, can be done, for example, by chemical coupling, genetic fusion, or non-covalent association. Multi-specific molecules can further include a third binding specificity, in addition to the first and second target epitope.

Bi-specific and multi-specific molecules can be prepared using methods known in the art. For example, each binding unit of the hi-specific molecule can be generated separately and then conjugated to one another. When the binding molecules are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitroberizoic acid) (DTNB), o-phenylenedimaleimide (oPDM), N-succinimidyl-3-(2-pyridyldithio) propionate (SPDP), and sulfosuccinimidyl 4-(N-maleimidomethyl)cyclohaxane-I-carboxylate (sulfo-SMCC) (Karpovsky et al. (1984) J. Exp. Med. 160:1686; Liu et al. (1985) Proc. Natl. Acad. Sci. USA 82:8648). When the binding molecules are antibodies, they can be conjugated by sulfhydryl bonding of the C-terminus hinge regions of the two heavy chains.

The antibodies disclosed herein may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

The antibodies also can be bound to many different carriers. Thus, this disclosure also provides compositions containing the antibodies and another substance, active or inert. Examples of well-known carriers include glass, polystyrene, polypropylene, polyethylene, dextran, nylon, amylase, natural and modified cellulose, polyacrylamide, agarose, and magnetite. The nature of the carrier can be either soluble or insoluble for purposes disclosed herein. Those skilled in the art will know of other suitable carriers for binding monoclonal antibodies, or will be able to ascertain such, using routine experimentation.

Provided herein are compositions and methods of use involving the above disclosed antibodies as interfering agents. Also disclosed are other interfering agents and compositions for use in the methods described herein. In some embodiments, the interfering agent disclosed herein is of the group:

(a) an isolated or recombinant integration host factor (IHF) polypeptide or a fragment or an equivalent of each thereof;

(b) an isolated or recombinant histone-like protein (HU) polypeptide or a fragment or an equivalent of each thereof;

(c) an isolated or recombinant polypeptide that comprising or consisting essentially of SEQ ID NOs. 12 to 17, SEQ ID NO. 31, SEQ ID NO. 33, a polypeptide comprising the amino acid sequence NPXT, or a fragment or an equivalent of each thereof;

(d) a polypeptide that competes with an integration host factor on binding to a microbial DNA;

(e) an isolated or recombinant polynucleotide encoding any one of (a) through (d) or an isolated, or a polynucleotide that hybridizes under stringent conditions to the polynucleotide its equivalent or its complement;

(f) an antibody or antigen binding fragment that specifically recognizes or binds any one of (a) through (e), or an equivalent or fragment of each antibody or antigen binding fragment thereof;

(g) isolated or recombinant polynucleotide encoding the antibody or antigen binding fragment of (f) or its complement;

(h) a small molecule that competes with the binding of a DNABII protein or polypeptide to a microbial DNA;

(i) an antibody from the group of (i) the antibody produced by hybridoma cell line IhfA5 nTHI 14G8.F5.G6, (ii) the antibody produced by hybridoma cell line IhfB4 NTHI 4E11.E5.G2, or (iii) the antibody produced by hybridoma cell line mIhfB4 NTHI 12E6.F8.D12.D5;

(j) an antibody or antigen binding fragment comprising one or more of the CDR sequences disclosed in SEQ ID NOs. 58-106, 108, and 109, the heavy chain sequence disclosed in SEQ ID NO. 51, and/or the light chain sequence disclosed in SEQ ID NO. 55, or an equivalent each thereof or (k) an antibody or antigen binding fragment comprising one or more of the CDR sequences disclosed in SEQ ID NOs. 110-159, the heavy chain sequence disclosed in SEQ ID NO. 53, and/or the light chain sequence disclosed in SEQ ID NO. 57, or an equivalent each thereof.

In some embodiments, the antibody or antigen binding fragment of (f), (i), (j), and/or (k) is not a polyclonal antibody.

Polypeptides

Aspects of the disclosure relate to isolated or recombinant DNABII polypeptides or fragments thereof, that comprise at least the the turn or "tip" portion of the protein, that in one aspect comprises the turn of the antiparallel beta ribbon and/or the consensus sequence NPXT, wherein "X" is any amino acid or alternatively X is selected from the amino acids Q, R, K, S, or T. Non-limiting examples of such are disclosed herein with the consensus amino acid sequence NPXT, in underlined and bolded text. In another aspect, a method is provided for obtaining an immunogen by mutating or selecting a tip region of a DNABII family member that contains the consensus sequence NPXT, wherein "X" is any amino acid or alternatively X is selected from the amino acids Q, R, K, S, or T. A skilled artisan will appreciate that in any one of these sequences, the residue in the X position (marked with a doubleunderline in the below examples) may be substituted with any amino acid—e.g., Q, R, K, S, or T. Examples include:

SEQ ID NO. 13: *Haemophilus influenzae* IhfA, A5 fragment:

RPGRNPKTGDVVPVSARRVV.

SEQ ID NO. 14: *Haemophilus influenzae* HU, A5 fragment:

RTGRNPQTGAEIQIAASKVP.

SEQ ID NO. 17: *Haemophilus influenzae* IhfB, modified B4 (mB4) fragment:

FSLHHRQPRLGRNPKTGDSV.

SEQ ID NO. 26: *Haemophilus influenzae* IhfA, A tip fragment:

NFELRDKSSRPGRNPKTGDVV.

SEQ ID NO. 27: *Haemophilus influenzae* IhfB, B tip fragment:

SLHHRQPRLGRNPKTGDSVNL.

SEQ ID NO. 31 *Haemophilus influenzae* HU, fragment:

VNERAARTGRNPQTGAEIQIAA.

In some embodiments, the polypeptide comprising NPXT is at least about 20 amino acids long and the NPXT is centrally in the sequence. Non-limiting examples of such sequences include SEQ ID NOs. 13, 14, and 31.

Aspects of the disclosure relate to isolated or recombinant integration host factor (IHF) polypeptides or a fragment or an equivalent of each thereof and an isolated or recombinant histone-like protein (HU) polypeptide or a fragment or an equivalent of each thereof as interfering agents. In some aspects, the interfering agent is an isolated or recombinant polypeptide that comprises or consisting essentially of an amino acid sequence selected from SEQ ID NOs. 12 to 17 or SEQ ID NO. 33, a polypeptide comprising the amino acid sequence NPXT, or an equivalent of each thereof.

This disclosure also provides isolated or recombinant polypeptides comprising or alternatively consisting essentially of, or yet further consisting of, two or more, or three or more, four or more, five or more, six or more, seven or more, eight or more, nine or more, ten or more, eleven or more, twelve or more, thirteen or more of all fourteen of the isolated polypeptides or a fragment or an equivalent of each thereof. Examples of such include isolated or recombinant polypeptides comprising SEQ ID NOs. 1, 2, 3, 12 to 17, and 33, a polypeptide comprising the amino acid sequence NPXT, and equivalents of each thereof. Biological equivalents of these polypeptides are further included in this disclosure with the proviso that the sequences do not include whole, isolated wildtype sequences.

In one embodiment, any polypeptide or protein having sequence identity to the wildtype polypeptides or those disclosed in Pedulla et al. (1996) PNAS 93:15411-15416 is excluded from this disclosure.

In any of the above embodiments, a peptide linker can be added to the N-terminus or C-terminus of the polypeptide. A "linker" or "peptide linker" refers to a peptide sequence linked to either the N-terminus or the C-terminus of a polypeptide sequence. In one aspect, the linker is from about 1 to about 20 amino acid residues long or alternatively 2 to about 10, about 3 to about 5 amino acid residues long. An example of a peptide linker is Gly-Pro-Ser-Leu-Lys-Leu (SEQ ID NO. 43). Other examples include Gly-Gly-Gly (SEQ ID NO. 44); Gly-Pro-Ser-Leu (SEQ ID NO. 45); Gly-Pro-Ser (SEQ ID NO. 46); Pro-Ser-Leu-Lys (SEQ ID NO. 47); Gly-Pro-Ser-Leu-Lys (SEQ ID NO. 48), and Ser-Leu-Lys-Leu (SEQ ID NO. 49).

The isolated polypeptides disclosed herein are intended to include isolated wildtype and recombinantly produced polypeptides and proteins from prokaryotic and eukaryotic host cells, as well as muteins, analogs and fragments thereof, examples of such cells are described above. In some embodiments, the term also includes antibodies and anti-idiotypic antibodies as described herein. Such polypeptides can be isolated or produced using the methods known in the art and briefly described herein.

It is understood that functional equivalents or variants of the wild type polypeptide or protein also are within the scope of this disclosure, for example, those having conservative amino acid substitutions of the amino acids. Other analogs include fusion proteins comprising a protein or polypeptide disclosed herein which can include a polypeptide joined to an antigen presenting matrix.

In a further aspect, the polypeptides are conjugated or linked to a detectable label. Suitable labels are known in the art and described herein.

In a yet further aspect, the polypeptides with or without a detectable label can be contained or expressed on the surface of a host prokaryotic or eukaryotic host cell, such as a dendritic cell.

The proteins and polypeptides are obtainable by a number of processes known to those of skill in the art, which include purification, chemical synthesis and recombinant methods. Polypeptides can be isolated from preparations such as host cell systems by methods such as immunoprecipitation with antibody, and standard techniques such as gel filtration, ion-exchange, reversed-phase, and affinity chromatography. For such methodology, see for example Deutscher et al. (1999) Guide To Protein Purification: Methods In Enzymology (Vol. 182, Academic Press). Accordingly, this disclosure also provides the processes for obtaining these polypeptides as well as the products obtainable and obtained by these processes.

The polypeptides also can be obtained by chemical synthesis using a commercially available automated peptide synthesizer such as those manufactured by Perkin/Elmer/Applied Biosystems, Inc., Model 430A or 431A, Foster City, Calif., USA. The synthesized polypeptide can be precipitated and further purified, for example by high performance liquid chromatography (HPLC). Accordingly, this disclosure also provides a process for chemically synthesizing the proteins disclosed herein by providing the sequence of the protein and reagents, such as amino acids and enzymes and linking together the amino acids in the proper orientation and linear sequence.

Alternatively, the proteins and polypeptides can be obtained by well-known recombinant methods as described, for example, in Sambrook et al. (1989) supra, using a host cell and vector systems described herein.

Also provided by this application are the polypeptides described herein conjugated to a detectable agent for use in the diagnostic methods. For example, detectably labeled polypeptides can be bound to a column and used for the detection and purification of antibodies. They also are useful as immunogens for the production of antibodies as described below. The polypeptides disclosed herein are useful in an in vitro assay system to screen for agents or drugs, which modulate cellular processes.

It is well known to those skilled in the art that modifications can be made to the peptides disclosed herein to provide them with altered properties. As used herein the term "amino acid" refers to either natural and/or unnatural or synthetic amino acids, including glycine and both the D or L optical isomers, and amino acid analogs and peptidomimetics. A peptide of three or more amino acids is commonly called an oligopeptide if the peptide chain is short. If the peptide chain is long, the peptide is commonly called a polypeptide or a protein.

Peptides disclosed herein can be modified to include unnatural amino acids. Thus, the peptides may comprise D-amino acids, a combination of and L-amino acids, and various "designer" amino acids (e.g., beta-methyl amino acids, C-alpha-methyl amino acids, and N-alpha-methyl amino acids, etc.) to convey special properties to peptides. Additionally, by assigning specific amino acids at specific coupling steps, peptides with alpha-helices, beta turns, beta sheets, gamma-turns, and cyclic peptides can be generated. Generally, it is believed that alpha-helical secondary structure or random secondary structure may be of particular use.

The polypeptides disclosed herein also can be combined with various solid phase carriers, such as an implant, a stent, a paste, a gel, a dental implant, or a medical implant or liquid phase carriers, such as beads, sterile or aqueous solutions, pharmaceutically acceptable carriers, pharmaceutically acceptable polymers, liposomes, micelles, suspensions and emulsions. Examples of non-aqueous solvents include propyl ethylene glycol, polyethylene glycol and vegetable oils. When used to prepare antibodies or induce an immune response in vivo, the carriers also can include an adjuvant that is useful to non-specifically augment a specific immune response. A skilled artisan can easily determine whether an adjuvant is required and select one. However, for the purpose of illustration only, suitable adjuvants include, but are not limited to Freund's Complete and Incomplete, mineral salts and polynucleotides. Other suitable adjuvants include monophosphoryl lipid A (MPL), mutant derivatives of the heat labile enterotoxin of *E. coli*, mutant derivatives of cholera toxin, CPG oligonucleotides, and adjuvants derived from squalene.

This disclosure also provides a pharmaceutical composition comprising or alternatively consisting essentially of, or yet further consisting of, any of a polypeptide, analog, mutein, or fragment disclosed herein, alone or in combination with each other or other agents, such an antibiotic and an acceptable carrier or solid support.

These compositions are useful for various diagnostic and therapeutic methods as described herein. In specific embodiments, it is envisioned that the polypeptides disclosed herein may be used in the generation of antibodies or a more generalized immune response. For example, the use of said polypeptides as immunogens may be useful in the generation of antibodies according to the above disclosed methods, as well as in diagnostic and therapeutic methods disclosed below. Conceivable embodiments according to the present disclosure include but are not limited to use of the isolated or recombinant polynucleotides to characterize, identify, purify, or otherwise assay the antibodies disclosed herein; use of the isolated or recombinant polynucleotides to generate the antibodies disclosed herein; or use of the isolated or recombinant polynucleotides alone or in combination with the antibodies disclosed herein in a vaccine or therapeutic formulation as contemplated herein.

Aspects of this disclosure relate to two or more of the polypeptides disclosed herein used as immunogens. For example, polypeptides including but not limited to:
 (a) SEQ ID NO. 12 (FLEEIRLSLESGQDVKLSGF);
 (b) SEQ ID NO. 13 (RPGRNPKTGDVVPVSARRVV);
 (c) SEQ ID NO. 14 (RTGRNPQTGAEIQIAASKVP);
 (d) SEQ ID NO. 15 (TLSAKEIENMVKDILEFISQ);
 (e) SEQ ID NO. 16 (RGFGSFSLHHRQPRLGRNPK);
 (f) SEQ ID NO. 17 (FSLHHRQPRLGRNPKTGDSV);
 (g) SEQ ID NO. 33 (KKQAKAALEATLDAITASLKEG);
 (h) SEQ ID NO. 31 (VNERAARTGRNPQTGAEIQIAA);
 (i) a polypeptide comprising the amino acid sequence NPXT; or
 (j) an equivalent of (a) through (i), wherein an equivalent comprises an amino acid sequence having at least about 80% homology or amino acid identity thereto, or an amino acid encoded by polynucleotide that hybridizes under conditions of high stringency to a polynucleotide encoding the amino acid sequence or its complement, wherein conditions of high stringency comprises incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water.

In some embodiments, the polypeptides disclosed herein may be used to determine binding affinity of the antibodies and/or screen for equivalent antibodies based on predicted affinity of a generated antibody to the peptide.

Polynucleotides

This disclosure also provides isolated or recombinant polynucleotides encoding one or more of the above-identified isolated or recombinant polypeptides and their respective complementary strands. This disclosure further provides isolated or recombinant polynucleotides encoding one or more of the above-identified antibodies. Vectors comprising the isolated or recombinant polynucleotides or antibodies are further provided examples of which are known in the art and briefly described herein. In one aspect where more than one isolated or recombinant polynucleotide is to be expressed as a single unit, the isolated or recombinant polynucleotides can be contained within a polycistronic vector. The polynucleotides can be DNA, RNA, mRNA or interfering RNA, such as siRNA, miRNA or dsRNA.

In another aspect, this disclosure provides an interfering agent that is a polynucleotide that interferes with the binding of the DNA to a polypeptide or protein in a microbial biofilm, or a four-way junction polynucleotide resembling a Holliday junction, a 3 way junction polynucleotide resembling a replication fork, a polynucleotide that has inherent flexibility or bent polynucleotide which can treat or inhibit DNABII polynucleotide from binding to microbial DNA as well treat, prevent or inhibit biofilm formation and associated infections and disorders. One of skill in the art can make such polynucleotides using the information provided herein and knowledge of those of skill in the art. See Goodman and Kay (1999) J. Biological Chem. 274(52):37004-37011 and Kamashev and Rouviere-Yaniv (2000) EMBO J. 19(23): 6527-6535.

The disclosure further provides the isolated or recombinant polynucleotide operatively linked to a promoter of RNA transcription, as well as other regulatory sequences for replication and/or transient or stable expression of the DNA or RNA. As used herein, the term "operatively linked" means positioned in such a manner that the promoter will direct transcription of RNA off the DNA molecule. Examples of such promoters are SP6, T4 and T7. In certain embodiments, cell-specific promoters are used for cell-specific expression of the inserted polynucleotide. Vectors which contain a promoter or a promoter/enhancer, with termination codons and selectable marker sequences, as well as a cloning site into which an inserted piece of DNA can be operatively linked to that promoter are known in the art and commercially available. For general methodology and cloning strategies, see Gene Expression Technology (Goeddel ed., Academic Press, Inc. (1991)) and references cited therein and Vectors: Essential Data Series (Gacesa and Ramji, eds., John Wiley & Sons, N.Y. (1994)) which contains maps, functional properties, commercial suppliers and a reference to GenEMBL accession numbers for various suitable vectors.

In one embodiment, polynucleotides derived from the polynucleotides disclosed herein encode polypeptides or proteins having diagnostic and therapeutic utilities as described herein as well as probes to identify transcripts of the protein that may or may not be present. These nucleic acid fragments can be prepared, for example, by restriction enzyme digestion of larger polynucleotides and then labeled with a detectable marker. Alternatively, random fragments can be generated using nick translation of the molecule. For methodology for the preparation and labeling of such fragments, see Sambrook et al. (1989) supra.

Expression vectors containing these nucleic acids are useful to obtain host vector systems to produce proteins and polypeptides. It is implied that these expression vectors must be replicable in the host organisms either as episomes or as an integral part of the chromosomal DNA. Non-limiting examples of suitable expression vectors include plasmids, yeast vectors, viral vectors and liposomes. Adenoviral vectors are particularly useful for introducing genes into tissues in vivo because of their high levels of expression and efficient transformation of cells both in vitro and in vivo. When a nucleic acid is inserted into a suitable host cell, e.g., a prokaryotic or a eukaryotic cell and the host cell replicates, the protein can be recombinantly produced. Suitable host cells will depend on the vector and can include mammalian cells, animal cells, human cells, simian cells, insect cells, yeast cells, and bacterial cells constructed using known methods. See Sambrook et al. (1989) supra. In addition to the use of viral vector for insertion of exogenous nucleic acid into cells, the nucleic acid can be inserted into the host cell by methods known in the art such as transformation for bacterial cells; transfection using calcium phosphate precipitation for mammalian cells; or DEAE-dextran; electroporation; or microinjection. See, Sambrook et al. (1989) supra, for methodology. Thus, this disclosure also provides a host cell, e.g., a mammalian cell, an animal cell (rat or mouse), a human cell, or a prokaryotic cell such as a bacterial cell, containing a polynucleotide encoding a protein or polypeptide or antibody.

A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment disclosed herein that is a polynucleotide encompasses both the double-stranded form and each of two complementary single-stranded forms known or predicted to make up the double-stranded form.

When the vectors are used for gene therapy in vivo or ex vivo, a pharmaceutically acceptable vector, such as a replication-incompetent retroviral or adenoviral vector, are exemplary (but non-limiting) and may be of particular use. Pharmaceutically acceptable vectors containing the nucleic acids disclosed herein can be further modified for transient or stable expression of the inserted polynucleotide. As used herein, the term "pharmaceutically acceptable vector" includes, but is not limited to, a vector or delivery vehicle having the ability to selectively target and introduce the nucleic acid into dividing cells. An example of such a vector is a "replication-incompetent" vector defined by its inability to produce viral proteins, precluding spread of the vector in the infected host cell. An example of a replication-incompetent retroviral vector is LNL6 (Miller et al. (1989) Bio-Techniques 7:980-990). The methodology of using replication-incompetent retroviruses for retroviral-mediated gene transfer of gene markers has been established. (Bordignon (1989) PNAS USA 86:8912-8952; Culver (1991) PNAS USA 88:3155; and Rill (1991) Blood 79(10):2694-2700).

This disclosure also provides genetically modified cells that contain and/or express the polynucleotides disclosed herein. The genetically modified cells can be produced by insertion of upstream regulatory sequences such as promoters or gene activators (see, U.S. Pat. No. 5,733,761).

The polynucleotides can be conjugated to a detectable and/or purification marker, e.g., an enzymatic label or a radioisotope for detection of nucleic acid and/or expression of the gene in a cell. A wide variety of appropriate detectable markers are known in the art, including fluorescent, radioactive, enzymatic or other ligands, such as avidin/biotin, which are capable of giving a detectable signal. In one aspect, one will likely desire to employ a fluorescent label or an enzyme tag, such as urease, alkaline phosphatase or peroxidase, instead of radioactive or other environmentally undesirable reagents. In the case of enzyme tags, calorimetric indicator substrates can be employed to provide a means visible to the human eye or spectrophotometrically, to identify specific hybridization with complementary nucleic acid-containing samples. Thus, this disclosure further provides a method for detecting a single-stranded polynucleotide or its complement, by contacting target single-stranded polynucleotide with a labeled, single-stranded polynucleotide (a probe) which is a portion of the polynucleotide disclosed herein under conditions permitting hybridization (optionally moderately stringent hybridization conditions) of complementary single-stranded polynucleotides, or optionally, under highly stringent hybridization conditions. Hybridized polynucleotide pairs are separated from un-hybridized, single-stranded polynucleotides. The hybridized polynucleotide pairs are detected using methods known to those of skill in the art and set forth, for example, in Sambrook et al, (1989) supra.

The polynucleotide embodied in this disclosure can be obtained using chemical synthesis, recombinant cloning methods, PCR, or any combination thereof. Methods of chemical polynucleotide synthesis are known in the art and need not be described in detail herein. One of skill in the art can use the sequence data provided herein to obtain a desired polynucleotide by employing a DNA synthesizer or ordering from a commercial service.

The polynucleotides disclosed herein can be isolated or replicated using PCR. The PCR technology is the subject matter of U.S. Pat. Nos. 4,683,195; 4,800,159; 4,754,065; and 4,683,202 and described in PCR: The Polymerase Chain Reaction (Mullis et al. eds., Birkhauser Press, Boston (199.4)) or MacPherson et al. (1991) and (1995) supra, and references cited therein. Alternatively, one of skill in the art can use the sequences provided herein and a commercial DNA synthesizer to replicate the DNA. Accordingly, this disclosure also provides a process for obtaining the polynucleotides disclosed herein by providing the linear sequence of the polynucleotide, nucleotides, appropriate primer molecules, chemicals such as enzymes and instructions for their replication and chemically replicating or linking the nucleotides in the proper orientation to obtain the polynucleotides. In a separate embodiment, these polynucleotides are further isolated. Still further, one of skill in the art can insert the poly-nucleotide into a suitable replication vector and insert the vector into a suitable host cell (prokaryotic or eukaryotic) for replication and amplification. The DNA so amplified can be isolated from the cell by methods known to those of skill in the art. A process for obtaining polynucleotides by this method is further provided herein as well as the polynucleotides so obtained.

RNA can be obtained by first inserting a DNA polynucleotide into a suitable host cell. The DNA can be delivered by any appropriate method, e.g., by the use of an appropriate gene delivery vehicle (e.g., liposome, plasmid or vector) or by electroporation. When the cell replicates and the DNA is transcribed into RNA; the RNA can then be isolated using methods known to those of skill in the art, for example, as set forth in Sambrook et al. (1989) supra. For instance, mRNA can be isolated using various lytic enzymes or chemical solutions according to the procedures set forth in Sambrook et al. (1989) supra, or extracted by nucleic-acid-binding resins following the accompanying instructions provided by manufactures.

Polynucleotides exhibiting sequence complementarity or homology to a polynucleotide disclosed herein are useful as hybridization probes or as an equivalent of the specific polynucleotides identified herein. Since the full coding sequence of the transcript is known, any portion of this sequence or homologous sequences, can be used in the methods disclosed herein.

It is known in the art that a "perfectly matched" probe is not needed for a specific hybridization. Minor changes in probe sequence achieved by substitution, deletion or insertion of a small number of bases do not affect the hybridization specificity. In general, as much as 20% base-pair mismatch (when optimally aligned) can be tolerated. In some embodiments, a probe useful for detecting the aforementioned mRNA is at least about 80% identical to the homologous region. In some embodiments, the probe is 85% identical to the corresponding gene sequence after alignment of the homologous region; in some embodiments, it exhibits 90% identity.

These probes can be used in radioassays (e.g., Southern and Northern blot analysis) to detect, prognose, diagnose or monitor various cells or tissues containing these cells. The probes also can be attached to a solid support or an array such as a chip for use in high throughput screening assays for the detection of expression of the gene corresponding a polynucleotide disclosed herein. Accordingly, this disclosure also provides a probe comprising or corresponding to a polynucleotide disclosed herein, or its equivalent, or its complement, or a fragment thereof, attached to a solid support for use in high throughput screens.

The total size of fragment, as well as the size of the complementary stretches, will depend on the intended use or application of the particular nucleic acid segment. Smaller fragments will generally find use in hybridization embodiments, wherein the length of the complementary region may be varied, such as between at least 5 to 10 to about 100 nucleotides, or even full length according to the complementary sequences one wishes to detect.

Nucleotide probes having complementary sequences over stretches greater than 5 to 10 nucleotides in length are generally well suited, so as to increase stability and selectivity of the hybrid, and thereby improving the specificity of particular hybrid molecules obtained. In certain embodiments, one can design polynucleotides having gene-complementary stretches of 10 or more or more than 50 nucleotides in length, or even longer where desired. Such fragments may be readily prepared by, for example, directly synthesizing the fragment by chemical means, by application of nucleic acid reproduction technology, such as the PCR technology with two priming oligonucleotides as described in U.S. Pat. No. 4,603,102 or by introducing selected sequences into recombinant vectors for recombinant production. In one aspect, a probe is about 50-75 or more alternatively, 50-100, nucleotides in length.

The polynucleotides of the present disclosure can serve as primers for the detection of genes or gene transcripts that are expressed in cells described herein. In this context, amplification means any method employing a primer-dependent polymerase capable of replicating a target sequence with reasonable fidelity. Amplification may be carried out by natural or recombinant DNA-polymerases such as T7 DNA polymerase, Klenow fragment of *E. coli* DNA polymerase, and reverse transcriptase. For illustration purposes only, a primer is the same length as that identified for probes.

One method to amplify polynucleotides is PCR and kits for PCR amplification are commercially available. After amplification, the resulting DNA fragments can be detected by any appropriate method known in the art, e.g., by agarose gel electrophoresis followed by visualization with ethidium bromide staining and ultraviolet illumination.

Methods for administering an effective amount of a gene delivery vector or vehicle to a cell have been developed and are known to those skilled in the art and described herein. Methods for detecting gene expression in a cell are known in the art and include techniques such as in hybridization to DNA microarrays, in situ hybridization, PCR, RNase protection assays and Northern blot analysis. Such methods are useful to detect and quantify expression of the gene in a cell. Alternatively expression of the encoded polypeptide can be detected by various methods. In particular it is useful to prepare polyclonal or monoclonal antibodies that are specifically reactive with the target polypeptide. Such antibodies are useful for visualizing cells that express the polypeptide using techniques such as immunohistology, ELISA, and Western blotting. These techniques can be used to determine expression level of the expressed polynucleotide.

Compositions

Compositions are further provided. The compositions comprise a carrier and one or more of an isolated polypeptide disclosed herein, an isolated polynucleotide disclosed herein, a vector disclosed herein, an isolated host cell disclosed herein, a small molecule or an antibody disclosed herein. The carriers can be one or more of a solid support or a pharmaceutically acceptable carrier. The compositions can further comprise an adjuvant or other components suitable for administrations as vaccines. In one aspect, the compositions are formulated with one or more pharmaceutically acceptable excipients, diluents, carriers and/or adjuvants. In addition, embodiments of the compositions of the present disclosure include one or more of an isolated polypeptide disclosed herein, an isolated polynucleotide disclosed herein, a vector disclosed herein, a small molecule, an isolated host cell disclosed herein, or an antibody of the disclosure, formulated with one or more pharmaceutically acceptable substances.

For oral preparations, any one or more of an isolated or recombinant polypeptide as described herein, an isolated or recombinant polynucleotide as described herein, a vector as described herein, an isolated host cell as described herein, a small molecule or an antibody as described herein can be used alone or in pharmaceutical formulations disclosed herein comprising, or consisting essentially of, the compound in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Pharmaceutical formulations and unit dose forms suitable for oral administration are particularly useful in the treatment of chronic conditions, infections, and therapies in which the patient self-administers the drug. In one aspect, the formulation is specific for pediatric administration.

The disclosure provides pharmaceutical formulations in which the one or more of an isolated polypeptide disclosed herein, an isolated polynucleotide disclosed herein, a vector disclosed herein, an isolated host cell disclosed herein, or an antibody disclosed herein can be formulated into preparations for injection in accordance with the disclosure by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives or other antimicrobial agents. A non-limiting example of such is another therapeutic agent is an antibody to other vaccine components such as surface antigens, e.g., an OMP P5, OMP 26, OMP P2, or a vaccine component such as Type IV Pilin protein (see Jurcisek and Bakaletz (2007) J. of Bacteriology 189(10):3868-3875 and Murphy, T. F. et al. (2009) The Pediatric Infectious Disease Journal 28:S121-S126) and antibacterial agents. For intravenous administration, suitable carriers include physiological bacteriostatic water, Cremophor EL™ (BASF, Parsippany, N.J.), or phosphate buffered saline (PBS). In all cases, a composition for parenteral administration must be sterile and should be fluid to the extent that easy syringability exists.

Aerosol formulations provided by the disclosure can be administered via inhalation and can be propellant or non-propellant based. For example, embodiments of the pharmaceutical formulations disclosed herein comprise a compound disclosed herein formulated into pressurized acceptable propellants such as dichlorodifluoromethane, propane, nitrogen and the like. For administration by inhalation, the compounds can be delivered in the form of an aerosol spray from a pressurized container or dispenser which contains a suitable propellant, e.g., a gas such as carbon dioxide, or a nebulizer. A non-limiting example of a non-propellant is a pump spray that is ejected from a closed container by means of mechanical force (i.e., pushing down a piston with one's finger or by compression of the container, such as by a compressive force applied to the container wall or an elastic force exerted by the wall itself (e.g., by an elastic bladder)).

Suppositories disclosed herein can be prepared by mixing a compound disclosed herein with any of a variety of bases such as emulsifying bases or water-soluble bases. Embodiments of this pharmaceutical formulation of a compound disclosed herein can be administered rectally via a suppository. The suppository can include vehicles such as cocoa butter, carbowaxes and polyethylene glycols, which melt at body temperature, yet are solidified at room temperature.

Unit dosage forms for oral or rectal administration, such as syrups, elixirs, and suspensions, may be provided wherein each dosage unit, for example, teaspoonful, tablespoonful, tablet or suppository, contains a predetermined amount of the composition containing one or more compounds disclosed herein. Similarly, unit dosage forms for injection or intravenous administration may comprise a compound disclosed herein in a composition as a solution in sterile water, normal saline or another pharmaceutically acceptable carrier.

Embodiments of the pharmaceutical formulations disclosed herein include those in which one or more of an isolated polypeptide disclosed herein, an isolated polynucleotide disclosed herein, a vector disclosed herein, a small molecule for use in the disclosure, an isolated host cell disclosed herein, or an antibody disclosed herein is formulated in an injectable composition. Injectable pharmaceutical formulations disclosed herein are prepared as liquid solutions or suspensions; or as solid forms suitable for solution in, or suspension in, liquid vehicles prior to injection. The preparation may also be emulsified or the active ingredient encapsulated in liposome vehicles in accordance with other embodiments of the pharmaceutical formulations disclosed herein.

In an embodiment, one or more of an isolated polypeptide disclosed herein, an isolated polynucleotide disclosed herein, a vector disclosed herein, an isolated host cell disclosed herein, or an antibody disclosed herein is formulated for delivery by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

Mechanical or electromechanical infusion pumps can also be suitable for use with the present disclosure. Examples of such devices include those described in, for example, U.S. Pat. Nos. 4,692,147; 4,360,019; 4,487,603; 4,360,019; 4,725,852; 5,820,589; 5,643,207; 6,198,966; and the like. In general, delivery of a compound disclosed herein can be accomplished using any of a variety of refillable, pump systems. Pumps provide consistent, controlled release over time. In some embodiments, a compound disclosed herein is in a liquid formulation in a drug-impermeable reservoir, and is delivered in a continuous fashion to the individual.

In one embodiment, the drug delivery system is an at least partially implantable device. The implantable device can be implanted at any suitable implantation site using methods and devices well known in the art. An implantation site is a site within the body of a subject at which a drug delivery device is introduced and positioned. Implantation sites include, but are not necessarily limited to, a subdermal, subcutaneous, intramuscular, or other suitable site within a subject's body. Subcutaneous implantation sites are used in some embodiments because of convenience in implantation and removal of the drug delivery device.

Drug release devices suitable for use in the disclosure may be based on any of a variety of modes of operation. For example, the drug release device can be based upon a diffusive system, a convective system, or an erodible system (e.g., an erosion-based system). For example, the drug release device can be an electrochemical pump, osmotic pump, an electro osmotic pump, a vapor pressure pump, or osmotic bursting matrix, e.g., where the drug is incorporated into a polymer and the polymer provides for release of drug formulation concomitant with degradation of a drug-impregnated polymeric material (e.g., a biodegradable, drug-impregnated polymeric material). In other embodiments, the drug release device is based upon an electro diffusion system, an electrolytic pump, an effervescent pump, a piezoelectric pump, a hydrolytic system, etc.

Drug release devices based upon a mechanical or electromechanical infusion pump can also be suitable for use with the present disclosure. Examples of such devices include those described in, for example, U.S. Pat. Nos. 4,692,147; 4,360,019; 4,487,603; 4,360,019; 4,725,852, and the like. In general, a subject treatment method can be accomplished using any of a variety of refillable, non-exchangeable pump systems. Pumps and other convective systems may be utilized due to their generally more consistent, controlled release over time. Osmotic pumps are used in some embodiments due to their combined advantages of more consistent controlled release and relatively small size (see, e.g., PCT International Pat. Application Publication No. WO 97/27840 and U.S. Pat. Nos. 5,985,305 and 5,728,396). Exemplary osmotically-driven devices suitable for use in the disclosure include, but are not necessarily limited to, those described in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,627,850; 4,865,845; 5,057,318; 5,059,423; 5,112,614; 5,137,727; 5,234,692; 5,234,693; 5,728,396; and the like. A further exemplary device that can be adapted for the present disclosure is the Synchromed infusion pump (Medtronic).

In some embodiments, the drug delivery device is an implantable device. The drug delivery device can be implanted at any suitable implantation site using methods and devices well known in the art. As noted herein, an implantation site is a site within the body of a subject at which a drug delivery device is introduced and positioned. Implantation sites include, but are not necessarily limited to a subdermal, subcutaneous, intramuscular, or other suitable site within a subject's body.

Suitable excipient vehicles for a compound disclosed herein are, for example, water, saline, dextrose, glycerol, ethanol, or the like, and combinations thereof. In addition, if desired, the vehicle may contain minor amounts of auxiliary substances such as wetting or emulsifying agents or pH buffering agents. Methods of preparing such dosage forms are known, or will be apparent upon consideration of this disclosure, to those skilled in the art. See, e.g., Remington's Pharmaceutical Sciences, Mack Publishing Company, Easton, Pa., 17th edition, 1985. The composition or formulation to be administered will, in any event, contain a quantity of the compound adequate to achieve the desired state in the subject being treated.

Compositions of the present disclosure include those that comprise a sustained-release or controlled release matrix. In addition, embodiments of the present disclosure can be used in conjunction with other treatments that use sustained-release formulations. As used herein, a sustained-release matrix is a matrix made of materials, usually polymers, which are degradable by enzymatic or acid-based hydrolysis or by dissolution. Once inserted into the body, the matrix is acted upon by enzymes and body fluids. A sustained-release matrix desirably is chosen from biocompatible materials such as liposomes, polylactides (polylactic acid), polyglycolide (polymer of glycolic acid), polylactide co-glycolide (copolymers of lactic acid and glycolic acid), polyanhydrides, poly(ortho)esters, polypeptides, hyaluronic acid, collagen, chondroitin sulfate, carboxcylic acids, fatty acids, phospholipids, polysaccharides, nucleic acids, polyamino acids, amino acids such as phenylatanine, tyrosine, isoleucine, polynucleotides, polyvinyl propylene, polyvinylpyrrolidone and silicone. Illustrative biodegradable matrices include a polylactide matrix, a polyglycolide matrix, and a polylactide co-glycolide (co-polymers of lactic acid and glycolic acid) matrix.

In another embodiment, the interfering agent or an antibody (as well as combination compositions) is delivered in a controlled release system. For example, a compound disclosed herein may be administered using intravenous infusion, an implantable osmotic pump, a transdermal patch, liposomes, or other modes of administration. In one embodiment, a pump may be used (Sefton (1987) CRC Crit. Ref. Biomed. Eng. 14:201; Buchwald et al. (1980) Surgery 88:507; Saudek et al. (1989) N. Engl. J. Med. 321:574). In another embodiment, polymeric materials are used. In yet another embodiment a controlled release system is placed in proximity of the therapeutic target, i.e., the liver, thus requiring only a fraction of the systemic dose. In yet another embodiment, a controlled release system is placed in proximity of the therapeutic target, thus requiring only a fraction of the systemic. Other controlled release systems are discussed in the review by Langer (1990) Science 249:1527-1533.

In another embodiment, the compositions of the present disclosure (as well as combination compositions separately or together) include those formed by impregnation of an inhibiting agent described herein into absorptive materials, such as sutures, bandages, and gauze, or coated onto the surface of solid phase materials, such as surgical staples, zippers and catheters to deliver the compositions. Other delivery systems of this type will be readily apparent to those skilled in the art in view of the instant disclosure.

The present disclosure provides methods and compositions for the administration of a one or more of an interfering agent to a host (e.g., a human) for the treatment of a microbial infection. In various embodiments, these methods disclosed herein span almost any available method and route suitable for drug delivery, including in vivo and ex vivo methods, as well as systemic and localized routes of administration.

Formulations and Co-Formulations

More specifically, the disclosure provided herein contemplates specific formulations and co-formulations of the interfering agents disclosed along with a pharmaceutically acceptable excipient, such as those disclosed herein above.

For the purpose of the above noted formulations and co-formulations, the interfering agent is of the group of:

(a) an isolated or recombinant integration host factor (IHF) polypeptide or a fragment or an equivalent of each thereof;

(b) an isolated or recombinant histone-like protein (HU) polypeptide or a fragment or an equivalent of each thereof;

(c) an isolated or recombinant polypeptide of SEQ ID NOs. 12 to 17, SEQ ID NO. 33, a polypeptide comprising the amino acid sequence NPXT, or a fragment or an equivalent of each thereof;

(d) a polypeptide that competes with an integration host factor on binding to a microbial DNA;

(e) an isolated or recombinant polynucleotide encoding any one of (a) through (f) or an isolated, or a polynucleotide that hybridizes under stringent conditions to the polynucleotide its equivalent or its complement;

(f) an antibody or antigen binding fragment that specifically recognizes or binds any one of (a) through (e), or an equivalent or fragment of each antibody or antigen binding fragment thereof;

(g) isolated or recombinant polynucleotide encoding the antibody or antigen binding fragment of (h) or its complement;

(i) a small molecule that competes with the binding of a DNABII protein or polypeptide to a microbial DNA;

(j) an antibody from the group of (i) the antibody produced by hybridoma cell line IhfA5 nTHI 14G8.F5.G6, (ii) the antibody produced by hybridoma cell line IhfB4 NTHI 4E11.E5.G2, or (iii) the antibody produced by hybridoma cell line mIhfB4 NTHI 12E6.F8.D12.D5;

(k) an antibody or antigen binding fragment comprising one or more of the CDR sequences disclosed herein that include those disclosed in SEQ ID NOs. 58-106, 108, and 109, the heavy chain sequence disclosed in SEQ ID NO. 51, and/or the light chain sequence disclosed in SEQ ID NO. 55, or an equivalent each thereof; or (l) an antibody or antigen binding fragment comprising one or more of the CDR sequences disclosed herein that include those disclosed in SEQ ID NOs. 110-159, the heavy chain sequence disclosed in SEQ ID NO. 53, and/or the light chain sequence disclosed in SEQ ID NO. 57, or an equivalent each thereof.

In some embodiments, the antibody or antigen binding fragment of (f), (j), (k), and/or (l) is not a polyclonal antibody.

In specific aspects, the disclosure provides for formulations or co-formulations comprising antibodies that specifically recognize or bind an isolated or recombinant polypeptide consisting essentially of an amino acid sequence selected from: SEQ ID NOs. 12 to 17, SEQ ID NO. 33, or an equivalent each thereof. Antibodies disclosed herein may be selected such that they have a high level of epitope binding specificity and high binding affinity to the biofilm.

In general, the higher the binding affinity of an antibody, the more stringent wash conditions can be performed in an immunoassay to remove nonspecifically bound material without removing the target. Accordingly, the antibodies of the present technology useful in the disclosed methods usually have binding affinities of at least $10^{-6}$, $10^{-7}$, $10^{-8}$, $10^{-9}$, $10^{-10}$, $10^{-11}$, or $10^{-12}$M. In certain aspects, the antibodies have a sufficient kinetic on-rate to reach equilibrium under standard conditions in at least 12 hours, at least 5 hours, at least 1 hour, or at least 30 minutes. In another aspect, the affinity of the antibody or antigen binding fragment is less than or about 1000 picoMole (pM), 900 pM, 800 pM, 700 pM, 600 pM, 500 pM, 400 pM, 300 pM, 200 pM, about 100 pM, 50 pM, 40 pM, 30 pM, 20 pM, 10 pM, 9 pM, 8 pM, 7 pM, 6 pM, 5 pM, or 4 pM.

In some embodiments, the antibodies are present in the formulation at a concentration from about 0.1 mg/mL to about 200 mg/mL, or alternatively from about 1 to about 150 mg/mL, or alternatively about 2 mg/mL to about 100 mg/mL, or alternatively about 3 mg/mL to about 80 mg/mL, or alternatively about 4 mg/mL to about 50 mg/mL, or alternatively about 5 mg/mL to about 20 mg/mL. In some embodiments, the antibodies are present at a concentration of at least about 1 mg/mL, or alternatively at least about 2 mg/mL, at least about 3 mg/mL, or alternatively at least about 4 mg/mL, or alternatively at least about 5 mg/mL, or alternatively at least about 6 mg/mL, or alternatively at least about 7 mg/mL, or alternatively at least about 8 mg/mL, or alternatively at least about 9 mg/mL, or alternatively at least about 10 mg/mL, or alternatively at least about 15 mg/mL, or alternatively at least about 20 mg/mL, or alternatively at least about 30 mg/mL, or alternatively at least about 40 mg/mL, or alternatively at least about 50 mg/mL, or alternatively at least about 60 mg/mL, or alternatively at least about 70 mg/mL, or alternatively at least about 80 mg/mL, or alternatively at least about 90 mg/mL, or alternatively at least about 100 mg/mL, or alternatively at least about 120 mg/mL, or alternatively at least about 150 mg/mL or alternatively at least about 200 mg/mL. In some embodiments, at least one of the plurality of antibodies is present at a concentration of at least about 1 mg/mL, or alternatively at least about 2 mg/mL, or alternatively at least about 3 mg/mL, or alternatively at least about 4 mg/mL, or alternatively at least about 5 mg/mL, or alternatively at least about 6 mg/mL, or alternatively at least about 7 mg/mL, or alternatively at least about 8 mg/mL, or alternatively at least about 9 mg/mL, or alternatively at least about 10 mg/mL, or alternatively at least about 15 mg/mL, or alternatively at least about 20 mg/mL, or alternatively at least about 30 mg/mL, or alternatively at least about 40 mg/mL, or alternatively at least about 50 mg/mL, or alternatively at least about 60 mg/mL, or alternatively at least about 70 mg/mL, or alternatively at least about 80 mg/mL, or alternatively at least about 90 mg/mL, or alternatively at least about 100 mg/mL, or alternatively at least about 120 mg/mL, or alternatively at least about 150 mg/mL, or alternatively at least about 200 mg/mL.

In some embodiments, wherein multiple different antibodies are included an antibody co-formulation, the different antibodies may be present in substantially equal concentrations. In another aspect of such embodiments, the different antibodies one or more of the antibodies may be present in a substantially higher concentration than the other antibodies, e.g., ratios of about 1.5:1, or alternatively about 1.5:1:1, or alternatively about 1.5:1:1:1, or alternatively about 2:1, or alternatively about 2:1:1, or alternatively about 2:1:1:1, or alternatively at least about 2.5:1, or alternatively at least about 2.5:1:1, or alternatively at least about 2.5:1:1:1.

In some embodiments the co-formulation comprises, or alternatively consists essentially of, or yet further comprises, (i) an antibody that specifically recognizes or binds an isolated or recombinant polypeptide consisting essentially of SEQ ID NO. 13 and/or SEQ ID NO. 14 or an equivalent of each thereof and (ii) an antibody that specifically recognizes or binds an isolated or recombinant polypeptide consisting essentially of SEQ ID NO. 16 and/or SEQ ID NO. 17 and/or SEQ ID NO. 31 and/or SEQ ID NO. 33 or an equivalent of each thereof. In some embodiments, one or more antibodies in the formulation is not a polyclonal antibody. In some embodiments, this formulation is used as a therapeutic.

In some embodiments the co-formulation comprises, or alternatively consists essentially of, or yet further comprises, (i) an antibody that specifically recognizes or binds an isolated or recombinant polypeptide consisting essentially of SEQ ID NO. 12 and/or SEQ ID NO. 31 and/or SEQ ID NO. 33 or an equivalent thereof and (ii) an antibody that specifically recognizes or binds an isolated or recombinant polypeptide consisting essentially of SEQ ID NO. 15 and/or SEQ ID NO. 31 and/or SEQ ID NO. 33 or an equivalent thereof. In some embodiments, one or more antibodies in the formulation is not a polyclonal antibody. In some embodiments, this formulation is used as a diagnostic.

Methods of stably formulating antibody formulations and co-formulations can be made according to techniques disclosed in the art—see, e.g., U.S. patent application Ser. No. 12/875,083 (published as US 2011/0059079).

Diagnostic and Therapeutic Methods

Also provided are methods for inhibiting, competing or titrating the binding of a DNABII polypeptide or protein to a microbial DNA, by contacting the DNABII polypeptide or protein or the microbial DNA with an interfering agent, thereby inhibiting, competing or titrating the binding of the DNABII protein or polypeptide to the microbial DNA. In a further aspect, the DNABII polypeptide and the microbial DNA are detectably labeled, for example with luminescent molecules that will emit a signal when brought into close contact with each other. The contacting can be performed in vitro or in vivo.

In another aspect, a method for inhibiting, preventing or breaking down a microbial biofilm is provided by contacting the biofilm with an interfering agent, thereby inhibiting, preventing or breaking down the microbial biofilm. In a further aspect, the DNABII polypeptide and the microbial DNA are detectably labeled, for example with luminescent molecules that will emit a signal when brought into close contact with each other. The contacting can be performed in vitro or in vivo.

When practiced in vitro, the methods are useful to screen for or confirm interfering agents having the same, similar or opposite ability as the polypeptides, polynucleotides, antibodies, host cells, small molecules and compositions disclosed herein. Alternatively, they can be used to identify which interfering agent is best suited to treat a microbial infection. For example, one can screen for new agents or combination therapies by having two samples containing for example, the DNABII polypeptide and microbial DNA and the agent to be tested. The second sample contains the DNABII polypeptide and microbial DNA and an agent known to active, e.g., an anti-IHF antibody or a small molecule to serve as a positive control. In a further aspect, several samples are provided and the interfering agents are added to the system in increasing dilutions to determine the optimal dose that would likely be effective in treating a subject in the clinical setting. As is apparent to those of skill in the art, a negative control containing the DNABII polypeptide and the microbial DNA can be provided. In a further aspect, the DNABII polypeptide and the microbial DNA are detectably labeled, for example with luminescent molecules that will emit a signal when brought into close contact with each other. The samples are contained under similar conditions for an effective amount of time for the agent to inhibit, compete or titrate the interaction between the DNABII polypeptide and microbial DNA and then the sample is assayed for emission of signal from the luminescent molecules. If the sample emits a signal, then the agent is not effective to inhibit binding.

In another aspect, the in vitro method is practiced in a miniaturized chamber slide system wherein the microbial (such as a bacterial) isolate causing an infection could be isolated from the human/animal then cultured to allow it to grow as a biofilm in vitro, see for example Experiment 1 below. The interfering agent (such as anti-IHF antibody) or potential interfering agent biofilm is added alone or in combination with another agent to the culture with or without increasing dilutions of the potential interfering agent or interfering agent such as an anti-IHF (or other antibody, small molecule, agent, etc.) to find the optimal dose that would likely be effective at treating that patient when delivered to the subject where the infection existed. As apparent to those of skill in the art, a positive and negative control can be performed simultaneously.

In a further aspect, the method is practiced in a high throughput platform with the interfering agent (such as anti-IHF antibody) and/or potential interfering agent (alone or in combination with another agent) in a flow cell. The interfering agent (such as anti-IHF antibody) or potential interfering agent biofilm is added alone or in combination with another agent to the culture with or without increasing dilutions of the potential interfering agent or interfering agent such as an anti-IHF (or other antibody, small molecule, agent, etc.) to find the optimal dose that would likely be effective at treating that patient when delivered to the subject where the infection existed. Biofilm isolates are sonicated to separate biofilm bacteria from DNABII polypeptide such as IHF bound to microbial DNA. The DNABII polypeptide-DNA complexes are isolated by virtue of the anti-IHF antibody on the platform. The microbial DNA is then be released with e.g., a salt wash, and used to identify the biofilm bacteria added. The freed DNA is then identified, e.g., by PCR sequenced. If DNA is not freed, then the interfering agent(s) successfully performed or bound the microbial DNA. If DNA is found in the sample, then the agent did not interfere with DNABII polypeptide-microbial DNA binding. As is apparent to those of skill in the art, a positive and/or negative control can be simultaneously performed.

In another aspect one or more of the interfering agents or antibodies disclosed herein are used in a method of detecting a biofilm in vivo. In further embodiments, the interfering agents or antibodies are detectably labeled, for example with a luminescent or fluorescent molecule. Further applications of the methods disclosed herein include methods of use of such interfering agents or antibodies to image a biofilm using, for example, a detectably labeled primary interfering agent or antibody which provides a detectable signal upon binding to the biofilm or a detectably labeled secondary antibody which binds to the primary interfering agent or antibody when it is bound to the biofilm.

The above methods also can be used as a diagnostic test since it is possible that a given bacterial species will respond better to reversal of its biofilm by one agent more than another, this rapid high throughput assay system could allow one skilled the art to assay a panel of possible anti-IHF-like agents to identify the most efficacious of the group.

The advantage of these methods is that most clinical microbiology labs in hospitals are already equipped to perform these sorts of assays (i.e., determination of MIC, MBC values) using bacteria that are growing in liquid culture (or planktonically). As is apparent to those of skill in die art, bacteria generally do not grow planktonically when they are causing diseases. Instead they are growing as a stable biofilm and these biofilms are significantly more resistant to treatment by antibiotics, antibodies or other therapeutics. This resistance is why most MIC/MBC values fail to accurately predict efficacy in vivo. Thus, by determining what "dose" of agent could reverse a bacterial biofilm in vitro (as described above) Applicants' pre-clinical assay would be a more reliable predictor of clinical efficacy, even as an application of personalized medicine.

In addition to the clinical setting, the methods can be used to identify the microbe causing the infection and/or confirm effective interfering agents in an industrial setting.

In a further aspect of the above methods, an antibiotic or antimicrobial known to inhibit growth of the underlying infection is added sequentially or concurrently, to determine if the infection can be inhibited. It is also possible to add the interfering agent to the microbial DNA or DNABII polypeptide before adding the complex to assay for biofilm inhibition.

When practiced in vivo in non-human animal such as a chinchilla, the method provides a pre-clinical screen to identify interfering agents that can be used alone or in combination with other agents to break down biofilms. Examples of this method are shown in Examples 4 through 9 below.

In another aspect, provided herein is a method of inhibiting, preventing or breaking down a biofilm in a subject by administering to the subject an effective amount of an interfering agent, thereby inhibiting, preventing or breaking down the microbial biofilm. Examples of this method are shown in Examples 4 through 7, below.

Alternatively or additionally, methods of inhibiting, preventing or breaking down a biofilm may be practiced in vitro and/or ex vivo and involve providing a sample of the biofilm—taken from a subject or generated in vitro—and administering an effective amount of an interfering agent, thereby inhibiting, preventing or breaking down the microbial biofilm. Similarly, the compositions disclosed herein may be used in method embodiments for inhibiting, preventing, or breaking down microbial biofilms on surfaces colonized by biofilms such as, but not limited to, hospital instruments, industrial equipment, and other materials not comprised of living tissue.

For the purpose of the above noted in vitro and in vivo methods, the interfering agent is of the group of:

(a) an isolated or recombinant integration host factor (IHF) polypeptide or a fragment or an equivalent of each thereof;

(b) an isolated or recombinant histone-like protein (HU) polypeptide or a fragment or an equivalent of each thereof;

(c) an isolated or recombinant polypeptide of SEQ ID NOs. 12 to 17, SEQ ID NO. 31, SEQ ID NO. 33, a polypeptide comprising the amino acid sequence NPXT, or a fragment or an equivalent of each thereof.

(d) a polypeptide that competes with an integration host factor on binding to a microbial DNA;

(e) an isolated or recombinant polynucleotide encoding any one of (a) through (f) or an isolated, or a polynucleotide that hybridizes under stringent conditions to the polynucleotide its equivalent or its complement;

(f) an antibody or antigen binding fragment that specifically recognizes or binds any one of (a) through (e), or an equivalent or fragment of each antibody or antigen binding fragment thereof.

(g) isolated or recombinant polynucleotide encoding the antibody or antigen binding fragment of (h) or its complement;

(i) a small molecule that competes with the binding of a DNABII protein or polypeptide to a microbial DNA;

(j) an antibody from the group of (i) the antibody produced by hybridoma cell line IhfA5 nTHI 14G8.F5.G6, (ii) the antibody produced by hybridoma cell line IhfB4 NTHI 4E11.E5.G2, or (iii) the antibody produced by hybridoma cell line mIhfB4 NTHI 12E6.F8.D12.D5;

(k) an antibody or antigen binding fragment comprising one or more of the CDR sequences disclosed herein that include those disclosed in SEQ ID NOs. 58-106, 108, and 109, the heavy chain sequence disclosed in SEQ ID NO. 51, and/or the light chain sequence disclosed in SEQ ID NO. 55, or an equivalent each thereof; or (l) an antibody or antigen binding fragment comprising one or more of the CDR sequences disclosed herein that include those disclosed in SEQ ID NOs. 110-159, the heavy chain sequence disclosed in SEQ ID NO. 53, and/or the light chain sequence disclosed in SEQ ID NO. 57, or an equivalent each thereof.

In some embodiments, the antibody or antigen binding fragment of (f), (j), (k), and/or (l) is not a polyclonal antibody.

In some embodiments the methods disclosed herein comprise, or alternatively consist essentially of, or yet further comprise, administering one or more antibodies alone or in combination. In some embodiments, such a method comprises, or alternatively consists essentially of, or yet further comprises, administering (i) an antibody that specifically recognizes or binds an isolated or recombinant polypeptide consisting essentially of SEQ ID NO. 13 and/or SEQ ID NO. 14 or an equivalent of each thereof and (ii) an antibody that specifically recognizes or binds an isolated or recombinant polypeptide consisting essentially of SEQ ID NO. 16 and/or SEQ ID NO. 17 or an equivalent of each thereof. In some embodiments, such a method comprises, or alternatively consists essentially of, or yet further comprises, administering (i) an antibody that specifically recognizes or binds an isolated or recombinant polypeptide consisting essentially of SEQ ID NO. 12 or an equivalent thereof and (ii) an antibody that specifically recognizes or binds an isolated or recombinant polypeptide consisting essentially of SEQ ID NO. 15 or an equivalent thereof. In further embodiments of the disclosed methods, the antibodies may be administered simultaneously. In alternative embodiments, the antibodies are administered sequentially.

Also provided herein is a method for inducing an immune response in or conferring passive immunity on subject in need thereof, comprising, or alternatively consisting essentially of, or yet further consisting of, administering to the subject an effective amount of one or more of the group:

(a) an isolated or recombinant integration host factor (IHF) polypeptide or a fragment or an equivalent of each thereof.

(b) an isolated or recombinant histone-like protein (HU) polypeptide or a fragment or an equivalent of each thereof.

(c) an isolated or recombinant polypeptide of SEQ ID NOs. 12 to 17, SEQ ID NO. 31, SEQ ID NO. 33, a polypeptide comprising the amino acid sequence NPXT, or a fragment or an equivalent of each thereof.

(d) a polypeptide that competes with an integration host factor on binding to a microbial DNA;

(e) an isolated or recombinant polynucleotide encoding any one of (a) through (f) or an isolated, or a polynucleotide that hybridizes under stringent conditions to the polynucleotide its equivalent or its complement;

(f) an antibody or antigen binding fragment that specifically recognizes or binds any one of (a) through (e), or an equivalent or fragment of each antibody or antigen binding fragment thereof.

(g) an antibody or antigen binding fragment comprising one or more of the CDR sequences disclosed herein that include those disclosed in SEQ ID NOs. 58-106, 108, and 109, the heavy chain sequence disclosed in SEQ ID NO. 51, and/or the light chain sequence disclosed in SEQ ID NO. 55, or an equivalent each thereof;

(h) an antibody or antigen binding fragment comprising one or more of the CDR sequences disclosed herein that include those disclosed in SEQ ID NOs. 110-159, the heavy chain sequence disclosed herein that include those disclosed in SEQ ID NO. 53, and/or the light chain sequence disclosed herein that include those disclosed in SEQ ID NO. 57, or an each equivalent thereof; or isolated or recombinant polynucleotide encoding the antibody or antigen binding fragment of (f) to (h)) or its complement or its equivalent.

In some embodiments, the antibody or antigen binding fragment of (f), (g), and/or (h) is not a polyclonal antibody.

In a further aspect, the methods further comprise, or alternatively consist essentially of, or yet further consist of administering to the subject an effective amount of one or more of an antimicrobial, an antigenic peptide or an adjuvant.

A non-limiting example of an antimicrobial agent are antibodies directed against vaccine component such as a surface antigen, e.g., an OMP P5, rsPilA, OMP 26, OMP P2, or Type IV Pilin protein (see Jurcisek and Bakaletz (2007) J. Bacteriology 189(10):3868-3875; Murphy et al. (2009) The Pediatric Infectious Disease Journal 28:S121-S126; Novotny et al. (2015) Mol Microbiol. 96(2):276-92).

The agents and compositions disclosed herein can be concurrently or sequentially administered with other antimicrobial agents and/or surface antigens. In one particular aspect, administration is locally to the site of the infection by direct injection or by inhalation for example. Other non-limiting examples of administration include by one or more method comprising transdermally, urethrally, sublingually, rectally, vaginally, ocularly, subcutaneous, intramuscularly, intraperitoneally, intranasally, by inhalation or orally.

Microbial infections and disease that can be treated by the methods disclosed herein include but are not limited to infection by various organisms associated with biofilm formation, including but not limited to those disclosed in Examples 4 through 9. Non-limiting examples of relevant organisms (and exemplary strains thereof in parentheses) include: Aggregatibacter *actinomycetemcomitans, Borrelia burgdorferi* (e.g., B31), *Bordetella pertussis* (e.g., Tohama I), *Burkholderia pseudomallei* (e.g., 668), *Burkholderia cenocepacia* (e.g., HI2424), *Escherichia coli* (e.g., K12 MG1655), *Enterococcus faecalis* (e.g., V583), *Haemophilus influenzae* (e.g., Rd KW20), *Helicobacter pylori* (e.g., 26695), *Klebsiella pneumoniae, Moraxella catarrhalis* (e.g., RH4), *Mycobacterium smegmatis* (e.g., MC2), *Mycobacte-*

*rium tuberculosis* (e.g., CDC1551), *Neisseria gonorrhoeae* (e.g., FA1090), *Neisseria meningitidis* (e.g., MC58), *Pseudomonas aeruginosa, Porphyromonas gingivalis* (e.g., W83), *Prevotella intermedia* (e.g., 17), *Prevotella melaninogenica* (e.g., ATCC® 25845), *Staphylococcus aureus* (e.g., MW2), *Staphylococcus epidermidis* (e.g., RP62A), *Streptococcus agalactiae* (e.g., 2603V/R), *Streptococcus bovis, Streptococcus gallolyticus* (e.g., UCN34), *Streptococcus gordonii* (e.g., NCTC 7868 (Challis)), *Streptococcus mutans* (e.g., UA159), *Streptococcus pneumoniae* (e.g., R6), *Streptococcus pyogenes* (e.g., MGAS10270), *Streptococcus sobrinus* (e.g., 6715), *Salmonella enterica* (e.g., typhi, CT18), *Treponema denticola* (e.g., ATCC® 35405), *Treponema palladum* (e.g., Nichols), *Vibrio cholera* (e.g., El Tor, N16961). Additional organisms known to associate with and/or form biofilms include but are not limited to *Campylobacter* spp., *Candida* spp., *Legionella pneumophila*, and *Listeria monocytogenes*. For example, cystic fibrosis patients have *Pseudomonas* infections that often result in antibiotic resistant biofilms. Exemplary diseases associated with biofilms include, but are not limited to, lung infections of cystic fibrosis patients, otitis media, native valve infectious endocarditis, osteomyelitis, rhinosinositis, prostatitis, recurrent urinary tract infection, wounds, dental caries and periodontitis. Conditions such as an infected artificial device, joint, catheter, stent or other surgical implant are also associated with biofilm formation.

These microbial infections may be present in the upper, mid and lower airway (otitis, sinusitis, bronchitis but also exacerbations of chronic obstructive pulmonary disease (COPD), chronic cough, complications of and/or primary cause of cystic fibrosis (CF) and community acquired pneumonia (CAP). Thus, by practicing the in vivo methods disclosed herein, these diseases and complications from these infections can also be prevented or treated.

Infections might also occur in the oral cavity (caries, periodontitis) and caused by *Streptococcus mutans, Porphyromonas gingivalis*, Aggregatibacter actinomvctemcomitans. Infections might also be localized to the skin (abscesses, 'staph' infections, impetigo, secondary infection of burns, Lyme disease) and caused by *Staphylococcus aureus, Staphylococcus epidermidis, Pseudomonas aeruginosa* and *Borrelia burdorferi*. Infections of the urinary tract (UTI) can also be treated and are typically caused by *Escherichia coli*. Infections of the gastrointestinal tract (GI) (diarrhea, cholera, gall stones, gastric ulcers) are typically caused by *Salmonella enterica* serovar, *Vibrio cholerae* and *Helicobacter pylori*. Infections of the genital tract include and are typically caused by *Neisseria gonorrhoeae*. Infections can be of the bladder or of an indwelling device caused by *Enterococcus faecalis*. Infections associated with implanted prosthetic devices, such as artificial hip or knee replacements, or dental implants, or medical devices such as pumps, catheters, stents, or monitoring systems, typically caused by a variety of bacteria, can be treated by the methods disclosed herein. These devices can be coated or conjugated to an agent as described herein. Thus, by practicing the in vivo methods disclosed herein, these diseases and complications from these infections can also be prevented or treated.

Infections caused by *Streptococcus agalactiae* can also be treated by the methods disclosed herein and it is the major cause of bacterial septicemia in newborns. Infections caused by *Neisseria meningitidis* which can cause meningitis can also be treated.

Thus, routes of administration applicable to the methods disclosed herein include intranasal, intramuscular, urethrally, intratracheal, subcutaneous, intradermal, topical application, intravenous, rectal, nasal, oral, inhalation, and other enteral and parenteral routes of administration. Routes of administration may be combined, if desired, or adjusted depending upon the agent and/or the desired effect. An active agent can be administered in a single dose or in multiple doses. Embodiments of these methods and routes suitable for delivery, include systemic or localized routes. In general, routes of administration suitable for the methods disclosed herein include, but are not limited to, direct injection, enteral, parenteral, or inhalational routes.

Parenteral routes of administration other than inhalation administration include, but are not limited to, topical, transdermal, subcutaneous, intramuscular, intraorbital, intracapsular, intraspinal, intrasternal, and intravenous routes, i.e., any route of administration other than through the alimentary canal. Parenteral administration can be conducted to effect systemic or local delivery of the inhibiting agent. Where systemic delivery is desired, administration typically involves invasive or systemically absorbed topical or mucosal administration of pharmaceutical preparations.

The interfering agents disclosed herein can also be delivered to the subject by enteral administration. Enteral routes of administration include, but are not limited to, oral and rectal (e.g., using a suppository) delivery.

Methods of administration of the active through the skin or mucosa include, but are not limited to, topical application of a suitable pharmaceutical preparation, transcutaneous transmission, transdermal transmission, injection and epidermal administration. For transdermal transmission, absorption promoters or iontophoresis are suitable methods. Iontophoretic transmission may be accomplished using commercially available "patches" that deliver their product continuously via electric pulses through unbroken skin for periods of several days or more.

In various embodiments of the methods disclosed herein, the interfering agent will be administered by inhalation, injection or orally on a continuous, daily basis, at least once per day (QD), and in various embodiments two (BID), three (TID), or even four times a day. Typically, the therapeutically effective daily dose will be at least about 1 mg, or at least about 10 mg, or at least about 100 mg, or about 200-about 500 mg, and sometimes, depending on the compound, up to as much as about 1 g to about 2.5 g.

This disclosure provides methods and compositions to inhibit or prevent infection of a host or host cell by a bacteria that exports an DNABII protein, the methods and compositions comprising, or alternatively consisting essentially of, or yet further consisting of, administering to a tissue exposed to or infected with the bacteria an effective amount of an bacteria-relevant antibody that specifically recognizes and binds the DNABII protein, thereby inhibiting or preventing infection of the host or host cell by the bacteria. The antibody can be polyclonal, monoclonal or a derivative of an antibody that recognizes and binds the bacteria-relevant DNABII protein. Multiple antibodies can be administered concurrently or sequentially along with supporting therapies as noted herein. Non-limiting exemplary antibodies include those disclosed herein, for example those generated against the disclosed polypeptide fragments, including but not limited to:

(a) SEQ ID NO. 12 (FLEEIRLSLESGQDVKLSGF);
(b) SEQ ID NO. 13 (RPGRNPKTGDVVPVSARRVV);
(c) SEQ ID NO. 14 (RTGRNPQTGAEIQIAASKVP);
(d) SEQ ID NO. 15 (TLSAKEIENMVKDILEFISQ);
(e) SEQ ID NO. 16 (RGFGSFSLHHRQPRLGRNPK);
(f) SEQ ID NO. 17 (FSLHHRQPRLGRNPKTGDSV);

(g) SEQ ID NO. 33 (KKQAKAALEATLDAI-TASLKEG);
(h) SEQ ID NO. 31 (VNERAARTGR NPQTGAEIQIAA);
(i) a polypeptide comprising the amino acid sequence NPXT; or
(j) an equivalent of (a) through (i), wherein an equivalent comprises an amino acid sequence having at least about 80% homology or amino acid identity thereto, or an amino acid encoded by polynucleotide that hybridizes under conditions of high stringency to a polynucleotide encoding the amino acid sequence or its complement, wherein conditions of high stringency comprises incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water.

In some embodiments, the antibody is not a polyclonal antibody.

Owing to the omnipresence of these DNABII proteins associated with the bacterial surface throughout the life cycle of the cell inclusive of all states, e.g. individual, aggregated or resident biofilm bacteria, antisera directed to DNABII proteins may interfere with interactions with the host cell surface including, attachment and subsequent invasion. Bacteria that can invade and propagate in host cells are protected from the host's immune system and antimicrobial therapy. Rendering bacteria incapable of binding and invasion makes them susceptible to clearance by the immune system and administered antimicrobials. The source of antibody against the DNABII protein can be elicited by either active vaccination of the host with DNABII protein or fragments thereof or passive transfer of antiserum or an antibody against the DNABII protein. Non-limiting examples of suitable polypeptide fragments, include but are not limited to:
(a) SEQ ID NO. 12 (FLEEIRLSLESGQDVKLSGF);
(b) SEQ ID NO. 13 (RPGRNPKTGDVVPVSARRVV);
(c) SEQ ID NO. 14 (RTGRNPQTGAEIQIAASKVP);
(d) SEQ ID NO. 15 (TLSAKEIENMVKDILEFISQ);
(e) SEQ ID NO. 16 (RGFGSFSLHHRQPRLGRNPK);
(f) SEQ ID NO. 17 (FSLHHRQPRLGRNPKTGDSV);
(g) SEQ ID NO. 33 (KKQAKAALEATLDAI-TASLKEG);
(h) SEQ ID NO. 31 (VNERAARTGR NPQTGAEIQIAA);
(i) a polypeptide comprising the amino acid sequence NPXT; or
(j) an equivalent of (a) through (i), wherein an equivalent comprises an amino acid sequence having at least about 80% homology or amino acid identity thereto, or an amino acid encoded by polynucleotide that hybridizes under conditions of high stringency to a polynucleotide encoding the amino acid sequence or its complement, wherein conditions of high stringency comprises incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water.

This disclosure provides a method to inhibit or prevent infection of a cell by a bacteria that exports an DNABII protein. The method comprises, or alternatively consists essentially of, or yet further consists of, administering to a tissue infected with the bacteria an effective amount of an antibody that specifically recognizes and binds the DNABII protein, thereby inhibiting or preventing infection of the bacteria. The source of antibody against the DNABII proteins can be elicited by either active vaccination of the host with the DNABII protein or passive transfer of antiserum or an antibody against proteins of the DNABII protein. The antibody can be polyclonal, monoclonal or a derivative of an antibody that recognizes and binds the bacteria-relevant DNABII protein. Multiple antibodies can be administered concurrently or sequentially along with supporting therapies as noted herein. Non-limiting exemplary antibodies include those disclosed herein, for example those generated against the disclosed polypeptide fragments, including but not limited to:
(a) SEQ ID NO. 12 (FLEEIRLSLESGQDVKLSGF);
(b) SEQ ID NO. 13 (RPGRNPKTGDVVPVSARRVV);
(c) SEQ ID NO. 14 (RTGRNPQTGAEIQIAASKVP);
(d) SEQ ID NO. 15 (TLSAKEIENMVKDILEFISQ);
(e) SEQ ID NO. 16 (RGFGSFSLHHRQPRLGRNPK);
(f) SEQ ID NO. 17 (FSLHHRQPRLGRNPKTGDSV);
(g) SEQ ID NO. 33 (KKQAKAALEATLDAI-TASLKEG);
(h) SEQ ID NO. 31 (VNERAARTGR NPQTGAEIQIAA);
(i) a polypeptide comprising the amino acid sequence NPXT; or
(j) an equivalent of (a) through (i), wherein an equivalent comprises an amino acid sequence having at least about 80% homology or amino acid identity thereto, or an amino acid encoded by polynucleotide that hybridizes under conditions of high stringency to a polynucleotide encoding the amino acid sequence or its complement, wherein conditions of high stringency comprises incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water.

In some embodiments, the antibody is not a polyclonal antibody.

The administration can be in vitro in a culture or in vivo, by administration to a patient infected with the bacteria. When practiced in vivo, the method can be used to treat a subject infected with the bacteria by administering to the infected subject an effective amount of the antibody. In addition, when the subject is a non-human animal, the method can be used to test possible therapies or combination therapies prior to administration to a human. When practiced in vitro, the method is useful to screen for other therapeutic agents and combination therapies, such as small molecule drugs, that inhibit or prevent infection of the bacteria in a tissue.

Also provided are methods to treat a bacterial infection in subject in need thereof, wherein the subject is infected with a bacteria that comprises an DNABII protein, the method comprising, or alternatively consisting essentially of, or yet further consisting of, administering to the subject an effective amount of an antibody that specifically recognizes and binds the DNABII protein, thereby inhibiting or preventing infection by the bacteria. The antibody can be polyclonal, monoclonal or a derivative of an antibody that recognizes and binds the bacteria-relevant DNABII protein. The source of antibody against the DNABII protein can be elicited by either active vaccination of the host with the DNABII protein or passive transfer of antiserum or an antibody against proteins of the DNABII protein. Multiple antibodies can be administered concurrently or sequentially along with supporting therapies as noted herein. Non-limiting exemplary antibodies include those disclosed herein, for example those generated against the disclosed polypeptide fragments, including but not limited to:

(a) SEQ ID NO. 12 (FLEEIRLSLESGQDVKLSGF);
(b) SEQ ID NO. 13 (RPGRNPKTGDVVPVSARRVV);
(c) SEQ ID NO. 14 (RTGRNPQTGAEIQIAASKVP);
(d) SEQ ID NO. 15 (TLSAKEIENMVKDILEFISQ);
(e) SEQ ID NO. 16 (RGFGSFSLHHRQPRLGRNPK);
(f) SEQ ID NO. 17 (FSLHHRQPRLGRNPKTGDSV);
(g) SEQ ID NO. 33 (KKQAKAALEATLDAI-TASLKEG);
(h) SEQ ID NO. 31 (VNERAARTGRNPQTGAEIQIAA);
(i) a polypeptide comprising the amino acid sequence NPXT; or
(j) an equivalent of (a) through (i), wherein an equivalent comprises an amino acid sequence having at least about 80% homology or amino acid identity thereto, or an amino acid encoded by polynucleotide that hybridizes under conditions of high stringency to a polynucleotide encoding the amino acid sequence or its complement, wherein conditions of high stringency comprises incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water.

In some embodiments, the antibody is not a polyclonal antibody.

Yet further provided are methods to treat a condition in a subject in need thereof, wherein the condition is associated with a bacterial infection wherein the bacteria expresses an DNABII protein, the method comprising, or alternatively consisting essentially of, or yet further consisting of, administering to the subject an effective amount of an antibody that specifically recognizes and binds the DNABII protein, thereby inhibiting or preventing infection of the bacteria. The source of antibody against the DNABII protein can be elicited by either active vaccination of the host with the DNABII protein or passive transfer of antiserum or an antibody against the DNABII protein. The antibody can be polyclonal, monoclonal or a derivative of an antibody that recognizes and binds the bacteria-relevant DNABII protein. Multiple antibodies can be administered concurrently or sequentially along with supporting therapies as noted herein. Non-limiting exemplary antibodies include those disclosed herein, for example those generated against the disclosed polypeptide fragments, including but not limited to:
(a) SEQ ID NO. 12 (FLEEIRLSLESGQDVKLSGF);
(b) SEQ ID NO. 13 (RPGRNPKTGDVVPVSARRVV);
(c) SEQ ID NO. 14 (RTGRNPQTGAEIQIAASKVP);
(d) SEQ ID NO. 15 (TLSAKEIENMVKDILEFISQ);
(e) SEQ ID NO. 16 (RGFGSFSLHHRQPRLGRNPK);
(f) SEQ ID NO. 17 (FSLHHRQPRLGRNPKTGDSV);
(g) SEQ ID NO. 33 (KKQAKAALEATLDAI-TASLKEG);
(h) SEQ ID NO. 31 (VNERAARTGRNPQTGAEIQIAA);
(i) a polypeptide comprising the amino acid sequence NPXT; or
(j) an equivalent of (a) through (i), wherein an equivalent comprises an amino acid sequence having at least about 80% homology or amino acid identity thereto, or an amino acid encoded by polynucleotide that hybridizes under conditions of high stringency to a polynucleotide encoding the amino acid sequence or its complement, wherein conditions of high stringency comprises incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water.

In some embodiments, the antibody is not a polyclonal antibody.

Any of the above methods can further comprise, or alternatively consist essentially of, or yet further consist of, administering to the subject or the tissue or cell culture in vitro, an effective amount of one or more of an antimicrobial, an antigenic peptide or an adjuvant. The subject, in some aspects, is a non-human animal or a human patient.

The antibody, polypeptide or composition is administered locally or systemically by any appropriate method, e.g., to the site of infection or biofilm, topically, rectally, vaginally, ocularly, subcutaneous, intramuscularly, intraperitoneally, urethrally, intranasally, by inhalation or orally.

In some aspects, the subject is a pediatric patient and the antibody is administered in a formulation for the pediatric patient.

A screen to identify potential therapeutic agents that inhibit or prevent infection of a cell by a bacteria that exports a DNABII protein and/or that disrupt or prevent biofilm formation is also disclosed. The screening method comprises, or alternatively consists essentially of, or yet consists of, contacting in vitro or administering in vivo to a tissue infected with the bacteria an agent and determining if the agent binds the DNABII protein. Methods to determining binding are known in the art and several non-limiting examples are described herein. In one aspect, if the agent binds the protein, the agent is a potential therapeutic agent and if the agent does not bind the protein, the agent is not a potential therapeutic agent. In another aspect, if the infection or biofilm is inhibited, disrupted, or prevented in vivo, the agent is a potential therapeutic agent and if infection is not inhibited or prevented, the agent is not a potential therapeutic agent. Methods of determining if the infection is inhibited or prevented are known in the art and several non-limiting examples are described herein; methods of determining if a biofilm is disrupted or prevented are known in the art and further disclosed herein. Non-limiting examples of potential therapeutic agents are from the group of: an antibody, an antibody derivative, a polypeptide or a small molecule. Multiple antibodies can be administered concurrently or sequentially along with supporting therapies as noted herein. Non-limiting exemplary antibodies include those disclosed herein, for example those generated against the disclosed polypeptide fragments, including but not limited to:
(a) SEQ ID NO. 12 (FLEEIRLSLESGQDVKLSGF);
(b) SEQ ID NO. 13 (RPGRNPKTGDVVPVSARRVV);
(c) SEQ ID NO. 14 (RTGRNPQTGAEIQIAASKVP);
(d) SEQ ID NO. 15 (TLSAKEIENMVKDILEFISQ);
(e) SEQ ID NO. 16 (RGFGSFSLHHRQPRLGRNPK);
(f) SEQ ID NO. 17 (FSLHHRQPRLGRNPKTGDSV);
(g) SEQ ID NO. 33 (KKQAKAALEATLDAI-TASLKEG);
(h) SEQ ID NO. 31 (VNERAARTGRNPQTGAEIQIAA);
(i) a polypeptide comprising the amino acid sequence NPXT; or
(j) an equivalent of (a) through (i), wherein an equivalent comprises an amino acid sequence having at least about 80% homology or amino acid identity thereto, or an amino acid encoded by polynucleotide that hybridizes under conditions of high stringency to a polynucleotide encoding the amino acid sequence or its complement, wherein conditions of high stringency comprises incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water.

In some embodiments, the antibody is not a polyclonal antibody.

In a further aspect, the agent binds the protein and the binding is compared to the binding of anti-DNABII antisera to the protein, e.g., antisera directed against an DNABII protein.

It should be appreciated that any of the general properties contemplated with respect of the interfering agent for inhibiting, titrating, or competing the binding of a DNABII protein to a microbial DNA should likewise apply to the above disclosed methods relating to bacterial infection.

Dosing can be accomplished in accordance with the methods disclosed herein using capsules, tablets, oral suspension, suspension for intra-muscular injection, suspension for intravenous infusion, get or cream for topical application, or suspension for intra-articular injection.

Dosage, toxicity and therapeutic efficacy of compositions described herein can be determined by standard pharmaceutical procedures in cell cultures or experimental animals, for example, to determine the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. In certain embodiments, compositions exhibit high therapeutic indices. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies (in certain embodiments, within a range of circulating concentrations that include the ED50 with little or no toxicity. The dosage may vary within this range depending upon the dosage form employed and the route of administration utilized. For any compound used in the methods, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In some embodiments, an effective amount of a composition sufficient for achieving a therapeutic or prophylactic effect, ranges from about 0.000001 mg per kilogram body weight per administration to about 10,000 mg per kilogram body weight per administration. Suitably, the dosage ranges are from about 0.0001 mg per kilogram body weight per administration to about 100 mg per kilogram body weight per administration. Administration can be provided as an initial dose, followed by one or more "booster" doses. Booster doses can be provided a day, two days, three days, a week, two weeks, three weeks, one, two, three, six or twelve months after an initial dose. In some embodiments, a booster dose is administered after an evaluation of the subject's response to prior administrations.

The skilled artisan will appreciate that certain factors may influence the dosage and timing required to effectively treat a subject, including but not limited to, the severity of the disease or disorder, previous treatments, the general health and/or age of the subject, and other diseases present. Moreover, treatment of a subject with a therapeutically effective amount of the therapeutic compositions described herein can include a single treatment or a series of treatments.

Functional Analysis with Antibodies

Antibodies disclosed herein can be used to purify the polypeptides disclosed herein and to identify biological equivalent polypeptide and/or polynucleotides. They also can be used to identify agents that modify the function of the polypeptides disclosed herein, e.g., aptamer, polynucleotides and small molecules. These antibodies include polyclonal antisera, monoclonal antibodies, and various reagents derived from these preparations that are familiar to those practiced in the art and described above.

Antibodies that neutralize the activities of proteins encoded by identified genes can also be used in vivo and in vitro to demonstrate function by adding such neutralizing antibodies into in vivo and in vitro test systems. They also are useful as pharmaceutical agents to modulate the activity of polypeptides disclosed herein.

Various antibody preparations can also be used in analytical methods such as ELISA assays or Western blots to demonstrate the expression of proteins encoded by the identified genes by test cells in vitro or in vivo. Fragments of such proteins generated by protease degradation during metabolism can also be identified by using appropriate polyclonal antisera with samples derived from experimental samples.

Further, in some embodiments, the antibodies disclosed herein may be used to visualize and/or detect biofilms. In such embodiments, the antibodies may be detectably labeled, e.g., with a radioisotope, an enzyme which generates a detectable product, a fluorescent protein, and the like or conjugated to other moieties, such as members of specific binding pairs, e.g., biotin (member of biotin-avidin specific binding pair), and the like. Detectably labeled antibodies may then be introduced to the sample suspected of being colonized by a biofilm and visualized and/or detected through microscopy or other methods known to detect the relevant label, e.g., spectroscopy, cytometry, or other common techniques. Conjugated antibodies or unlabeled antibodies may likewise be identified through known analytical methods targeting the conjugated moiety or antibody, respectively. For example, in some embodiments, a detectably labeled secondary antibody specific to the isotype of the antibodies disclosed herein may be used in the visualization and/or detection of a biofilm; such embodiments may entail the administration of the antibody specific to the "tail" of a DNABII protein to the surface suspected of being colonized by a biofilm, followed by the administration of the detectably labeled secondary antibody and the subsequent detection of the relevant label.

In some embodiments, use of antibodies specific to the "tail" of a DNABII protein (e.g., SEQ ID NOs. 12, 15, and 33), an amino acid sequence of a DNABII protein that does not comprise or is engineered to exclude the consensus amino acid sequence NPXT,oranequivalenteachthereof is envisioned to visualize or detect the presence of a biofilm on a surface according to the methods described hereinabove. In some embodiments, the antibody is not a polyclonal antibody. In further embodiments, one or more antibodies disclosed herein above may be used for the treatment of the detected biofilm according to the methods described hereinabove. Non-limiting examples of the antibodies that may be used in this step include, but are not limited to, antibodies specific to the "tip" of a DNABII protein (e.g., SEQ ID NOs. 13, 14, 16, and 17), an amino acid sequence that conforms to a sharp turn as part of an anti-parallel beta ribbon, a polypeptide comprising the amino acid sequence sequence NPXT, SEQ ID NO. 31, or an equivalent each thereof. In some embodiments, the antibody is not a polyclonal antibody.

The antibodies disclosed herein may be used for vaccination or to boost vaccination, alone or in combination with peptides or protein-based vaccines or dendritic-cell based vaccines.

Screening Assays

The present disclosure provides methods for screening for equivalent agents, such as equivalent monoclonal antibodies and fragments thereof to exemplified antibodies as described herein and various agents that modulate the activity of the active agents and pharmaceutical compositions disclosed herein or the function of a polypeptide or peptide product encoded by the polynucleotide disclosed herein. For the purposes of this disclosure, an "agent" is intended to include, but not be limited to a biological or chemical compound such as a simple or complex organic or inorganic molecule, a peptide, a protein (e.g., antibody), a polynucleotide anti-sense) or a ribozyme. A vast array of compounds can be synthesized, for example polymers, such as polypeptides and polynucleotides, and synthetic organic compounds based on various core structures, and these are also included in the term "agent." In addition, various natural sources can provide compounds for screening, such as plant or animal extracts, and the like. It should be understood, although not always explicitly stated that the agent is used alone or in combination with another agent, having the same or different biological activity as the agents identified by the inventive screen.

To practice the screening method in vitro, suitable cell culture or tissue infected with the microbial to be treated are first provided. The cells are cultured under conditions (temperature, growth or culture medium and gas ($CO_2$) and for an appropriate amount of time to attain exponential proliferation without density dependent constraints. It also is desirable to maintain an additional separate cell culture that is not infected as a control.

As is apparent to one of skill in the art, suitable cells can be cultured in micro-titer plates and several agents can be assayed at the same time by noting genotypic changes, phenotypic changes or a reduction in microbial titer.

When the agent is a composition other than a DNA or RNA, such as a small molecule as described above, the agent can be directly added to the cell culture or added to culture medium for addition. As is apparent to those skilled in the art, an "effective" a mount must be added which can be empirically determined.

When the agent is an antibody or antigen binding fragment, the agent can be contacted or incubated with the target antigen and polyclonal antibody as described herein under conditions to perform a competitive ELISA. Such methods are known to the skilled artisan.

The assays also can be performed in a subject. When the subject is an animal such as a rat, chinchilla, mouse or simian, the method provides a convenient animal model system that can be used prior to clinical testing of an agent in a human patient. In this system, a candidate agent is a potential drug if symptoms of the disease or microbial infection is reduced or eliminated, each as compared to untreated, animal having the same infection. It also can be useful to have a separate negative control group of cells or animals that are healthy and not treated, which provides a basis for comparison.

Additional screening assays specific to antibodies contemplated herein include those methods suitable for identifying an antibody or agent which specifically binds to one or more of the polypeptides disclosed herein. This method involves identifying an antibody binding to a site on the antigen to which the antibody of the present invention binds.

An antibody binding site can be determined through methods known to those skilled in the art. For example, when the antibody binds to or recognizes the partial conformation of the antigen, the binding site for the antibody can be determined by identifying amino acid residues on the antigen adjacent to the antibody using X-ray structural analysis. For example, the antibody or its fragment and the antigen or its fragment can be bound to each other and crystallized, followed by structural analysis to identify each amino acid residue on the antigen having an interactional distance with the antibody. The interactional distance is 8 angstroms or shorter, preferably 6 angstroms or shorter, more preferably 4 angstroms or shorter. One or more such amino acid residues having an interactional distance with the antibody can constitute a site (epitope) on the antigen to which the antibody binds. Two or more such amino acid residues may not be adjacent to each other on the primary sequence. Such structural analysis can provide the three-dimensional structure of the protein, therefore yielding both the sequence and conformation of the identified epitope.

A test antibody or agent may be contacted with one or more of the polypeptides disclosed herein. Subsequently, the distance is measured between the substance and amino acid residues constituting the epitope to which any one of the antibodies disclosed herein bind. The test antibody or agent can be determine to specifically bind if it has an appropriate interaction distance with each of the residues. In some embodiments, the test antibody is not a polyclonal antibody.

In some embodiments, the test antibody or agent is analyzed based on its interaction with a the conformational epitope identified by structural analysis of the antibody-antigen interaction. A non-limiting example of such a conformational epitope is a 0 hairpin, which may be comprised in one or more of the polypeptides disclosed herein. An additional non-limiting exemplary epitope is an amino acid sequence that conforms to a sharp turn as part of an anti-parallel beta ribbon, such as the consensus amino acid sequence NPXT, wherein "X" refers to any amino acid. In some embodiments, X is selected from the amino acids Q, R, K, S, or T. Non-limiting examples of such are disclosed herein with the consensus amino acid sequence NPXT, in underlined and bolded text. A skilled artisan will appreciate that in any one of these sequences, the residue in the X position (marked with a doubleunderline in the below examples) may be substituted with any amino acid—e.g., Q, R, K, S, or T. Examples include:

SEQ ID NO. 13: *Haemophilus influenzae* IhfA, A5 fragment:

RPGRNPKTGDVVPVSARRVV.

SEQ ID NO. 14: *Haemophilus influenzae* HU, A5 fragment:

RTGRNPQTGAEIQIAASKVP.

SEQ ID NO. 17: *Haemophilus influenzae* IhfB, modified B4 (mB4) fragment:

FSLHHRQPRLGRNPKTGDSV.

SEQ ID NO. 26: *Haemophilus influenzae* IhfA, A tip fragment:

NFELRDKSSRPGRNPKTGDVV.

SEQ ID NO. 27: *Haemophilus influenzae* IhfB, B tip fragment:

SLHHRQPRLGRNPKTGDSVNL.

SEQ ID NO. 31 *Haemophilus influenzae* HU, fragment:

VNERAARTGRNPQTGAEIQIAA.

In some embodiments, the polypeptide comprising NPXT is at least about 20 amino acids long and the NPXT is located approximately centrally in the sequence. Non-limiting examples of such sequences include SEQ ID NOs. 13, 14, and 31.

The agents and compositions can be used in the manufacture of medicaments and for the treatment of humans and other animals by administration in accordance with conventional procedures, such as an active ingredient in pharmaceutical compositions.

Combination Therapy

The compositions and related methods of the present disclosure may be used in combination with the administration of other therapies. These include, but are not limited to, the administration of DNase enzymes, antibiotics, antimicrobials, or other antibodies.

In some embodiments, the methods and compositions include a deoxyribonuclease (DNase) enzyme that acts synergistically with the anti-DNABII antibody. A DNase is any enzyme that catalyzes the cleavage of phosphodiester linkages in the DNA backbone. Three non-limiting examples of DNase enzymes that are known to target not only cruciform structures, but also a variety of secondary structure of DNA include DNAse I, T4 EndoVII and T7 Endo I. In certain embodiments, the effective amount of anti-DNABII antibody needed to destabilize the biofilm is reduced when combined with a DNase. When administered in vitro, the DNase can be added directly to the assay or in a suitable buffer known to stabilize the enzyme. The effective Unit dose of DNase and the assay conditions may vary, and can be optimized according to procedures known in the art.

In other embodiments, the methods and compositions can be combined with antibiotics and/or antimicrobials. Antimicrobials are substances that kill or inhibit the growth of microorganisms such as bacteria, fungi, or protozoans. Although biofilms are generally resistant to the actions of antibiotics, compositions and methods described herein can be used to sensitize the infection involving a biofilm to traditional therapeutic methods for treating infections. In other embodiments, the use of antibiotics or antimicrobials in combination with methods and compositions described herein allow for the reduction of the effective amount of the antimicrobial and/or biofilm reducing agent. Some non-limiting examples of antimicrobials and antibiotics useful in combination with methods of the current disclosure include amoxicillin, amoxicillin-clavulanate, cefdinir, azithromycin, and sulfamethoxazole-trimethoprim. The therapeutically effective dose of the antimicrobial and/or antibiotic in combination with the biofilm reducing agent can be readily determined by traditional methods. In some embodiments the dose of the antimicrobial agent in combination with the biofilm reducing agent is the average effective dose which has been shown to be effective in other bacterial infections, for example, bacterial infections wherein the etiology of the infection does not include a biofilm. In other embodiments, the dose is 0.1, 0.15, 0.2, 0.25, 0.30, 0.35, 0.40, 0.45, 0.50, 0.55, 0.60, 0.65, 0.70, 0.75, 0.8, 0.85, 0.9, 0.95, 1.1, 1.2, 1.3, 1.4, 1.5, 1.6, 1.7, 1.8, 1.9, 2.0, 2.5, 3.0 or 5 times the average effective dose. The antibiotic or antimicrobial can be added prior to, concurrent with, or subsequent to the addition of the anti-DNABII antibody.

In other embodiments, the methods and compositions can be combined with antibodies that treat the bacterial infection. One example of an antibody useful in combination with the methods and compositions described herein is an antibody directed against an unrelated outer membrane protein (i.e., OMP P5). Treatment with this antibody alone does not debulk a biofilm in vitro. Combined therapy with this antibody and a biofilm reducing agent results in a greater effect than that which could be achieved by either reagent used alone at the same concentration. Other antibodies that may produce a synergistic effect when combined with a biofilm reducing agent or methods to reduce a biofilm include anti-rsPilA anti-OMP26, anti-OMP P2, and anti-whole OMP preparations.

The compositions and methods described herein can be used to sensitize the bacterial infection involving a biofilm to common therapeutic modalities effective in treating bacterial infections without a biofilm but are otherwise ineffective in treating bacterial infections involving a biofilm. In other embodiments, the compositions and methods described herein can be used in combination with therapeutic modalities that are effective in treating bacterial infections involving a biofilm, but the combination of such additional therapy and biofilm reducing agent or method produces a synergistic effect such that the effective dose of either the biofilm reducing agent or the additional therapeutic agent can be reduced. In other instances the combination of such additional therapy and biofilm reducing agent or method produces a synergistic effect such that the treatment is enhanced. An enhancement of treatment can be evidenced by a shorter amount of time required to treat the infection.

The additional therapeutic treatment can be added prior to, concurrent with, or subsequent to methods or compositions used to reduce the biofilm, and can be contained within the same formation or as a separate formulation.

Kits

Kits containing the agents and instructions necessary to perform the in vitro and in vivo methods as described herein also are claimed. Accordingly, the disclosure provides kits for performing these methods which may include an interfering disclosed herein as well as instructions for carrying out the methods disclosed herein such as collecting tissue and/or performing the screen, and/or analyzing the results, and/or administration of an effective amount of an interfering agent as defined herein. These can be used alone or in combination with other suitable antimicrobial agents.

For example, a kit can comprise, or alternatively consist essentially of, or yet further consist of any one or more agent of the group of an isolated or recombinant integration host factor (IHF) polypeptide or a fragment or an equivalent of each thereof; an isolated or recombinant polypeptide of SEQ ID NO. 12 to 17, SEQ ID NO. 33, or a fragment or an equivalent of each thereof or a polynucleotide encoding same; a polypeptide that competes with an integration host factor on binding to a microbial DNA; an isolated or recombinant polynucleotide encoding any one of the above noted polypeptides; an antibody that specifically recognizes or binds any one of the above noted polypeptides, or an equivalent or fragment thereof; or a small molecule that competes with the binding of a DNABII protein or polypeptide to a microbial DNA, and instructions for use. The kit can further comprising one or more of an adjuvant, an antigenic peptide or an antimicrobial. Examples of carriers include a liquid carrier, a pharmaceutically acceptable carrier, a solid phase carrier, a pharmaceutically acceptable carrier, a pharmaceutically acceptable polymer, a liposome, a micelle, an implant, a stent, a paste, a gel, a dental implant, or a medical implant.

The following examples are intended to illustrate, and not limit the embodiments disclosed herein.

EXAMPLES

Example 1: Generation of Antibodies

IHF and HU antibodies, proteins and polypeptides were generated to IHF and HU as a whole and to specific fragments.

The methods to produce them are well known to the skilled artisan, e.g., as described in Granston and Nash (1993) J. Mol. Biol. 234:45-59; Nash et al. (1987) Journal of Bacteriology 169(9):4124-4127; and Rice et al. (1996) Cell, 87:1295-1306. Briefly, to overproduce IHF-α (SEQ ID NO. 6), the himA gene was inserted downstream from the $P_L$ promoter in the bacterial plasmid pAD284. Transformants of strain K5607, a lambda lysogen of strain C600himA42 that had received the desired plasmid, were identified by screening ampicillin-resistant transformants for the ability to grow bacteriophage Mu. DNA was prepared from himA$^+$ transformants according to standard DNA isolation techniques, and the orientation of the himA gene was determined by restriction enzyme cleavage. Plasmid pPLhimA-1, which has the himA gene in the proper orientation for expression by the $P^L$ promoter, was transformed into strain N5271, which contains a cryptic lambda prophage expressing the cI857 thermoinducible repressor, to yield strain K5770.

To overproduce IHF-β (SEQ ID NO. 7), plasmid pKT23-hip323, which contains a fusion of the IHF-, -coding sequence to the bacteriophage lambda $P_L$ promoter was used. pKT23-hip323 was introduced into N5271 to give strain E443. To facilitate the selection of pKT23-hip323 in the presence of another plasmid, changed its selectable marker was changed from ampicillin resistance (bla$^+$) to chloramphenicol resistance (cat$^-$). A cat-containing fragment was isolated from plasmid pBR325 as described by Flamm and Weisberg and was inserted into the unique ScaI site in bla. The ligated DNA was introduced into strain E403, which carries a hip mutation and which synthesizes temperature-sensitive X repressor, and chloramphenicol-resistant transformants were selected at low temperature. One such transformant (E735) was hip$^+$ and ampicillin sensitive; it therefore appears to carry a bla cat$^+$ derivative of pKT23-hip323 (pE735).

To generate a strain that overproduces both subunits of IHF, E735 was transformed with plasmid pP$_L$himA-1, selecting transformant (E738) that had become ampicillin resistant and had retained chloramphenicol resistance. The generation of a second strain that overproduces both subunits of depended on the construction of plasmid pP$_L$hip himA-5, which was made by ligating blunted (SstII restriction enzyme site) containing the pheT and himA genes into the pKT23-hip323 plasmid. This is described in further detail in (Nash et al. (1987) J. Bacteriology 169(9):4124-4127. himA$^+$ transformants of strain K5607 were identified by screening for HimA$^+$, and the plasmid DNA was analyzed by restriction digestion. In all cases where the plasmid structure was obvious, two copies of himA had been ligated as a tandem direct repeat into the vector. It is not known if the presence of two copies of the himA gene on this plasmid is demanded by the selection, but it should be recalled that a single copy of the himA gene in plasmid pP$_L$himA-1 is sufficient to complement a himA mutant. Plasmid pP$_L$hiphimA-5 was used to transform strain N5271 to yield strain K5746.

The same procedure was replicated to overproduce HU (SEQ ID NO. 3).

Cells were grown in shaking water bath at 31° C. in TBY medium (10 g of tryptone, 5 g of yeast extract, and 5 g of sodium chloride per liter). At mid-log phase (optical density at 650 nm, ca. 0.6), the cells were shifted to a 42° C. water bath and shaking was continued. Typically, 300 ml of culture was centrifuged and suspended in 0.6 to 0.9 ml of TEG (20 mM Tris hydrochloride (pH 7.4), 1 mM sodium EDTA, 10% glycerol) containing 20 mM NaCl. The cells were disrupted with six 20-s bursts of sonication, with 40 s between each burst. A portion of the sonic extract was centrifuged in a Somali SS34 rotor for 20 min at 15,000 rpm. Samples of the sonic extract were analyzed by sodium dodecyl sulfate (SDS) gel electrophoresis according to standard molecular biology techniques.

Purification of was done according to the following: A 3.6-liter batch of cells was induced for 3 h. All subsequent steps were carried out at 0 to 4° C. The cell pellet from 3.3-liters was suspended in 10 ml of TEG containing 20 mM NaCl to give a total volume of 29 ml; this suspension was disrupted in two batches, each receiving six bursts of 3 min of sonication separated by 90-s intervals. The sonic extract was centrifuged for 20 min at 15,000 rpm, yielding 16.9 ml of clarified extract. A 10% (vol/vol) solution (1.1 ml) of polymin P (BDH Chemicals Ltd.) was added slowly to the clarified extract; after being stirred for 20 mm, the mixture was centrifuged for 30 mm at 10,000 rpm. The resulting pellet was suspended in 10 ml of TEG containing 500 mM NaCl; after being stirred for 15 min, the mixture was centrifuged for 20 min at 12,000 rpm. The supernatant (10.3 ml) was adjusted to 50% saturation by the addition of 3.2 g of ammonium sulfate, stirred for 20 min, and centrifuged for 15 min at 15,000 rpm. The resulting supernatant was adjusted to 70% saturation by the addition of 1.64 g of ammonium sulfate, stirred for 20 min, and centrifuged for 15 min at 15,000 rpm. The resulting pellet was suspended in 1 ml of TG (50 mM Tris hydrochloride (pH 7.4) containing 10% glycerol) and dialyzed against two changes of TG. The dialyzed material (2.0 ml) was loaded onto a 1-ml column (0.5 by 5.8 cm) of phosphocellulose (P11; Whatman, Inc.) that had been equilibrated with TG. The column was washed with 3 ml of TG and developed with 20 ml of a linear gradient (0 to 1.2 M) of KCl in TG. Fractions of 0.5 ml were collected, stored at −20° C., and assayed for IHF activity.

Polyclonal anti-IHF was prepared as follows. Rabbits were injected with 250 μg of purified IHF with Freund's complete adjuvant. Booster immunizations of 250 μg of IHF with Freund's incomplete adjuvant were given 1, 7, and 12 weeks later. As determined by immunoblotting of IHF, sera collected 13 weeks after the initial injection had a high titer of IHF-reactive material. The animals were maintained for several years and, when necessary, given further booster immunization in order to maintain a high titer of anti-IHF in their sera. The antibody was not purified further. Crude sera was stored at −70° C. Polyclonal anti-HU was prepared according to the same manner.

Hybridomas producing murine monoclonal antibodies specific to each subunit of IHF or HU were generated by using synthetic polypeptides corresponding to SEQ ID NOs. 12-17 were ordered from Rockland Immunochemicals, Limerick, Pa. Three of the hybridomas were deposited and validated for viability by ATCC. Table 1, reproduced herein below, lists the deposited hybridomas and their corresponding ATCC Accession Number.

TABLE 1

(reproduced from above)

| Specificity | SEQ ID NO. | ATCC Accession No. | Hybridoma Cell Line |
|---|---|---|---|
| IhfA frag. A5 | SEQ ID NO. 13 | PTA-122334 | IhfA5 NTHI 14G8.F5.G6 |
| IhfB frag. B4 | SEQ ID NO. 16 | PTA-122336 | IhfB4 NTHI 4E11.E5.G2 |
| IhfB frag. mB4 | SEQ ID NO. 17 | PTA-122335 | mIhfB4 NTHI 12E6.F8.D12.D5 |
| IhfA frag. A3 | SEQ ID NO. 12 | | IhfA3 NTHI 9B10.F2.H3 |
| IhfB frag. B2 | SEQ ID NO. 15 | | IhfB2 NTHI 7A4.E4.G4 IhfB2 NTHI 7A4.E4.G11 |

Example 2: Reduction of Biofilm Analysis Using Polyclonal Antibodies

This experiment describes an in vitro model for disruption of an established biofilm in 8-well chamber slide. The materials used in this experiment were: Chocolate Agar; sBHI (BHI with 2 mg heme/mL and 2 mg b-NAD/mL); 8-well Chamber slides (Nunc*Lab-Tek*Fisher catalog #12-565-18); Sterile 0.9% saline; LIVE/DEAD BacLight Bacterial Viability Kit (Fisher catalog #NC9439023) and Formalin.

On day 1, NTHI was struck for isolation on chocolate agar. It was then incubated for 20 hrs at 37° C. and 5% $CO_2$. The next day, bacteria were suspended in 5 mL equilibrated (37° C., 5% $CO_2$) and optical density was adjusted to $OD_{490}$≈0.65 in sBHI. Bacteria were diluted 1:6 in equilibrated sBHI (1 mL bacterial suspension+5 mL sBHI). Bacteria were then incubated for 3 hours at 37° C. in 5% $CO_2$, static ($OD_{490}$ should be approx 0.65). Next, the bacteria were again diluted 1:2500 in equilibrated sBHI and 200 mL of the bacterial suspension was added to each well of the chamber slide. For dilution, 10 µL bacteria was added to 990 µL sBHI in an eppendorf tube and 8 µL dilution was added to 192 µL sBHI in each chamber and incubated at 37° C., 5% $CO_2$, static.

On the third day after 16 hours of incubation medium was aspirated from chamber by aspirating medium from the corner of the well so as not to disturb biofilm. Then 200 mL of equilibrated sBHI was added to each chamber and incubated for 37° C., 5% $CO_2$, static for 8 hours. After 8 hours, the medium was aspirated and 200 mL equilibrated sBHI was added to each untreated chamber; and 200 mL of interfering agent such as Rabbit anti-rsPilA; diluted 1:50 in sBHI and 200 mL Naïve rabbit serum (or other appropriate serum control) diluted 1:50 in sBHI was added. They were then incubated at 37° C. and 5% $CO_2$, static.

On day 4, after approximately 16 hours of incubation, aspirate sBHI was aspirated and the biofilm was washed twice with 200 mL sterile saline. The saline was aspirated and 200 mL Live/Dead stain was added. Next, 3 mL component A plus 3 mL component B in 1 mL sterile 10 mM phosphate buffered saline was added. It was then incubated for 15 minutes at room temperature, static, protected from light. Stain was aspirated and biofilm was washed twice with 200 mL sterile saline. Saline was aspirated and 200 mL formalin was added to fix biofilm. It was then incubated 15 minutes at room temperature, static, protected from light. Formalin was aspirated and biofilm was washed twice with 200 mL sterile saline. Gasket was removed and coverslip were placed on slide; coverslip were sealed with nail polish and dried prior to viewing by confocal microscopy.

Polyclonal antibodies directed against the *E. coli* IHF and *Haemophilus influenzae* IHF and HU was prepared in rabbits according to standard techniques using purified Integration Host Factor (IHF). Example 1 describes the generation of polyclonal antibodies. Polyclonal antibodies generated from *Haemophilus influenzae* DNABII polypeptides were demonstrated to have robust disruption of biofilms relative to anti-*E. coli* IHF, native rabbit antiserum, and medium controls (FIG. 1). Polyclonal antisera was used at a 1:50 dilution.

Example 3: Reduction of Biofilm Analysis Using Monoclonal Antibodies and Combinations Thereof Using this method of Example 2 and the antibodies or combinations thereof listed Table 2 generated according to the methods described in Example 1, Applicants reduced a biofilm produced by *Haemophilus influenzae* which is prevalent in sinusitis, bronchitis, otitis media and exacerbations of chronic obstructive pulmonary disease (COPD). Polyclonal antiserum was used at a 1:25 dilution. Monoclonal antibodies were used at 4.4 µg/well—with 4.4 µg/well of each monoclonal antibody where more than one monoclonal was used.

TABLE 2

| Antibody | Specificity |
|---|---|
| Ihf A3 (A3) | SEQ ID NO. 12 |
| Ihf A5 (A5) | SEQ ID NO. 13 |
| Ihf B2 (B2) | SEQ ID NO. 15 |
| Ihf B4 (B4) | SEQ ID NO. 16 |
| Ihf mB4 (mB4) | SEQ ID NO. 17 |

| Combination | Contents |
|---|---|
| A3 + B2 | Ihf A3 and Ihf B2 |
| A5 + B4 | Ihf A5 and Ihf B4 |
| A5 + mB4 | Ihf A5 and Ihf mB4 |

Figure 3A:
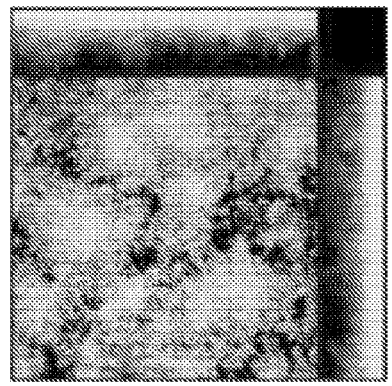
FIG. 3A depicts the disruption of biofilms formed by *Haemophilus influenzae* upon incubation with monoclonal anti-IHF and combinations thereof. Specifically anti-IHF A5 and anti-IHF B4 or mB4 demonstrated robust disruption of biofilms both alone or in combination with one another.
Figure 3A:
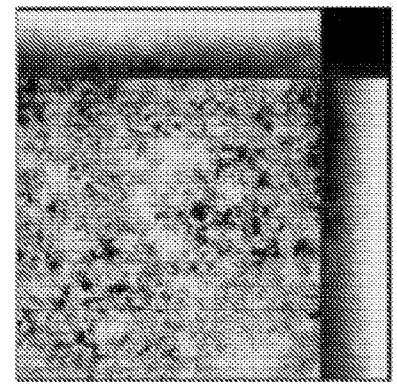
Figure 3A:
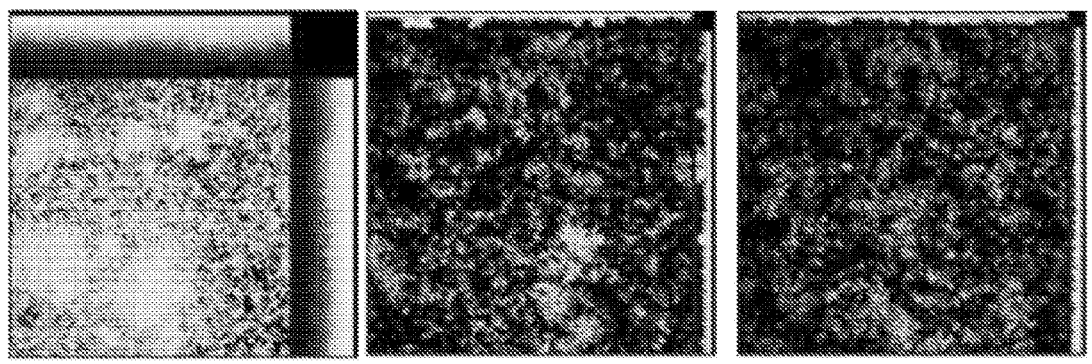
Figure 3A:
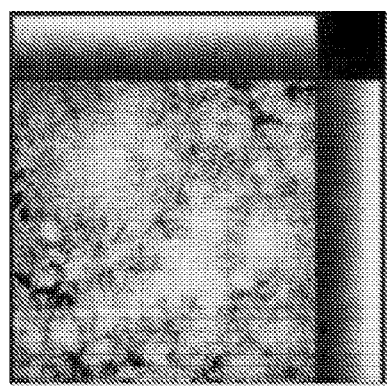
Figure 3A:
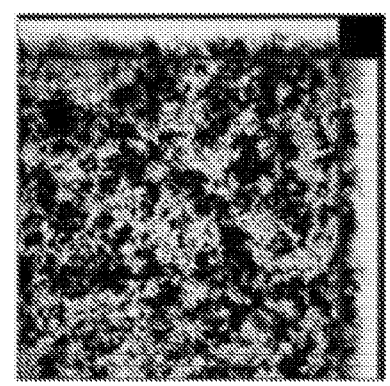
Figure 3A:
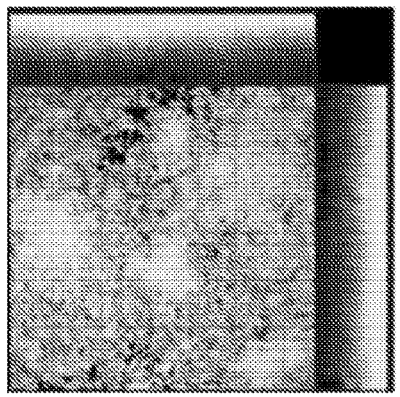
Figure 3A:
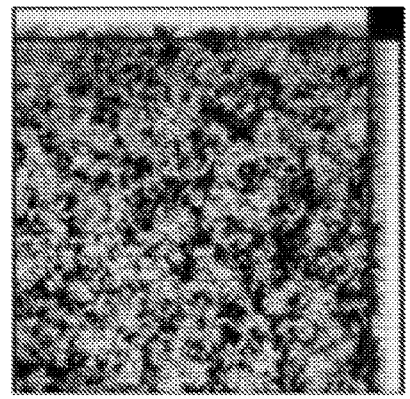
Figure 3A:
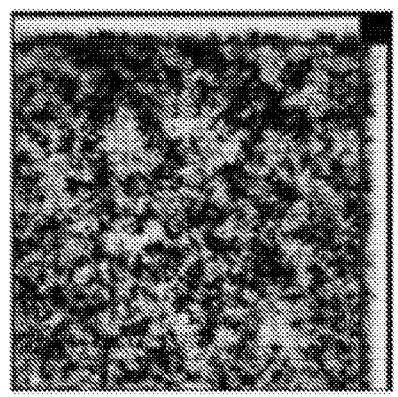
Figure 3B:
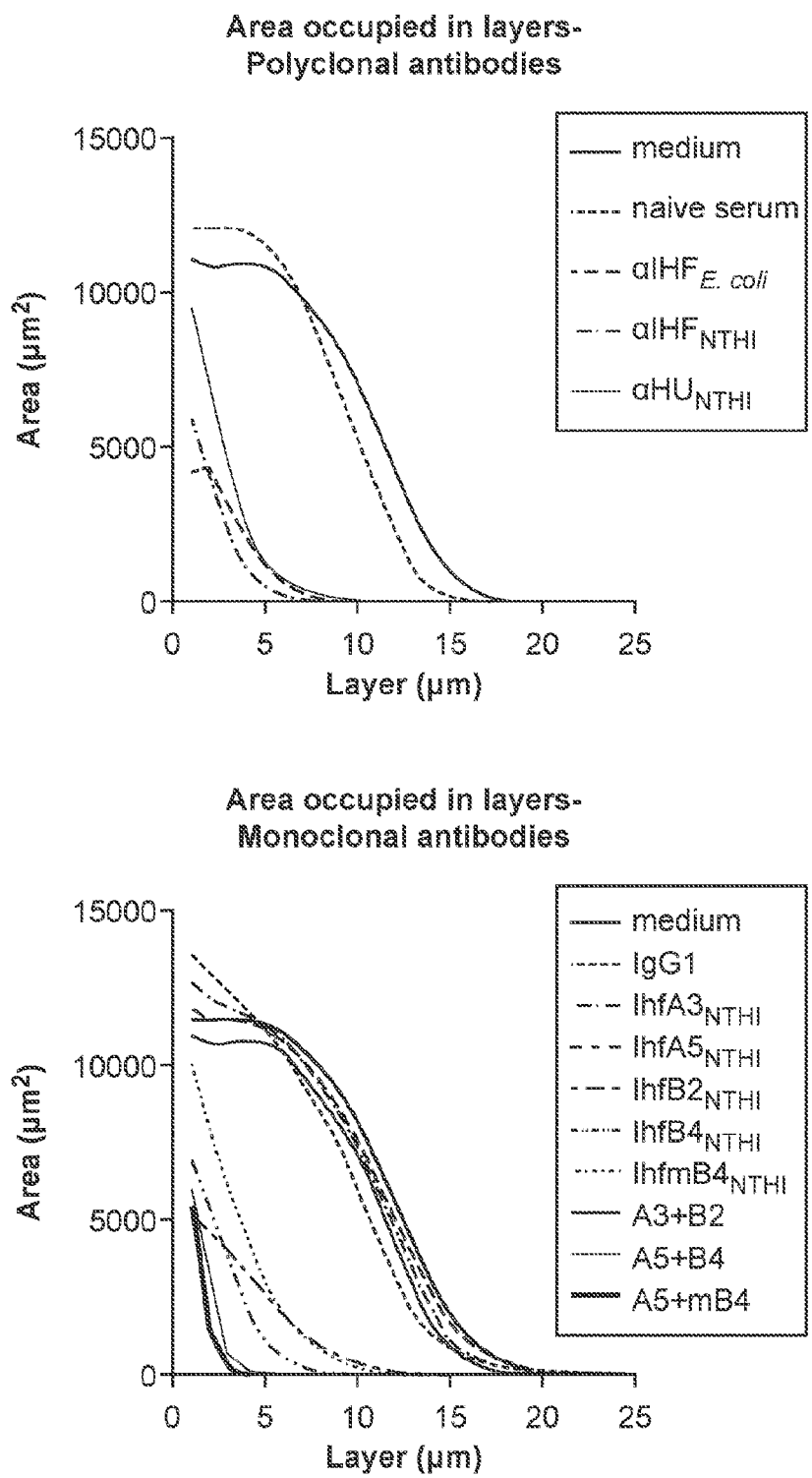
FIG. 3B depicts a COMSTAT plot of the thickness of the biofilm layers after administration of the respective antibodies or combinations thereof. Again, anti-IHF A5 and anti-IHF B4 or mB4 demonstrated robust reductions in thickness of the biofilm layers both alone or in combination with one another.
Figure 3B:
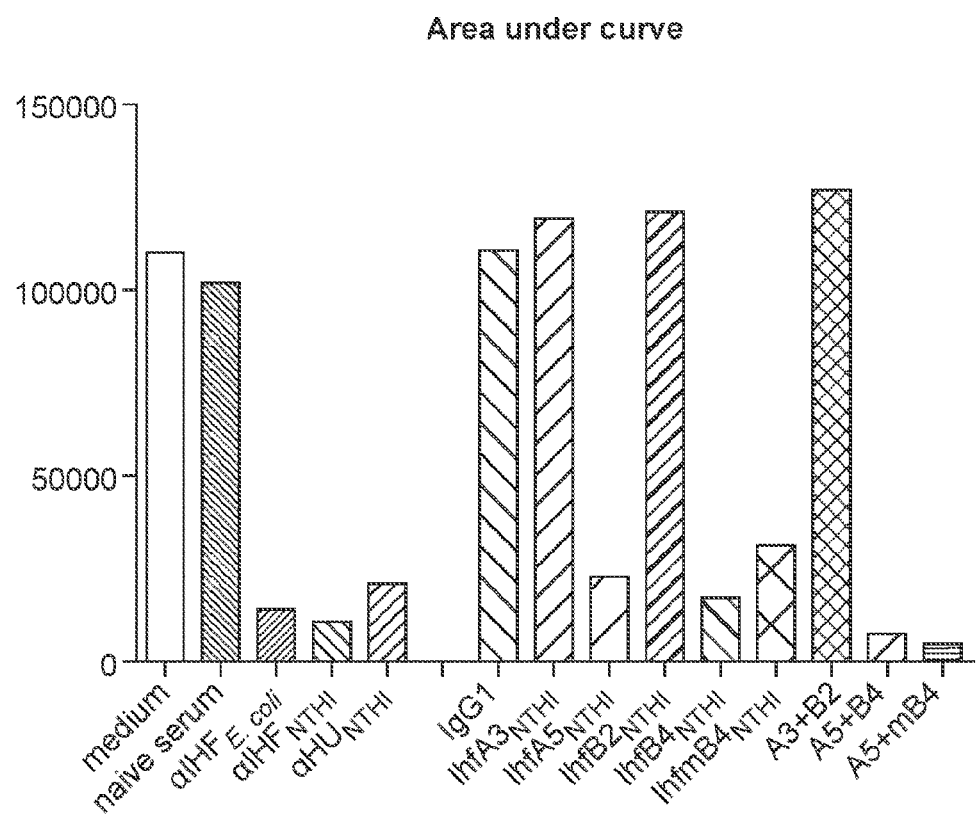
Figure 3C:
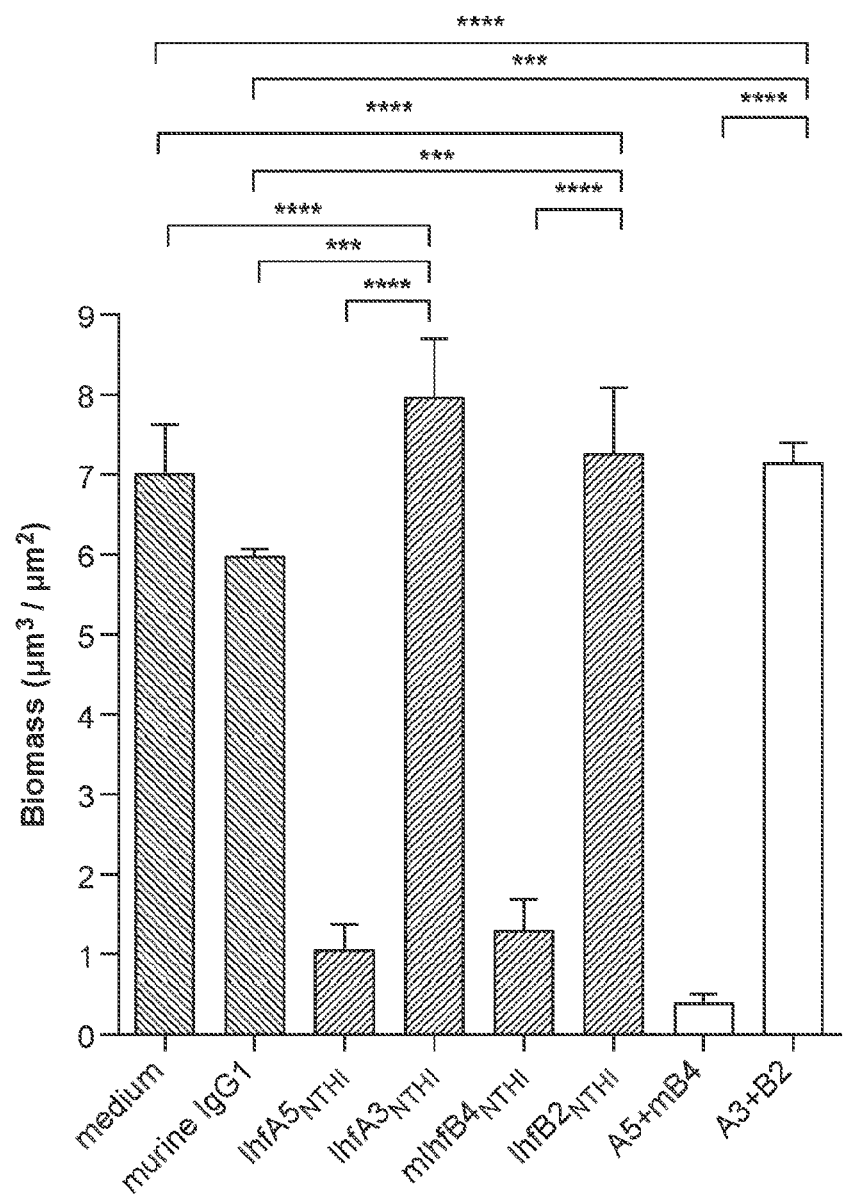
FIG. 3C depicts the mean biofilm biomass that remained after treatment as determined by COMSTAT2 analyses. *, p≤0.001, **, p≤0.0001.
Figure 9C:
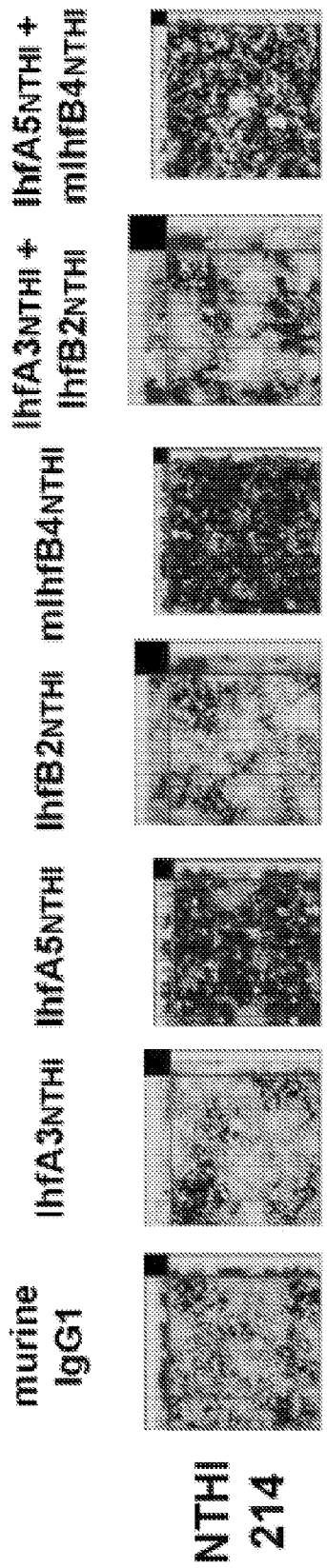
FIG. 9C depicts the disruption of biofilms formed by *Haemophilus influenzae* NTHI strain #214 upon incubation with monoclonal anti-IHF and combinations thereof.
Figure 10A:
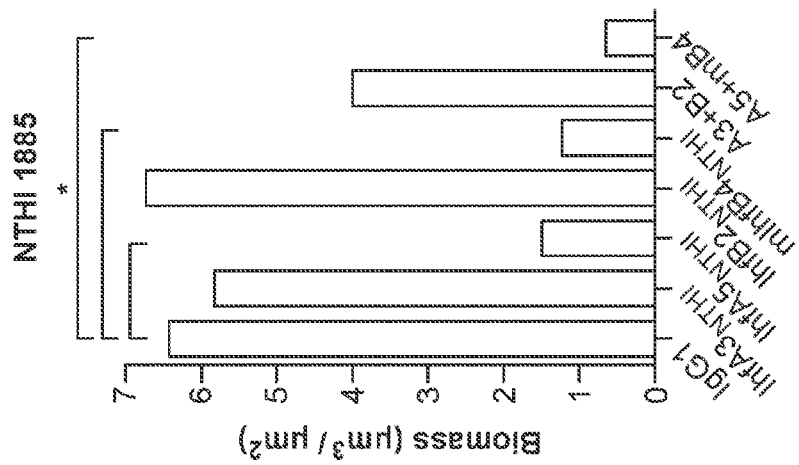
FIG. 10A depicts the mean *Haemophilus influenzae* NTHI 1885 biofilm biomass that remained after treatment as determined by COMSTAT2 analyses.
Figure 10B:
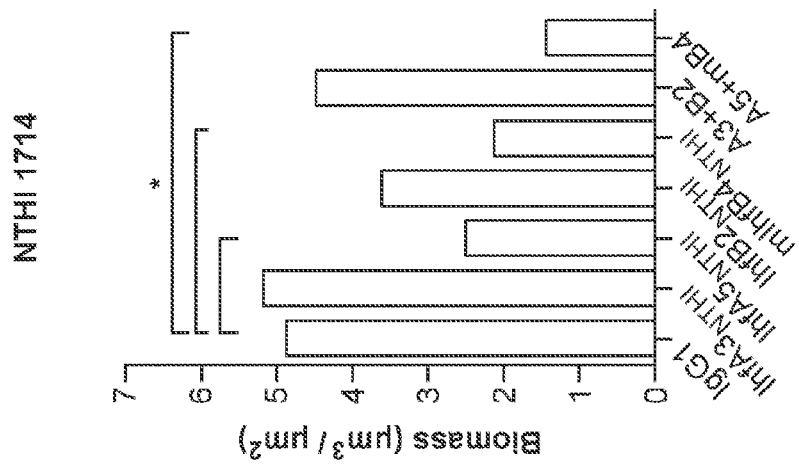
FIG. 10B depicts the mean *Haemophilus influenzae* NTHI 1714 biofilm biomass that remained after treatment as determined by COMSTAT2 analyses.
Figure 10C:
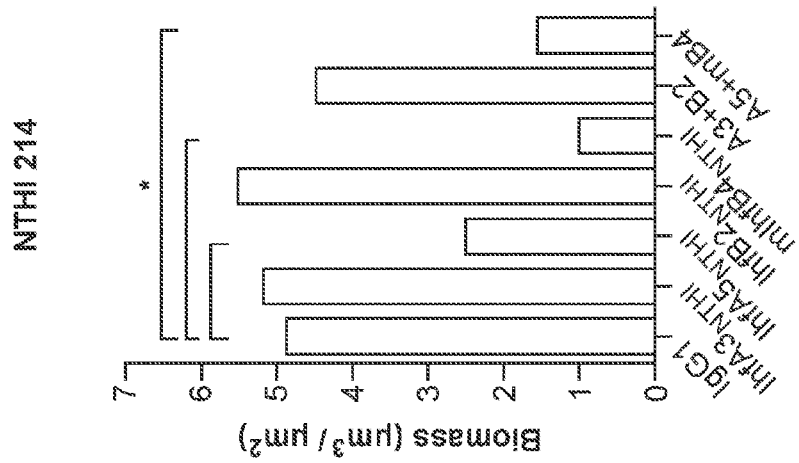
FIG. 10C depicts the mean *Haemophilus influenzae* NTHI 214 biofilm biomass that remained after treatment as determined by COMSTAT2 analyses.

Biofilm mass was examined visually and via COMSTAT. Significant disruptions in biofilm biomass were visible in biofilms treated with A5, B4, mB4, A5+B4, and A5+mB4 relative to biofilms treated with IgG1 or IgG2 (FIG. 3A); a COMSTAT2 analysis confirmed these results, demonstrating significant disruptions in biofilm mass as a result of the administration of A5, B4, mB4, A5+B4, and A5+mB4 (FIG. 3B and FIG. 3C). This was repeated with multiple NTHI strain types (FIG. 9 and FIG. 10).

Using this method of Example 2 and the antibodies or combinations thereof listed Table 3, Applicants disrupt a biofilm produced by *Streptococcus mutans* which is prevalent in initiation and progression of dental caries.

Figure 7A:
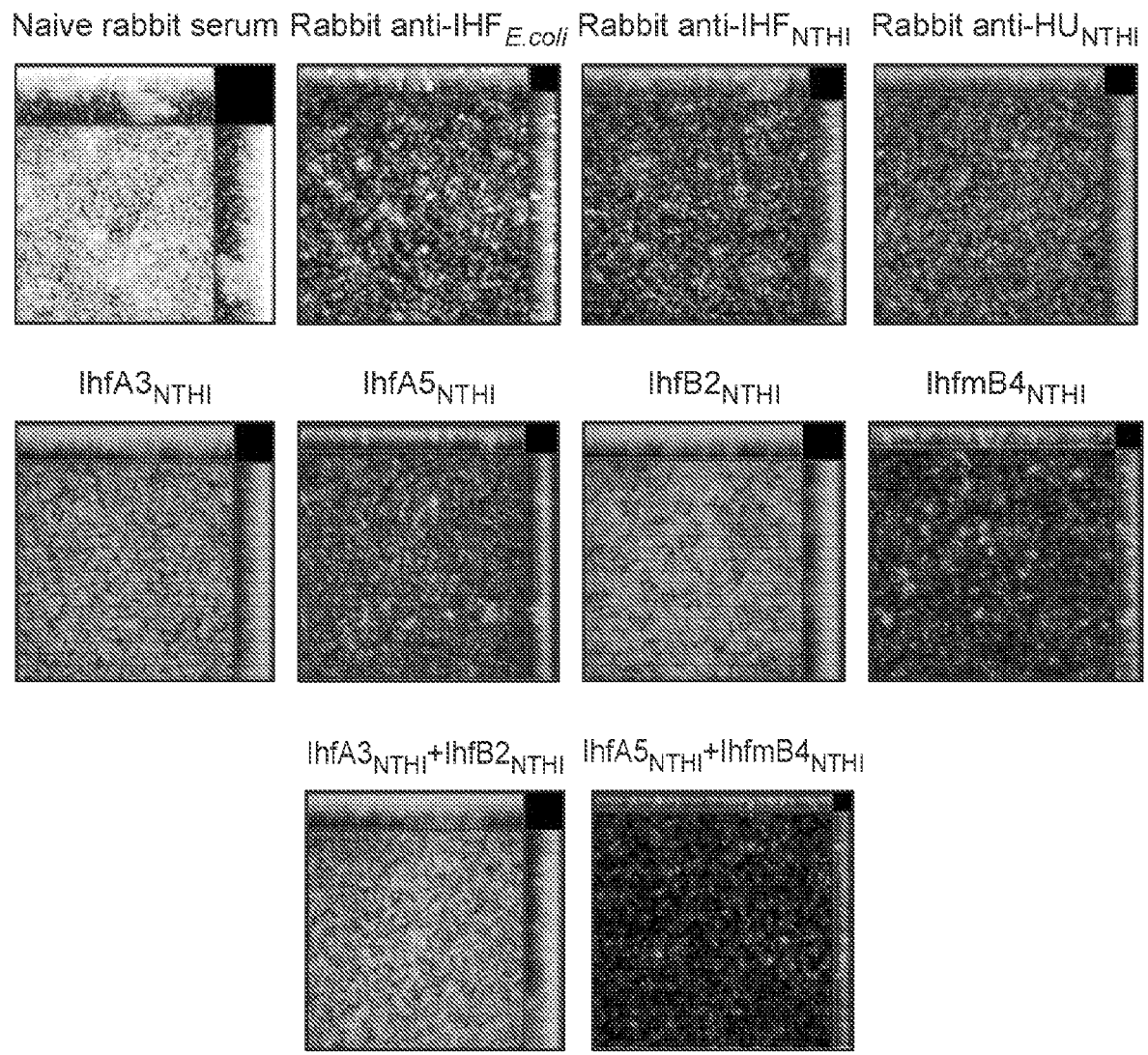
FIG. 7A depicts the reduction of biofilms formed by *B. cenocepacia* K56 upon incubation with monoclonal anti-IHF and combinations thereof, as well as polyclonal anti-IHF. Specifically anti-IHF A-5 and anti-IHF mB-4 demonstrated robust disruption of biofilms either alone or in combination with one another.
Figure 7B:
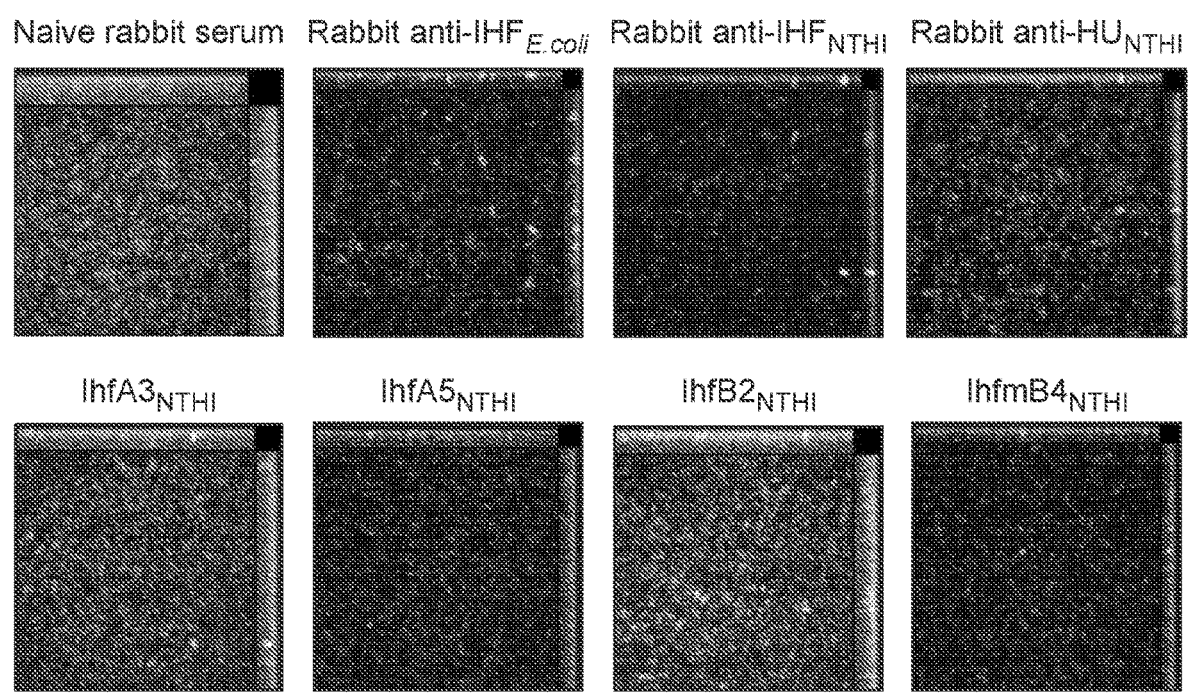
FIG. 7B depicts similar results for biofilms formed by *Pseudomonas aeruginosa* 28753.
Figure 7C:
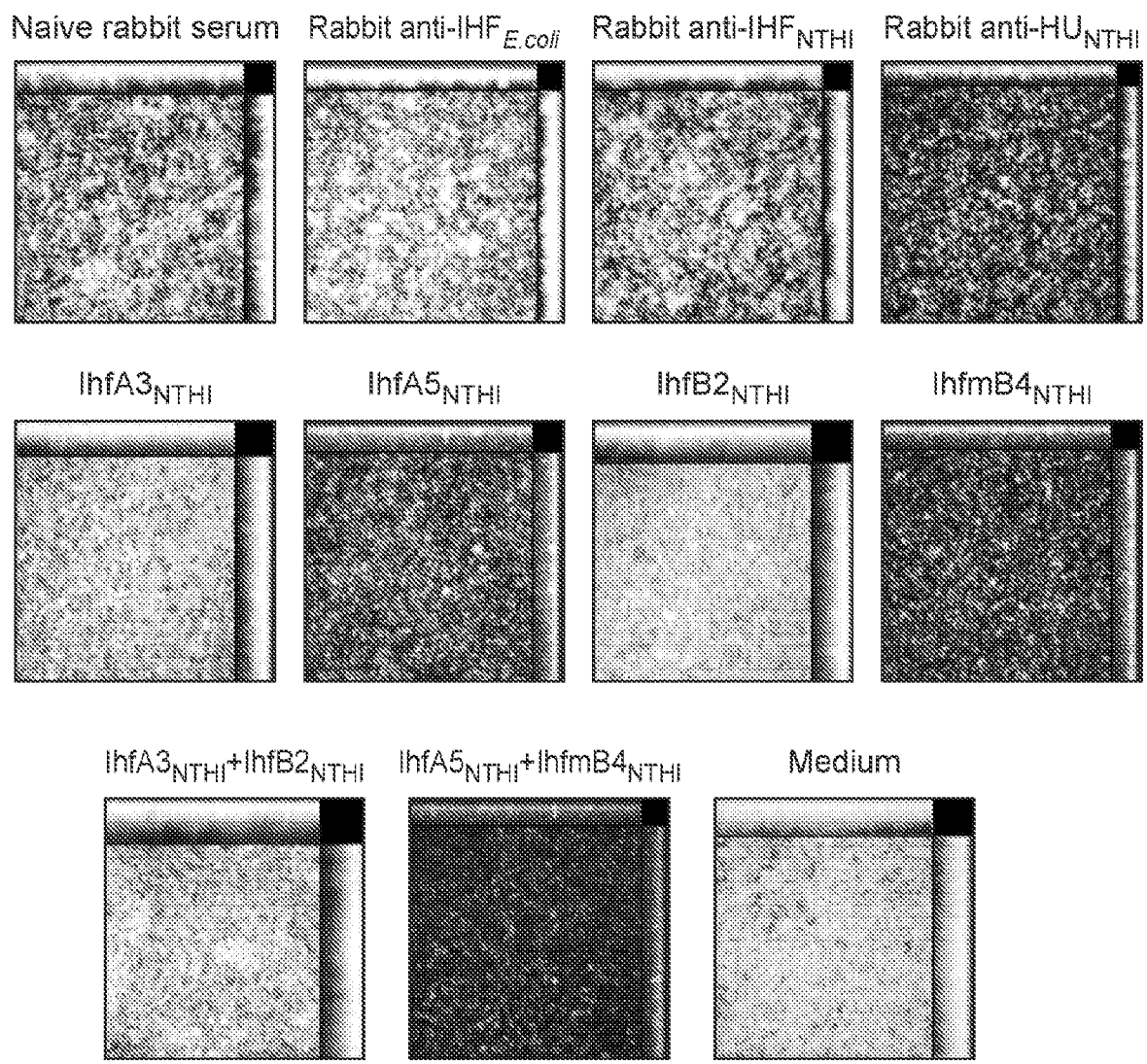
FIG. 7C depicts similar results for biofilms formed by *Staphylococcus aureus* 29213.
Figure 11B:
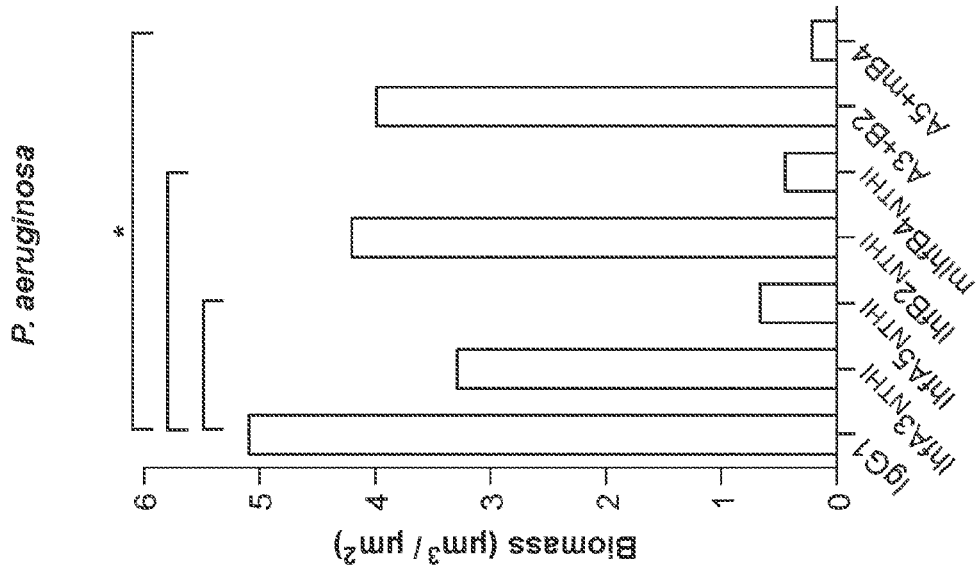
FIG. 11B depicts the mean *Pseudomonas aeruginosa* 28753 biofilm biomass that remained after treatment as determined by COMSTAT2 analyses.
Figure 11A:
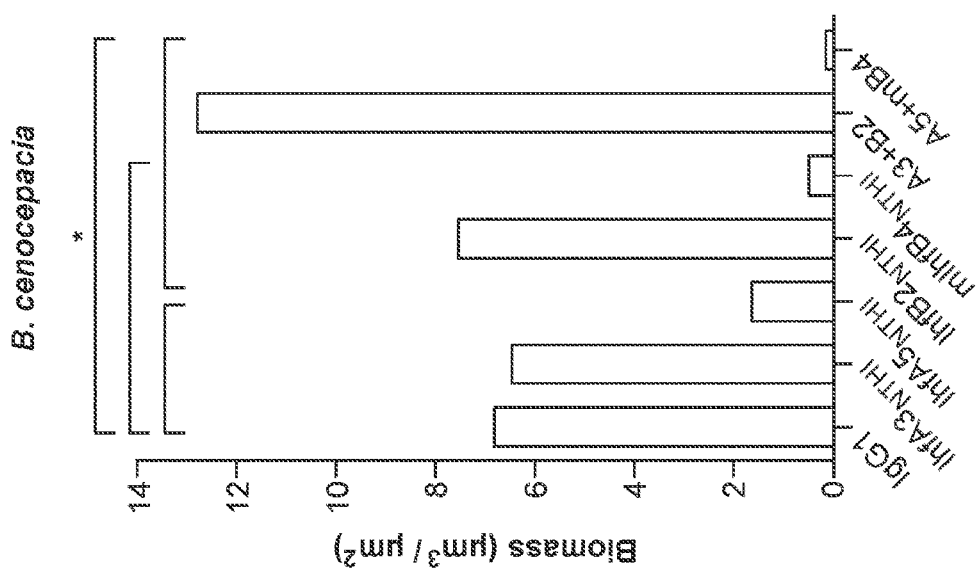
FIG. 11A depicts the mean *B. cenocepacia* K56 biofilm biomass that remained after treatment as determined by COMSTAT2 analyses.
Figure 11C:
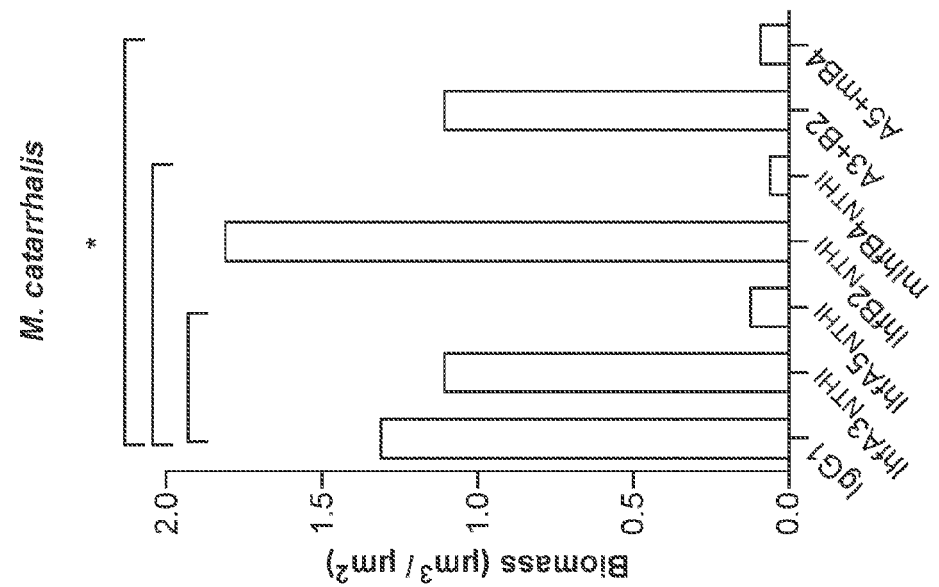
FIG. 11C depicts the mean *Staphylococcus aureus* 29213 biofilm biomass that remained after treatment as determined by COMSTAT2 analyses.

Using this method of Example 2 and the antibodies or combinations thereof listed Table 3, Applicants disrupted a biofilm produced by *Staphylococcus aureus* which is prevalent in localized and diffuse skin infections, chronic rhinosinusitis and nosocomial infections (FIG. 7C and FIG. 11C). Polyclonal antiserum was used at a 1:50 dilution. Monoclonal antibodies were used at 5—with 5 µg/well of each monoclonal antibody where more than one monoclonal was used.

Figure 7D:
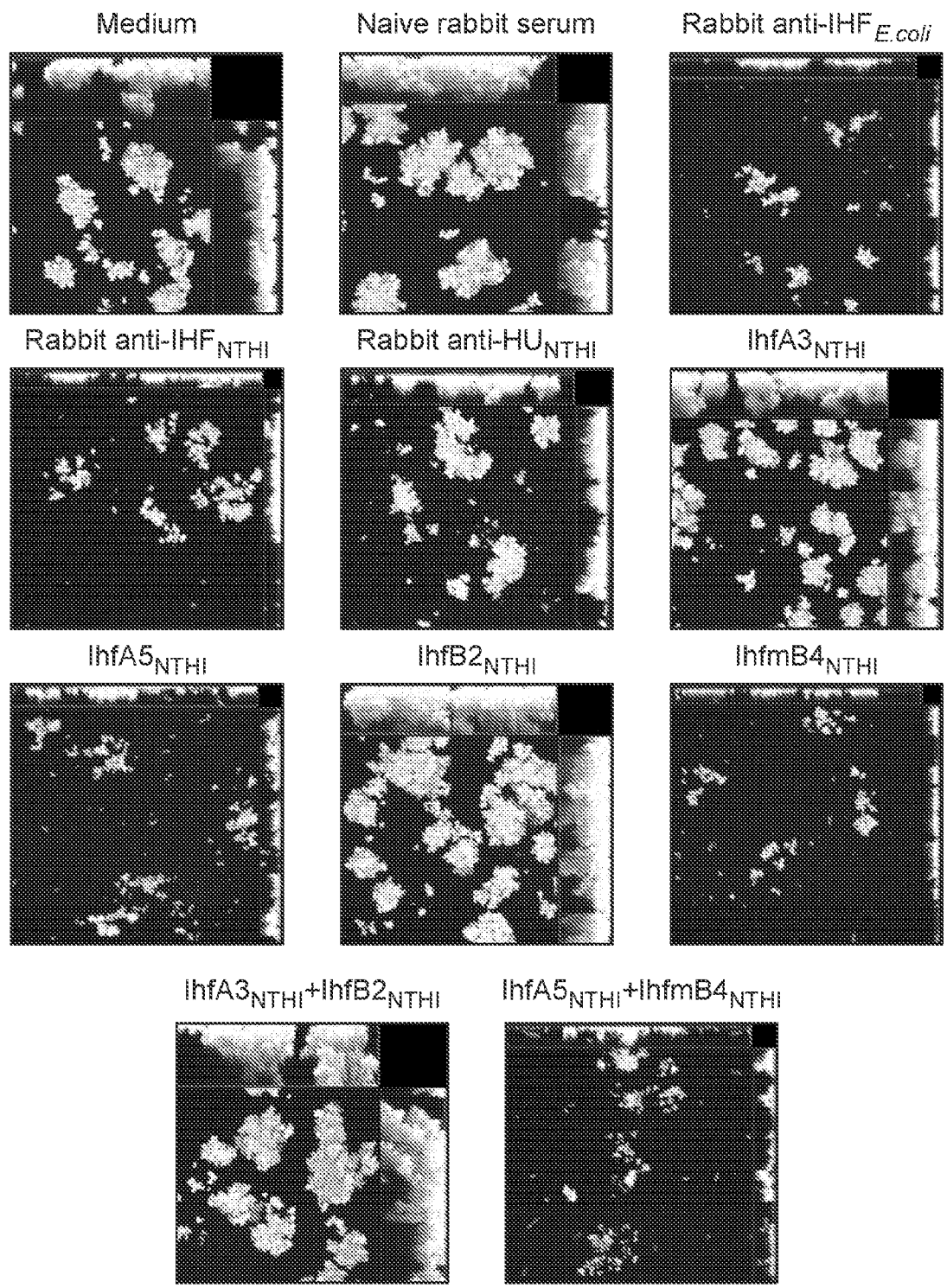
FIG. 7D depicts similar results for biofilms formed by *Moraxella catarrhalis* 7169.
Figure 8A:
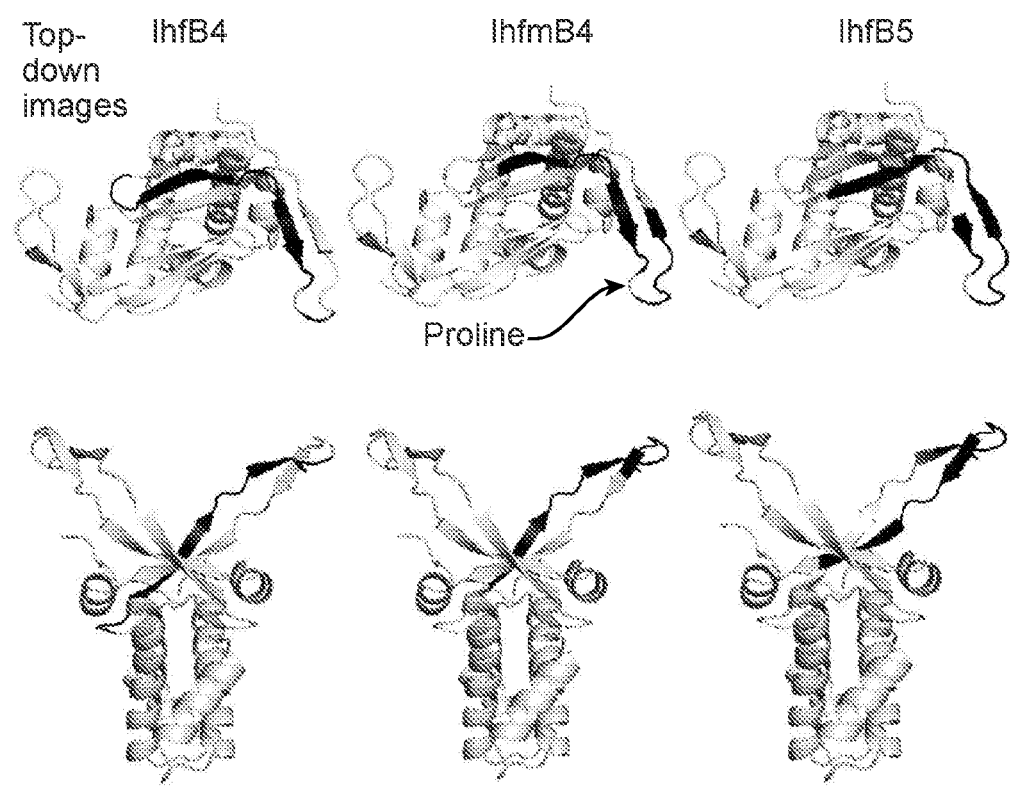
Figure 11D:
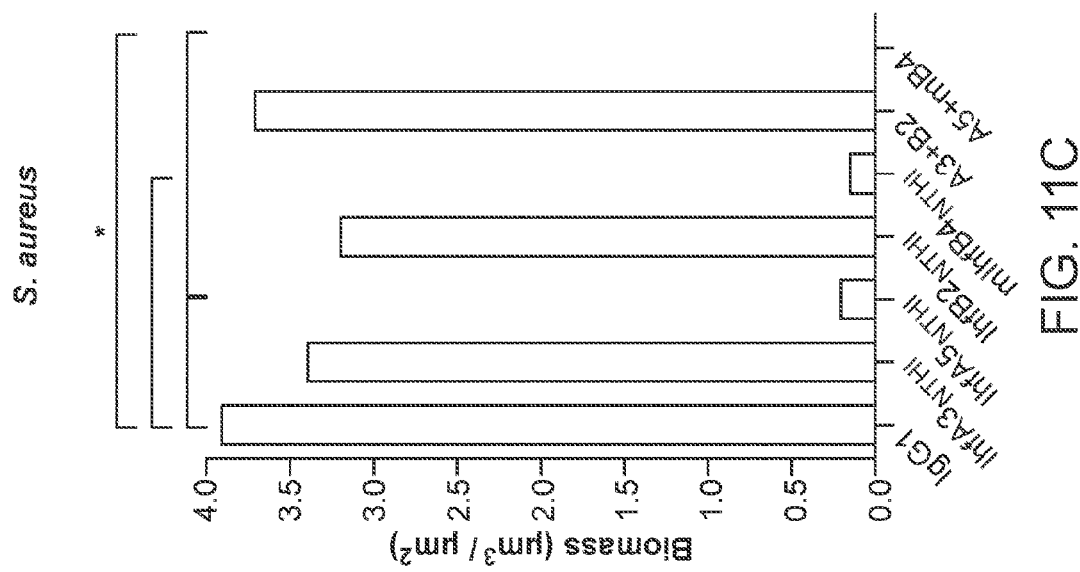
FIG. 11D depicts the mean *Moraxella catarrhalis* 7169 biofilm biomass that remained after treatment as determined by COMSTAT2 analyses.

Using this method of Example 2 and the antibodies or combinations thereof listed Table 3, Applicants disrupt a biofilm produced by *Moraxella catarrhalis* which is prevalent in exacerbation of COPD and otitis media (FIG. 7D and FIG. 11D). Polyclonal antiserum was used at a 1:50 dilution. Monoclonal antibodies were used at 5—with 5 µg/well of each monoclonal antibody where more than one monoclonal was used.

Using this method of Example 2 and the antibodies or combinations thereof listed Table 3, Applicants disrupt a biofilm produced by *Streptococcus pneumoniae* which is prevalent in sinusitis, pneumonia and otitis media.

Using this method of Example 2 and the antibodies or combinations thereof listed Table 3, Applicants disrupt a biofilm produced by *Pseudomonas aeruginosa* which is prevalent in cystic fibrosis, pneumonia, skin and soft tissue infections and on medical devices (FIG. 7B and FIG. 11B). Polyclonal antiserum was used at a 1:50 dilution. Monoclonal antibodies were used at 5—with 5 µg/well of each monoclonal antibody where more than one monoclonal was used.

Using this method of Example 2 and the antibodies or combinations thereof listed Table 3, Applicants disrupt a biofilm produced by *Neisseria gonorrhoeae* which is in gonorrhea.

Using this method of Example 2 and the antibodies or combinations thereof listed Table 3, Applicants disrupt a biofilm produced by Uropathogenic *E. coli* which is prevalent in urinary tract infections.

Using this method of Example 2 and the antibodies or combinations thereof listed Table 3, Applicants disrupt a biofilm produced by *Staphylococcus epidermidis* which is prevalent in infections of the skin.

Using this method of Example 2 and the antibodies or combinations thereof listed Table 3, Applicants disrupt a biofilm produced by *Burkholderia cenocepacia* which is prevalent in cystic fibrosis and chronic granulomatous disease (FIG. 7A and FIG. 11A). Polyclonal antiserum was used at a 1:50 dilution. Monoclonal antibodies were used at 5 µg/well—with 5 µg/well of each monoclonal antibody where more than one monoclonal was used.

Using this method of Example 2, Applicants demonstrated that while neither the naïve serum control (IgG1+ IgG2a) nor the "tail" cocktail (A3 and B2) disrupt a pre-existing *B. cenocepacia* biofilm, the "tip" cocktail (A5 and mB4) did. Similarly, when admixed with the antibiotic ceftazidime (at 16 ug/ml), neither the naïve control or the tail cocktail disrupted the biofilm or caused significant bacterial cell death (visible as yellow color in the color images), however admixing of the tip cocktail with ceftazidime both disrupted the biofilm and induced marked bacterial cell death.

These experiments are repeated for antibodies directed at HU A5 generated specific to SEQ ID NO. 14.

Example 4: Otitis Media

Middle ear infection (or otitis media, OM) is a highly prevalent disease worldwide, with the most severe form (called chronic suppurative OM or CSOM) afflicting 50-330 million children globally each year. The socioeconomic burden of OM is also great, with cost estimates between $5-6 billion in the United States alone annually. All three of the predominant bacterial pathogens of OM are known to form biofilms both in vitro and in vivo and recently, clinicians have come to appreciate that the chronicity and recurrence of OM is due, at least in part, to the formation of bacterial biofilms within the middle ear cavity.

In fact, results of labeling of otorrhea solids from pediatric patients with tympanostomy tubes and persistent otorrhea for eDNA and IHF in combination with microbiological culture indicate that biofilms play a role in chronic otorrhea. Specifically, of 15 pediatric otorrhea samples analyzed, 9 (60%) contained solids positive for labeling IHF in association with a lattice of eDNA (labeled using rabbit anti-IHF, detected with goat anti-rabbit IgG conjugated to ALEXA FLUOR® 594 fluorescent dye) and 75% yielded positive bacterial cultures. Bacterial culture results demonstrated the presence of *H. influenzae*, MRSA, *S. pneumonia*, *M catarrhalis*, and *P. aeruginosa*. These data suggest that DNABII proteins may serve as a therapeutic target in post-tympaostomy tube otorrhea among other otic disease.

In one chinchilla model of OM, juvenile chinchillas are first given a viral 'cold', followed a week later by their being challenged intranasally with an inoculum viable bacteria. Similar to the human condition wherein "my child has a cold and a week later gets an ear infection" chinchillas will also develop a bacterial OM approximately one week after a challenge, and while experiencing the viral upper respiratory tract infection. Once bacteria gain access to the middle ear (either via ascension of the Eustachian tube or following direct challenge to the middle ear space), they will form a robust biofilm. Applicants thus contemplate and indeed have already used chinchilla models as reported herein to demonstrate the protective efficacy of IHF immunization which results in rapid resolution of existing biofilms. This model is also useful for therapeutic approaches via either passive delivery of anti-DNABII antibody or via delivery of a small molecule or other agent known to bind to IHF or other DNABII family members.

Because the chinchilla model is used for development and pre-clinical testing of human vaccines, it is important to establish meaningful immunological parallels with the human host, particularly the child. Applicants have shown that effusions recovered from children with AOM due to NTHI, and middle ear fluids from chinchillas with experimental NTHI-induced OM, recognized immunodominant regions of OMP P5 in a similar hierarchical manner (see for e.g., Novotny et al. (2000) Infect 68(4):2119-2128; Novotny et al. (2007) 9$^{th}$ International Symposium on Recent Advances in Otitis Media; St. Pete Beach, Fla.; Novotny et al. (2002) Vaccine 20(29-30):3590-3597). Applicants have also shown that chinchillas with experimental OM, children with natural OM, and adults with exacerbations of COPD, all recognized peptides representing PilA in a highly analogous manner (see, e.g., Adams et al. (2007) 107th General Meeting, American Society for Microbiology, 2007, Toronto, ON; Adams et al. (2007) 9th International Symposium on Recent Advances in Otitis Media, St. Pete Beach, Fla.). Thus, chinchillas with experimental OM and children with natural disease respond similarly immunologically to at least two unrelated NTHI protein adhesins. This parallel was put to the ultimate test recently, when the chinchilla AV-NTHI superinfection model was used to conduct pre-clinical efficacy testing of a novel 11-valent Protein D-pneumococcal polysaccharide conjugate vaccine. Data obtained in the chinchilla predicted an efficacy of 34% whereas, when tested in children, the efficacy obtained against *H. influenzae*- induced OM was 35.6% (see, e.g., Novotny et al. (2006) Vaccine 24(22):4804-11 and Prymula et al. (2006) Lancet. 367(9512):740-8), thus lending strong support to the relevancy of this model for the development and testing of OM vaccine candidates.

In order to determine the efficacy of the generated antibodies, NTHI bacteria were injected into the middle ear space of the chinchillas and allowed to form a biofilm. After four days, the respective treatments were initiated. Using this model, Applicants demonstrated a reduction in or eradication of a pre-formed biofilm in the middle ear of chinchillas after receipt the polyclonal and/or monoclonal antibodies described in Examples 2 and 3 and listed in Table 3 below (FIG. 4).

TABLE 3

| Polyclonal Abs | Monoclonal Abs | Combinations |
| --- | --- | --- |
| Poly naive rabbit serum | mAb IhfA3$_{NTHI}$ | mAb IhfA3$_{NTHI}$ + IhfB2$_{NTHI}$ (synergy) |
| Poly Rabbit anti-IHF$_{E.\ coli}$ | mAb IhfA5$_{NTHI}$ | mAb IhfA3$_{NTHI}$ + IhfB2$_{NTHI}$ (power) |
| Poly rabbit anti-IHF$_{NTHI}$ | mAb IhfB2$_{NTHI}$ | mAb IhfA5$_{NTHI}$ + IhfmB4$_{NTHI}$ (synergy) |
| Poly rabbit anti-IHF$_{HU}$ | mAb IhfmB4$_{NTHI}$ | mAb IhfA5$_{NTHI}$ + IhfmB4$_{NTHI}$ (power) |

For combinations labeled "synergy" each animal received 2.5 µg of each of the two monoclonal antibodies indicated in the table such that the total antibody concentration of the treatment is the same as treatments comprising just one type of antibody—monoclonal or polyclonal—5 µg total antibody.

For combinations labeled "power" each animal received 5.0 µg of each of the two monoclonal antibodies indicated in the table, such that the total antibody concentration of the treatment is twice that of treatments comprising just one type of antibody—monoclonal or polyclonal. Thus, a combination labeled power comprises 10 µg total antibody.

Thirty-six adults were ordered from Rauscher's Chinchilla Ranch (La Rue, Ohio) and were acclimated to the vivarium for 7-10 days prior to the beginning of the study. Prior to TB challenge, baseline otoscopy and tympanometry was performed, as well as a limited volume prebleed to collect serum. Chinchillas were anesthetized and 1000 cfu of NTHI (strain #86-028NP) is introduced into the middle ear space via transbullar challenge. Routine otoscopy and tympanometry was performed daily through the study.

Four days after challenge (day +4), chinchillas were infused with 100 µl antibody via hypodermic needle inserted through the bone or bulla surrounding the middle ear space of the chinchilla for three consecutive days. Seven days after challenge (day +7), chinchillas were sacrificed.

Figure 4A:
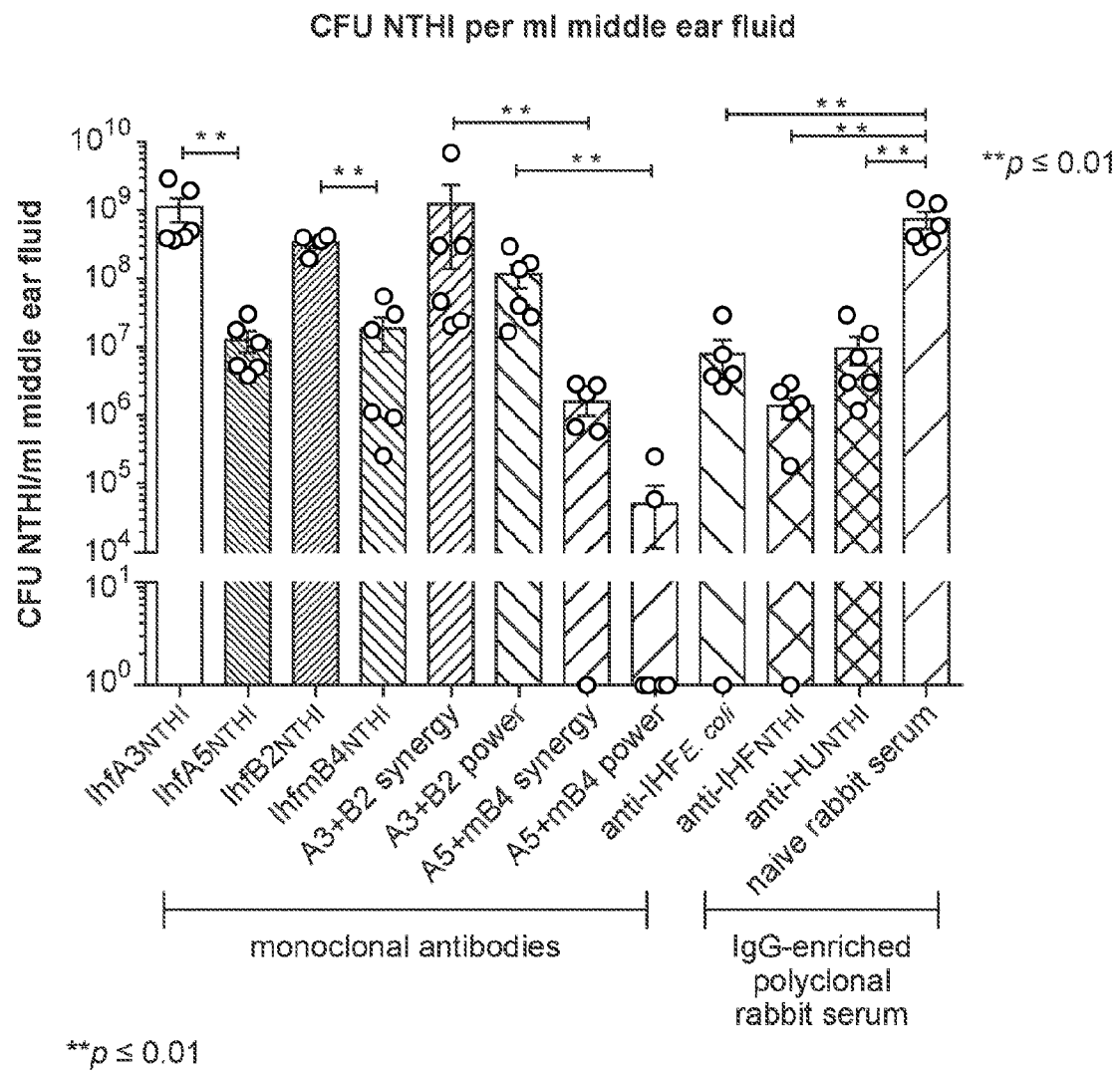
FIG. 4A shows the concentration of colony forming units of non-typeable *Haemophilus influenzae* (NTHI) per ml fluid extracted from the middle ear of chinchillas by treatment group.
Figure 4B:
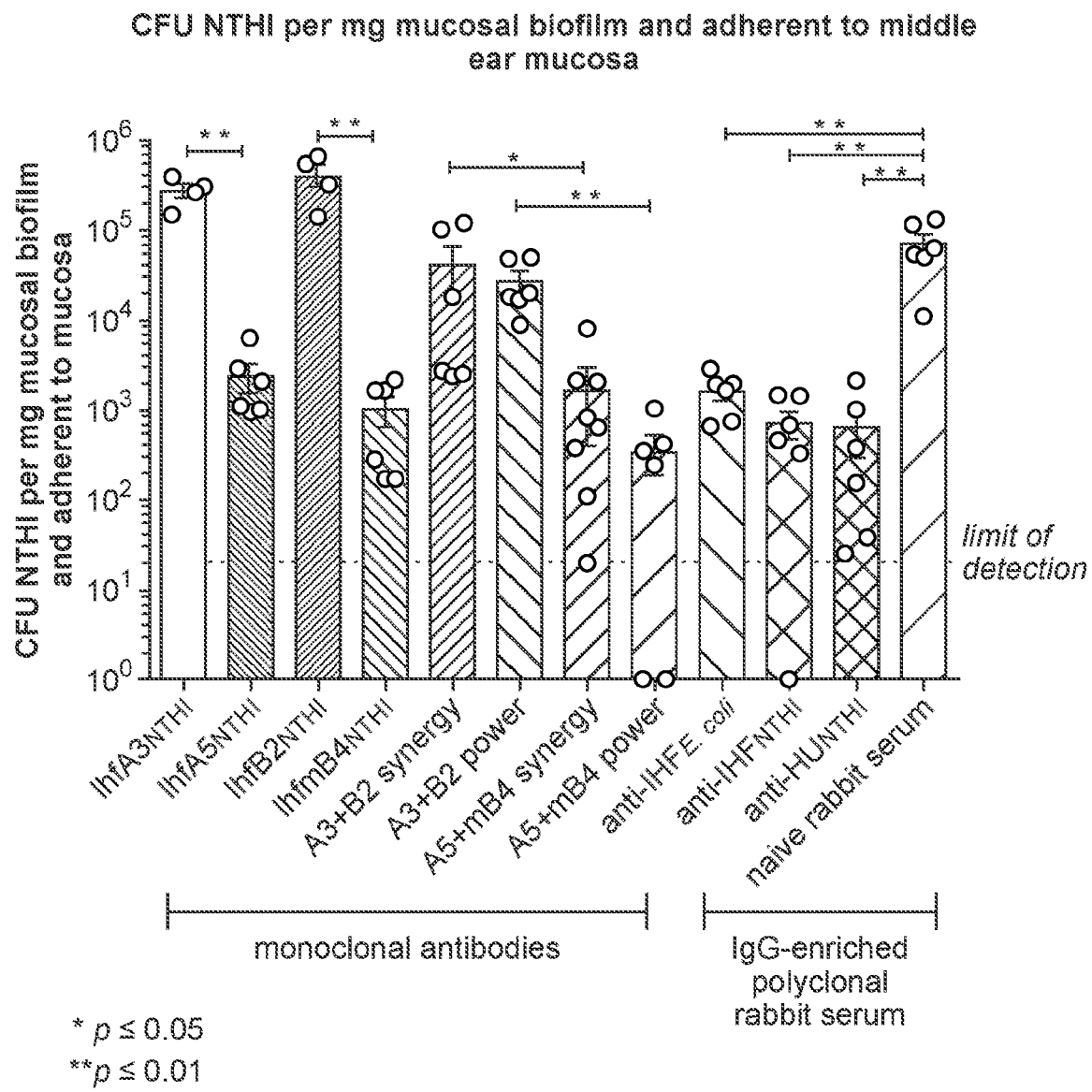
FIG. 4B shows the concentration of colony forming units of non-typeable *Haemophilus influenzae* (NTHI) per mg biofilm adherent to middle ear mucosa by treatment group.

The bullae are dissected and any fluids present were aseptically collected and plated to determine cfu NTHI/mL supernatant (FIG. 4A). The bullae were then opened to visualize the inferior bulla and any biofilm present. Images were collected and the bulla were washed with 1 ml of sterile saline and re-imaged. The mucosa, along with any biofilm present, were collected from the right bulla and placed in a pre-weighed tube. These tissues are homogenized, serially diluted, and plated to determine cfu NTHI/mg wet weight tissue (FIG. 4B). The left bullae were filled with OCT compound and snap frozen for histological analysis. Images of the left and right middle ear cavities, with resident biofilms, were scrambled and two images per animal were compiled into a single file for ranking by blinded evaluators.

Figure 4C:
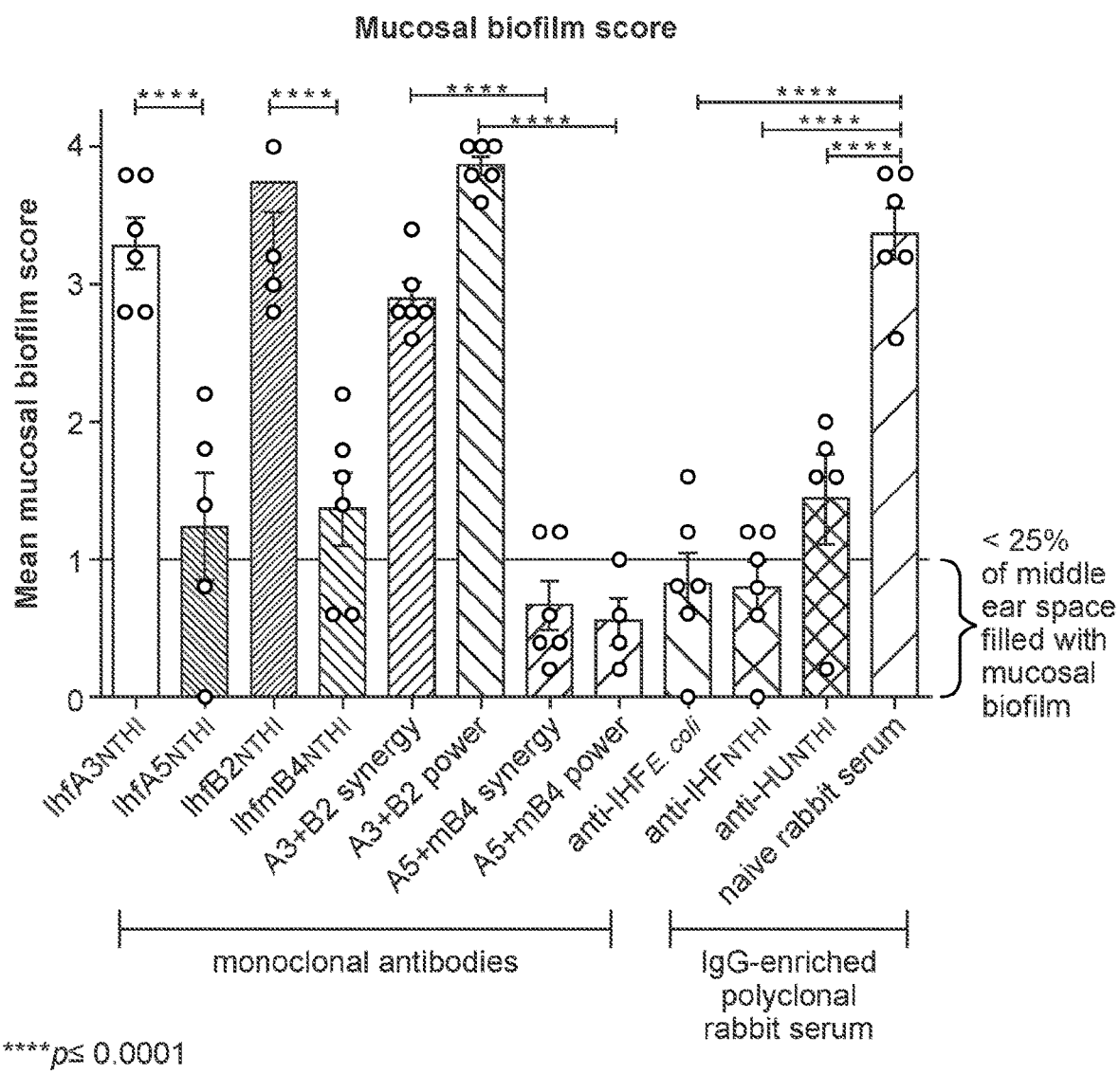
FIG. 4C depicts mucosal biofilm scoring by treatment group.
Figure 4D:
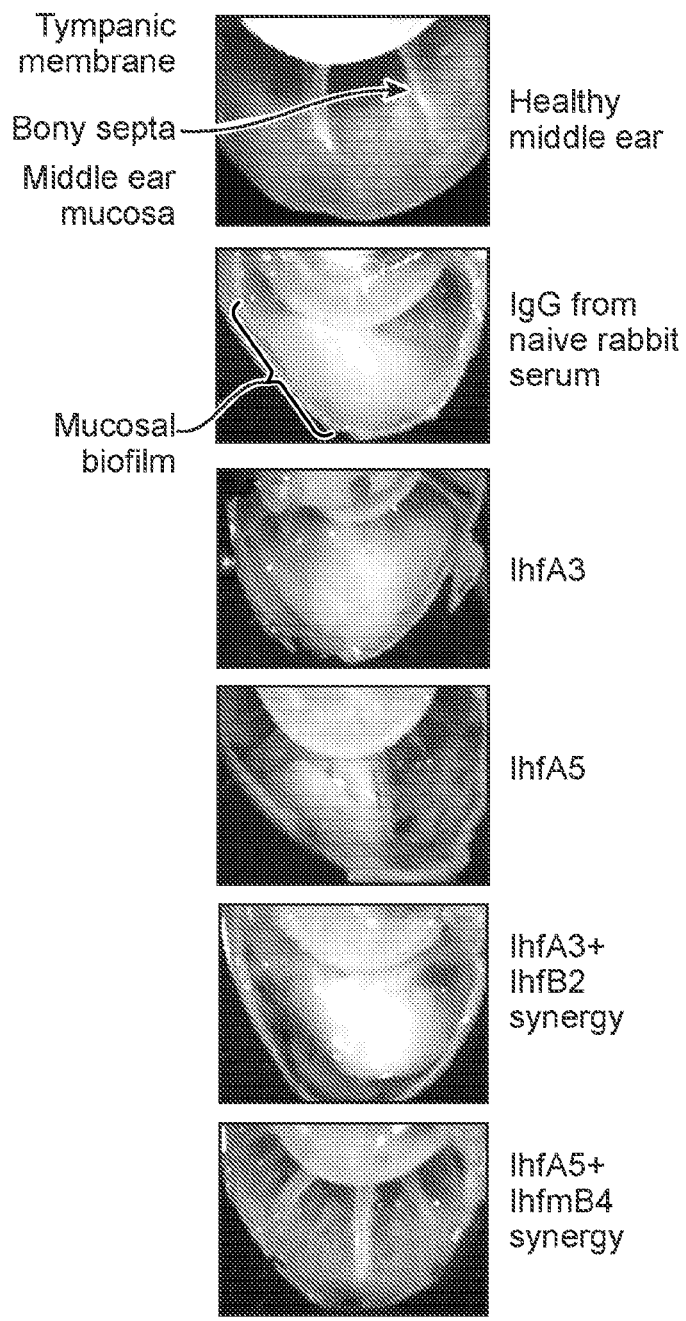
FIG. 4D provides images of middle ear biofilms (or the lack thereof) in dissected bullae recovered from chinchillas stained by treatment group.

The relative amount of biomass remaining within the middle ear of each animal was ranked on a 0 to 4+ scale by blinded reviewers using the scale shown in Table 4 below (FIG. 4C).

TABLE 4

| Score | Criteria |
| --- | --- |
| 0 | No evidence of biomass. |
| 1+ | Biomass fills ≤25% of middle ear space. Junction of the bony septa to inferior bulla is visible. |
| 2+ | Biomass fills >25% to ≤50% of middle ear space. Unable to visualize where the bony septa meet the inferior bulla. |
| 3+ | Biomass fills >50% to ≤75% of middle ear space. Biomass covers >50% of the length of bony septa. |
| 4+ | Biomass fills >75% to ≤100% of middle ear space. Bony septa not visible; obscured by biomass. |

Significant differences in mean CFU/mg tissue and mean CFU NTHI/ml supernatant were determined by paired t-test. A p-value≤0.05 was considered significant. Significance in relative biomass among cohorts is assessed by unpaired t-test. A p-value≤0.05 was considered significant.

Results demonstrate a significant reduction in biofilm severity, especially as a result of administration of monoclonal antibodies A5 and mB4 alone or in combination as well as polyclonal antibodies to E. coli IHF and Haemophilus influenzae IHF and HU.

Figure 5A:
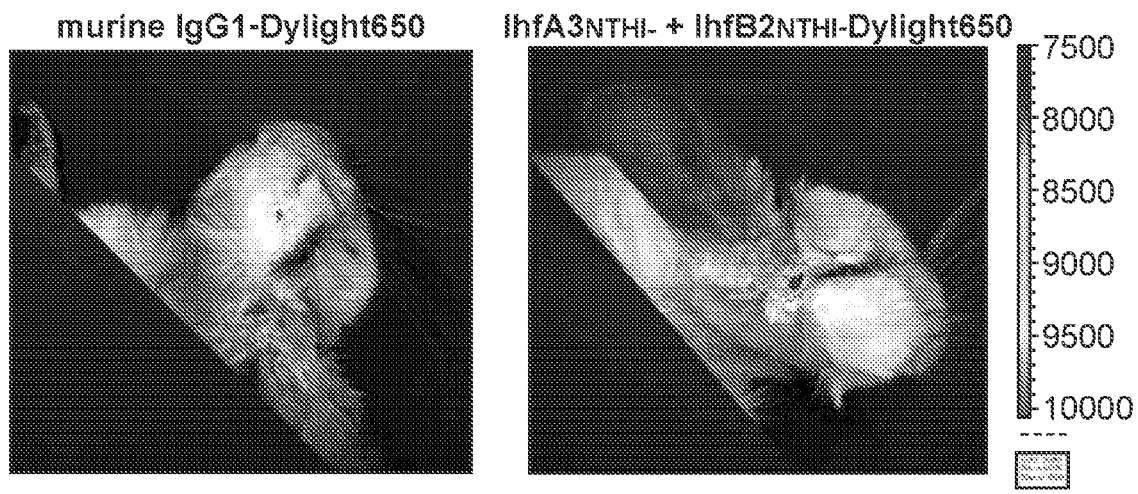
FIG. 5A depicts antibody labeling of an in situ biofilm using IhfA3, demonstrating detection of DNABII proteins within a 2 week old NTHI.
Figure 5B:
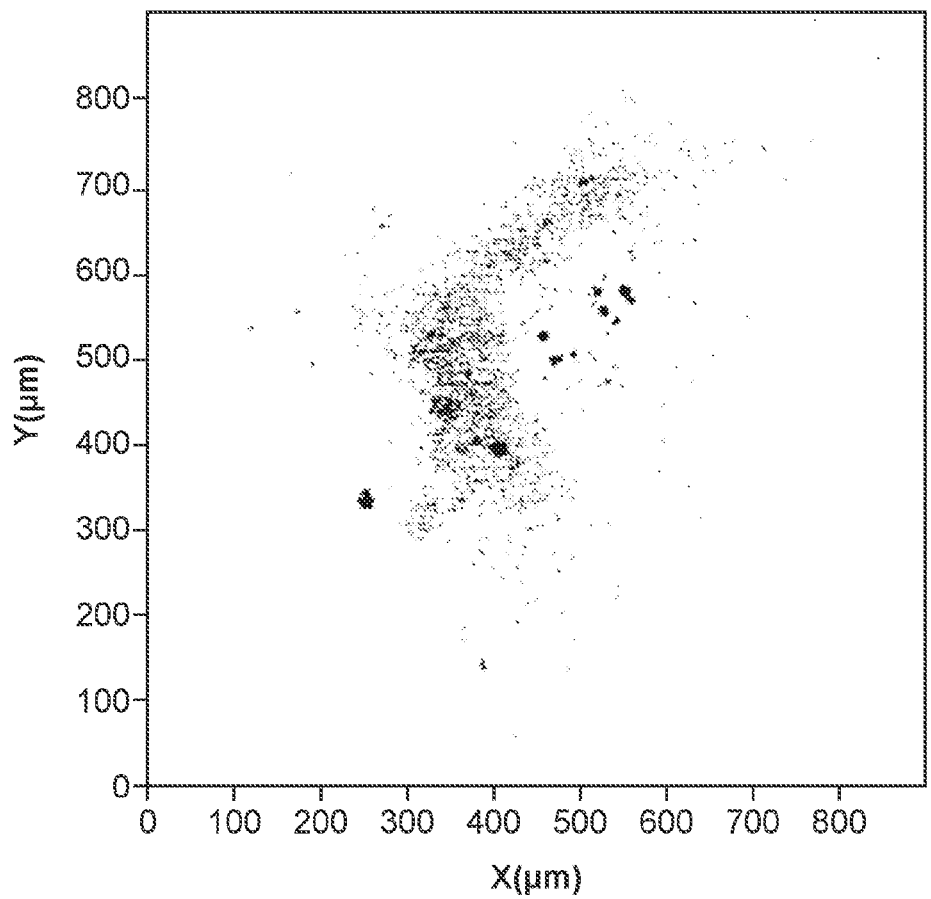
FIG. 5B depicts antibody labeling of an in vitro biofilm using IhfA3.

A biofilm that was not cleared from a chinchilla treated with monoclonal antibody A3 was extracted and incubated with goat anti-mouse IgG-Alexa594 (1:200, 30 min) and imaged at 10× magnification (FIG. 5A). The A3 antibody was localized to the biofilm; thus, antibodies of the present disclosure are useful in diagnostics such as but not limited to the labeling and/or imaging of biofilms.

These experiments are repeated for antibodies directed at HU A5 generated specific to SEQ ID NO. 14.

Example 5: Oral Cavity Biofilms

A number of oral bacteria (e.g., Aggregatibacter actinomycetemcomitans, Porphyromonas gingivalis) have been implicated in the pathogenesis of inflammatory diseases such as periodontitis and peri-implantitis, which destroy alveolar bone and gingiva. Investigations of the pathogenesis of these bacteria are hampered by lack of effective animal models. One of the challenges of investigating the pathogenicity of specific bacteria is the difficulty of establishing a biofilm when exogenous bacteria are introduced into the oral cavity of animals. Though animal models of periodontitis have been developed, cultivable bacteria are rarely recovered from the oral cavity of inoculated animals. Developing an effective animal model which can assess the pathogenicity of specific bacteria wilt greatly aid in elucidating their pathogenic mechanisms.

The surface of machined titanium dental implants (1.2× 4.5 mm) was modified by grit blasting with A103 (100 µm) and HCl etching (pH 7.8 for 20 min at 80° C.). Machined and nano-textured implants are incubated in TSB medium inoculated with D7S clinical strain of Aggregatibacter actinomycetemcomitans (Aa) for 1 to 3 days at 37° C. The bacterial biofilm on the implants are analyzed by SEM, as well as by confocal laser scanning microscopy following staining with LIVE/DEAD® BacLight™. Implants with and without established Aa biofilm are transmucosally placed into the alveolar bone of female rats between premolar and incisor region of the maxillae. To detect the presence of Aa biofilm on the implants placed in vivo, bacterial samples are collected from saliva and the oral surfaces of implants after 2 days. Aa was detected by culture, as well as by PCR analysis. Micro-CT and histological analysis of peri-implant bone and mucosal tissues is performed six weeks after implantation.

Example 6: Lyme Disease

This experiment provides a mouse model for pre-clinical testing of interfering agents to treat lyme disease. See Dresser et al. Pathogens 5(12)e1000680, Epub 2009 Dec. 4. Lyme disease is the most common tick-borne disease in the United States. Reported cases have more than doubled between 1992 and 2006, with approximately 29,000 new cases confirmed in 2008. Estimates are that the actual number of cases of Lyme disease may exceed that reported by a factor of 6-12 in endemic areas. By definition, these endemic areas are expanding as populations continue to move from cities to suburban and rural areas and whitetail deer (which carry the tick species *ixodes*) increasingly roam these areas. Lyme disease is caused by the microorganism *Borrelia burgdorferi*, a spirochete. *B. burgdorferi* is transmitted via the bite of the *ixodes* tick and subsequently disseminates, via the bloodstream, to other tissues and organs.

In this animal model, C3H/HeN mice are injected with spirochetes via dorsal subcutaneous and intraperitoneal injection, or via intravenous injection. Blood and biopsy specimens are recovered at approximately 7 days post infection for evaluation of microbial burden and assessment of pathology in tissues and organs. The methods and compositions disclosed herein are contemplated to develop both therapeutic as well as preventative strategies for reduction and/or elimination of the resulting *B. burgdorferi* biofilms which form subsequent to challenge and are believed to contribute to both the pathogenesis and chronic nature of the disease.

Example 7: Cystic Fibrosis

This experiment provides a porcine model for pre-clinical testing of interfering agents to treat cystic fibrosis. See Stoltz et al. (2010) Science Translational Medicine 2(29):29-31. Cystic fibrosis is an autosomal recessive disease due to mutations in a gene that encodes the CF transmembrane conductance regulator (called CFTR) anion channel. In this model, pigs which have been specifically bred to carry a defect in the genes called "CFTR" and called CF pigs spontaneously develop hallmark features of CF lung disease that includes infection of the lower airway by multiple bacterial species. The pigs can be immunized with the interfering agents to either 1) immunize these CF pigs with a polypeptide or other immunogenic agent thereby inducing the formation of antibodies which will eradicate bacterial biofilms in the lungs (similarly to how antibodies eradicated biofilms resident within the middle ears of chinchillas following active immunization as shown in Example 4) to the lungs of these animals by nebulization to assess the amelioration of the signs of disease and associated pathologies.

A study was designed to test the therapeutic efficacy afforded by monoclonal antibodies directed against specific epitopes of the DNABII family protein, $IHF_{NTHI}$, to resolve infection with *Pseudomonas aeruginosa* in a murine model of lung disease.

Thirty-five male C57BL/6 mice were obtained from Charles River Laboratories International, Inc. All mice were inoculated with *P. aeruginosa* strain 27853 (ATCC) by intratracheal (IT) instillation using BioLite Intubation System (Braintree Scientific, Inc.). Target challenge dose: $1\times10^7$ CFU/0.03 ml. Actual dose administered: $9\times10^6$ CFU/0.03 ml.

One day after IT challenge, 5 mice were sacrificed to determine the relative bacterial load per lung prior to treatment with monoclonal antibodies. Lungs were aseptically collected and then homogenized using GentleMACs C-tubes (Miltenyi Biotec) with 1.0 ml sterile 0.9% sodium chloride. Lung homogenates were serially diluted in saline and plated on to Trypic Soy agar (BBL). Due to the presence of lung tissue within homogenate aliquots, agar plates were incubated for 48 hrs to allow sufficient *P. aeruginosa* growth prior to enumerating the colony forming units per lung.

Also at this time point (1 day after challenge with *P. aeruginosa*), the remaining 30 mice were divided into 3 cohorts of 10 animals each and administered the following treatment by IT instillation detailed in Table 5 below.

TABLE 5

| Cohort number | Antibody administered | Monoclonal antibody isotype | Concentration of antibody administered | Total volume administered | Source of antibody |
|---|---|---|---|---|---|
| Cohort 1 | Murine IgG | IgG1 | 10 µg | 0.03 ml | Santa Cruz Biotechnology |
| Cohort 2 | Monoclonal antibody against $IhfA3_{NTHI}$ + monoclonal antibody against $IhfB2_{NTHI}$ | IgG1 ($IhfA3_{NTHI}$ & $IhfB2_{NTHI}$) | 5 µg each monoclonal antibody; total of 10 µg delivered | 0.03 ml | 9B10.F2.H3 ($IhfA3_{NTHI}$) and 7A4.E4.G11 ($IhfB2_{NTHI}$) |
| Cohort 3 | Monoclonal antibody against $IhfA5_{NTHI}$ + monoclonal antibody against $IhfmB4_{NTHI}$ | IgM/IgG2a ($IhfA5_{NTHI}$); IgG1 ($IhfmB4_{NTHI}$) | 5 µg each monoclonal antibody; total of 10 µg delivered | 0.03 ml | 14G8.F5.G6 ($IhfA5_{NTHI}$) and 12E6.F8.D12.D5 ($IhfmB4_{NTHI}$) |

To assess the efficacy of treatment with the $IHF_{NTHI}$-targeted monoclonal antibodies to reduce the bacterial load within the lung, five mice from each cohort were sacrificed 1 and 6 days after treatment (2 and 7 days after *P. aeruginosa* challenge). Lungs were collected, processed and plated as before.

Figure 6A:
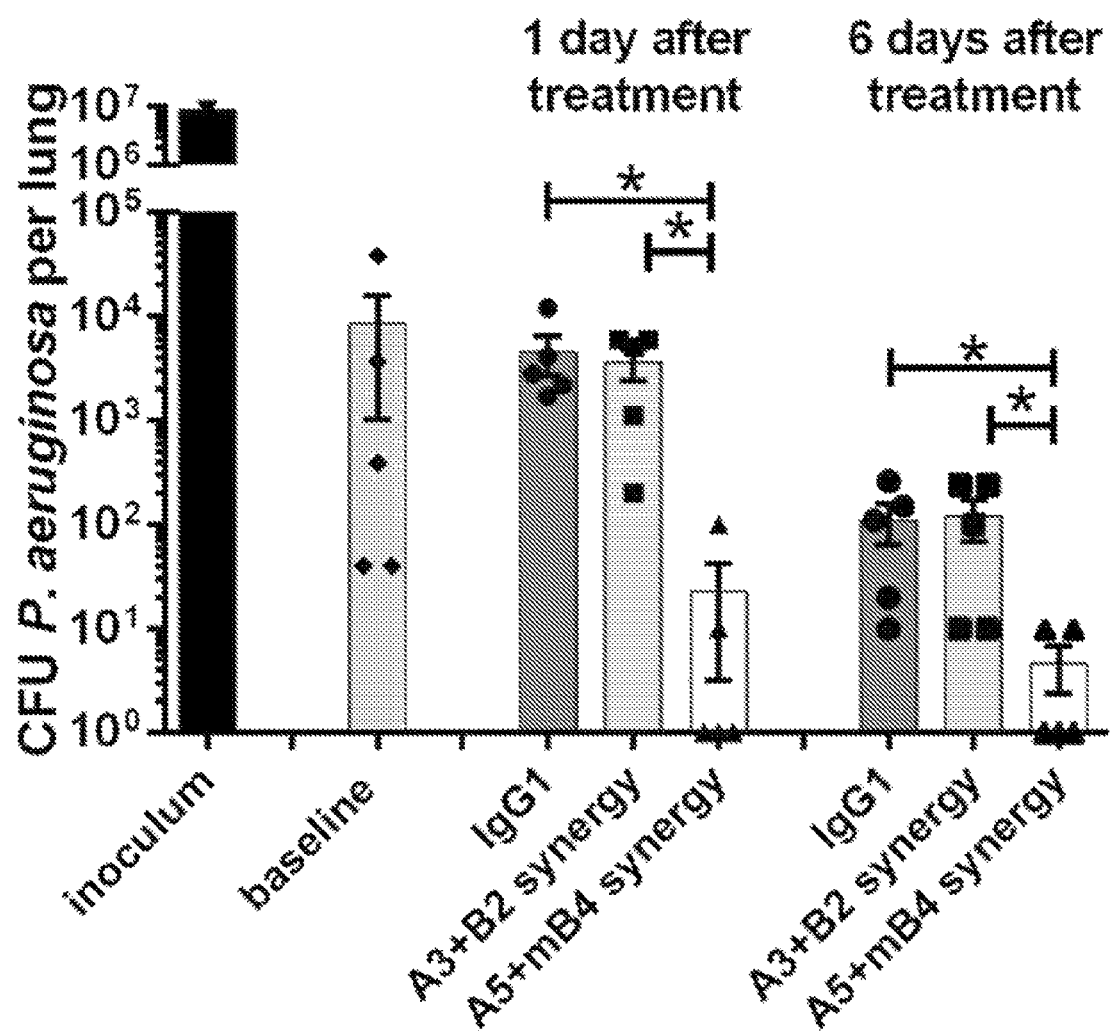
FIG. 6A shows the concentration of colony forming units of *Pseudomonas aeruginosa* per mouse lung by treatment group.
Figure 6B:
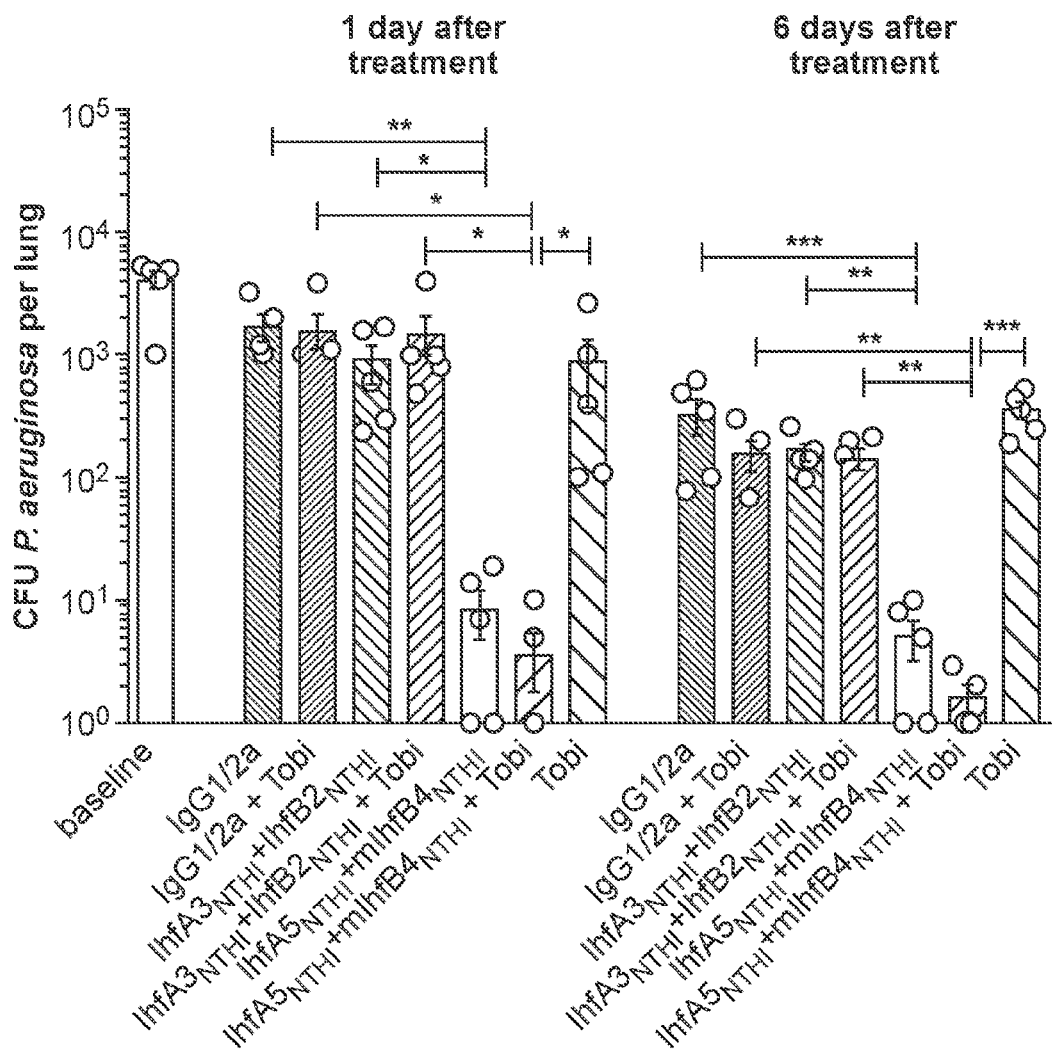
FIG. 6B shows the concentration of colony forming units of *Pseudomonas aeruginosa* per mouse lung by treatment group (with and without tobramycin).

Results demonstrate a significant reduction in biofilm severity, especially as a result of administration of monoclonal antibodies A5 and mB4 which demonstrated synergy (FIG. 6A and FIG. 6B).

The efficacy of the monoclonals as a combination therapy was assessed with tobramycin (Tobi) (FIG. 6C). One day after treatment, there was no reduction in CFU *P. aeruginosa* per lung homogenate in animals that received either: naïve murine IgG1/2a with or without tobramycin, a cocktail of tail peptide-directed monoclonal antisera with or without tobramycin or tobramycin alone. Those cohorts of mice that received a cocktail of tip-directed monoclonal antibodies either with or without tobramycin showed a significant reduction in bacterial load compared to either naïve serum treated mice ($p \leq 0.01$), those treated with tail peptide directed monoclonal antibody cocktail ($p \leq 0.05$) or those treated with tobramycin alone ($p \leq 0.05$). The level of significance of these differences increased at 6 days after treatment. The addition of tobramycin to a cocktail of tip peptide directed monoclonal antibodies appeared to confer an added benefit although all cohorts that received this cocktail of antibodies generated very low CFU counts in lung homogenates, thereby this is difficult to assess and was not statistically significant.

Figure 12A:
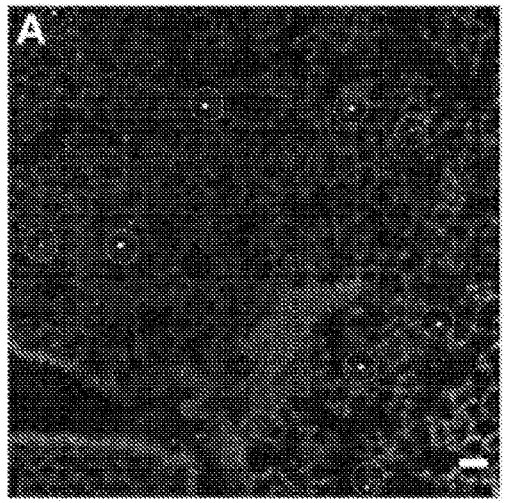
FIGS. 12A-12C depict reduction in both *P. aeruginosa* aggregate number and size within lungs treated with $IHF_{NTHI}$ tip-directed MAbs in an experimental murine model of lung infection.
Figure 12B:
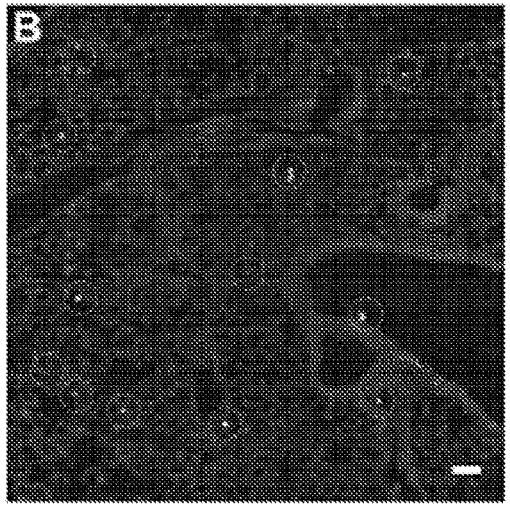
Figure 12C:
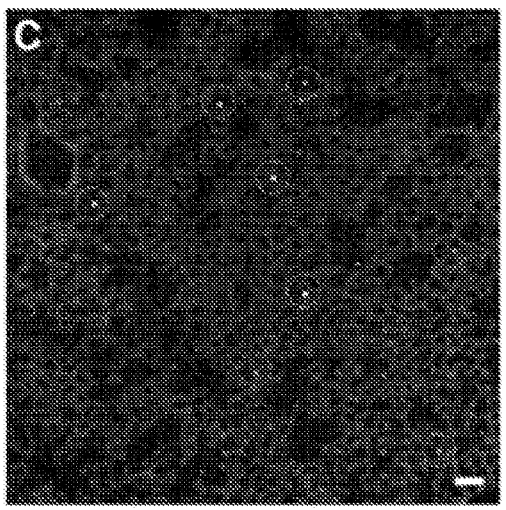
Figure 12D:
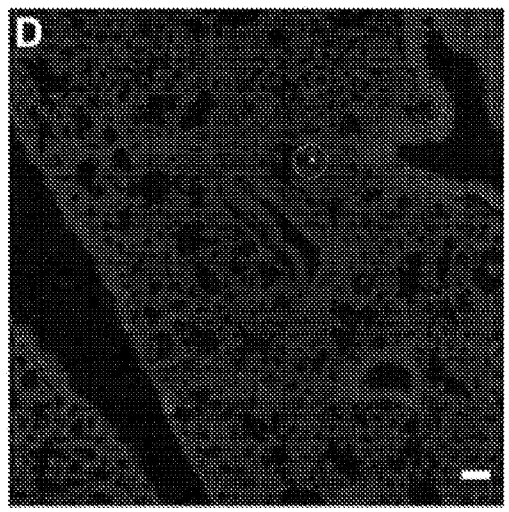
(FIG. 12D) In contrast, few *P. aeruginosa* were detected after delivery of tip-directed MAbs $IhfA5_{NTHI}$ $mIhfB4_{NTHI}$ thus demonstrating the efficacy of this therapeutic strategy. DAPI counterstain (blue); scale bars, 50 μm.
Figure 12H:
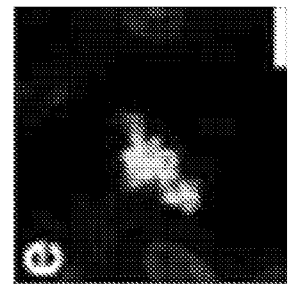
FIGS. 12E-12H show higher magnification images of representative aggregates for each cohort showing either relative size of the aggregates or the presence of single bacteria [FIG. 12E—prior to treatment.
Figure 12G:
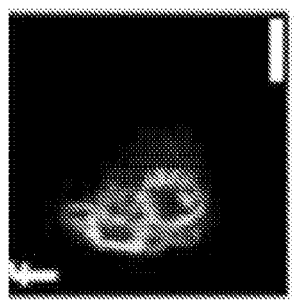
Figure 12F:
Figure 12E:
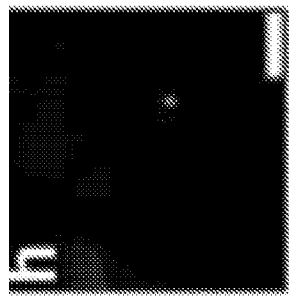
Figure 12I:
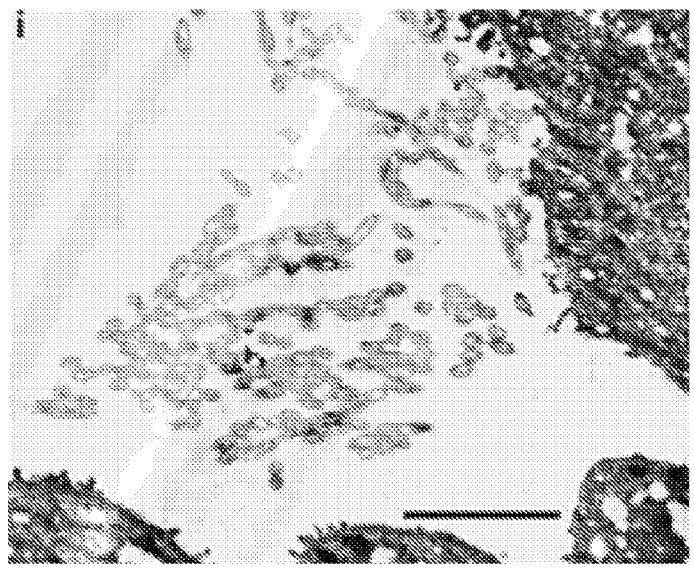
Figure 13A:
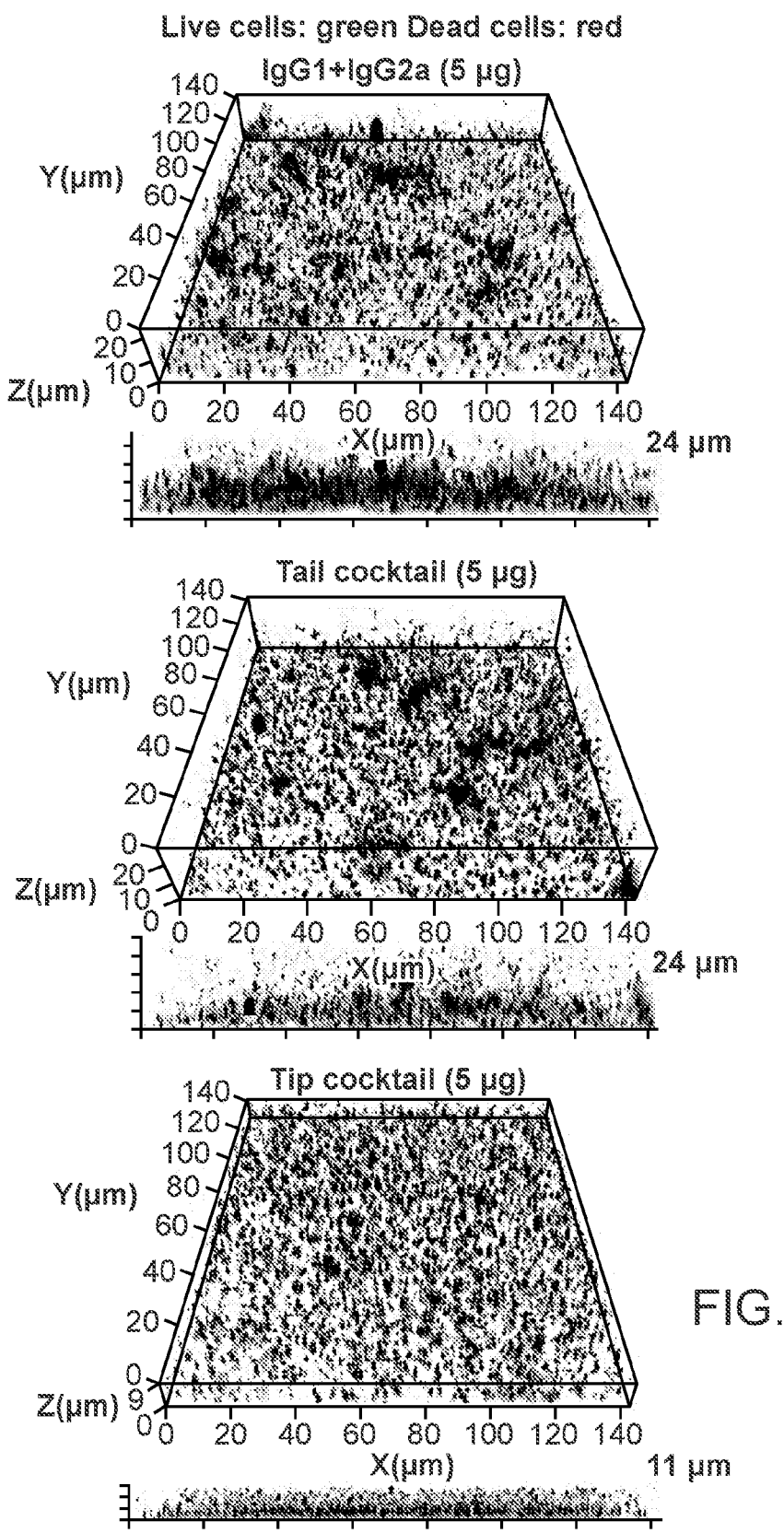
FIGS. 13A-13B show disruption of *B. cenocepacia* biofilms with monoclonal antibodies against DNA-binding 'tip' regions of IHF (A5 and mB4) and synergy with antibiotics in vitro.
Figure 13A:
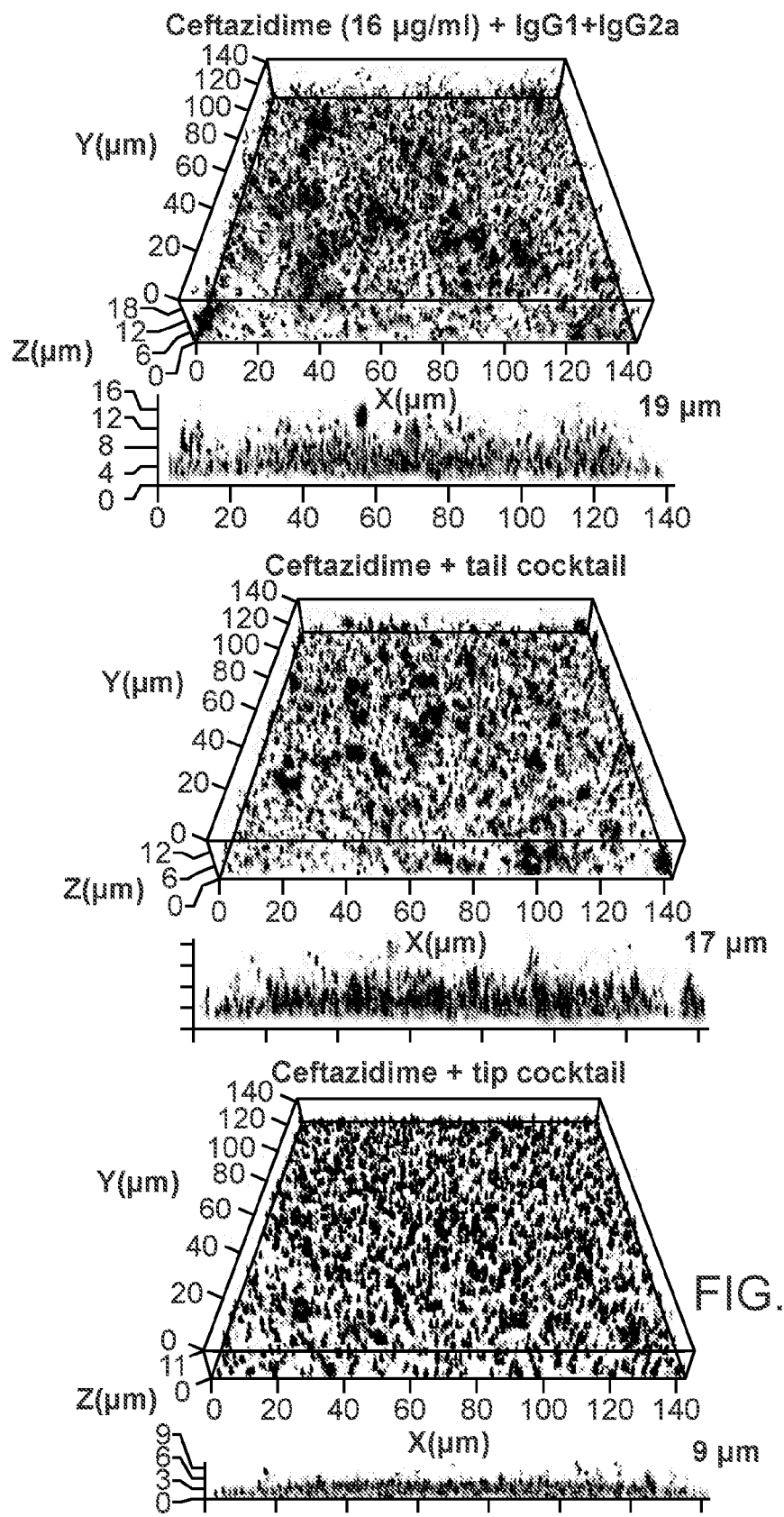
Figure 13B:
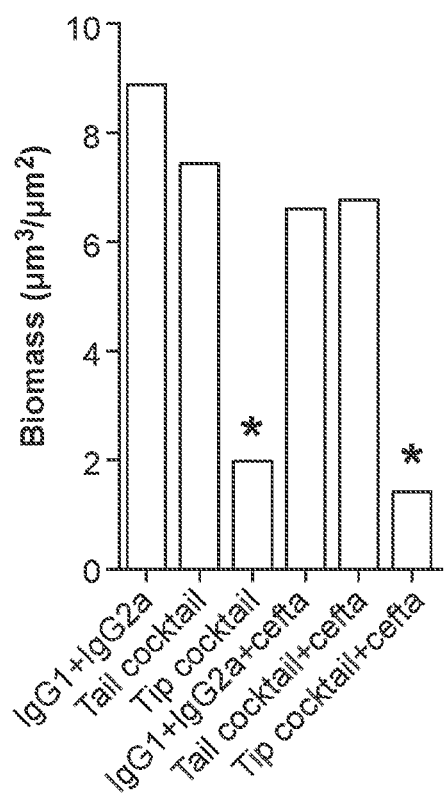

Histological evaluation of the lungs of mice following treatment revealed multiple small aggregates of positively labeled *Pseudomonas* in sections of lung recovered from both non-treated mice (FIG. 12A), mice that had been treated with naïve murine IgG (FIG. 12B) or those treated with the cocktail of monoclonal antibodies directed against the tail peptides IHFA3+IHFB2 (FIG. 12C). Small aggregates were observed dispersed through the lung with between 7 to 15 aggregates of 3-10 bacterial cells each observed in any single 10× field of view. There was a notable reduction in both number as well as the relative size of aggregates observed in the lungs recovered from mice treated with the cocktail of monoclonal antibodies directed against the tip peptides IHFA5+IHFmB4 compared to those observed in the other cohorts (FIG. 12D). Whereas in this latter cohort of mice bacterial aggregates were only rarely observed and when observed, aggregates were few in number (<1 per 10× field of view) and comprised of only 1-2 bacterial cells.

Example 8: Tuberculosis

Applicants also provide a pre-clinical model for tuberculosis (TB). See Ordway et al. (2010) Anti. Agents and Chemotherapy 54:1820. The microorganism *Mycobacterium tuberculosis* is responsible for a growing global epidemic. Current figures suggest that there are approximately 8 million new cases of TB and about 2.7 million deaths due to TB annually. In addition to the role of this microbe as a co-infection of individuals with HIV (of the ~45 million infected with HIV, estimates are that ~⅓ are also co-infected with *M. tuberculosis*), its particularly troublesome that isolates have become highly resistant to multiple drugs and no new drug for TB has been introduced in over a quarter of a century. In this animal model, SPF guinea pigs are maintained in a barrier colony and infected via aerosolized spray to deliver ~20 cfu of *M. tuberculosis* strain Erdman K01 bacilli into their lungs. Animals are sacrificed with determination of bacterial load and recovery of tissues for histopathological assessment on days 25, 50, 75, 100, 125 and 150 days post-challenge. Unlike mice which do not develop classic signs of TB, guinea pigs challenged in this manner develop well-organized granulomas with central necrosis, a hallmark of human disease. Further, like humans, guinea pigs develop severe pyogranulomatous and necrotizing lymphadenitis of the draining lymph nodes as part of the primary lesion complex. Use of this model will provide a pre-clinical screen to confirm and identify therapeutic as well as preventative strategies for reduction and/or elimination of the resulting *M. tuberculosis* biofilms which have been observed to form in the lungs of these animals subsequent to challenge and are believed to contribute to both the pathogenesis and chronicity of the disease.

Example 9: Nosocomial Infections

Multiple animal models of catheter/indwelling device biofilm infections are known. See Otto (2009) Nature Reviews Microbiology, 7:555. While typically considered normal skin flora, the microbe *Staphylococcus epidermidis* has become what many regard as a key opportunistic pathogen, ranking first among causative agents of nosocomial infections. Primarily, this bacterium is responsible for the majority of infections that develop on indwelling medical devices which are contaminated by this common skin colonizer during device insertion. While not typically life-threatening, the difficulty associated with treatment of these biofilm infections, combined with their frequency, makes them a serious public health burden. Current costs associated with treatment of vascular catheter associated bloodstream infections alone that are due to *S. epidermidis* amount to $2 billion annually in the United States. In addition to *S. epidermidis*, *E. faecalis* and *S. aureus* are also contaminations found on indwelling medical devices. There are several animal models of catheter-associated *S. epidermidis* infections including rabbits, mice, guinea pigs and rats all of which are used to study the molecular mechanisms of pathogenesis and which lend themselves to studies of prevention and/or therapeutics. Rat jugular vein catheters have been used to evaluate therapies that interfere with *E. faecalis*, *S. aureus* and *S. epidermidis* biofilm formation. Biofilm reduction is often measured three ways—(i) sonicate catheter and calculate CFUs, (ii) cut slices of catheter or simply lay on a plate and score, or (iii) the biofilm can be stained with crystal violet or another dye, eluted, and OD measured as a proxy for CFUs.

Example 10: Generation of an Immune Response

Methods described herein may be used to elicit immune responses in humans and animals. Immunogenic compositions may be administered to a human and animal subjects in the presence of adjuvants such as but not limited to aluminum salts and liposomes. Those skilled in the art will understand that any number of pharmaceutically acceptable adjuvants can also be used. Immunogenic compositions may be administered to a human or animal subjects intramuscularly, subdermally, intranasally, or through any other suitable route. Immunogenic compositions may be prepared in a manner consistent with the selected mode of administration. Immunogenic compositions may take the form of polypeptides, nucleic acids, or a combination thereof, and may comprise full-length or partial antigens. Additionally or alternatively, immunogenic compositions may take the form of APCs pulsed with a particular antigen, or APCs transfected with one or more polynucleotides encoding a particular antigen. Administration may comprise a single dose of an immunogenic composition, or an initial administration, followed by one or more booster doses. Booster doses may be provided a day, two days, three days, a week, two weeks, three weeks, one, two, three, six or twelve months, or at any other time point after an initial dose. A booster dose may be administered after an evaluation of the subject's antibody titer.

Example 11: Passive Immunity

Methods described herein may be used to confer passive immunity on a non-immune subject. Passive immunity against a given antigen may be conferred through the transfer of antibodies or antigen binding fragments that specifically recognize or bind to a particular antigen. Antibody donors and recipients may be human or non-human subjects. Additionally or alternatively, the antibody composition may comprise an isolated or recombinant polynucleotide encoding an antibody or antigen binding fragment that specifically recognizes or binds to a particular antigen.

Passive immunity may be conferred in cases where the administration of immunogenic compositions poses a risk for the recipient subject, the recipient subject is immunocompromised, or the recipient subject requires immediate immunity. Immunogenic compositions may be prepared in a manner consistent with the selected mode of administration. Compositions may comprise whole antibodies, antigen binding fragments, polyclonal antibodies, monoclonal antibodies, antibodies generated in vivo, antibodies generated in vitro, purified or partially purified antibodies, or whole serum. Administration may comprise a single dose of an antibody composition, or an initial administration followed by one or more booster doses. Booster doses may be provided a day, two days, three days, a week, two weeks, three weeks, one, two, three, six or twelve months, or at any other time point after an initial dose. A booster dose may be administered after an evaluation of the subject's antibody titer.

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

Unless otherwise defined, all technical and scientific terms used herein have the same meaning as commonly understood by one of ordinary skill in the art to which this disclosure belongs. All nucleotide sequences provided herein are presented in the 5' to 3' direction.

The embodiments illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure.

Thus, it should be understood that although the present disclosure has been specifically disclosed by specific embodiments and optional features, modification, improvement and variation of the embodiments therein herein disclosed may be resorted to by those skilled in the art, and that such modifications, improvements and variations are considered to be within the scope of this disclosure. The materials, methods, and examples provided here are representative of particular embodiments, are exemplary, and are not intended as limitations on the scope of the disclosure.

The scope of the disclosure has been described broadly and generically herein. Each of the narrower species and subgeneric groupings falling within the generic disclosure also form part of the disclosure. This includes the generic description with a proviso or negative limitation removing any subject matter from the genus, regardless of whether or not the excised material is specifically recited herein.

In addition, where features or aspects of the disclosure are described in terms of Markush groups, those skilled in the art will recognize that embodiments of the disclosure may also thereby be described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

What is claimed is:

1. An isolated antibody or antigen binding fragment comprising:

(a) a heavy chain (HC) variable domain comprising a complementarity determining region H1 (CDRH1) as set forth in SEQ ID NO: 58, a complementarity determining region H2 (CDRH2) as set forth in SEQ ID NO: 62, and a complementarity determining region H3 (CDRH3) as set forth in SEQ ID NO: 77; and (b) a light chain (LC) variable domain comprising a complementarity determining region L1 (CDRL1) as set forth in SEQ ID NO: 79, a complementarity determining region L2 (CDRL2) as set forth in SEQ ID NO: 82, and a complementarity determining region L3 (CDRL3) as set forth in SEQ ID NO: 108.

2. The isolated antibody or antigen binding fragment of claim 1, wherein the heavy chain variable domain comprises the polypeptide as set forth in SEQ ID NO: 51 or an equivalent thereof, and the light chain variable domain comprises the polypeptide as set forth in SEQ ID NO: 55 or an equivalent thereof.

3. The isolated antibody or antigen binding fragment of claim 2, wherein the equivalent of SEQ ID NO. 51 or 55 has at least about 80% amino acid identity to SEQ ID NO. 51 or 55, respectively.

4. The isolated antibody or antigen binding fragment of claim 1, wherein the heavy chain variable domain comprises the polypeptide as set forth in SEQ ID NO: 51 and a light chain variable domain comprises the polypeptide as set forth in SEQ ID NO: 55.

5. The isolated antibody or antigen binding fragment of claim 1, wherein the antigen binding fragment is selected from Fab, Fab', F(ab')₂, Fv, scFv, dsFv, Fd fragment, minibody, diabody, triabody, tetrabody or kappa body.

6. The isolated antibody or antigen binding fragment of claim 1, wherein the antibody or antigen binding fragment is monospecific or multispecific.

7. The isolated antibody or antigen binding fragment of claim 1, further comprising an Fc domain.

8. The isolated antigen binding fragment of claim 7, wherein the Fc domain is of an isotype selected from IgA1, IgA2, IgD, IgE, IgG1, IgG2, IgG3, IgG4 or IgM.

9. The isolated antibody or antigen binding fragment of claim 1, further comprising a detectable label or a purification label.

10. A composition comprising the isolated antibody or antigen binding fragment of claim 1.

11. The composition of claim 10, further comprising one or more of the following:
(a) an isolated antibody or antigen binding fragment that comprises a heavy chain (HC) variable domain and a light chain (LC) variable domain, wherein the heavy chain variable domain comprises:
complementarity determining region H1 (CDRH1) as set forth in SEQ ID NO. 110,
complementarity determining region H2 (CDRH2) as set forth in SEQ ID NO. 114, and
complementarity determining region H3 (CDRH3) as set forth in SEQ ID NO. 129, and
the light chain variable domain comprises:
complementarity determining region L1 (CDRL1) as set forth in SEQ ID NO. 130,
complementarity determining region L2 (CDRL2) as set forth in SEQ ID NO. 133, and
complementarity determining region L3 (CDRL3) as set forth in SEQ ID NO. 158,
(b) an antibody or antigen binding fragment of (a), wherein the heavy chain variable domain comprises the polypeptide as set forth in SEQ ID NO. 53 or an equivalent having at least 80% homology thereto and the light chain variable domain comprises the polypeptide as set forth in SEQ ID NO. 57 or an equivalent having at least 80% homology thereto;
(c) one or more polypeptides selected from
(i) SEQ ID NO. 12 (FLEEIRLSLESGQDVKLSGF);
(ii) SEQ ID NO. 13 (RPGRNPKTGDVVPVSARRVV);
(iii) SEQ ID NO. 14 (RTGRNPQTGAEIQIAASKVP);
(iv) SEQ ID NO. 15 (TLSAKEIENMVKDILEFISQ);
(v) SEQ ID NO. 16 (RGFGSFSLHHRQPRLGRNPK);
(vi) SEQ ID NO. 17 (FSLHHRQPRLGRNPKTGDSV);
(vii) SEQ ID NO. 33 (KKQAKAALEATLDAITASLKEG);
(viii) SEQ ID NO. 31 (VNERAARTGRNPQTGAEIQIAA);
(ix) a polypeptide comprising NPXT, wherein X is any amino acid or wherein X is selected from the amino acids Q, R, K, S or T; or
(x) an equivalent of any one of (i) through (ix), wherein an equivalent has at least about 80% homology or amino acid identity thereto;
(d) one or more of an adjuvant, a deoxyribonuclease (DNase), amoxicillin, amoxicillin-clavulanate, cefdinir, azithromycin, sulfamethoxazole-trimethoprim, or an antibody directed against outer membrane protein ("OMP") P5, rsPilA, OMP 26, OMP P2, Type IV Pilin protein or any one of (c) (i)-(x); or
(e) a carrier, which is selected from the group of a liquid carrier or a solid phase carrier, optionally which is selected from the group of a pharmaceutically acceptable polymer, a liposome, a micelle, an implant, a stent, a paste, a gel, a dental implant, and a medical implant.

12. A method of treating a subject in need thereof, comprising administering to the subject an effective amount of the isolated antibody or antigen binding fragment of claim 1.

13. The method of claim 12, further comprising administering the isolated or recombinant polypeptide comprising SEQ ID NO. 13 (RPGRNPKTGDVVPVSARRVV) or an equivalent of SEQ ID NO: 13, wherein an equivalent has at least about 80% amino acid identity to SEQ ID NO: 13.

14. The method of claim 12, further comprising administering an effective amount of an antimicrobial.

15. The method of claim 12, further comprising administering an effective amount of one or more of the following:
(a) an antibody directed against OMP P5, rsPilA, OMP 26, OMP P2, or Type IV Pilin protein;
(b) one or more of amoxicillin, amoxicillin-clavulanate, cefdinir, azithromycin, or sulfamethoxazole-trimethoprim;
(c) a deoxyribonuclease (DNase) enzyme;
(d) a polypeptide selected from
(i) SEQ ID NO. 12 (FLEEIRLSLESGQDVKLSGF);
(ii) SEQ ID NO. 13 (RPGRNPKTGDVVPVSARRVV);
(iii) SEQ ID NO. 14 (RTGRNPQTGAEIQIAASKVP);
(iv) SEQ ID NO. 15 (TLSAKEIENMVKDILEFISQ);
(v) SEQ ID NO. 16 (RGFGSFSLHHRQPRLGRNPK);
(vi) SEQ ID NO. 17 (FSLHHRQPRLGRNPKTGDSV);
(vii) SEQ ID NO. 33 (KKQAKAALEATLDAITASLKEG);
(viii) SEQ ID NO. 31 (VNERAARTGRNPQTGAEIQIAA);
(ix) a polypeptide comprising NPXT, wherein "X" refers to any amino acid; or
(x) an equivalent of any one of (i) through (ix), wherein an equivalent has at least about 80% amino acid identity thereto; or
(e) an antibody or an antigen binding fragment comprising:
(xi) a heavy chain (HC) variable domain comprising complementarity determining region H1 (CDRH1) as set forth in SEQ ID NO: 110, complementarity determining region H2 (CDRH2) as set forth in SEQ ID NO: 114, and complementarity determining region H3 (CDRH3) as set forth in SEQ ID NO: 129; and (xii) a light chain (LC) variable domain comprising complementarity determining region L1 (CDRL1) as set forth in SEQ ID NO: 130, complementarity determining region L2 (CDRL2) as set forth in SEQ ID NO: 133, and complementarity determining region L3 (CDRL3) as set forth in SEQ ID NO: 158;

(f) an isolated antibody or antigen binding fragment of (e), wherein the heavy chain variable domain comprises the polypeptide as set forth in SEQ ID NO. 53 or an equivalent thereof and the light chain variable domain comprises the polypeptide as set forth in SEQ ID NO. 57 or an equivalent thereof, wherein an equivalent has at least 80% homology thereto.

16. The method of claim 12, wherein the isolated antibody comprises a heavy chain variable domain is as set forth in SEQ ID NO: 51 and a light chain variable domain is as set forth in SEQ ID NO: 55, or an equivalent of each thereof, wherein or an equivalent has at least 80% homology thereto.

17. The method of claim 12, wherein the subject is suffering from sinusitis, bronchitis, otitis media, exacerbations of chronic obstructive pulmonary disease (COPD), dental caries, pneumonia, cystic fibrosis, skin and soft tissue infections, gonorrhea, urinary tract infection, or chronic granulomatous disease.

18. The method of claim 12, wherein the subject has a biofilm generated by one or more microorganisms selected from *Haemophilus influenza, Streptococcus mutans, Staphylococcus aureus, Moraxella catarrhalis, Streptococcus pneumonia, Pseudomonas aeruginosa, Neisseria gonorrhoeae, E. coli, Staphylococcus epidermidis*, and *Burkholderia cenocepacia*.

19. The method of claim 18, wherein *Staphylococcus aureus* is Methicillin-resistant *S. aureus* (MRSA).

20. A method of treating a subject having been selected for the treatment by detection of the presence of one or more DNABII proteins in a sample isolated from the subject, comprising administering to the subject an effective amount of the isolated antibody or antigen binding fragment of claim 1.

21. The method of claim 20, wherein the isolated antibody or antigen binding fragment comprises the heavy chain variable domain as set forth in SEQ ID NO: 51 and the light chain variable domain as set forth in SEQ ID NO: 55 or an equivalent of each thereof, wherein an equivalent has at least 80% homology thereto.

22. The method of claim 20, wherein the subject has a biofilm associated disease selected from sinusitis, bronchitis, otitis media, exacerbations of chronic obstructive pulmonary disease (COPD), dental caries, pneumonia, cystic fibrosis, skin and soft tissue infections, gonorrhea, urinary tract infection, or chronic granulomatous disease.

23. The method of claim 20, wherein the subject has a biofilm generated by one or more microorganisms selected from *Haemophilus influenza, Streptococcus mutans, Staphylococcus aureus, Moraxella catarrhalis, Streptococcus pneumonia, Pseudomonas aeruginosa, Neisseria gonorrhoeae, E. coli, Staphylococcus epidermidis*, and *Burkholderia cenocepacia*.

24. The method of claim 23, wherein *Staphylococcus aureus* is Methicillin-resistant *S. aureus* (MRSA).

25. The method of claim 20, further comprising administering to the subject an effective amount of an antimicrobial.

26. The method of claim 20, further comprising administering an effective amount of one or more of the following:
(a) an isolated antibody directed against OMP P5, rsPilA, OMP 26, OMP P2, or Type IV Pilin protein;
(b) one or more of amoxicillin, amoxicillin-clavulanate, cefdinir, azithromycin, or sulfamethoxazole-trimethoprim;
(c) a deoxyribonuclease (DNase) enzyme;
(d) a polypeptide selected from
(i) SEQ ID NO. 12 (FLEEIRLSLESGQDVKLSGF);
(ii) SEQ ID NO. 13 (RPGRNPKTGDVVPVSARRVV);
(iii) SEQ ID NO. 14 (RTGRNPQTGAEIQIAASKVP);
(iv) SEQ ID NO. 15 (TLSAKEIENMVKDILEFISQ);
(v) SEQ ID NO. 16 (RGFGSFSLHHRQPRLGRNPK);
(vi) SEQ ID NO. 17 (FSLHHRQPRLGRNPKTGDSV);
(vii) SEQ ID NO. 33 (KKQAKAALEATLDAITASLKEG);
(viii) SEQ ID NO. 31 (VNERAARTGRNPQTGAEIQIAA);
(ix) a polypeptide comprising NPXT, wherein "X" refers to any amino acid; or
(x) an equivalent of any one of (i) through (ix), wherein an equivalent has at least about 80% amino acid identity thereto; or
(e) an antibody or an antigen binding fragment comprising:
(xi) a heavy chain (HC) variable domain comprising complementarity determining region H1 (CDRH1) as set forth in SEQ ID NO: 110, complementarity determining region H2 (CDRH2) as set forth in SEQ ID NO: 114, and complementarity determining region H3 (CDRH3) at set forth in SEQ ID NO: 129; and
(xii) a light chain (LC) variable domain comprising complementarity determining region L1 (CDRL1) as set forth in SEQ ID NO: 130, complementarity determining region L2 (CDRL2) as set forth in SEQ ID NO: 133, and complementarity determining region L3 (CDRL3) as set forth in SEQ ID NO: 158;
(f) an antibody or antigen binding fragment of (e), wherein the heavy chain variable domain comprises the polypeptide as set forth in SEQ ID NO. 53 or an equivalent thereof and the light chain variable domain comprises the polypeptide as set forth in SEQ ID NO. 57 or an equivalent thereof, wherein an equivalent has at least 80% homology thereto.

* * * * *

SEQUENCE LISTING

```
<160> NUMBER OF SEQ ID NOS: 160

<210> SEQ ID NO 1
<211> LENGTH: 96
<212> TYPE: PRT
<213> ORGANISM: Haemophilus influenzae

<400> SEQUENCE: 1

Met Ala Thr Ile Thr Lys Leu Asp Ile Ile Glu Tyr Leu Ser Asp Lys
1               5                   10                  15

Tyr His Leu Ser Lys Gln Asp Thr Lys Asn Val Val Glu Asn Phe Leu
            20                  25                  30

Glu Glu Ile Arg Leu Ser Leu Glu Ser Gly Gln Asp Val Lys Leu Ser
        35                  40                  45

Gly Phe Gly Asn Phe Glu Leu Arg Asp Lys Ser Ser Arg Pro Gly Arg
    50                  55                  60

Asn Pro Lys Thr Gly Asp Val Val Pro Val Ser Ala Arg Arg Val Val
65                  70                  75                  80

Ile Thr Lys Pro Gly Gln Lys Leu Arg Ala Arg Val Glu Lys Ile Lys
                85                  90                  95
```

<210> SEQ ID NO 2
<211> LENGTH: 94
<212> TYPE: PRT
<213> ORGANISM: Haemophilus influenzae

<400> SEQUENCE: 2

Met Thr Lys Ser Glu Leu Met Glu Lys Leu Ser Ala Lys Gln Pro Thr
1               5                   10                  15

Leu Ser Ala Lys Glu Ile Glu Asn Met Val Lys Asp Ile Leu Glu Phe
            20                  25                  30

Ile Ser Gln Ser Leu Glu Asn Gly Asp Arg Val Glu Val Arg Gly Phe
        35                  40                  45

Gly Ser Phe Ser Leu His His Arg Gln Pro Arg Leu Gly Arg Asn Pro
    50                  55                  60

Lys Thr Gly Asp Ser Val Asn Leu Ser Ala Lys Ser Val Pro Tyr Phe
65                  70                  75                  80

Lys Ala Gly Lys Glu Leu Lys Ala Arg Val Asp Val Gln Ala
                85                  90

<210> SEQ ID NO 3
<211> LENGTH: 136
<212> TYPE: PRT
<213> ORGANISM: Haemophilus influenzae

<400> SEQUENCE: 3

Met Arg Phe Val Thr Ile Phe Ile Asn His Ala Phe Asn Ser Ser Gln
1               5                   10                  15

Val Arg Leu Ser Phe Ala Gln Phe Leu Arg Gln Ile Arg Lys Asp Thr
            20                  25                  30

Phe Lys Glu Ser Asn Phe Leu Phe Asn Arg Arg Tyr Lys Phe Met Asn
        35                  40                  45

Lys Thr Asp Leu Ile Asp Ala Ile Ala Asn Ala Ala Glu Leu Asn Lys
    50                  55                  60

Lys Gln Ala Lys Ala Ala Leu Glu Ala Thr Leu Asp Ala Ile Thr Ala
65                  70                  75                  80

Ser Leu Lys Glu Gly Glu Pro Val Gln Leu Ile Gly Phe Gly Thr Phe
                85                  90                  95

Lys Val Asn Glu Arg Ala Ala Arg Thr Gly Arg Asn Pro Gln Thr Gly
            100                 105                 110

Ala Glu Ile Gln Ile Ala Ala Ser Lys Val Pro Ala Phe Val Ser Gly
        115                 120                 125

Lys Ala Leu Lys Asp Ala Ile Lys
    130                 135

<210> SEQ ID NO 4
<211> LENGTH: 96
<212> TYPE: PRT
<213> ORGANISM: Haemophilus influenzae

<400> SEQUENCE: 4

Met Ala Thr Ile Thr Lys Leu Asp Ile Ile Glu Tyr Leu Ser Asp Lys
1               5                   10                  15

Tyr His Leu Ser Lys Gln Asp Thr Lys Asn Val Val Glu Asn Phe Leu
            20                  25                  30

Glu Glu Ile Arg Leu Ser Leu Glu Ser Gly Gln Asp Val Lys Leu Ser
        35                  40                  45

Gly Phe Gly Asn Phe Glu Leu Arg Asp Lys Ser Ser Arg Pro Gly Arg
50                  55                  60

Asn Pro Lys Thr Gly Asp Val Val Pro Val Ser Ala Arg Arg Val Val
65                  70                  75                  80

Thr Phe Lys Pro Gly Gln Lys Leu Arg Ala Arg Val Glu Lys Thr Lys
                85                  90                  95

<210> SEQ ID NO 5
<211> LENGTH: 96
<212> TYPE: PRT
<213> ORGANISM: Haemophilus influenzae

<400> SEQUENCE: 5

Met Ala Thr Ile Thr Lys Leu Asp Ile Ile Glu Tyr Leu Ser Asp Lys
1               5                   10                  15

Tyr His Leu Ser Lys Gln Asp Thr Lys Asn Val Val Glu Asn Phe Leu
                20                  25                  30

Glu Glu Ile Arg Leu Ser Leu Glu Ser Gly Gln Asp Val Lys Leu Ser
            35                  40                  45

Gly Phe Gly Asn Phe Glu Leu Arg Asp Lys Ser Ser Arg Pro Gly Arg
50                  55                  60

Asn Pro Lys Thr Gly Asp Val Val Pro Val Ser Ala Arg Arg Val Val
65                  70                  75                  80

Thr Phe Lys Pro Gly Gln Lys Leu Arg Ala Arg Val Glu Lys Thr Lys
                85                  90                  95

<210> SEQ ID NO 6
<211> LENGTH: 99
<212> TYPE: PRT
<213> ORGANISM: Escherichia coli

<400> SEQUENCE: 6

Met Ala Leu Thr Lys Ala Glu Met Ser Glu Tyr Leu Phe Asp Lys Leu
1               5                   10                  15

Gly Leu Ser Lys Arg Asp Ala Lys Glu Leu Val Glu Leu Phe Phe Glu
                20                  25                  30

Glu Ile Arg Arg Ala Leu Glu Asn Gly Glu Gln Val Lys Leu Ser Gly
            35                  40                  45

Phe Gly Asn Phe Asp Leu Arg Asp Lys Asn Gln Arg Pro Gly Arg Asn
50                  55                  60

Pro Lys Thr Gly Glu Asp Ile Pro Ile Thr Ala Arg Arg Val Val Thr
65                  70                  75                  80

Phe Arg Pro Gly Gln Lys Leu Lys Ser Arg Val Glu Asn Ala Ser Pro
                85                  90                  95

Lys Asp Glu

<210> SEQ ID NO 7
<211> LENGTH: 94
<212> TYPE: PRT
<213> ORGANISM: Escherichia coli

<400> SEQUENCE: 7

Met Thr Lys Ser Glu Leu Ile Glu Arg Leu Ala Thr Gln Gln Ser His
1               5                   10                  15

Ile Pro Ala Lys Thr Val Glu Asp Ala Val Lys Glu Met Leu Glu His
                20                  25                  30

Met Ala Ser Thr Leu Ala Gln Gly Glu Arg Ile Glu Ile Arg Gly Phe
            35                  40                  45

```
Gly Ser Phe Ser Leu His Tyr Arg Ala Pro Arg Thr Gly Arg Asn Pro
        50                  55                  60

Lys Thr Gly Asp Lys Val Glu Leu Glu Gly Lys Tyr Val Pro His Phe
 65                  70                  75                  80

Lys Pro Gly Lys Glu Leu Arg Asp Arg Ala Asn Ile Tyr Gly
                85                  90
```

<210> SEQ ID NO 8
<211> LENGTH: 90
<212> TYPE: PRT
<213> ORGANISM: Escherichia coli

<400> SEQUENCE: 8

```
Met Asn Lys Thr Gln Leu Ile Asp Val Ile Ala Glu Lys Ala Glu Leu
 1               5                  10                  15

Ser Lys Thr Gln Ala Lys Ala Ala Leu Glu Ser Thr Leu Ala Ala Ile
                20                  25                  30

Thr Glu Ser Leu Lys Glu Gly Asp Ala Val Gln Leu Val Gly Phe Gly
                35                  40                  45

Thr Phe Lys Val Asn His Arg Ala Glu Arg Thr Gly Arg Asn Pro Gln
 50                  55                  60

Thr Gly Lys Glu Ile Lys Ile Ala Ala Ala Asn Val Pro Ala Phe Val
 65                  70                  75                  80

Ser Gly Lys Ala Leu Lys Asp Ala Val Lys
                85                  90
```

<210> SEQ ID NO 9
<211> LENGTH: 88
<212> TYPE: PRT
<213> ORGANISM: Escherichia coli

<400> SEQUENCE: 9

```
Met Asn Lys Ser Gln Leu Ile Asp Lys Ile Ala Ala Gly Ala Asp Ile
 1               5                  10                  15

Ser Lys Ala Ala Ala Gly Arg Ala Leu Asp Ala Ile Ile Ala Ser Val
                20                  25                  30

Thr Glu Ser Leu Lys Glu Gly Asp Asp Val Ala Leu Val Gly Phe Gly
                35                  40                  45

Thr Phe Ala Val Lys Glu Arg Ala Ala Arg Thr Gly Arg Asn Pro Gln
 50                  55                  60

Thr Gly Lys Glu Ile Ala Ala Ala Lys Val Pro Ser Phe Arg Ala Gly
 65                  70                  75                  80

Lys Ala Leu Lys Asp Ala Val Asn
                85
```

<210> SEQ ID NO 10
<211> LENGTH: 100
<212> TYPE: PRT
<213> ORGANISM: Pseudomonas aeruginosa

<400> SEQUENCE: 10

```
Met Gly Ala Leu Thr Lys Ala Glu Ile Ala Glu Arg Leu Tyr Glu Glu
 1               5                  10                  15

Leu Gly Leu Asn Lys Arg Glu Ala Lys Glu Leu Val Glu Leu Phe Phe
                20                  25                  30

Glu Glu Ile Arg Gln Ala Leu Glu His Asn Glu Gln Val Lys Leu Ser
                35                  40                  45
```

```
Gly Phe Gly Asn Phe Asp Leu Arg Asp Lys Arg Gln Arg Pro Gly Arg
            50                  55                  60

Asn Pro Lys Thr Gly Glu Glu Ile Pro Ile Thr Ala Arg Arg Val Val
 65                  70                  75                  80

Thr Phe Arg Pro Gly Gln Lys Leu Lys Ala Arg Val Glu Ala Tyr Ala
                    85                  90                  95

Gly Thr Lys Ser
            100

<210> SEQ ID NO 11
<211> LENGTH: 94
<212> TYPE: PRT
<213> ORGANISM: Pseudomonas aeruginosa

<400> SEQUENCE: 11

Met Thr Lys Ser Glu Leu Ile Glu Arg Ile Val Thr His Gln Gly Gln
 1               5                  10                  15

Leu Ser Ala Lys Asp Val Glu Leu Ala Ile Lys Thr Met Leu Glu Gln
            20                  25                  30

Met Ser Gln Ala Leu Ala Thr Gly Asp Arg Ile Glu Ile Arg Gly Phe
        35                  40                  45

Gly Ser Phe Ser Leu His Tyr Arg Ala Pro Arg Val Gly Arg Asn Pro
    50                  55                  60

Lys Thr Gly Glu Ser Val Arg Leu Asp Gly Lys Phe Val Pro His Phe
 65                  70                  75                  80

Lys Pro Gly Lys Glu Leu Arg Asp Arg Val Asn Glu Pro Glu
                85                  90

<210> SEQ ID NO 12
<211> LENGTH: 20
<212> TYPE: PRT
<213> ORGANISM: Haemophilus influenzae

<400> SEQUENCE: 12

Phe Leu Glu Glu Ile Arg Leu Ser Leu Glu Ser Gly Gln Asp Val Lys
 1               5                  10                  15

Leu Ser Gly Phe
            20

<210> SEQ ID NO 13
<211> LENGTH: 20
<212> TYPE: PRT
<213> ORGANISM: Haemophilus influenzae

<400> SEQUENCE: 13

Arg Pro Gly Arg Asn Pro Lys Thr Gly Asp Val Val Pro Val Ser Ala
 1               5                  10                  15

Arg Arg Val Val
            20

<210> SEQ ID NO 14
<211> LENGTH: 20
<212> TYPE: PRT
<213> ORGANISM: Haemophilus influenzae

<400> SEQUENCE: 14

Arg Thr Gly Arg Asn Pro Gln Thr Gly Ala Glu Ile Gln Ile Ala Ala
 1               5                  10                  15

Ser Lys Val Pro
            20
```

<210> SEQ ID NO 15
<211> LENGTH: 20
<212> TYPE: PRT
<213> ORGANISM: Haemophilus influenzae

<400> SEQUENCE: 15

Thr Leu Ser Ala Lys Glu Ile Glu Asn Met Val Lys Asp Ile Leu Glu
1               5                   10                  15

Phe Ile Ser Gln
            20

<210> SEQ ID NO 16
<211> LENGTH: 20
<212> TYPE: PRT
<213> ORGANISM: Haemophilus influenzae

<400> SEQUENCE: 16

Arg Gly Phe Gly Ser Phe Ser Leu His His Arg Gln Pro Arg Leu Gly
1               5                   10                  15

Arg Asn Pro Lys
            20

<210> SEQ ID NO 17
<211> LENGTH: 20
<212> TYPE: PRT
<213> ORGANISM: Haemophilus influenzae

<400> SEQUENCE: 17

Phe Ser Leu His His Arg Gln Pro Arg Leu Gly Arg Asn Pro Lys Thr
1               5                   10                  15

Gly Asp Ser Val
            20

<210> SEQ ID NO 18
<211> LENGTH: 20
<212> TYPE: PRT
<213> ORGANISM: Haemophilus influenzae

<400> SEQUENCE: 18

Met Ala Thr Ile Thr Lys Leu Asp Ile Ile Glu Tyr Leu Ser Asp Lys
1               5                   10                  15

Tyr His Leu Ser
            20

<210> SEQ ID NO 19
<211> LENGTH: 20
<212> TYPE: PRT
<213> ORGANISM: Haemophilus influenzae

<400> SEQUENCE: 19

Lys Tyr His Leu Ser Lys Gln Asp Thr Lys Asn Val Val Glu Asn Phe
1               5                   10                  15

Leu Glu Glu Ile
            20

<210> SEQ ID NO 20
<211> LENGTH: 20
<212> TYPE: PRT
<213> ORGANISM: Haemophilus influenzae

<400> SEQUENCE: 20

-continued

```
Lys Leu Ser Gly Phe Gly Asn Phe Glu Leu Arg Asp Lys Ser Ser Arg
1               5                   10                  15

Pro Gly Arg Asn
            20

<210> SEQ ID NO 21
<211> LENGTH: 21
<212> TYPE: PRT
<213> ORGANISM: Haemophilus influenzae

<400> SEQUENCE: 21

Ala Arg Arg Val Val Thr Phe Lys Pro Gly Gln Lys Leu Arg Ala Arg
1               5                   10                  15

Val Glu Lys Thr Lys
            20

<210> SEQ ID NO 22
<211> LENGTH: 20
<212> TYPE: PRT
<213> ORGANISM: Haemophilus influenzae

<400> SEQUENCE: 22

Met Thr Lys Ser Glu Leu Met Glu Lys Leu Ser Ala Lys Gln Pro Thr
1               5                   10                  15

Leu Ser Ala Lys
            20

<210> SEQ ID NO 23
<211> LENGTH: 20
<212> TYPE: PRT
<213> ORGANISM: Haemophilus influenzae

<400> SEQUENCE: 23

Glu Phe Ile Ser Gln Ser Leu Glu Asn Gly Asp Arg Val Glu Val Arg
1               5                   10                  15

Gly Phe Gly Ser
            20

<210> SEQ ID NO 24
<211> LENGTH: 20
<212> TYPE: PRT
<213> ORGANISM: Haemophilus influenzae

<400> SEQUENCE: 24

Gly Arg Asn Pro Lys Thr Gly Asp Ser Val Asn Leu Ser Ala Lys Ser
1               5                   10                  15

Val Pro Tyr Phe
            20

<210> SEQ ID NO 25
<211> LENGTH: 19
<212> TYPE: PRT
<213> ORGANISM: Haemophilus influenzae

<400> SEQUENCE: 25

Ser Val Pro Tyr Phe Lys Ala Gly Lys Glu Leu Lys Ala Arg Val Asp
1               5                   10                  15

Val Gln Ala

<210> SEQ ID NO 26
<211> LENGTH: 21
<212> TYPE: PRT
```

```
<213> ORGANISM: Haemophilus influenzae

<400> SEQUENCE: 26

Asn Phe Glu Leu Arg Asp Lys Ser Ser Arg Pro Gly Arg Asn Pro Lys
1               5                   10                  15

Thr Gly Asp Val Val
            20

<210> SEQ ID NO 27
<211> LENGTH: 21
<212> TYPE: PRT
<213> ORGANISM: Haemophilus influenzae

<400> SEQUENCE: 27

Ser Leu His His Arg Gln Pro Arg Leu Gly Arg Asn Pro Lys Thr Gly
1               5                   10                  15

Asp Ser Val Asn Leu
            20

<210> SEQ ID NO 28
<211> LENGTH: 22
<212> TYPE: PRT
<213> ORGANISM: Haemophilus influenzae

<400> SEQUENCE: 28

Met Asn Lys Thr Asp Leu Ile Asp Ala Ile Ala Asn Ala Ala Glu Leu
1               5                   10                  15

Asn Lys Lys Gln Ala Lys
            20

<210> SEQ ID NO 29
<211> LENGTH: 22
<212> TYPE: PRT
<213> ORGANISM: Haemophilus influenzae

<400> SEQUENCE: 29

Lys Lys Gln Ala Lys Ala Ala Leu Glu Ala Thr Leu Asp Ala Ile Thr
1               5                   10                  15

Ala Ser Leu Lys Glu Gly
            20

<210> SEQ ID NO 30
<211> LENGTH: 22
<212> TYPE: PRT
<213> ORGANISM: Haemophilus influenzae

<400> SEQUENCE: 30

Ser Leu Lys Glu Gly Glu Pro Val Gln Leu Ile Gly Phe Gly Thr Phe
1               5                   10                  15

Lys Val Asn Glu Arg Ala
            20

<210> SEQ ID NO 31
<211> LENGTH: 22
<212> TYPE: PRT
<213> ORGANISM: Haemophilus influenzae

<400> SEQUENCE: 31

Val Asn Glu Arg Ala Ala Arg Thr Gly Arg Asn Pro Gln Thr Gly Ala
1               5                   10                  15

Glu Ile Gln Ile Ala Ala
            20
```

<210> SEQ ID NO 32
<211> LENGTH: 22
<212> TYPE: PRT
<213> ORGANISM: Haemophilus influenzae

<400> SEQUENCE: 32

Ile Gln Ile Ala Ala Ser Lys Val Pro Ala Phe Val Ser Gly Lys Ala
1               5                   10                  15

Leu Lys Asp Ala Ile Lys
            20

<210> SEQ ID NO 33
<211> LENGTH: 22
<212> TYPE: PRT
<213> ORGANISM: Haemophilus influenzae

<400> SEQUENCE: 33

Lys Lys Gln Ala Lys Ala Ala Leu Glu Ala Thr Leu Asp Ala Ile Thr
1               5                   10                  15

Ala Ser Leu Lys Glu Gly
            20

<210> SEQ ID NO 34
<211> LENGTH: 384
<212> TYPE: PRT
<213> ORGANISM: Homo sapiens

<400> SEQUENCE: 34

Ala Pro Thr Lys Ala Pro Asp Val Phe Pro Ile Ile Ser Gly Cys Arg
1               5                   10                  15

His Pro Lys Asp Asn Ser Pro Val Val Leu Ala Cys Leu Ile Thr Gly
            20                  25                  30

Tyr His Pro Thr Ser Val Thr Val Thr Trp Tyr Met Gly Thr Gln Ser
        35                  40                  45

Gln Pro Gln Arg Thr Phe Pro Glu Ile Gln Arg Arg Asp Ser Tyr Tyr
    50                  55                  60

Met Thr Ser Ser Gln Leu Ser Thr Pro Leu Gln Gln Trp Arg Gln Gly
65                  70                  75                  80

Glu Tyr Lys Cys Val Val Gln His Thr Ala Ser Lys Ser Lys Lys Glu
                85                  90                  95

Ile Phe Arg Trp Pro Glu Ser Pro Lys Ala Gln Ala Ser Ser Val Pro
            100                 105                 110

Thr Ala Gln Pro Gln Ala Glu Gly Ser Leu Ala Lys Ala Thr Thr Ala
        115                 120                 125

Pro Ala Thr Thr Arg Asn Thr Gly Arg Gly Gly Glu Glu Lys Lys Lys
    130                 135                 140

Glu Lys Glu Lys Glu Glu Gln Glu Glu Arg Glu Thr Lys Thr Pro Glu
145                 150                 155                 160

Cys Pro Ser His Thr Gln Pro Leu Gly Val Tyr Leu Leu Thr Pro Ala
                165                 170                 175

Val Gln Asp Leu Trp Leu Arg Asp Lys Ala Thr Phe Thr Cys Phe Val
            180                 185                 190

Val Gly Ser Asp Leu Lys Asp Ala His Leu Thr Trp Glu Val Ala Gly
        195                 200                 205

Lys Val Pro Thr Gly Gly Val Glu Glu Gly Leu Leu Glu Arg His Ser
    210                 215                 220

```
Asn Gly Ser Gln Ser Gln His Ser Arg Leu Thr Leu Pro Arg Ser Leu
225                 230                 235                 240

Trp Asn Ala Gly Thr Ser Val Thr Cys Thr Leu Asn His Pro Ser Leu
            245                 250                 255

Pro Pro Gln Arg Leu Met Ala Leu Arg Glu Pro Ala Ala Gln Ala Pro
        260                 265                 270

Val Lys Leu Ser Leu Asn Leu Leu Ala Ser Ser Asp Pro Pro Glu Ala
    275                 280                 285

Ala Ser Trp Leu Leu Cys Glu Val Ser Gly Phe Pro Pro Asn Ile
290                 295                 300

Leu Leu Met Trp Leu Glu Asp Gln Arg Glu Val Asn Thr Ser Gly Phe
305                 310                 315                 320

Ala Pro Ala Arg Pro Pro Gln Pro Gly Ser Thr Thr Phe Trp Ala
                325                 330                 335

Trp Ser Val Leu Arg Val Pro Ala Pro Pro Ser Pro Gln Pro Ala Thr
            340                 345                 350

Tyr Thr Cys Val Val Ser His Glu Asp Ser Arg Thr Leu Leu Asn Ala
            355                 360                 365

Ser Arg Ser Leu Glu Val Ser Tyr Val Thr Asp His Gly Pro Met Lys
370                 375                 380

<210> SEQ ID NO 35
<211> LENGTH: 330
<212> TYPE: PRT
<213> ORGANISM: Homo sapiens

<400> SEQUENCE: 35

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220
```

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 36
<211> LENGTH: 326
<212> TYPE: PRT
<213> ORGANISM: Homo sapiens

<400> SEQUENCE: 36

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr

```
                   260                 265                 270
Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 37
<211> LENGTH: 377
<212> TYPE: PRT
<213> ORGANISM: Homo sapiens

<400> SEQUENCE: 37

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300
```

```
Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
370                 375
```

<210> SEQ ID NO 38
<211> LENGTH: 452
<212> TYPE: PRT
<213> ORGANISM: Homo sapiens

<400> SEQUENCE: 38

```
Gly Ser Ala Ser Ala Pro Thr Leu Phe Pro Leu Val Ser Cys Glu Asn
1               5                   10                  15

Ser Pro Ser Asp Thr Ser Ser Val Ala Val Gly Cys Leu Ala Gln Asp
            20                  25                  30

Phe Leu Pro Asp Ser Ile Thr Leu Ser Trp Lys Tyr Lys Asn Asn Ser
        35                  40                  45

Asp Ile Ser Ser Thr Arg Gly Phe Pro Ser Val Leu Arg Gly Gly Lys
    50                  55                  60

Tyr Ala Ala Thr Ser Gln Val Leu Leu Pro Ser Lys Asp Val Met Gln
65                  70                  75                  80

Gly Thr Asp Glu His Val Val Cys Lys Val Gln His Pro Asn Gly Asn
                85                  90                  95

Lys Glu Lys Asn Val Pro Leu Pro Val Ile Ala Glu Leu Pro Pro Lys
            100                 105                 110

Val Ser Val Phe Val Pro Pro Arg Asp Gly Phe Phe Gly Asn Pro Arg
        115                 120                 125

Lys Ser Lys Leu Ile Cys Gln Ala Thr Gly Phe Ser Pro Arg Gln Ile
    130                 135                 140

Gln Val Ser Trp Leu Arg Glu Gly Lys Gln Val Gly Ser Gly Val Thr
145                 150                 155                 160

Thr Asp Gln Val Gln Ala Glu Ala Lys Glu Ser Gly Pro Thr Thr Tyr
                165                 170                 175

Lys Val Thr Ser Thr Leu Thr Ile Lys Glu Ser Asp Trp Leu Gly Gln
            180                 185                 190

Ser Met Phe Thr Cys Arg Val Asp His Arg Gly Leu Thr Phe Gln Gln
        195                 200                 205

Asn Ala Ser Ser Met Cys Val Pro Asp Gln Asp Thr Ala Ile Arg Val
    210                 215                 220

Phe Ala Ile Pro Pro Ser Phe Ala Ser Ile Phe Leu Thr Lys Ser Thr
225                 230                 235                 240

Lys Leu Thr Cys Leu Val Thr Asp Leu Thr Thr Tyr Asp Ser Val Thr
                245                 250                 255

Ile Ser Trp Thr Arg Gln Asn Gly Glu Ala Val Lys Thr His Thr Asn
            260                 265                 270

Ile Ser Glu Ser His Pro Asn Ala Thr Phe Ser Ala Val Gly Glu Ala
        275                 280                 285

Ser Ile Cys Glu Asp Asp Trp Asn Ser Gly Glu Arg Phe Thr Cys Thr
    290                 295                 300
```

Val Thr His Thr Asp Leu Pro Ser Pro Leu Lys Gln Thr Ile Ser Arg
305                 310                 315                 320

Pro Lys Gly Val Ala Leu His Arg Pro Asp Val Tyr Leu Leu Pro Pro
            325                 330                 335

Ala Arg Glu Gln Leu Asn Leu Arg Glu Ser Ala Thr Ile Thr Cys Leu
            340                 345                 350

Val Thr Gly Phe Ser Pro Ala Asp Val Phe Val Gln Trp Met Gln Arg
            355                 360                 365

Gly Gln Pro Leu Ser Pro Glu Lys Tyr Val Thr Ser Ala Pro Met Pro
            370                 375                 380

Glu Pro Gln Ala Pro Gly Arg Tyr Phe Ala His Ser Ile Leu Thr Val
385                 390                 395                 400

Ser Glu Glu Glu Trp Asn Thr Gly Glu Thr Tyr Thr Cys Val Ala His
            405                 410                 415

Glu Ala Leu Pro Asn Arg Val Thr Glu Arg Thr Val Asp Lys Ser Thr
            420                 425                 430

Gly Lys Pro Thr Leu Tyr Asn Val Ser Leu Val Met Ser Asp Thr Ala
            435                 440                 445

Gly Thr Cys Tyr
            450

<210> SEQ ID NO 39
<211> LENGTH: 327
<212> TYPE: PRT
<213> ORGANISM: Homo sapiens

<400> SEQUENCE: 39

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg

```
                210                 215                 220
Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
                275                 280                 285

Arg Leu Thr Val Asp Lys Ser Arg Trp Gln Glu Gly Asn Val Phe Ser
                290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 40
<211> LENGTH: 353
<212> TYPE: PRT
<213> ORGANISM: Homo sapiens

<400> SEQUENCE: 40

Ala Ser Pro Thr Ser Pro Lys Val Phe Pro Leu Ser Leu Cys Ser Thr
1               5                   10                  15

Gln Pro Asp Gly Asn Val Val Ile Ala Cys Leu Val Gln Gly Phe Phe
                20                  25                  30

Pro Gln Glu Pro Leu Ser Val Thr Trp Ser Glu Ser Gly Gln Gly Val
                35                  40                  45

Thr Ala Arg Asn Phe Pro Pro Ser Gln Asp Ala Ser Gly Asp Leu Tyr
                50                  55                  60

Thr Thr Ser Ser Gln Leu Thr Leu Pro Ala Thr Gln Cys Leu Ala Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Ser Thr Pro Pro Thr Pro Ser Pro
                100                 105                 110

Ser Thr Pro Pro Thr Pro Ser Pro Ser Cys Cys His Pro Arg Leu Ser
                115                 120                 125

Leu His Arg Pro Ala Leu Glu Asp Leu Leu Leu Gly Ser Glu Ala Asn
                130                 135                 140

Leu Thr Cys Thr Leu Thr Gly Leu Arg Asp Ala Ser Gly Val Thr Phe
145                 150                 155                 160

Thr Trp Thr Pro Ser Ser Gly Lys Ser Ala Val Gln Gly Pro Pro Glu
                165                 170                 175

Arg Asp Leu Cys Gly Cys Tyr Ser Val Ser Ser Val Leu Pro Gly Cys
                180                 185                 190

Ala Glu Pro Trp Asn His Gly Lys Thr Phe Thr Cys Thr Ala Ala Tyr
                195                 200                 205

Pro Glu Ser Lys Thr Pro Leu Thr Ala Thr Leu Ser Lys Ser Gly Asn
                210                 215                 220

Thr Phe Arg Pro Glu Val His Leu Leu Pro Pro Pro Ser Glu Glu Leu
225                 230                 235                 240

Ala Leu Asn Glu Leu Val Thr Leu Thr Cys Leu Ala Arg Gly Phe Ser
                245                 250                 255
```

```
Pro Lys Asp Val Leu Val Arg Trp Leu Gln Gly Ser Gln Glu Leu Pro
            260                 265                 270

Arg Glu Lys Tyr Leu Thr Trp Ala Ser Arg Gln Glu Pro Ser Gln Gly
        275                 280                 285

Thr Thr Thr Phe Ala Val Thr Ser Ile Leu Arg Val Ala Ala Glu Asp
        290                 295                 300

Trp Lys Lys Gly Asp Thr Phe Ser Cys Met Val Gly His Glu Ala Leu
305                 310                 315                 320

Pro Leu Ala Phe Thr Gln Lys Thr Ile Asp Arg Leu Ala Gly Lys Pro
                325                 330                 335

Thr His Val Asn Val Ser Val Val Met Ala Glu Val Asp Gly Thr Cys
                340                 345                 350

Tyr

<210> SEQ ID NO 41
<211> LENGTH: 340
<212> TYPE: PRT
<213> ORGANISM: Homo sapiens

<400> SEQUENCE: 41

Ala Ser Pro Thr Ser Pro Lys Val Phe Pro Leu Ser Leu Asp Ser Thr
1               5                   10                  15

Pro Gln Asp Gly Asn Val Val Ala Cys Leu Val Gln Gly Phe Phe Pro
            20                  25                  30

Pro Gln Glu Pro Leu Ser Val Thr Trp Ser Glu Ser Gly Gln Asn Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Pro Asp Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Pro Pro Pro Cys Cys His Pro Arg
            100                 105                 110

Arg Leu Ser Leu His Arg Pro Ala Leu Glu Asp Leu Leu Leu Gly Ser
        115                 120                 125

Glu Ala Asn Leu Thr Cys Thr Leu Thr Gly Leu Arg Asp Ala Ser Gly
    130                 135                 140

Ala Thr Phe Thr Trp Thr Pro Ser Ser Gly Lys Ser Ala Val Gln Gly
145                 150                 155                 160

Pro Pro Glu Arg Asp Leu Cys Gly Cys Tyr Ser Val Ser Ser Val Leu
                165                 170                 175

Pro Gly Cys Ala Gln Pro Trp Asn His Gly Glu Thr Phe Thr Cys Thr
            180                 185                 190

Ala Ala His Pro Glu Leu Lys Thr Pro Leu Thr Ala Asn Ile Thr Lys
        195                 200                 205

Ser Gly Asn Thr Phe Arg Pro Glu Val His Leu Leu Pro Pro Pro Ser
    210                 215                 220

Glu Glu Leu Ala Leu Asn Glu Leu Val Thr Leu Thr Cys Leu Ala Arg
225                 230                 235                 240

Gly Phe Ser Pro Lys Asp Val Leu Val Arg Trp Leu Gln Gly Ser Gln
                245                 250                 255

Glu Leu Pro Arg Glu Lys Tyr Leu Thr Trp Ala Ser Arg Gln Glu Pro
            260                 265                 270
```

-continued

```
Ser Gln Gly Thr Thr Thr Phe Ala Val Thr Ser Ile Leu Arg Val Ala
        275                 280                 285
Ala Glu Asp Trp Lys Lys Gly Asp Thr Phe Ser Cys Met Val Gly His
    290                 295                 300
Glu Ala Leu Pro Leu Ala Phe Thr Gln Lys Thr Ile Asp Arg Met Ala
305                 310                 315                 320
Gly Lys Pro Thr His Val Asn Val Ser Val Val Met Ala Glu Val Asp
                325                 330                 335
Gly Thr Cys Tyr
            340

<210> SEQ ID NO 42
<211> LENGTH: 106
<212> TYPE: PRT
<213> ORGANISM: Homo sapiens

<400> SEQUENCE: 42

Thr Val Ala Ala Pro Ser Val Phe Ile Phe Pro Pro Ser Asp Glu Gln
1               5                   10                  15
Leu Lys Ser Gly Thr Ala Ser Val Val Cys Leu Leu Asn Asn Phe Tyr
            20                  25                  30
Pro Arg Glu Ala Lys Val Gln Trp Lys Val Asp Asn Ala Leu Gln Ser
        35                  40                  45
Gly Asn Ser Gln Glu Ser Val Thr Glu Gln Asp Ser Lys Asp Ser Thr
    50                  55                  60
Tyr Ser Leu Ser Ser Thr Leu Thr Leu Ser Lys Ala Asp Tyr Glu Lys
65                  70                  75                  80
His Lys Val Tyr Ala Cys Glu Val Thr His Gln Gly Leu Ser Ser Pro
                85                  90                  95
Val Thr Lys Ser Phe Asn Arg Gly Glu Cys
            100                 105

<210> SEQ ID NO 43
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gly Pro Ser Leu Lys Leu
1               5

<210> SEQ ID NO 44
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gly Gly Gly
1

<210> SEQ ID NO 45
<211> LENGTH: 4
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 45

Gly Pro Ser Leu
1

<210> SEQ ID NO 46
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gly Pro Ser
1

<210> SEQ ID NO 47
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Pro Ser Leu Lys
1

<210> SEQ ID NO 48
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gly Pro Ser Leu Lys
1               5

<210> SEQ ID NO 49
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ser Leu Lys Leu
1

<210> SEQ ID NO 50
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50
gaggtgcagc tgcaggagtc tggacctggc ctggtgacgc cctcacagag cctgtccatg      60
acttgcactg tctctgggtt ttcattaacc agctatagtg tacactgggt tcgccagcct     120
ccaggaaaga gtctggagtg gctgggagta atatgggctg gtggaagcac aaattataat     180
tcggctctca tgtccagact gagcatcagc aaagacaact ccaagagcca agttttctta    240
aaaatggaca gtctgcaaac tgatgacaca gccatatact actgtgccag agaggactcc    300
tggggtcaag aacctcagt caccgtctcc tca    333

```
<210> SEQ ID NO 51
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51
```

Glu Val Gln Leu Gln Glu Ser Gly Pro Gly Leu Val Thr Pro Ser Gln
1               5                   10                  15

Ser Leu Ser Met Thr Cys Thr Val Ser Gly Phe Ser Leu Thr Ser Tyr
            20                  25                  30

Ser Val His Trp Val Arg Gln Pro Pro Gly Lys Ser Leu Glu Trp Leu
        35                  40                  45

Gly Val Ile Trp Ala Gly Gly Ser Thr Asn Tyr Asn Ser Ala Leu Met
    50                  55                  60

Ser Arg Leu Ser Ile Ser Lys Asp Asn Ser Lys Ser Gln Val Phe Leu
65                  70                  75                  80

Lys Met Asp Ser Leu Gln Thr Asp Asp Thr Ala Ile Tyr Tyr Cys Ala
                85                  90                  95

Arg Glu Asp Ser Trp Gly Gln Gly Thr Ser Val Thr Val Ser Ser
            100                 105                 110

```
<210> SEQ ID NO 52
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52
```
gaggtgcagc tgcaggagtc tgggcagag cttgtgaggt caggggcctc agtcaagttg    60
tcctgcacag cttctggctt caacattaaa gactactata tgcactgggt gaagcagagg    120
cctgaacagg gcctggagtg gattggatgg attgatcctg aaaatgatga tactgaatat    180
gtcccgaagt tccagggcaa ggccagtatg actgcagaca catcctccaa cacagcctac    240
ctgcagctca gcagcctgac atctgaggac actgccgtct attactgtac agagctcgga    300
gcttactggg gccaggggac tctggtc    327

```
<210> SEQ ID NO 53
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53
```

Glu Val Gln Leu Gln Glu Ser Gly Ala Glu Leu Val Arg Ser Gly Ala
1               5                   10                  15

Ser Val Lys Leu Ser Cys Thr Ala Ser Gly Phe Asn Ile Lys Asp Tyr
            20                  25                  30

Tyr Met His Trp Val Lys Gln Arg Pro Glu Gln Gly Leu Glu Trp Ile
            35                  40                  45

Gly Trp Ile Asp Pro Glu Asn Asp Thr Glu Tyr Val Pro Lys Phe
 50                  55                  60

Gln Gly Lys Ala Ser Met Thr Ala Asp Thr Ser Asn Thr Ala Tyr
65                  70                  75                  80

Leu Gln Leu Ser Ser Leu Thr Ser Glu Asp Thr Ala Val Tyr Tyr Cys
                85                  90                  95

Thr Glu Leu Gly Ala Tyr Trp Gly Gln Gly Thr Leu Val
            100                 105

<210> SEQ ID NO 54
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54
gacattgtga tgacccagtc tcaaaaattc atgtccacat cagtaggaga cagggtcagc    60
gtcacctgca aggccagtca gaatgtgggt actaatgtag cctggtatca acagaaacca   120
gggcaatctc ctaaagcact gatttactcg gcatcctacc ggtacagtgg agtccctgat   180
cgcttcacag gcagtggatc tgggacagat ttcactctca ccatcagcaa tgtgcagtct   240
gaagacttgg cagagtattt ctgtcagcaa tataacagct atcccacgtt cggagggggg   300
accaagttgg aaataaaa                                                 318

<210> SEQ ID NO 55
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Asp Ile Val Met Thr Gln Ser Gln Lys Phe Met Ser Thr Ser Val Gly
 1               5                  10                  15

Asp Arg Val Ser Val Thr Cys Lys Ala Ser Gln Asn Val Gly Thr Asn
                20                  25                  30

Val Ala Trp Tyr Gln Gln Lys Pro Gly Gln Ser Pro Lys Ala Leu Ile
            35                  40                  45

Tyr Ser Ala Ser Tyr Arg Tyr Ser Gly Val Pro Asp Arg Phe Thr Gly
 50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Thr
                85                  90                  95

Phe Gly Gly Gly Thr Lys Leu Glu Ile Lys
            100                 105

<210> SEQ ID NO 56
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide -continued

<400> SEQUENCE: 56

```
gatgttgtga tgacccagat tccactcact ttgtcggtta ccattggaca accagcctcc      60
atctcttgca agtcaagtca gagcctctta gatagtaatg gaaagacata tttgaattgg     120
ttgtttcaga ggccaggcca gtctccaaag cgcctaatct atctggtgtc taaactggac     180
tctggagtcc ctgacaggtt cactggcagt ggatcaggga cagatttcac actgaaaatc     240
agcagagttg aggctgagga tttgggaatt tattattgct ggcaaagtac acattttcct     300
cacacgttcg gagggggac caagttggaa atcaaa                                 336
```

<210> SEQ ID NO 57
<211> LENGTH: 112
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 57

```
Asp Val Val Met Thr Gln Ile Pro Leu Thr Leu Ser Val Thr Ile Gly
 1               5                  10                  15
Gln Pro Ala Ser Ile Ser Cys Lys Ser Ser Gln Ser Leu Leu Asp Ser
            20                  25                  30
Asn Gly Lys Thr Tyr Leu Asn Trp Leu Phe Gln Arg Pro Gly Gln Ser
        35                  40                  45
Pro Lys Arg Leu Ile Tyr Leu Val Ser Lys Leu Asp Ser Gly Val Pro
    50                  55                  60
Asp Arg Phe Thr Gly Ser Gly Ser Gly Thr Asp Phe Thr Leu Lys Ile
65                  70                  75                  80
Ser Arg Val Glu Ala Glu Asp Leu Gly Ile Tyr Tyr Cys Trp Gln Ser
                85                  90                  95
Thr His Phe Pro His Thr Phe Gly Gly Gly Thr Lys Leu Glu Ile Lys
               100                 105                 110
```

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 58

```
Phe Ser Leu Thr Ser Tyr Ser
 1               5
```

<210> SEQ ID NO 59
<211> LENGTH: 8
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 59

```
Phe Ser Leu Thr Ser Tyr Ser Val
 1               5
```

<210> SEQ ID NO 60
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 60

Phe Ser Leu Thr Ser Tyr Ser Val His
1               5

<210> SEQ ID NO 61
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gly Phe Ser Leu Thr Ser Tyr Ser
1               5

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Ile Trp Ala Gly Gly Ser Thr
1               5

<210> SEQ ID NO 63
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Val Ile Trp Ala Gly Gly Ser Thr
1               5

<210> SEQ ID NO 64
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gly Val Ile Trp Ala Gly Gly Ser Thr
1               5

<210> SEQ ID NO 65
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Leu Gly Val Ile Trp Ala Gly Gly Ser Thr
1               5                   10
```

<210> SEQ ID NO 66
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Trp Leu Gly Val Ile Trp Ala Gly Gly Ser Thr
1               5                   10

<210> SEQ ID NO 67
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Ile Trp Ala Gly Gly Ser Thr Asn
1               5

<210> SEQ ID NO 68
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Val Ile Trp Ala Gly Gly Ser Thr Asn
1               5

<210> SEQ ID NO 69
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gly Val Ile Trp Ala Gly Gly Ser Thr Asn
1               5                   10

<210> SEQ ID NO 70
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Leu Gly Val Ile Trp Ala Gly Gly Ser Thr Asn
1               5                   10

<210> SEQ ID NO 71
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Trp Leu Gly Val Ile Trp Ala Gly Gly Ser Thr Asn
1               5                   10

<210> SEQ ID NO 72
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Ile Trp Ala Gly Gly Ser Thr Asn Tyr
1               5

<210> SEQ ID NO 73
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Val Ile Trp Ala Gly Gly Ser Thr Asn Tyr
1               5                   10

<210> SEQ ID NO 74
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gly Val Ile Trp Ala Gly Gly Ser Thr Asn Tyr
1               5                   10

<210> SEQ ID NO 75
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Leu Gly Val Ile Trp Ala Gly Gly Ser Thr Asn Tyr
1               5                   10

<210> SEQ ID NO 76
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Trp Leu Gly Val Ile Trp Ala Gly Gly Ser Thr Asn Tyr
1               5                   10

<210> SEQ ID NO 77
<211> LENGTH: 4
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 77

Arg Glu Asp Ser
1

<210> SEQ ID NO 78
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Ala Arg Glu Asp Ser
1               5

<210> SEQ ID NO 79
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Gln Asn Val Gly Thr Asn
1               5

<210> SEQ ID NO 80
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gln Asn Val Gly Thr Asn Val
1               5

<210> SEQ ID NO 81
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Gln Asn Val Gly Thr Asn Val Ala
1               5

<210> SEQ ID NO 82
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Ser Ala Ser
1

<210> SEQ ID NO 83
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Tyr Ser Ala Ser
1

<210> SEQ ID NO 84
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Ile Tyr Ser Ala Ser
1               5

<210> SEQ ID NO 85
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Leu Ile Tyr Ser Ala Ser
1               5

<210> SEQ ID NO 86
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Ala Leu Ile Tyr Ser Ala Ser
1               5

<210> SEQ ID NO 87
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Ser Ala Ser Tyr
1

<210> SEQ ID NO 88
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Tyr Ser Ala Ser Tyr
1               5

<210> SEQ ID NO 89
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Ile Tyr Ser Ala Ser Tyr
1               5

<210> SEQ ID NO 90
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Leu Ile Tyr Ser Ala Ser Tyr
1               5

<210> SEQ ID NO 91
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Ala Leu Ile Tyr Ser Ala Ser Tyr
1               5

<210> SEQ ID NO 92
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Ser Ala Ser Tyr Arg
1               5

<210> SEQ ID NO 93
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Tyr Ser Ala Ser Tyr Arg
1               5

<210> SEQ ID NO 94
<211> LENGTH: 7

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Ile Tyr Ser Ala Ser Tyr Arg
1               5

<210> SEQ ID NO 95
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Leu Ile Tyr Ser Ala Ser Tyr Arg
1               5

<210> SEQ ID NO 96
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Ala Leu Ile Tyr Ser Ala Ser Tyr Arg
1               5

<210> SEQ ID NO 97
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Ser Ala Ser Tyr Arg Tyr
1               5

<210> SEQ ID NO 98
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Tyr Ser Ala Ser Tyr Arg Tyr
1               5

<210> SEQ ID NO 99
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Ile Tyr Ser Ala Ser Tyr Arg Tyr
```

```
1               5
```

<210> SEQ ID NO 100
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

```
Leu Ile Tyr Ser Ala Ser Tyr Arg Tyr
1               5
```

<210> SEQ ID NO 101
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

```
Ala Leu Ile Tyr Ser Ala Ser Tyr Arg Tyr
1               5                   10
```

<210> SEQ ID NO 102
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

```
Ser Ala Ser Tyr Arg Tyr Ser
1               5
```

<210> SEQ ID NO 103
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

```
Tyr Ser Ala Ser Tyr Arg Tyr Ser
1               5
```

<210> SEQ ID NO 104
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

```
Ile Tyr Ser Ala Ser Tyr Arg Tyr Ser
1               5
```

<210> SEQ ID NO 105
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 105

Leu Ile Tyr Ser Ala Ser Tyr Arg Tyr Ser
1               5                   10

<210> SEQ ID NO 106
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Ala Leu Ile Tyr Ser Ala Ser Tyr Arg Tyr Ser
1               5                   10

<210> SEQ ID NO 107
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Gly Gly Ser Gly Gly Ser
1               5

<210> SEQ ID NO 108
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Gln Gln Tyr Asn Ser Tyr Pro
1               5

<210> SEQ ID NO 109
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Gln Gln Tyr Asn Ser Tyr Pro Thr
1               5

<210> SEQ ID NO 110
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Phe Asn Ile Lys Asp Tyr Tyr
1               5

<210> SEQ ID NO 111

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Phe Asn Ile Lys Asp Tyr Tyr Met
1               5

<210> SEQ ID NO 112
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Phe Asn Ile Lys Asp Tyr Tyr Met His
1               5

<210> SEQ ID NO 113
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Gly Phe Asn Ile Lys Asp Tyr Tyr
1               5

<210> SEQ ID NO 114
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Ile Asp Pro Glu Asn Asp Asp Thr
1               5

<210> SEQ ID NO 115
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Trp Ile Asp Pro Glu Asn Asp Asp Thr
1               5

<210> SEQ ID NO 116
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116
```

```
Gly Trp Ile Asp Pro Glu Asn Asp Asp Thr
1               5                   10

<210> SEQ ID NO 117
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Ile Gly Trp Ile Asp Pro Glu Asn Asp Asp Thr
1               5                   10

<210> SEQ ID NO 118
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Trp Ile Gly Trp Ile Asp Pro Glu Asn Asp Asp Thr
1               5                   10

<210> SEQ ID NO 119
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Ile Asp Pro Glu Asn Asp Asp Thr Glu
1               5

<210> SEQ ID NO 120
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Trp Ile Asp Pro Glu Asn Asp Asp Thr Glu
1               5                   10

<210> SEQ ID NO 121
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Gly Trp Ile Asp Pro Glu Asn Asp Asp Thr Glu
1               5                   10

<210> SEQ ID NO 122
<211> LENGTH: 12
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 122

Ile Gly Trp Ile Asp Pro Glu Asn Asp Asp Thr Glu
1               5                   10

<210> SEQ ID NO 123
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Trp Ile Gly Trp Ile Asp Pro Glu Asn Asp Asp Thr Glu
1               5                   10

<210> SEQ ID NO 124
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Ile Asp Pro Glu Asn Asp Asp Thr Glu Tyr
1               5                   10

<210> SEQ ID NO 125
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Trp Ile Asp Pro Glu Asn Asp Asp Thr Glu Tyr
1               5                   10

<210> SEQ ID NO 126
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Gly Trp Ile Asp Pro Glu Asn Asp Asp Thr Glu Tyr
1               5                   10

<210> SEQ ID NO 127
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Ile Gly Trp Ile Asp Pro Glu Asn Asp Asp Thr Glu Tyr
1               5                   10

```
<210> SEQ ID NO 128
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Trp Ile Gly Trp Ile Asp Pro Glu Asn Asp Asp Thr Glu Tyr
1               5                   10

<210> SEQ ID NO 129
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Thr Glu Leu Gly Ala Tyr
1               5

<210> SEQ ID NO 130
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Gln Ser Leu Leu Asp Ser Asn Gly Lys Thr Tyr
1               5                   10

<210> SEQ ID NO 131
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Gln Ser Leu Leu Asp Ser Asn Gly Lys Thr Tyr Leu
1               5                   10

<210> SEQ ID NO 132
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Gln Ser Leu Leu Asp Ser Asn Gly Lys Thr Tyr Leu Asn
1               5                   10

<210> SEQ ID NO 133
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133
```

Leu Val Ser
1

<210> SEQ ID NO 134
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Tyr Leu Val Ser
1

<210> SEQ ID NO 135
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Ile Tyr Leu Val Ser
1               5

<210> SEQ ID NO 136
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Leu Ile Tyr Leu Val Ser
1               5

<210> SEQ ID NO 137
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Arg Leu Ile Tyr Leu Val Ser
1               5

<210> SEQ ID NO 138
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Leu Val Ser Lys
1

<210> SEQ ID NO 139
<211> LENGTH: 5
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 139

Tyr Leu Val Ser Lys
1               5

<210> SEQ ID NO 140
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Ile Tyr Leu Val Ser Lys
1               5

<210> SEQ ID NO 141
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Leu Ile Tyr Leu Val Ser Lys
1               5

<210> SEQ ID NO 142
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Arg Leu Ile Tyr Leu Val Ser Lys
1               5

<210> SEQ ID NO 143
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Leu Val Ser Lys Leu
1               5

<210> SEQ ID NO 144
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Tyr Leu Val Ser Lys Leu
1               5
```

<210> SEQ ID NO 145
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Ile Tyr Leu Val Ser Lys Leu
1               5

<210> SEQ ID NO 146
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Leu Ile Tyr Leu Val Ser Lys Leu
1               5

<210> SEQ ID NO 147
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Arg Leu Ile Tyr Leu Val Ser Lys Leu
1               5

<210> SEQ ID NO 148
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Leu Val Ser Lys Leu Asp
1               5

<210> SEQ ID NO 149
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Tyr Leu Val Ser Lys Leu Asp
1               5

<210> SEQ ID NO 150
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 150

Ile Tyr Leu Val Ser Lys Leu Asp
1               5

<210> SEQ ID NO 151
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Leu Ile Tyr Leu Val Ser Lys Leu Asp
1               5

<210> SEQ ID NO 152
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Arg Leu Ile Tyr Leu Val Ser Lys Leu Asp
1               5                   10

<210> SEQ ID NO 153
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Leu Val Ser Lys Leu Asp Ser
1               5

<210> SEQ ID NO 154
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Tyr Leu Val Ser Lys Leu Asp Ser
1               5

<210> SEQ ID NO 155
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Ile Tyr Leu Val Ser Lys Leu Asp Ser
1               5

<210> SEQ ID NO 156
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 156

Leu Ile Tyr Leu Val Ser Lys Leu Asp Ser
1               5                   10

<210> SEQ ID NO 157
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Arg Leu Ile Tyr Leu Val Ser Lys Leu Asp Ser
1               5                   10

<210> SEQ ID NO 158
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Trp Gln Ser Thr His Phe Pro His
1               5

<210> SEQ ID NO 159
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Trp Gln Ser Thr His Phe Pro His Thr
1               5

<210> SEQ ID NO 160
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(10)
<223> OTHER INFORMATION: a, c, t, g, unknown or other

<400> SEQUENCE: 160
watcaannnn ttr                                                        13
```